US012589156B2

(12) United States Patent
Sparks et al.

(10) Patent No.: US 12,589,156 B2
(45) Date of Patent: Mar. 31, 2026

(54) BENZIMIDAZOLE AND BENZIMIDAZOLONE BASED PROTAC COMPOUNDS FOR THE TARGETED DEGRADATION OF LEUCINE RICH REPEAT KINASE 2 (LRRK2)

(71) Applicant: Arvinas Operations, Inc., New Haven, CT (US)

(72) Inventors: Steven M. Sparks, Guilford, CT (US); Michael Berlin, Yardley, PA (US)

(73) Assignee: Arvinas Operations, Inc., New Haven, CT (US)

(*) Notice: Subject to any disclaimer, the term of this patent is extended or adjusted under 35 U.S.C. 154(b) by 0 days.

(21) Appl. No.: 19/088,147

(22) Filed: Mar. 24, 2025

(65) Prior Publication Data

US 2025/0228952 A1 Jul. 17, 2025

Related U.S. Application Data

(63) Continuation of application No. PCT/US2024/048800, filed on Sep. 27, 2024.

(60) Provisional application No. 63/586,344, filed on Sep. 28, 2023.

(51) Int. Cl.

| | |
|---|---|
| ***A61K 47/55*** | (2017.01) |
| ***A61K 47/54*** | (2017.01) |
| ***C07D 401/14*** | (2006.01) |
| ***C07D 471/04*** | (2006.01) |

(52) U.S. Cl.

CPC ............ *A61K 47/55* (2017.08); *A61K 47/545* (2017.08); *C07D 401/14* (2013.01); *C07D 471/04* (2013.01)

(58) Field of Classification Search

CPC .... A61K 47/55; A61K 47/545; C07D 401/14; C07D 471/04; A61P 25/28

USPC .......................................................... 514/252

See application file for complete search history.

(56) References Cited

U.S. PATENT DOCUMENTS

| | | | |
|---|---|---|---|
| 11,981,683 | B2 | 5/2024 | Araujo et al. |
| 12,053,469 | B2 | 8/2024 | Araujo et al. |
| 2011/0301141 | A1 | 12/2011 | Baker-Glenn et al. |
| 2016/0009681 | A1 | 1/2016 | Miller et al. |
| 2016/0009689 | A1 | 1/2016 | Miller et al. |
| 2016/0176916 | A1 | 6/2016 | Bradner et al. |
| 2018/0099940 | A1 | 4/2018 | Crew et al. |
| 2021/0238193 | A1 | 8/2021 | Mainolfi et al. |
| 2021/0361774 | A1 | 11/2021 | Gray et al. |
| 2023/0083376 | A1 | 3/2023 | Lu et al. |
| 2023/0097358 | A1 | 3/2023 | Araujo et al. |
| 2024/0360152 | A1 | 10/2024 | Araujo et al. |
| 2025/0114356 | A1 | 4/2025 | Araujo et al. |

FOREIGN PATENT DOCUMENTS

| | | | |
|---|---|---|---|
| CN | 110621322 | A | 12/2019 |
| CN | 112888460 | A | 6/2021 |
| WO | 2011/141756 | A1 | 11/2011 |
| WO | 2014/134774 | A1 | 9/2014 |
| WO | 2014/134776 | A1 | 9/2014 |
| WO | 2014/137723 | A1 | 9/2014 |
| WO | 2015/160842 | A1 | 10/2015 |
| WO | 2015/160845 | A2 | 10/2015 |
| WO | 2018/148443 | A1 | 8/2018 |
| WO | 2019/199816 | A1 | 10/2019 |
| WO | 2019/222173 | A1 | 11/2019 |
| WO | 2020/081682 | A1 | 4/2020 |
| WO | 2021/127278 | A1 | 6/2021 |
| WO | 2021/194878 | A1 | 9/2021 |
| WO | 2021/194879 | A1 | 9/2021 |
| WO | 2022/198112 | A1 | 9/2022 |

(Continued)

OTHER PUBLICATIONS

CID 175666551, also known as ARV-102, retrieved from Pubchem database https://pubchem.ncbi.nlm.nih.gov/compound/175666551 (Year: 2025).*

(Continued)

*Primary Examiner* — Jared Barsky
*Assistant Examiner* — Liyuan Mou
(74) *Attorney, Agent, or Firm* — McCarter & English, LLP; Michael J. DeGrazia; James M. Alburger

(57) ABSTRACT

Provided herein are compounds (e.g., compounds of Formula (Ia)) that function to recruit LRRK2 protein or a mutated version thereof to an E3 ubiquitin ligase for targeted ubiquitination and subsequent proteasomal degradation.

(Ia)

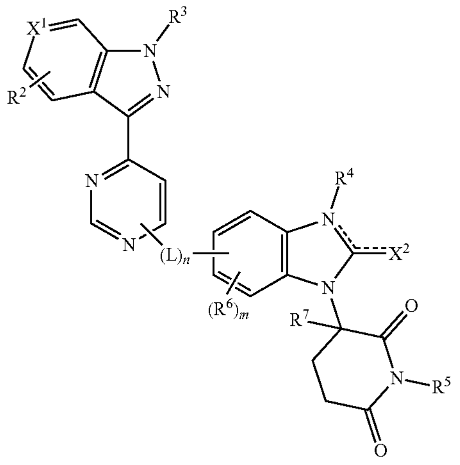

12 Claims, No Drawings

(56) References Cited

FOREIGN PATENT DOCUMENTS

| | | | |
|---|---|---|---|
| WO | 2023/283606 | A1 | 1/2023 |
| WO | 2024/054876 | A1 | 3/2024 |

OTHER PUBLICATIONS

Liu et al., Discovery of XL01126: A Potent, Fast, Cooperative, Selective, Orally Bioavailable, and Blood—Brain Barrier Penetrant PROTAC Degrader of Leucine-Rich Repeat Kinase 2. Journal of the American Chemical Society. 2022;144:16930-16952.
PubChem SID No. 447021161, LIJMLEVZYKFYAF-YYFFZOGMSA-N. 3 pages, Nov. 10, 2021.
International Preliminary Report on Patentability for Application No. PCT/US2021/023183, dated Oct. 8, 2022, 8 pages.
International Preliminary Report on Patentability for Application No. PCT/US2022/021049, dated Sep. 28, 2023, 8 pages.
International Preliminary Report on Patentability for Application No. PCT/US2023/075389, dated Mar. 20, 2025, 6 pages.
International Search Report and Written Opinion for Application No. PCT/US2021/023179, dated Jun. 10, 2021, 10 pages.
International Search Report and Written Opinion for Application No. PCT/US2021/023183, dated Jun. 10, 2021, 13 pages.
International Search Report and Written Opinion for Application No. PCT/US2024/048800, dated Jan. 23, 2025, 9 pages.
International Search Report for International Application No. PCT/US2022/021049, mailed Jun. 30, 2022, 5 pages.

* cited by examiner

BENZIMIDAZOLE AND BENZIMIDAZOLONE BASED PROTAC COMPOUNDS FOR THE TARGETED DEGRADATION OF LEUCINE RICH REPEAT KINASE 2 (LRRK2)

RELATED APPLICATIONS

This application is a continuation of International Patent Application No. PCT/US2024/048800, filed Sep. 27, 2024, which in turn claims the benefit of priority to U.S. provisional application No. 63/586,344, filed Sep. 28, 2023. The entire contents of each of the foregoing applications are incorporated herein by reference.

BACKGROUND

Lewy bodies are the main histological hallmark of Parkinson's disease (PD). Lewy bodies are composed primarily of alpha-synuclein aggregates, and mutations in alpha-synuclein that increase this aggregation also increase the risk of developing PD (Meade R M, et al. Mol Neurodegener 2019, 14. 29-29). Depletion of Leucine-rich repeat kinase 2 (LRRK2) with ASOs and deletion of LRRK2 at a genomic level have been shown to reduce alpha-synuclein mediated pathology in mouse models of PD (Lin X, et al. Neuron 2009, 64:807-27). Mutations increasing LRRK2 activity, such as G2019S, increase the aggregation of alpha-synuclein in neurons and mouse models of PD. This increase was reversed with LRRK2 kinase inhibitors (Volpicelli-Daley L A, et al. J Neurosci. 2016 Jul. 13; 36 (28): 7415-27). There is some evidence to suggest that the G2019S mutant form of LRRK2 is resistant to inhibition by kinase inhibitors in the central nervous system (CNS), potentially reducing their disease modifying effect (Kelly K, et al. Exp Neurol. 2018 November; 309:1-13). Even though most cases of PD also have Lewy bodies upon post-mortem examination, Lewy bodies are not present in a high number of LRRK2 G2019S mutation associated PD cases (Kalia L V, et al. JAMA neurol 2015, 72:100-05). In addition to Lewy bodies being a common feature of PD, Tau pathology is also a major feature of LRRK2 mutation carriers at post-mortem (Henderson M X, et al. Acta Neuropathol Commun 2019, 7. 183).

LRRK2 is highly expressed in the immune system in neutrophils, monocytes, and macrophages, as well as in brain microglia, and is a modulator of the intrinsic regulation of microglial activation and of lysosomal degradation processes (Ma et al. Hum Mol Genet. 2014 Feb. 1; 23 (3): 831-41). Prolonged activation of these immune cells through PD processes or mutations in LRRK2 could increase neuroinflammation and lead to a greater risk of developing PD and/or Tau pathology. In addition to PD, LRRK2 has been linked to other diseases such as cancer, leprosy, and Crohn's disease (Lewis P A, (2012). Sci Signal. 5 (207), pe2).

An ongoing need exists in the art for effective treatments for LRRK2 related disease and disorders, e.g., idiopathic PD, LRRK2 mutation associated PD (e.g., PD associated with one or more LRRK2 activating mutations), primary tauopathies (e.g., progressive supranuclear palsy (PSP) or corticobasal degeneration (CBD)), lewy body dementia, Crohn's Disease, Leprosy (e.g., Leprosy with type 1 inflammatory reactions), and/or neuroinflammation.

SUMMARY

Provided herein are compounds, pharmaceutically acceptable salts thereof, and pharmaceutical compositions comprising these compounds and salts, that function to recruit LRRK2 protein or a mutated version thereof to an E3 ubiquitin ligase for targeted ubiquitination and subsequent proteasomal degradation. As such, these compounds are useful in the treatment of a variety of indications, including Parkinson's Disease (PD).

In particular, provided herein are compounds of Formula (Ia):

(Ia)

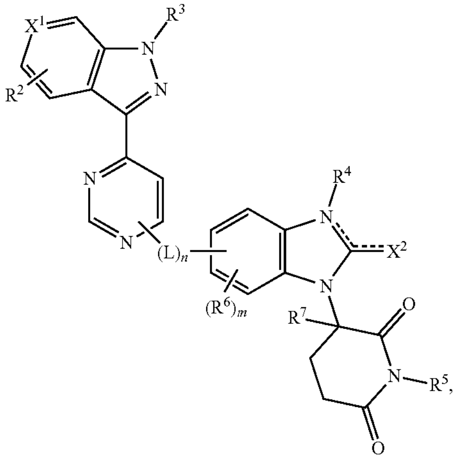

or pharmaceutically acceptable salts thereof, wherein the variables are defined herein.

Also provided herein are pharmaceutical compositions comprising the compounds described herein, or pharmaceutically acceptable salts thereof, and a pharmaceutically acceptable carrier.

Further, provided herein are methods of treating a disease, a disorder, or a symptom causally related to LRRK2 comprising administering to a subject an effective amount of any of the compounds described herein, or a pharmaceutical composition comprising an effective amount of one or more compounds described herein or a pharmaceutically acceptable salt thereof.

Further, provided herein are uses of an effective amount of any of the compounds described herein, or a pharmaceutically acceptable salt thereof, or a pharmaceutical composition comprising an effective amount of one or more compounds described herein or a pharmaceutically acceptable salt thereof for treating a disease, a disorder, or a symptom causally related to LRRK2.

Further, provided herein are uses of an effective amount of any of the compounds described herein, or a pharmaceutically acceptable salt thereof, or a pharmaceutical composition comprising an effective amount of one or more compounds described herein or a pharmaceutically acceptable salt thereof, for the manufacture of a medicament for treating a disease, a disorder, or a symptom causally related to LRRK2.

DETAILED DESCRIPTION

Leucine-rich repeat kinase 2 (LRRK2) is a member of the leucine-rich repeat kinase family. Catalytic activities of LRRK2 are associated with the kinase and GTPase domain, and LRRK2 is a heterodimer in its active form (Greggio E, et al. J Biol Chem 2008, 283:16906-16914). GTP binding is essential for kinase activity, and mutations that prevent GTP binding have been shown to ablate LRRK2 kinase activity (Ito G, et al. Biochemistry 2007, 46:1380-88). Expression levels of LRRK2 are highest in immune cells, such as neutrophils, monocytes and B cells, lung, and kidney, with lower levels in the brain where it is expressed in dopaminergic neurons of the substantia nigra (West A B, et al. J Comp Neurol 2014, 522:2465-2480).

There are several dominant gain-of-function pathogenic and characterized mutations to LRRK2 located either in the Roco domains (N1437H, R1441G/C/H, Y1699C) effecting GTP hydrolysis or in the kinase domains (G2019S and I2020T). The G2019S is the most common LRRK2 mutation linked to Parkinson's disease (PD), which is a progressive neurodegenerative disorder characterized by resting tremors, rigidity, decreased movement (bradykinesia), and postural instability. The histological hallmarks of PD include neurodegeneration of the dopaminergic neurons in the substantia nigra pars compacta as well as intracellular inclusions called Lewy bodies and neurites consisting of the aggregated form of the alpha-synuclein protein. G2019S is associated with 1-2% of all PD patients and causes an increase in kinase activity of 2-fold in vitro (West A B, et al. Proc Natl Acad Sci USA 2005, 102:16842-47) and autophosphorylation at Ser1292 is increased 4-fold (Sheng Z, et al. Sci Transl Med 2012, 4:164ra161). Several of the above Parkinson disease-associated mutations (R1441C/G, Y1699C and I2020T) suppress phosphorylation of LRRK2 at Ser910 and Ser935, which in turn reduces LRRK2 association with 14-3-3 proteins, thought to represent an inactive form of LRRK2 (Nichols J, et al. Biochem J 2010, 430: 393-404).

Furthermore, LRRK2 is linked to autosomal dominant inherited PD through a mutation within a region of chromosome 12, termed PARK8, which is linked to the LRRK2 gene (Funayama M, et al. Ann Neurol 2002, 51:296-301; Zimprich A, et al. Neuron 2004, 44:601-607; Paisan-Ruiz C, et al. Neuron 2004, 44:595-600).

LRRK2 is highly expressed in the immune system in neutrophils, monocytes, and macrophages, as well as in brain microglia, and is a modulator of the intrinsic regulation of microglial activation and of lysosomal degradation processes (Ma et al. Hum Mol Genet. 2014 Feb. 1; 23 (3): 831-41). Prolonged activation of these immune cells through PD processes or mutations in LRRK2 could increase neuroinflammation and lead to a greater risk of developing PD and/or Tau pathology. In addition to PD, LRRK2 has been linked to other diseases such as cancer, leprosy, and Crohn's disease (Lewis P A, (2012). Sci Signal. 5 (207), pe2).

Provided herein are compounds (e.g., compounds of Formula (Ia)), pharmaceutically acceptable salts of these compounds, and pharmaceutical compositions comprising these compounds and salts, that function to recruit LRRK2 protein or a mutated version thereof to an E3 ubiquitin ligase for targeted ubiquitination and subsequent proteasomal degradation.

As such, these compounds, as well as pharmaceutically acceptable salts of these compounds, and pharmaceutical compositions comprising these compounds or pharmaceutically acceptable salts thereof, are useful in the treatment of a variety of indications, including Parkinson's Disease.

Definitions

Listed below are definitions of various terms used to describe the compounds and compositions described herein. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting.

As used herein, the term "about" will be understood by persons of ordinary skill in the art and will vary to some extent on the context in which it is used. The terms "administering," "administer," and "administration" as used herein refer to the providing of a therapeutic agent to a subject. Multiple techniques of administering a therapeutic agent exist in the art including, but not limited to, intravenous, oral, aerosol, parenteral, ophthalmic, pulmonary, and topical administration.

The term "treat," "treated," "treating," or "treatment" includes the diminishment or alleviation of at least one symptom associated or caused by the state, disorder or disease being treated. In embodiments, the treatment comprises alleviating the symptoms of inflammation and age-related disorders.

As used herein, the terms "preventing," "prevent," and "prevention" means no disorder or disease development occurred, or no further disorder or disease development occurred if there had already been prior development of the disorder or disease. Also considered is the ability of one to prevent some or all the symptoms associated with the disorder or disease.

"Bioactive agent" refers to an agent, other than a compound according to the present disclosure, which is used in combination with a present compound as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents, antiviral agents, especially including anti-HIV agents and anti-HCV agents, antimicrobial agents, antifungal agents, etc.

As used herein, the term "contacting" refers to the bringing together of indicated moieties in an in vitro system or an in vivo system. For example, "contacting" a cell with a compound includes the administration of a compound of the present invention to an individual, subject, or patient, such as a human, as well as, for example, introducing a compound into a sample containing a purified preparation containing the cell.

As used herein, the term "cell" is meant to refer to a cell that is in vitro, ex vivo, or in vivo. In some embodiments, an ex vivo cell can be part of a tissue sample excised from an organism such as a mammal. In some embodiments, an in vitro cell can be a cell in a cell culture. In embodiments, an in vivo cell is a cell living in an organism such as a mammal.

As used herein, the term "patient," "individual," or "subject" refers to a human or a non-human mammal. Non-human mammals include, for example, livestock and pets, such as ovine, bovine, porcine, canine, feline and marine mammals. Preferably, the patient, subject, or individual is human.

As used herein, the term "effective amount" refers to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the described compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. The phrase "pharmaceutically acceptable salt" is not limited to a mono, or 1:1, salt. For example, "pharmaceutically acceptable salt" also includes bis-salts, such as a bis-hydrochloride salt. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound useful within the disclosure with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

As used herein, the term "pharmaceutically acceptable carrier" means a pharmaceutically acceptable material, composition, or carrier, such as a liquid or solid filler, stabilizer, dispersing agent, suspending agent, diluent, excipient, thickening agent, solvent, or encapsulating material, involved in carrying or transporting a compound useful within the disclosure within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the disclosure, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

The term "pharmaceutically acceptable carrier" also includes any and all coatings, antibacterial and antifungal agents, and absorption delaying agents, and the like that are compatible with the activity of the compound useful within the present disclosure and are physiologically acceptable to the patient. Supplementary active compounds may also be incorporated into the compositions. The "pharmaceutically acceptable carrier" may further include a pharmaceutically acceptable salt of the compound described herein. Other additional ingredients that may be included in the pharmaceutical compositions are known in the art and described, for example, in Remington's Pharmaceutical Sciences (Genaro, Ed., Mack Publishing Co., 1985, Easton, PA), which is incorporated herein by reference.

The language "pharmaceutically effective amount" or "pharmaceutically acceptable amount" of the compound is that amount necessary or sufficient to treat or prevent a disorder, e.g., prevent the various morphological and somatic symptoms of a disorder, disease, or condition described herein. The effective amount can vary depending on such factors as the size and weight of the subject, the type of illness, or the particular compound of the invention. For example, the choice of the compound provided herein can affect what constitutes an "effective amount." One of ordinary skill in the art would be able to study the factors contained herein and make the determination regarding the effective amount of the compounds of the invention without undue experimentation.

As used herein, the term "alkyl," by itself or as part of another substituent means, unless otherwise stated, a straight or branched chain hydrocarbon having the number of carbon atoms designated (i.e., $C_{1-6}$ alkyl means an alkyl having one to six carbon atoms) and includes straight and branched chains. Examples include methyl, ethyl, propyl, isopropyl, butyl, isobutyl, tert butyl, pentyl, neopentyl, and hexyl. Other examples of $C_{1-6}$ alkyl include ethyl, methyl, isopropyl, isobutyl, n-pentyl, and n-hexyl.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

"Alkoxy" means an alkyl radical attached through an oxygen linking atom, represented by —O-alkyl. For example, "$C_{1-4}$ alkoxy" includes methoxy, ethoxy, proproxy, and butoxy.

The term "haloalkyl" includes mono, poly, and perhaloalkyl groups where the halogens are independently selected from fluorine, chlorine, bromine, and iodine.

The term “acyl” refers to the group —$COCH_3$.

The term “alkynyl” as used herein refers to an unsaturated straight or branched hydrocarbon having at least one carbon-carbon triple bond. Exemplary alkynyl groups include, but are not limited to, ethynyl, propynyl, butynyl, pentynyl, hexynyl, methylpropynyl, etc.

As used herein, the term “cycloalkyl” means a non-aromatic carbocyclic system that is fully saturated having 1, 2, or 3 rings wherein such rings may be fused. The term “fused” means that a second ring is present (i.e., attached or formed) by having two adjacent atoms in common (i.e., shared) with the first ring. Cycloalkyl also includes bicyclic structures that may be bridged or spirocyclic in nature with each individual ring within the bicycle varying from 3-8 atoms. The term “cycloalkyl” includes, but is not limited to, cyclopropyl, cyclobutyl, cyclopentyl, cyclohexyl, bicyclo[3.1.0]hexyl, spiro[3.3]heptanyl, and bicyclo[1.1.1]pentyl. In embodiments, cycloalkyl refers to $C_{3-11}$ cycloalkyl. In embodiments, cycloalkyl refers to $C_{3-6}$ cycloalkyl. In embodiments, cycloalkyl refers to $C_{3-5}$ cycloalkyl. In embodiments, cycloalkyl refers to $C_3$ cycloalkyl.

As used herein, the term “heterocyclyl” means a non-aromatic carbocyclic system containing 1, 2, 3, or 4 heteroatoms independently selected from N, O, and S and having 1, 2, or 3 rings wherein such rings may be fused, wherein fused is defined above. The term “heterocyclyl” includes unsaturated compounds such as dihydropyridinyl, dihydropyridazinyl, dihydropyrimidinyl, and dihydropyrazinyl. Heterocyclyl also includes bicyclic structures that may be bridged or spirocyclic in nature with each individual ring within the bicycle varying from 3-8 atoms, and containing 0, 1, or 2 N, O, or S atoms. The term “heterocyclyl” includes cyclic esters (i.e., lactones) and cyclic amides (i.e., lactams) and also specifically includes, but is not limited to, epoxidyl, oxetanyl, tetrahydro-furanyl, tetrahydropyranyl (i.e., oxanyl), pyranyl, dioxanyl, aziridinyl, azetidinyl, pyrrolidinyl, 2,5-dihydro-1H-pyrrolyl, oxazolidinyl, thiazolidinyl, piperidinyl, morpholinyl, piperazinyl, thiomorpholinyl, 1,3-oxazinanyl, 1,3-thiazinanyl, 2-azabicyclo[2.1.1]hexanyl, 5-azabicyclo[2.1.1]-hexanyl, 6-azabicyclo[3.1.1]heptanyl, 2-azabicyclo[2.2.1]heptanyl, 3-azabicyclo[3.1.1]heptanyl, 2-azabicyclo[3.1.1]heptanyl, 3-azabicyclo[3.1.0]hexanyl, 2-azabicyclo[3.1.0]hexanyl, 3-azabicyclo[3.2.1]octanyl, 8-azabicyclo[3.2.1]octanyl, 3-oxa-7-azabicyclo[3.3.1]nonanyl, 3-oxa-9-azabicyclo[3.3.1]nonanyl, 2-oxa-5-azabicyclo[2.2.1]heptanyl, 6-oxa-3-azabicyclo[3.1.1]heptanyl, 2-azaspiro[3.3]heptanyl, 2-oxa-6-azaspiro[3.3]heptanyl, 2-oxaspiro[3.3]heptanyl, 2-oxaspiro[3.5]nonanyl, 3-oxaspiro[5.3]nonanyl, and 8-oxabicyclo[3.2.1]octanyl. In embodiments, heterocyclyl refers to 4-12-membered heterocyclyl. In embodiments, heterocyclyl refers to 5-10-membered heterocyclyl. In embodiments, heterocyclyl refers to 6-10-membered heterocyclyl. In embodiments, heterocyclyl refers to 5-8-membered heterocyclyl. In embodiments, heterocyclyl refers to 6-8-membered heterocyclyl. In embodiments, heterocyclyl refers to 4-7-membered heterocyclyl. In embodiments, heterocyclyl refers to 6-membered heterocyclyl.

A 6-membered heterocyclyl ring is a heterocyclyl group having six ring atoms wherein one or more (e.g., 1, 2, or 3) ring atoms are independently selected from N, O, and S. Exemplary 6-membered ring heterocyclyls include piperidinyl, piperazinyl, dioxanyl thianyl, dithianyl, morpholinyl, thiomorpholinyl, and dihydropyridinyl.

The term “heterocycloalkyl” refers to a heterocyclyl which is fully saturated.

It is to be understood that if a cycloalkyl or heterocyclyl moiety may be bonded or otherwise attached to a designated moiety through differing ring atoms (i.e., shown or described without denotation of a specific point of attachment), then all possible points are intended, whether through a carbon atom or, for example, a trivalent nitrogen atom.

The compounds described herein may exist as tautomers and optical isomers (e.g., enantiomers, diastereomers, diastereomeric mixtures, racemic mixtures, and the like).

When the stereochemical configuration at a chiral center in a compound having one or more chiral centers is depicted by its chemical name (e.g., where the configuration is indicated in the chemical name by “R” or “S”) or structure (e.g., the configuration is indicated by “wedge” bonds), the enrichment of the indicated configuration relative to the opposite configuration is greater than 50%, 60%, 70%, 80%, 90%, 99% or 99.9%. “Enrichment of the indicated configuration relative to the opposite configuration” is a mole percent and is determined by dividing the number of compounds with the indicated stereochemical configuration at the chiral center(s) by the total number of all of the compounds with the same or opposite stereochemical configuration in a mixture.

When a geometric isomer is depicted by name or structure, the enrichment of the indicated isomer relative to the opposite isomer is greater than 50%, 60%, 70%, 80%, 90%, 99% or 99.9%. “Enrichment of the indicated isomer relative to the opposite isomer” is a mole percent and is determined by dividing the number of compounds with the indicated geometrical configuration by the total number of all of the compounds with the same or opposite geometrical configuration in a mixture.

When the stereochemistry of the groups for compounds comprising a 1,4-substituted cyclohexyl or a 1,3-substituted cyclobutyl in variable L is depicted using “wedge” bonds, the stereochemistry of the groups on the ring are defined relative to one another. That is, the groups on the ring have either a trans or cis orientation towards one another, which can be depicted via either of the trans confirmations or either of the cis confirmations. For example, the stereochemistry for the groups on a cyclohexyl ring in variable L can be depicted using either 1,4-trans stereochemistry, both of which depict the same compound. Thus, a compound of Formula (Ia) can be depicted as either:

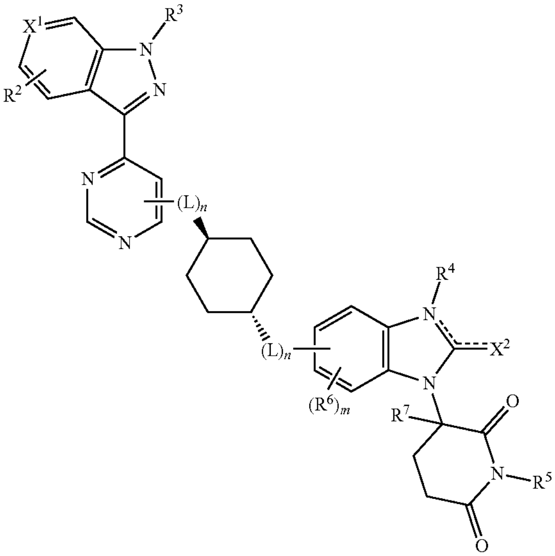
or

-continued

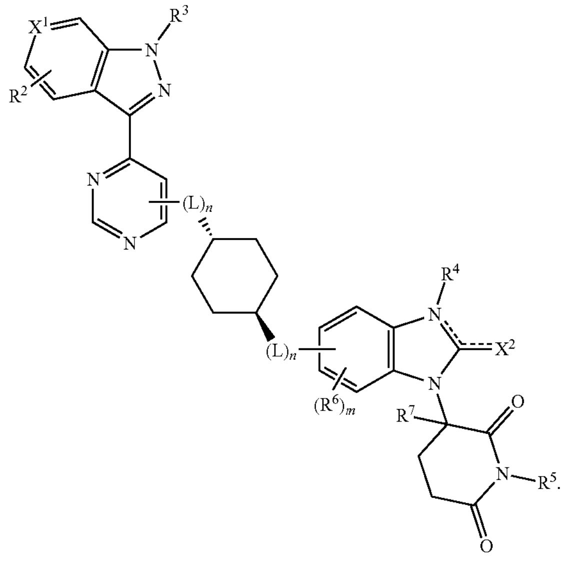

-continued

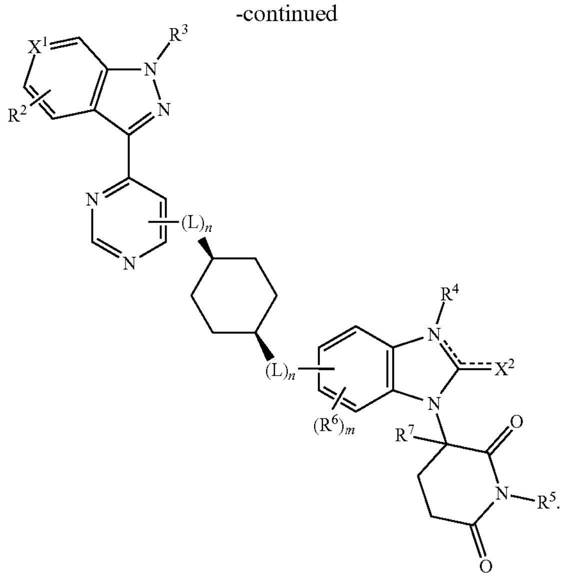

Similarly, the stereochemistry for the groups on a cyclohexyl ring in the variable L can be depicted using either 1,4-cis stereochemistry, both of which depict the same compound. Thus, a compound of Formula (Ia) can be depicted as either:

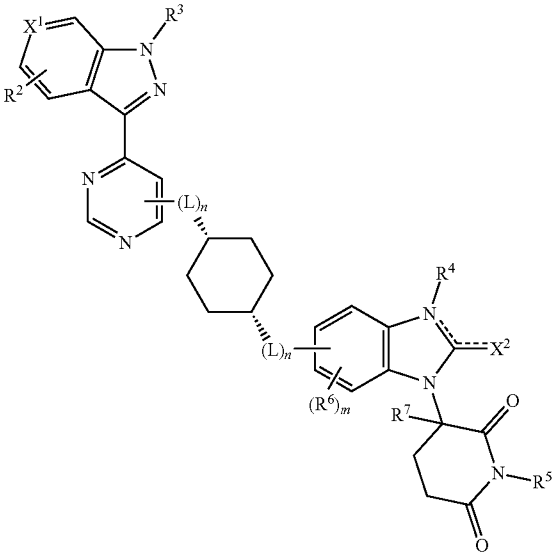

or

It will be understood that that selection of which trans or which cis isomer is depicted is arbitrary and is only intended to show the relative configuration of the groups on the ring.

When a described compound is named or depicted by a structure without indicating stereochemistry, it is understood that the name or the structure encompasses one of the possible stereoisomers or geometric isomers free of the others, or a mixture of the encompassed stereoisomers or geometric isomers.

To the extent there is a discrepancy between the structure of a compound and its name, the structure will control.

The terms "independently selected" or "each independently" are used herein to indicate that, for a variable which occurs in more than one location in a genus, the identity of the variable is determined separately in each instance. For example, if Rx appears as a substituent on two different atoms, the two instances of RX may be the same moiety, or different moieties. The same is true if a single atom is substituted with more than one instance of Rx. The identity of Rx in each instance is determined independently of the identity of the other(s).

Compounds

Provided herein are compounds of Formula (Ia):

(Ia)

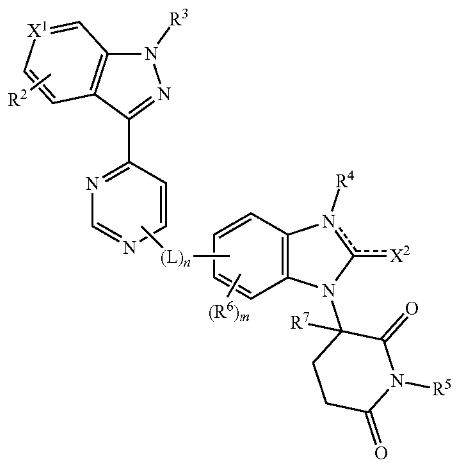

or a pharmaceutically acceptable salt thereof, wherein:

$X^1$ is $CR^1$ or N;

$X^2$ is H, $C_{1-3}$ alkyl, or O;

$R^1$, $R^2$, $R^3$, $R^4$, and $R^5$ are each independently selected from H, acetyl, halo, $C_{1-6}$ alkyl, $C_{1-6}$ haloalkyl, $C_{3-10}$ cycloalkyl, $OC_{3-6}$ cycloalkyl, and $C_{1-6}$ alkoxy, wherein the $C_{3-10}$ cycloalkyl, $OC_{3-6}$ cycloalkyl and $C_{1-6}$ alkoxy are optionally substituted with 1 or 2 $C_{1-6}$ alkyl or cyano;

$R^6$ is halo or $C_{1-3}$ alkyl;

$R^7$ is H or $C_{1-3}$ alkyl;

one ⎓ is a double bond, and one ⎓ is a single bond; provided that when $R^4N$⎓C is a double bond, then $R^4$ is absent; and provided that when $X^2$ is O, C⎓$X^2$ is a double bond;

each L is independently selected from $C_{1-6}$ alkyl, $C_{2-6}$ alkynyl, $C_{1-6}$ haloalkyl, $C_{1-6}$ alkoxy, O, $C_{3-11}$ cycloalkyl, and 4-12-membered heterocycloalkyl, wherein $C_{3-11}$ cycloalkyl and 4-12-membered heterocycloalkyl are optionally substituted with 1, 2, or 3 substituents $R^L$, wherein each $R^L$ is independently selected from halo, CN, and $C_{1-6}$ alkyl;

n is 1, 2, 3, 4, 5, 6, 7, 8, 9, or 10;

m is 0, 1, or 2.

In embodiments of Formula (Ia), $R^7$ is H or $-CH_3$.

In embodiments of Formula (Ia), m is 0 or 1 and $R^6$, when present, is halo.

In embodiments, the compound of Formula (Ia) is a compound of Formula (I):

(I)

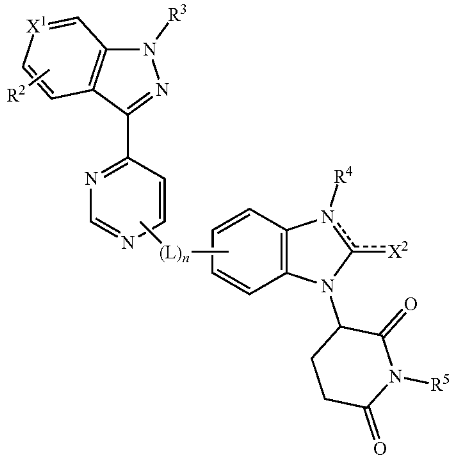

or pharmaceutically acceptable salts thereof, wherein:

$X^1$ is $CR^1$ or N;

$X^2$ is H or O;

$R^1$, $R^2$, $R^3$, $R^4$, and $R^5$ are each independently selected from H, acetyl, halo, $C_{1-6}$ alkyl, $C_{1-6}$ haloalkyl, $C_{3-6}$ cycloalkyl, $OC_{3-6}$ cycloalkyl, and $C_{1-6}$ alkoxy, wherein $C_{3-6}$ cycloalkyl, $OC_{3-6}$ cycloalkyl and $C_{1-6}$ alkoxy are optionally substituted with 1 or 2 $C_{1-6}$ alkyl;

one ⎓ is a double bond, and one ⎓ is a single bond; provided that when $R^4N$ ⎓ C is a double bond, then $R^4$ is absent; and provided that when $X^2$ is O, C⎓ $X^2$ is a double bond;

each L is independently selected from $C_{1-6}$ alkyl, $C_{2-6}$ alkynyl, $C_{1-6}$ haloalkyl, $C_{1-6}$ alkoxy, O, $C_{3-11}$ cycloalkyl, and 4-12-membered heterocycloalkyl, wherein $C_{3-11}$ cycloalkyl and 4-12-membered heterocycloalkyl are optionally substituted with 1, 2, or 3 substituents $R^L$, wherein each $R^L$ is independently selected from halo, CN, and $C_{1-6}$ alkyl; and n is 1, 2, 3, 4, 5, 6, 7, 8, 9, or 10.

In embodiments of Formulae (Ia) and (I), $X^1$ is $CR^1$ or N;

$X^2$ is H or O;

$R^1$, $R^2$, $R^3$, $R^4$, and $R^5$ are each independently selected from H, halo, $C_{1-6}$ alkyl, $C_{3-6}$ cycloalkyl, $OC_{3-6}$ cycloalkyl, and $C_{1-6}$ alkoxy, wherein $C_{3-6}$ cycloalkyl, $OC_{3-6}$ cycloalkyl, and $C_{1-6}$ alkoxy are optionally substituted with 1 or 2 $C_{1-6}$ alkyl;

each L is independently selected from $C_{1-6}$ alkyl, $C_{2-6}$ alkynyl, $C_{1-6}$ alkoxy, O, $C_{3-11}$ cycloalkyl, and 4-12-membered heterocycloalkyl, wherein 4-12-membered heterocycloalkyl is optionally substituted with 1 or 2 substituents $R^L$, wherein each $R^L$ is independently selected from halo, CN, and $C_{1-6}$ alkyl; and n is 1, 2, 3, 4, 5, 6, 7, or 8.

In embodiments of Formulae (Ia) and (I), $X^1$ is CH or N;

$X^2$ is H or O;

$R^2$, $R^3$, $R^4$, and $R^5$ are each independently selected from H, $C_{1-6}$ alkyl, $OC_{3-6}$ Cycloalkyl, and $C_{1-6}$ alkoxy, wherein $OC_{3-6}$ cycloalkyl, and $C_{1-6}$ alkoxy are optionally substituted with 1 or 2 $C_{1-4}$ alkyl;

each L is independently selected from $C_{1-6}$ alkyl, $C_{2-6}$ alkynyl, $C_{1-6}$ alkoxy, O, $C_{3-11}$ cycloalkyl, and 4-12-membered heterocycloalkyl, wherein 4-12-membered heterocycloalkyl is optionally substituted with 1 or 2 substituents $R^L$, wherein each $R^L$ is halo or $C_{1-6}$ alkyl; and n is 1, 2, 3, 4, 5, or 6.

In embodiments of Formulae (Ia) and (I), $X^1$ is CH or N;

$X^2$ is H or O;

$R^3$, $R^4$, and $R^5$ are each independently H or $C_{1-6}$ alkyl;

$R^2$ is $OC_{3-6}$ cycloalkyl, optionally substituted with 1 or 2 $C_{1-4}$ alkyl;

each L is independently selected from $C_{1-6}$ alkyl, $C_{2-6}$ alkynyl, $C_{1-6}$ alkoxy, O, $C_{3-11}$ cycloalkyl, and 4-12-membered heterocycloalkyl, wherein 3-12-membered heterocycloalkyl is optionally substituted with 1 or 2 substituents $R^L$, wherein each $R^L$ is halo or $C_{1-6}$ alkyl; and n is 1, 2, 3, 4, 5, or 6.

In embodiments of Formulae (Ia) and (I), $R^3$ is H.

In embodiments, the compound of Formula (I) is a compound of Formula (II):

(II)

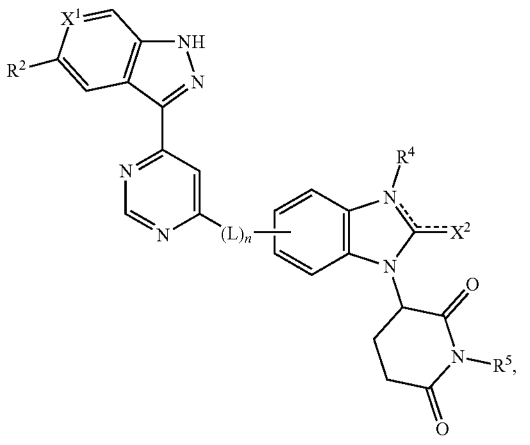

or a pharmaceutically acceptable salt thereof.

In embodiments of Formulae (Ia), (I), and (II), $R^4N$ === C is a double bond;

$X^2$ is H; and $R^4$ is absent.

In embodiments of Formulae (Ia), (I), and (II), $X^2$=== C is a double bond; and $X^2$ is O.

In embodiments, the compound of Formula (Ia), (I), or (II) is a compound of Formula (IIA):

(IIA)

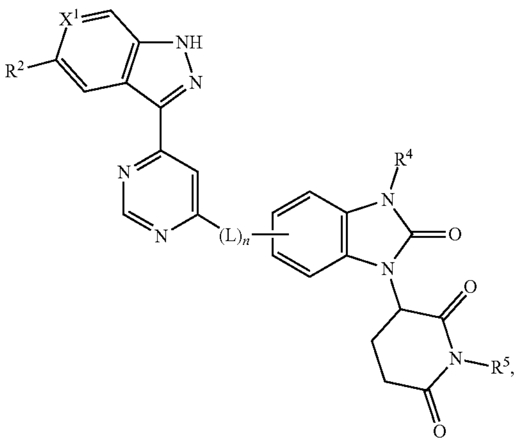

or a pharmaceutically acceptable salt thereof.

In embodiments, the compound of Formula (Ia), (I), or (II), is a compound of Formula (IIB):

(IIB)

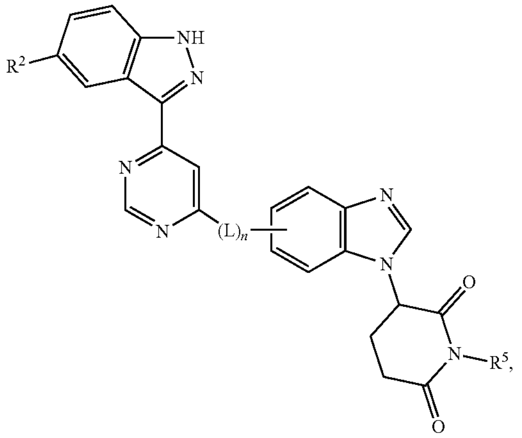

or a pharmaceutically acceptable salt thereof.

In embodiments of Formulae (Ia), (I), (II), (IIA), and (IIB), $R^1$ is H.

In embodiments of Formulae (Ia), (I), (II), (IIA), and (IIB), $R^2$ is $C_{1-4}$alkoxy, $C_{3-8}$ cycloalkyl, or $OC_{3-5}$ cycloalkyl, wherein the $C_{3-8}$ cycloalkyl and $OC_{3-5}$ cycloalkyl are each optionally substituted with 1 or 2 $C_{1-4}$ alkyl or cyano. In embodiments of Formulae (Ia), (I), (II), (IIA), and (IIB), $R^2$ is $OC_{3-5}$ cycloalkyl optionally substituted with 1 or 2 $C_{1-4}$ alkyl. In further embodiments of Formulae (I)-(IIB), $R^2$ is $OC_{3-5}$ cycloalkyl optionally substituted with $C_{1-3}$ alkyl. In still further embodiments of Formulae (I)-(IIB), $R^2$ is $OC_{3-5}$ cycloalkyl substituted with $CH_3$.

In embodiments of Formulae (Ia), (I), (II), (IIA), and (IIB), $R^2$ is $—OCH_3$, $—OCH_2CH_3$, $—OCH(CH_3)_2$, $—OC(CH_3)_3$,

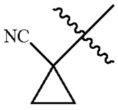, 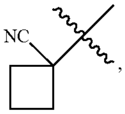, 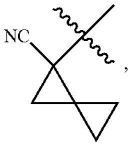,

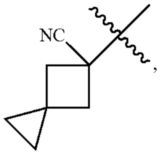, or 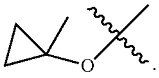.

In embodiments of Formulae (Ia), (I), (II), (IIA), and (IIB), $R^2$ is selected from

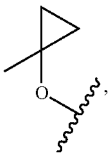, 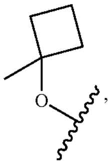, 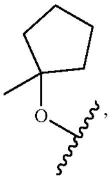, 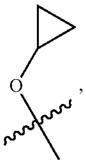,

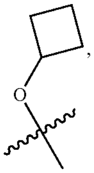, and 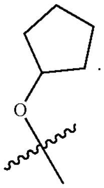.

In embodiments of Formulae (Ia), (I), (II), (IIA), and (IIB), $R^2$ is selected from:

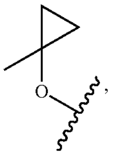, 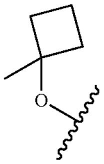, 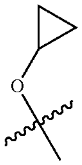, and 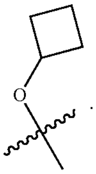.

In embodiments of Formulae (Ia), (I), (II), (IIA), and (IIB), $R^2$ is:

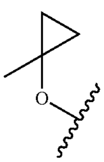 or 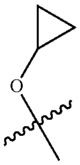.

In embodiments of Formulae (Ia), (I), (II), (IIA), and (IIB), $R^2$ is:

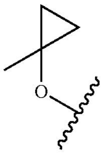.

In embodiments of Formulae (Ia), (I), (II), and (IIA), $R^4$ is H, $C_{1-6}$ alkyl, $C_{1-6}$ haloalkyl, or $C_{3-10}$ cycloalkyl, wherein the $C_{3-10}$ cycloalky is optionally substituted with 1 or 2 $C_{1-6}$ alkyl or cyano. In embodiments of Formulae (Ia), (I), (II), and (IIA), $R^4$ is $C_{1-3}$ alkyl. In embodiments of Formulae (Ia), (I), (II), and (IIA), $R^4$ is methyl. In embodiments of Formulae (I)-(IIA), $R^4$ is $C_3$ alkyl. In embodiments of Formulae (I)-(IIA), $R^4$ is isopropyl.

In embodiments of Formulae (Ia), (I), (II), (IIA), and (IIB), $R^5$ is H, $C_{1-6}$ alkyl, $C_{1-6}$ haloalkyl, or $C_{3-10}$ cycloalkyl, wherein the $C_{3-10}$ cycloalky is optionally substituted with 1 or 2 $C_{1-6}$ alkyl or cyano. In embodiments of Formulae (Ia), (I), (II), (IIA), and (IIB), $R^5$ is H.

In embodiments of Formulae (Ia), (I), (II), (IIA), and (IIB), each L is independently selected from $C_{1-6}$ alkyl, $C_{2-6}$ alkynyl, $C_{1-6}$ alkoxy, O, $C_{3-11}$ cycloalkyl, and 4-12-membered heterocycloalkyl, wherein 4-12-membered heterocycloalkyl is optionally substituted with 1 or 2 substituents $R^L$, wherein $R^L$ is $C_{1-6}$ alkyl.

In embodiments of Formulae (Ia), (I), (II), (IIA), and (IIB), at least two L are 4-12-membered heterocycloalkyl, optionally substituted with 1 or 2 substituents $R^L$, wherein $R^L$ is $C_{1-6}$ alkyl. In embodiments of Formulae (Ia), (I), (II), (IIA), and (IIB), at least three L are 4-12-membered heterocycloalkyl, wherein the 4-12-membered heterocycloalkyl is optionally substituted with 1 or 2 substituents $R^L$, wherein $R^L$ is $C_{1-6}$ alkyl. In embodiments of Formulae (Ia), (I), (II), (IIA), and (IIB), each L is independently selected from $C_{1-6}$ alkyl, $C_{2-4}$ alkynyl, $C_{1-6}$ alkoxy, O, $C_{3-7}$ cycloalkyl, and 6-8-membered heterocycloalkyl, wherein 6-8-membered heterocycloalkyl is optionally substituted with 1 or 2 substituents $R^L$, and wherein $R^L$ is $C_{1-3}$ alkyl. In embodiments of Formulae (Ia), (I), (II), (IIA), and (IIB), each L is independently selected from $C_{1-3}$ alkyl, $C_{2-4}$ alkynyl, $C_{1-3}$ alkoxy, O, $C_{3-7}$ cycloalkyl, and 6-8-membered heterocycloalkyl, wherein 6-8-membered heterocycloalkyl is optionally substituted with 1 or 2 substituents $R^L$, and wherein $R^L$ is methyl.

In embodiments of Formulae (Ia), (I), (II), (IIA), and (IIB), n is 1, 2, 3, 4, 5, 6, 7, 8, or 9. In embodiments of Formulae (Ia), (I), (II), (IIA), and (IIB), n is 1, 2, 3, 4, 5, 6, 7, or 8. In embodiments of Formulae (Ia), (I), (II), (IIA), and (IIB), n is 2, 3, 4, 5, 6, or 7. In embodiments of Formulae (Ia), (I), (II), (IIA), and (IIB), n is 3, 4, 5, 6, 7, or 8. In embodiments of Formulae (Ia), (I), (II), (IIA), and (IIB), n is 1, 2, 3, 4, 5, 6. In embodiments of Formulae (Ia), (I), (II), (IIA), and (IIB), n is 2, 3, 4, 5, or 6. In embodiments of Formulae (Ia), (I), (II), (IIA), and (IIB), n is 3, 4, 5, or 6. In embodiments of Formulae (Ia), (I), (II), (IIA), and (IIB), n is 4, 5, or 6.

In embodiments of Formulae (Ia), (I), (II), (IIA), and (IIB), n is 1. In embodiments of Formulae (Ia), (I), (II), (IIA), and (IIB), n is 2. In embodiments of Formulae (Ia), (I), (II), (IIA), and (IIB), n is 3. In embodiments of Formulae (Ia), (I), (II), (IIA), and (IIB), n is 4. In embodiments of Formulae (Ia), (I), (II), (IIA), and (IIB), n is 5. In embodiments of Formulae (Ia), (I), (II), (IIA), and (IIB), n is 6. In embodiments of Formulae (Ia), (I), (II), (IIA), and (IIB), n is 7. In embodiments of Formulae (Ia), (I), (II), (IIA), and (IIB), n is 8. In embodiments of Formulae (Ia), (I), (II), (IIA), and (IIB), n is 9. In embodiments of Formulae (Ia), (I), (II), (IIA), and (IIB), n is 10.

In embodiments of Formulae (I)-(IIB), n is 2, 3, 4, 5, 6, 7, or 8, and at least two L are 4-12-membered heterocycloalkyl, optionally substituted with 1 or 2 substituents $R^L$, wherein $R^L$ is $C_{1-6}$ alkyl. In further embodiments of Formulae (I)-(IIB), n is 3, 4, 5, 6, 7 or 8, and at least three L are 4-12-membered heterocycloalkyl, wherein the 4-12-membered heterocycloalkyl is optionally substituted with 1 or 2 substituents $R^L$, wherein $R^L$ is $C_{1-6}$ alkyl.

In embodiments of Formulae (Ia), (I), (II), (IIA), and (IIB), n is 5, and each L, taken together, forms a linker selected from (4-12-membered heterocycloalkyl)-($C_{1-6}$ alkyl)-(4-12-membered heterocycloalkyl)-($C_{1-6}$ alkyl)-(4-12-membered heterocycloalkyl); (4-12-membered heterocycloalkyl)-($C_{1-6}$ alkyl)-($C_{3-12}$ cycloalkyl)-(O)-(4-12-membered heterocycloalkyl); (4-12-membered heterocycloalkyl)-($C_{1-6}$ alkyl)-(4-12-membered heterocycloalkyl)-($C_{1-6}$ alkoxy)-($C_{3-6}$ alkynyl); and (4-12-membered heterocycloalkyl)-($C_{1-6}$ alkyl)-(4-12-membered heterocycloalkyl)-(O)—($C_{3-6}$ alkynyl), wherein each 4-12-membered heterocycloalkyl is optionally substituted with 1 or 2 substituents $R^L$, wherein $R^L$ is $C_{1-6}$ alkyl.

In embodiments of Formulae (Ia), (I), (II), (IIA), and (IIB), n is 5, and each L, taken together, forms a linker selected from (5-6-membered heterocycloalkyl)-($C_{1-6}$ alkyl)-(5-6-membered heterocycloalkyl)-($C_{1-6}$ alkyl)-(5-6-membered heterocycloalkyl); (5-6-membered heterocycloalkyl)-($C_{1-6}$ alkyl)-($C_{5-6}$ cycloalkyl)-(O)-(5-6-membered heterocycloalkyl); (5-6-membered heterocycloalkyl)-($C_{1-6}$ alkyl)-(5-6-membered heterocycloalkyl)-($C_{1-6}$ alkoxy)-($C_{3-6}$ alkynyl); and (5-6-membered heterocycloalkyl)-($C_{1-6}$ alkyl)-(5-6-membered heterocycloalkyl)-(O)—($C_{3-6}$ alkynyl), wherein each 5-6-membered heterocycloalkyl is optionally substituted with 1 or 2 substituents $R^L$, wherein $R^L$ is $C_{1-6}$ alkyl.

In embodiments of Formulae (Ia), (I), (II), and (IIA), the compound is a compound of Formula (IIAa):

(IIAa)

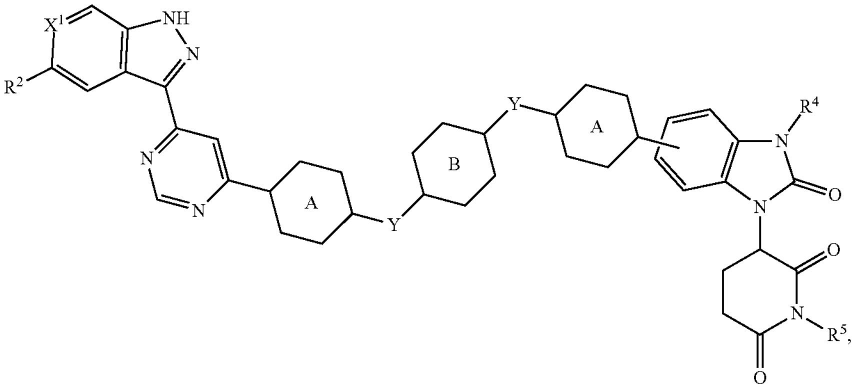

or a pharmaceutically acceptable salt thereof, wherein:

each ring A is independently selected from piperidinyl, hexahydropyridazinyl, hexahydropyrimidinyl, and piperazinyl, wherein each ring A is optionally substituted with 1 or 2 substituents $R^L$, wherein $R^L$ is $C_{1-6}$ alkyl;

ring B is selected from cyclohexyl, piperidinyl, hexahydropyridazinyl, hexahydropyrimidinyl, and piperazinyl, wherein each ring B is optionally substituted with 1 or 2 substituents $R^L$, wherein $R^L$ is $C_{1-6}$ alkyl; and each Y is independently O, $C_{1-6}$ alkyl, or $C_{1-6}$ alkoxy.

In embodiments of Formulae (Ia), (I), (II), and (IIA), the compound is a compound of Formula (IIAb):

(IIAb)

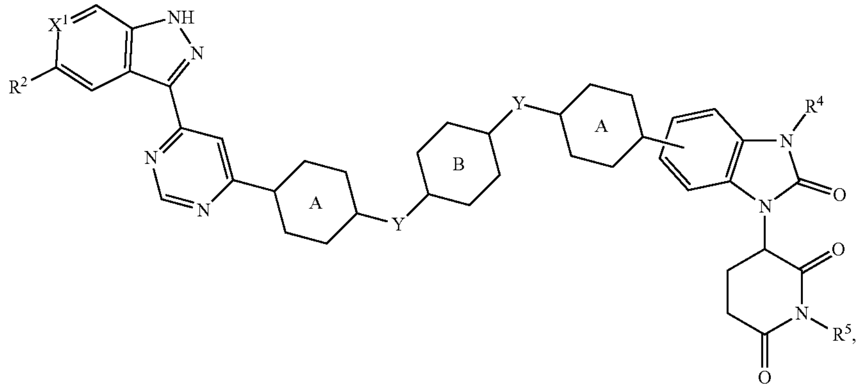

or a pharmaceutically acceptable salt thereof, wherein:

each ring A is independently selected from piperidinyl, hexahydropyridazinyl, hexahydropyrimidinyl, and piperazinyl, wherein each ring A is optionally substituted with 1 or 2 substituents $R^L$, wherein $R^L$ is $C_{1-6}$ alkyl;

ring B is selected from cyclohexyl, piperidinyl, hexahydropyridazinyl, hexahydropyrimidinyl, and piperazinyl, wherein each ring B is optionally substituted with 1 or 2 substituents $R^L$, wherein $R^L$ is $C_{1-6}$ alkyl; and each Y is independently O, $C_{1-6}$ alkyl, or $C_{1-6}$ alkoxy.

In embodiments of Formulae (I), (II), and (IIB), the compound is a compound of Formula (IIBa):

(IIBa)

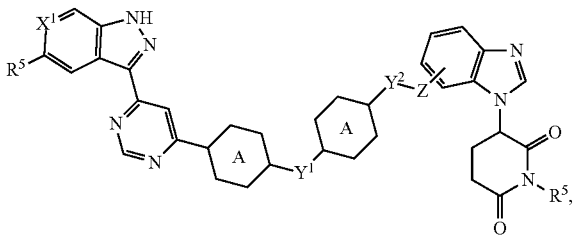

or a pharmaceutically acceptable salt thereof, wherein:

each ring A is independently selected from piperidinyl, hexahydropyridazinyl, hexahydropyrimidinyl, and piperazinyl;

$Y^1$ is $C_{1-6}$ alkyl;

$Y^2$ is O or $C_{1-6}$ alkoxy; and

Z is $C_{3-6}$ alkynyl.

In embodiments of Formulae (Ia)-(IIBa), $R^L$ is $C_{1-4}$ alkyl. In embodiments of Formulae (Ia), (I), (II), (IIA), and (IIB), $R^L$ is $C_{1-3}$ alkyl. In embodiments of Formulae (Ia)-(IIBa), $R^L$ is methyl.

In embodiments of Formulae (Ia)-(IIBa), $(L)_n$ is selected from:

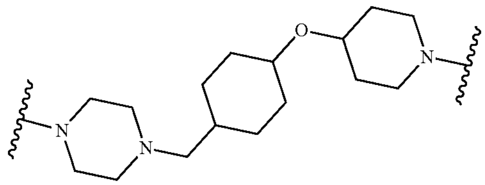

,

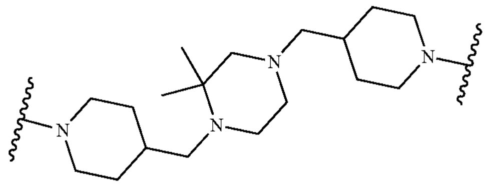

,

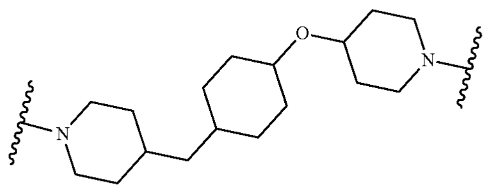

,

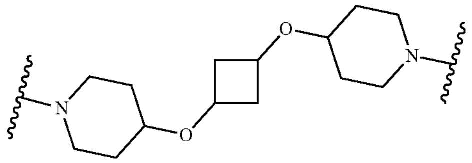

,

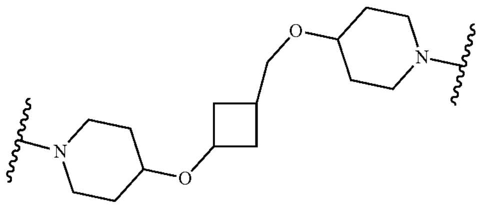

,

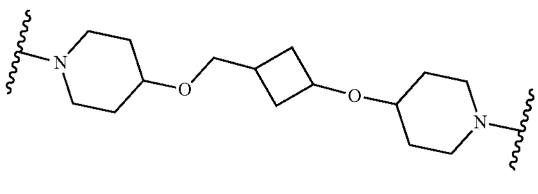

,

-continued

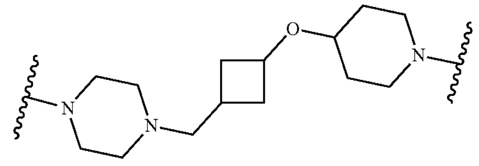

,

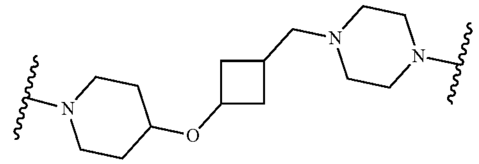

,

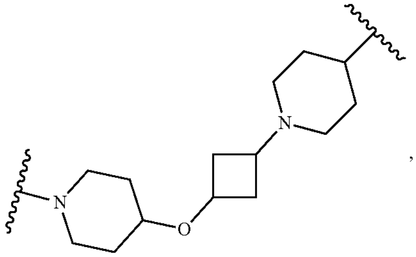 [SMILES: *C1CCN(C2CC(OC3CCN(*)CC3)C2)CC1]

,

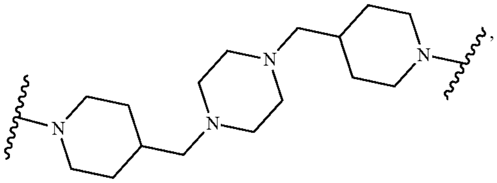 [SMILES: *N1CCC(CN2CCN(CC3CCN(*)CC3)CC2)CC1]

, and

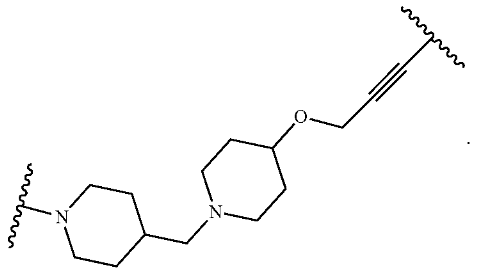 [SMILES: *C#CCOC1CCN(CC2CCN(*)CC2)CC1]

.

In embodiments of Formulae (Ia)-(IIBa), $(L)_n$ is selected from:

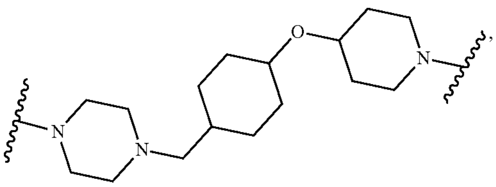 [SMILES: *N1CCC(OC2CCC(CN3CCN(*)CC3)CC2)CC1]

,

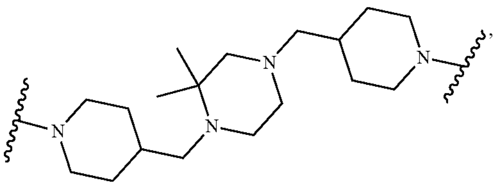 [SMILES: *N1CCC(CN2CCN(CC3CCN(*)CC3)C(C)(C)C2)CC1]

,

-continued

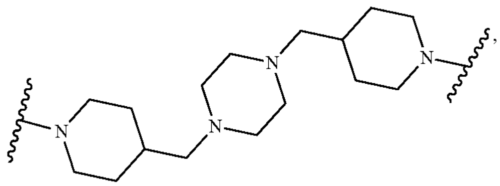 [SMILES: *N1CCC(CN2CCN(CC3CCN(*)CC3)CC2)CC1]

, and

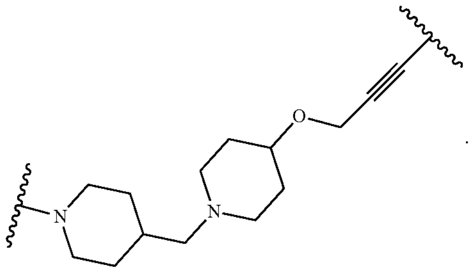 [SMILES: *C#CCOC1CCN(CC2CCN(*)CC2)CC1]

.

In embodiments of Formula (Ia), the compound is a compound of Formula (II):

(III)

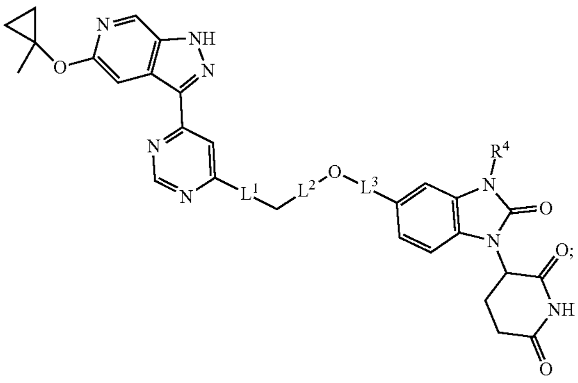

;

or a pharmaceutically acceptable salt thereof, wherein $R^4$ is $C_{1-3}$ alkyl;

$L^1$ and $L^3$ are each independently 5- to 6-membered heterocyclyl; and $L^2$ is $C_{3-6}$ cycloalkyl.

In embodiments of Formulae (Ia) and (III), the compound is a compound of Formula (IIIa):

(IIIa)

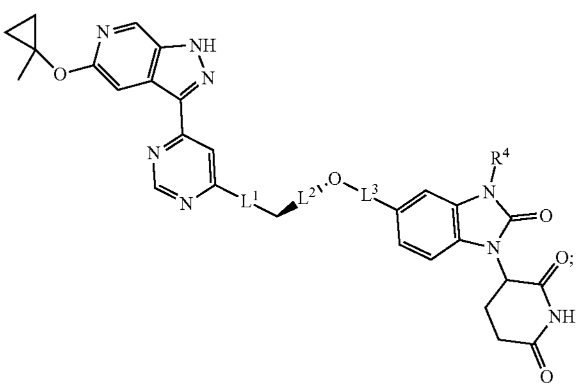

or a pharmaceutically acceptable salt thereof.

In embodiments of Formulae (III) and (IIIa), $L^1$ is a 6-membered heterocyclyl. In embodiments of Formulae (III) and (IIIa), $L^1$ is piperdinyl or piperazinyl. In embodiments of Formulae (III) and (IIIa), $L^1$ is piperazinyl.

In embodiments of Formulae (III) and (IIIa), $L^3$ is a 6-membered heterocyclyl. In embodiments of Formulae (III) and (IIIa), $L^3$ is piperdinyl or piperazinyl. In embodiments of Formulae (III) and (IIIa), $L^3$ is piperdinyl.

In embodiments of Formulae (III) and (IIIa), $L^2$ is cyclopropyl. In embodiments of Formulae (III) and (IIIa), $L^2$ is cyclobutyl. In embodiments of Formulae (III) and (IIIa), $L^2$ is cyclopentyl. In embodiments of Formulae (III) and (IIIa), $L^2$ is cyclohexyl.

In embodiments, the compound of Formula (Ia) is selected from:

| Compound No. | Structure |
| --- | --- |
| 1 | 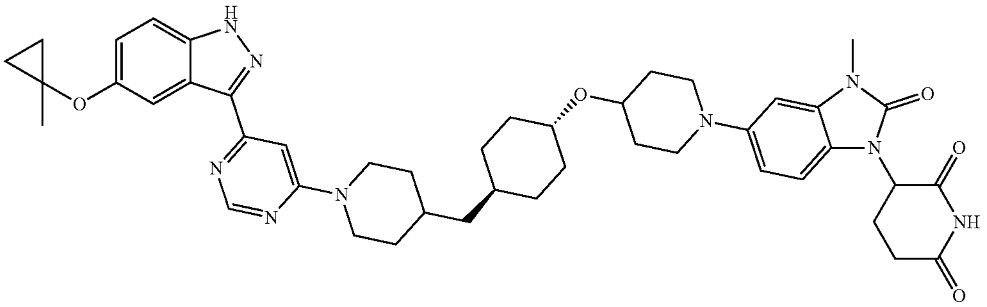 [SMILES: Cn1c(=O)n(C2CCC(=O)NC2=O)c2ccc(N3CCC(O[C@H]4CC[C@H](CC5CCN(c6cc(-c7n[nH]c8ccc(OC9(C)CC9)cc78)ncn6)CC5)CC4)CC3)cc21] |
| 2 | 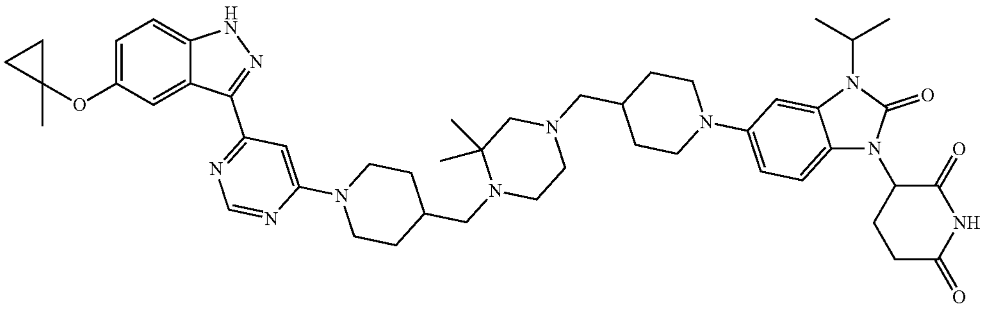 [SMILES: CC(C)n1c(=O)n(C2CCC(=O)NC2=O)c2ccc(N3CCC(CN4CCN(CC5CCN(c6cc(-c7n[nH]c8ccc(OC9(C)CC9)cc78)ncn6)CC5)C(C)(C)C4)CC3)cc21] |
| 3 | 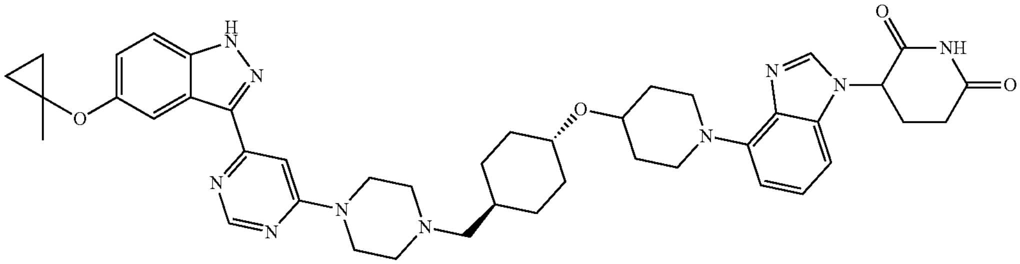 [SMILES: CC1(Oc2ccc3[nH]nc(-c4cc(N5CCN(C[C@H]6CC[C@H](OC7CCN(c8cccc9c8ncn9C8CCC(=O)NC8=O)CC7)CC6)CC5)ncn4)c3c2)CC1] |

-continued
| Compound No. | Structure |
| --- | --- |
| 4 | 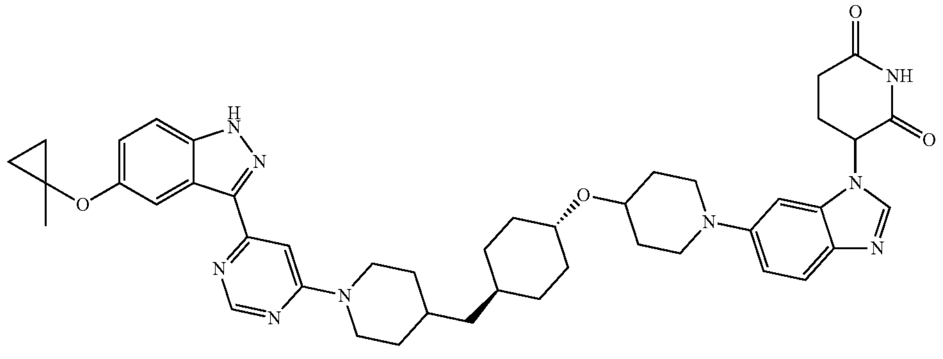 [SMILES: CC1(Oc2ccc3[nH]nc(-c4cc(N5CCC(C[C@H]6CC[C@H](OC7CCN(c8ccc9ncn(C%10CCC(=O)NC%10=O)c9c8)CC7)CC6)CC5)ncn4)c3c2)CC1] |
| 5 | 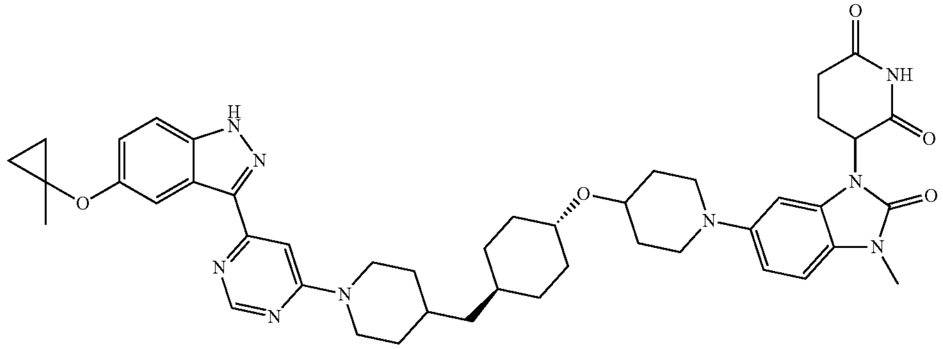 [SMILES: Cn1c(=O)n(C2CCC(=O)NC2=O)c2cc(N3CCC(O[C@H]4CC[C@H](CC5CCN(c6cc(-c7n[nH]c8ccc(OC9(C)CC9)cc78)ncn6)CC5)CC4)CC3)ccc21] |
| 6 | 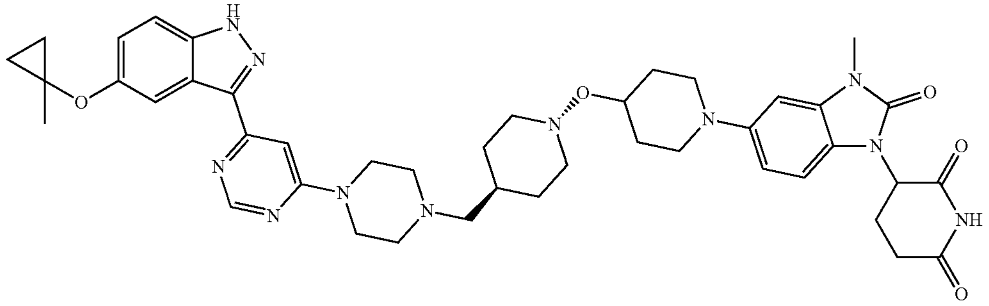 |
| 7 | 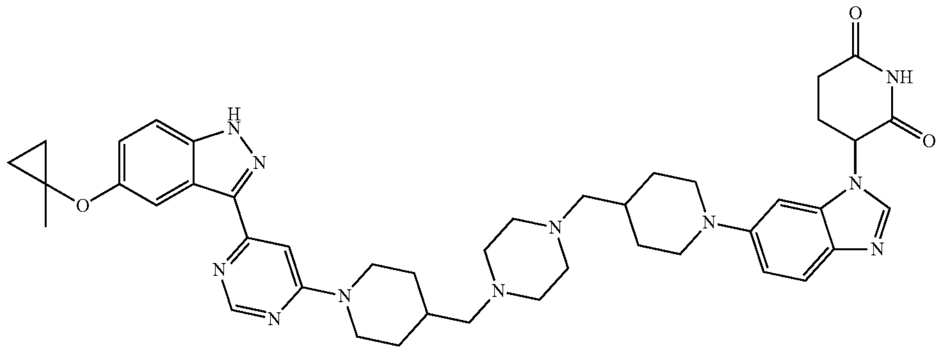 [SMILES: CC1(Oc2ccc3[nH]nc(-c4cc(N5CCC(CN6CCN(CC7CCN(c8ccc9ncn(C%10CCC(=O)NC%10=O)c9c8)CC7)CC6)CC5)ncn4)c3c2)CC1] |

-continued
| Compound No. | Structure |
|---|---|
| 8 | 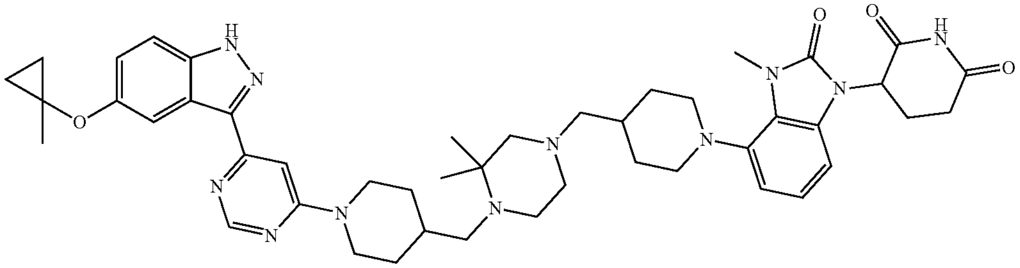 [SMILES: Cn1c(=O)n(C2CCC(=O)NC2=O)c2cccc(N3CCC(CN4CCN(CC5CCN(c6cc(-c7n[nH]c8ccc(OC9(C)CC9)cc78)ncn6)CC5)C(C)(C)C4)CC3)c21] |
| 9 | 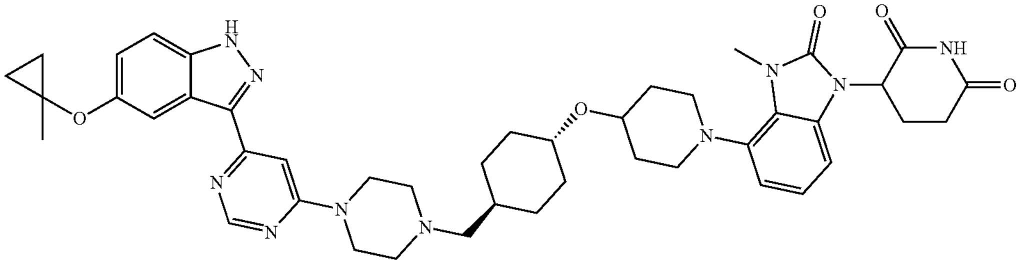 [SMILES: Cn1c(=O)n(C2CCC(=O)NC2=O)c2cccc(N3CCC(O[C@H]4CC[C@H](CN5CCN(c6cc(-c7n[nH]c8ccc(OC9(C)CC9)cc78)ncn6)CC5)CC4)CC3)c21] |
| 10 | 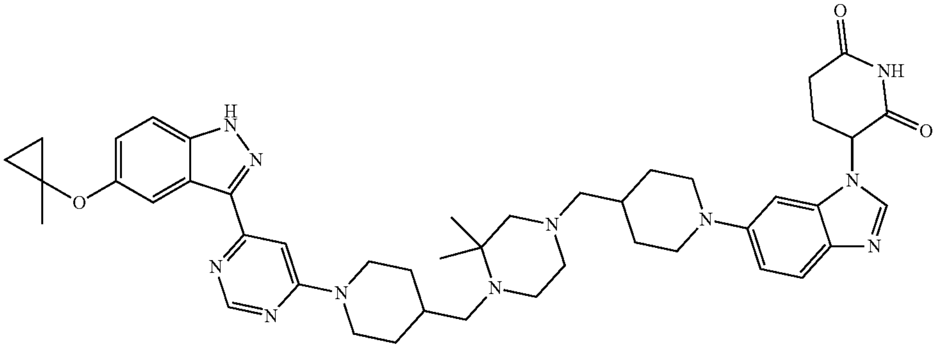 [SMILES: CC1(Oc2ccc3[nH]nc(-c4cc(N5CCC(CN6CCN(CC7CCN(c8ccc9ncn(C%10CCC(=O)NC%10=O)c9c8)CC7)CC6(C)C)CC5)ncn4)c3c2)CC1] |
| 11 | 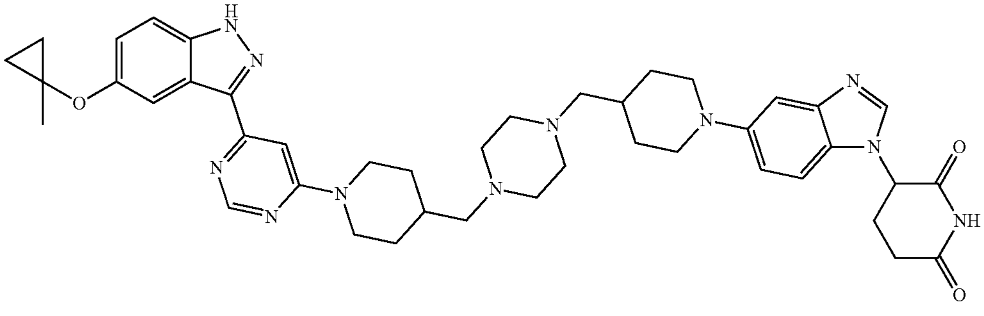 [SMILES: CC1(Oc2ccc3[nH]nc(-c4cc(N5CCC(CN6CCN(CC7CCN(c8ccc9c(c8)ncn9C8CCC(=O)NC8=O)CC7)CC6)CC5)ncn4)c3c2)CC1] |
| 12 | 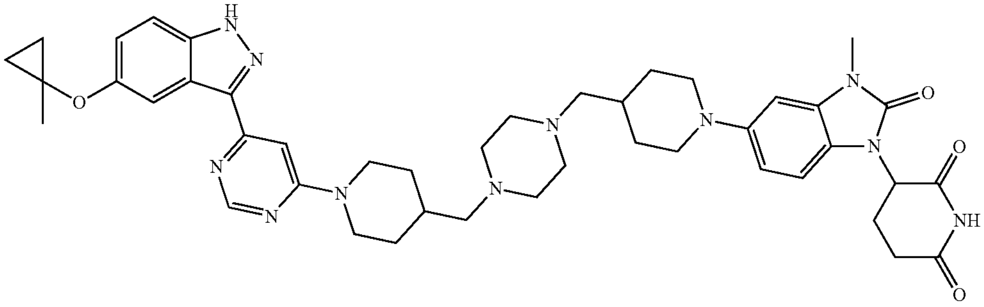 [SMILES: Cn1c(=O)n(C2CCC(=O)NC2=O)c2ccc(N3CCC(CN4CCN(CC5CCN(c6cc(-c7n[nH]c8ccc(OC9(C)CC9)cc78)ncn6)CC5)CC4)CC3)cc21] |

-continued
| Compound No. | Structure |
| --- | --- |
| 13 | 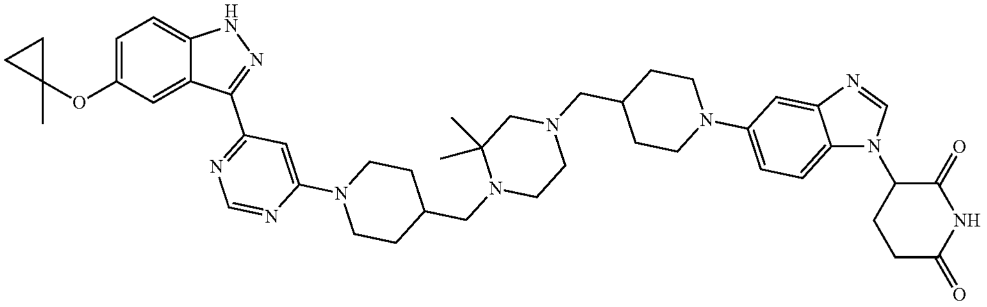 [SMILES: CC1(Oc2ccc3[nH]nc(-c4cc(N5CCC(CN6CCN(CC7CCN(c8ccc9c(c8)ncn9C8CCC(=O)NC8=O)CC7)CC6(C)C)CC5)ncn4)c3c2)CC1] |
| 14 | 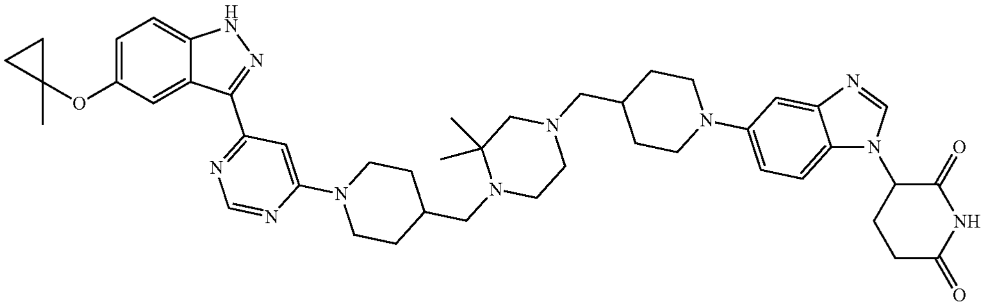 [SMILES: CC1(Oc2ccc3[nH]nc(-c4cc(N5CCC(CN6CCN(CC7CCN(c8ccc9c(c8)ncn9C8CCC(=O)NC8=O)CC7)CC6(C)C)CC5)ncn4)c3c2)CC1] |
| 15 | 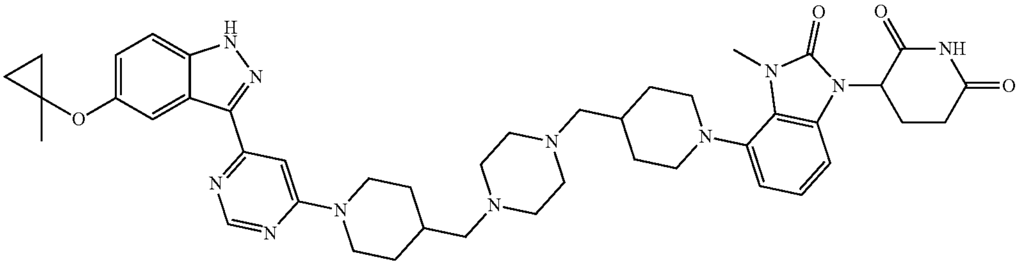 [SMILES: Cn1c(=O)n(C2CCC(=O)NC2=O)c2cccc(N3CCC(CN4CCN(CC5CCN(c6cc(-c7n[nH]c8ccc(OC9(C)CC9)cc78)ncn6)CC5)CC4)CC3)c21] |
| 16 | 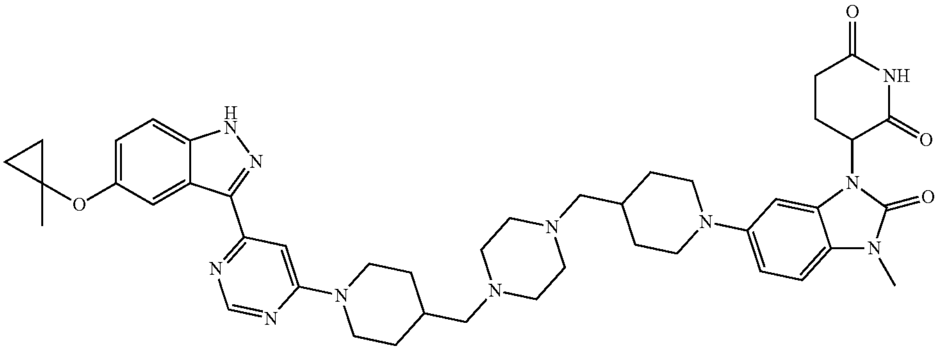 [SMILES: Cn1c(=O)n(C2CCC(=O)NC2=O)c2cc(N3CCC(CN4CCN(CC5CCN(c6cc(-c7n[nH]c8ccc(OC9(C)CC9)cc78)ncn6)CC5)CC4)CC3)ccc21] |

-continued
| Compound No. | Structure |
|---|---|
| 17 | 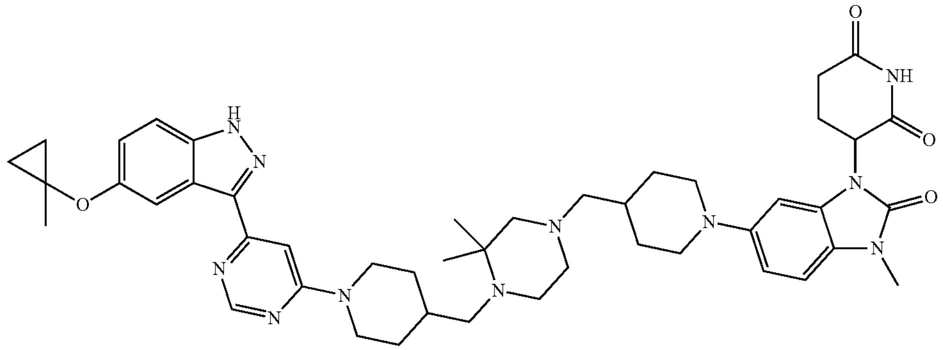 [SMILES: Cn1c(=O)n(C2CCC(=O)NC2=O)c2cc(N3CCC(CN4CCN(CC5CCN(c6cc(-c7n[nH]c8ccc(OC9(C)CC9)cc78)ncn6)CC5)C(C)(C)C4)CC3)ccc21] |
| 18 | 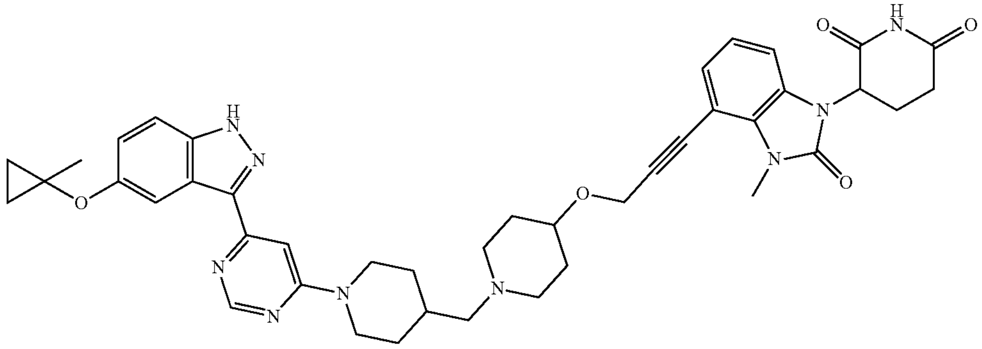 [SMILES: Cn1c(=O)n(C2CCC(=O)NC2=O)c2cccc(C#CCOC3CCN(CC4CCN(c5cc(-c6n[nH]c7ccc(OC8(C)CC8)cc67)ncn5)CC4)CC3)c21] |
| 19 | 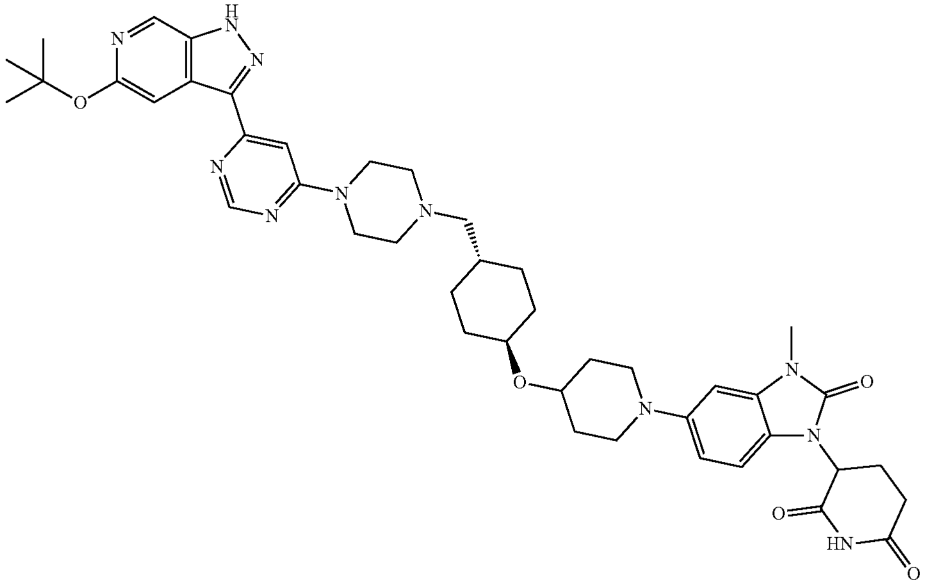 [SMILES: Cn1c(=O)n(C2CCC(=O)NC2=O)c2ccc(N3CCC(O[C@H]4CC[C@H](CN5CCN(c6cc(-c7n[nH]c8cnc(OC(C)(C)C)cc78)ncn6)CC5)CC4)CC3)cc21] |

-continued
| Compound No. | Structure |
|---|---|
| 20 | 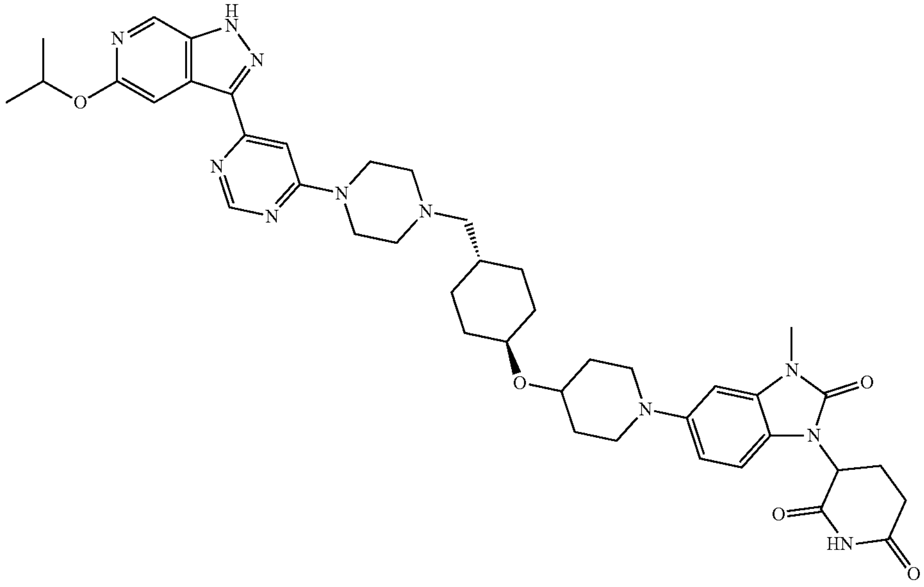 [SMILES: CC(C)Oc1cc2c(-c3cc(N4CCN(C[C@H]5CC[C@H](OC6CCN(c7ccc8c(c7)n(C)c(=O)n8C7CCC(=O)NC7=O)CC6)CC5)CC4)ncn3)n[nH]c2cn1] |
| 21 | 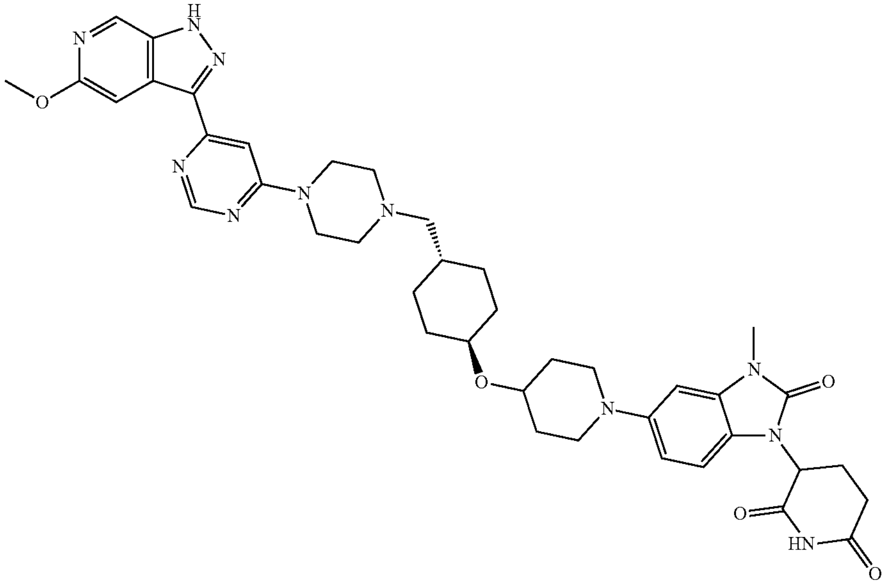 [SMILES: COc1cc2c(-c3cc(N4CCN(C[C@H]5CC[C@H](OC6CCN(c7ccc8c(c7)n(C)c(=O)n8C7CCC(=O)NC7=O)CC6)CC5)CC4)ncn3)n[nH]c2cn1] |

-continued
| Compound No. | Structure |
|---|---|
| 22 | 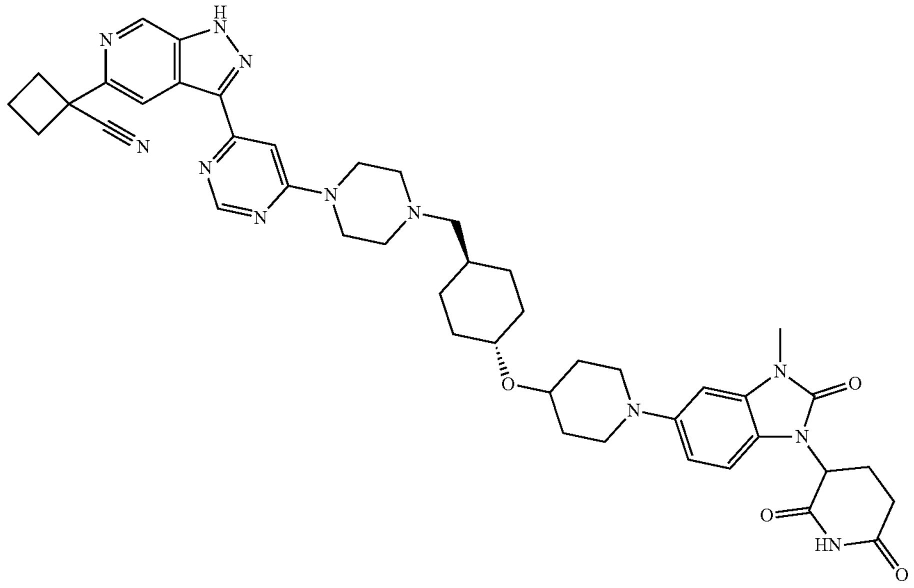 [SMILES: Cn1c(=O)n(C2CCC(=O)NC2=O)c2ccc(N3CCC(O[C@H]4CC[C@H](CN5CCN(c6cc(-c7n[nH]c8cnc(C9(C#N)CCC9)cc78)ncn6)CC5)CC4)CC3)cc21] |
| 23 | 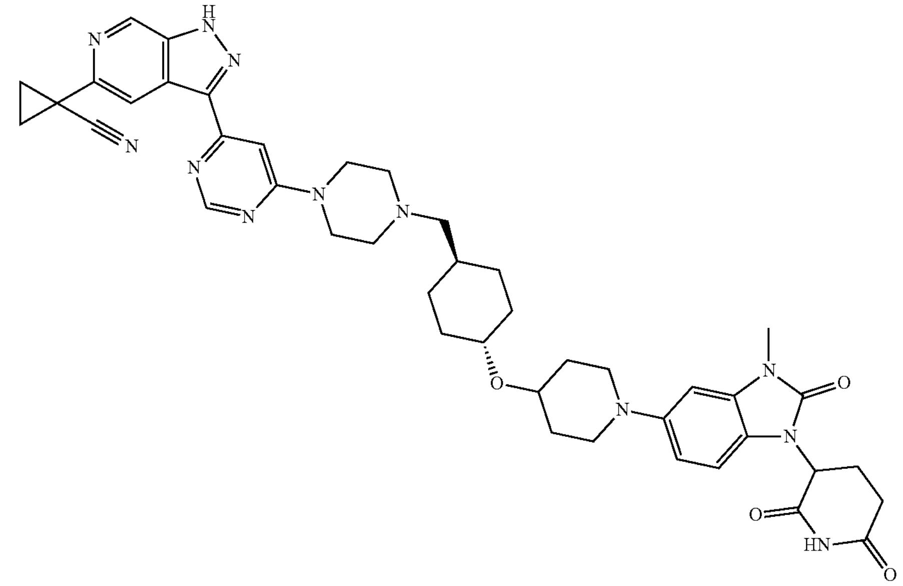 [SMILES: Cn1c(=O)n(C2CCC(=O)NC2=O)c2ccc(N3CCC(O[C@H]4CC[C@H](CN5CCN(c6cc(-c7n[nH]c8cnc(C9(C#N)CC9)cc78)ncn6)CC5)CC4)CC3)cc21] |

-continued
| Compound No. | Structure |
|---|---|
| 24 | 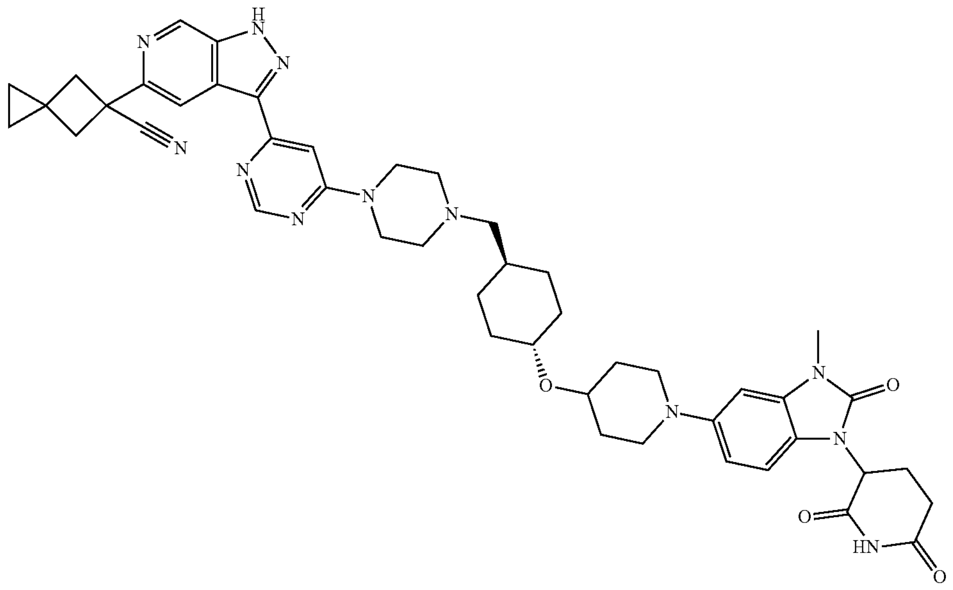 [SMILES: Cn1c(=O)n(C2CCC(=O)NC2=O)c2ccc(N3CCC(O[C@H]4CC[C@H](CN5CCN(c6cc(-c7n[nH]c8cnc(C9(C#N)CC%10(CC%10)C9)cc78)ncn6)CC5)CC4)CC3)cc21] |
| 25 | 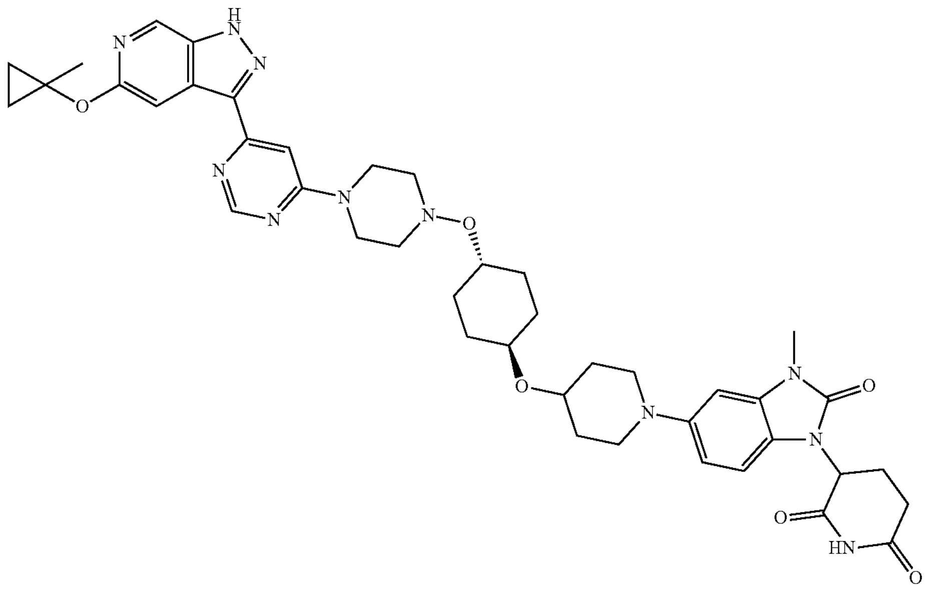 [SMILES: Cn1c(=O)n(C2CCC(=O)NC2=O)c2ccc(N3CCC(O[C@H]4CC[C@H](ON5CCN(c6cc(-c7n[nH]c8cnc(OC9(C)CC9)cc78)ncn6)CC5)CC4)CC3)cc21] |

-continued
| Compound No. | Structure |
| --- | --- |
| 26 | 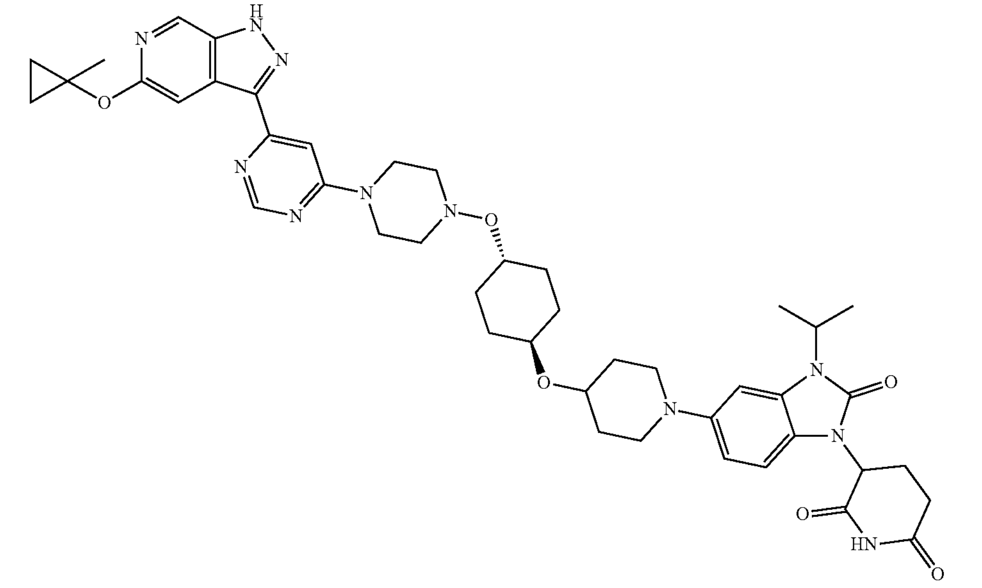 [SMILES: CC(C)n1c(=O)n(C2CCC(=O)NC2=O)c2ccc(N3CCC(O[C@H]4CC[C@H](ON5CCN(c6cc(-c7n[nH]c8cnc(OC9(C)CC9)cc78)ncn6)CC5)CC4)CC3)cc21] |
| 27 | 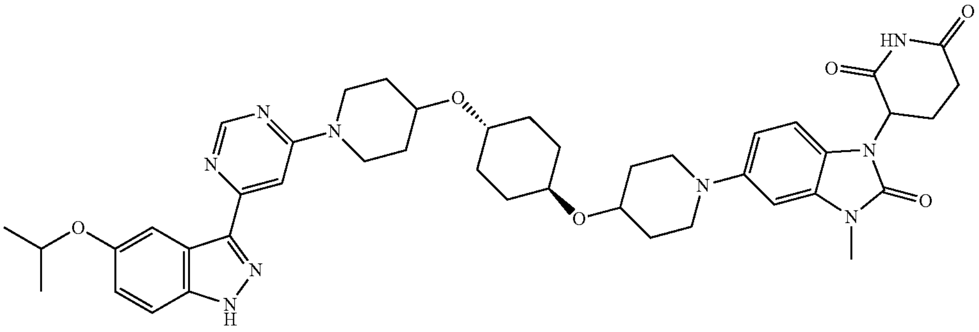 [SMILES: CC(C)Oc1ccc2[nH]nc(-c3cc(N4CCC(O[C@H]5CC[C@H](OC6CCN(c7ccc8c(c7)n(C)c(=O)n8C7CCC(=O)NC7=O)CC6)CC5)CC4)ncn3)c2c1] |
| 28 | 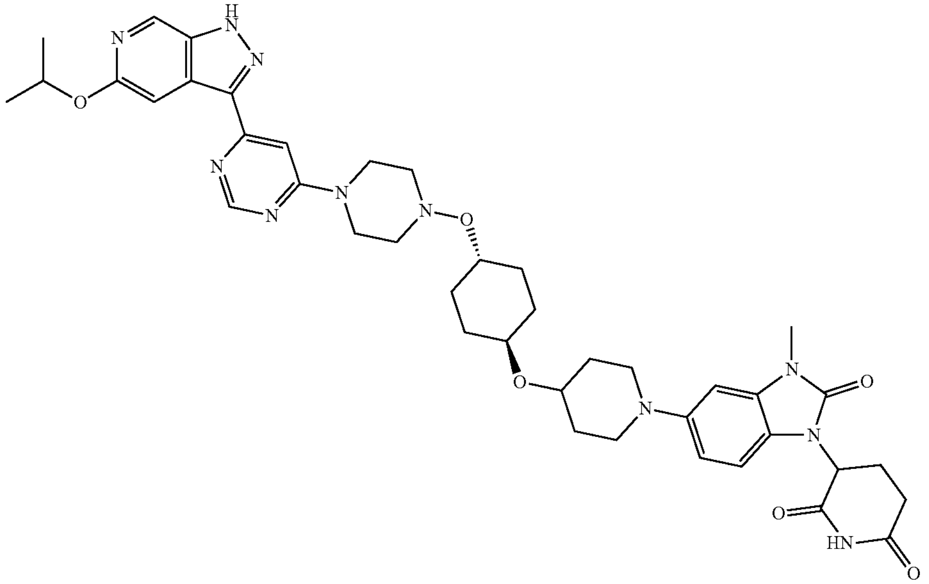 [SMILES: CC(C)Oc1cc2c(-c3cc(N4CCN(O[C@H]5CC[C@H](OC6CCN(c7ccc8c(c7)n(C)c(=O)n8C7CCC(=O)NC7=O)CC6)CC5)CC4)ncn3)n[nH]c2cn1] |

-continued
| Compound No. | Structure |
| --- | --- |
| 29 | 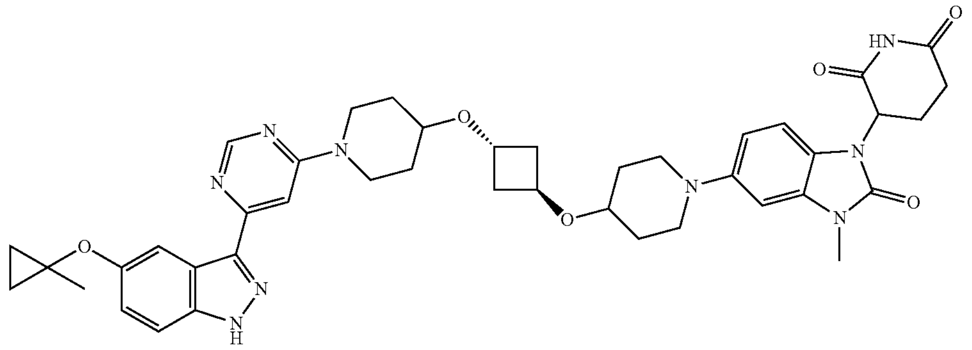 [SMILES: Cn1c(=O)n(C2CCC(=O)NC2=O)c2ccc(N3CCC(O[C@H]4C[C@H](OC5CCN(c6cc(-c7n[nH]c8ccc(OC9(C)CC9)cc78)ncn6)CC5)C4)CC3)cc21] |
| 30 | 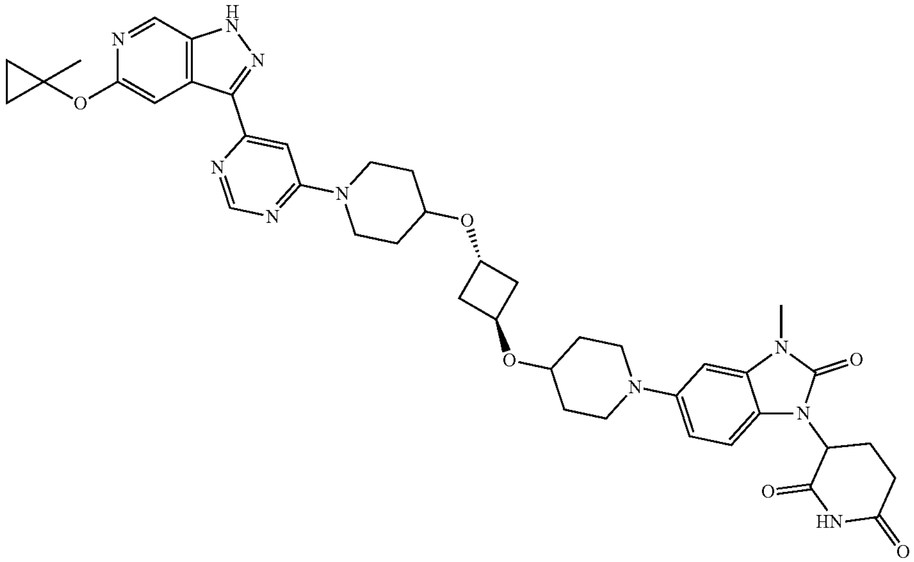 [SMILES: Cn1c(=O)n(C2CCC(=O)NC2=O)c2ccc(N3CCC(O[C@H]4C[C@H](OC5CCN(c6cc(-c7n[nH]c8cnc(OC9(C)CC9)cc78)ncn6)CC5)C4)CC3)cc21] |
| 31 | 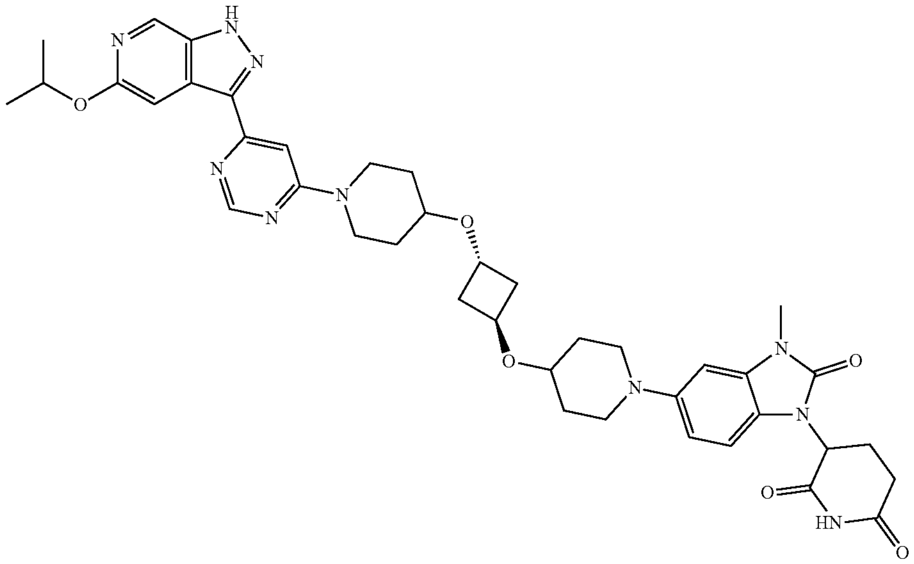 [SMILES: CC(C)Oc1cc2c(-c3cc(N4CCC(O[C@H]5C[C@H](OC6CCN(c7ccc8c(c7)n(C)c(=O)n8C7CCC(=O)NC7=O)CC6)C5)CC4)ncn3)n[nH]c2cn1] |

-continued
| Compound No. | Structure |
|---|---|
| 32 | 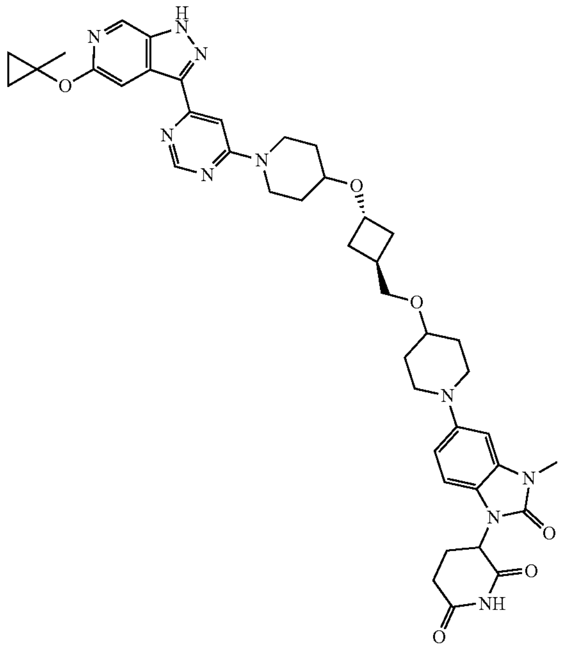 [SMILES: Cn1c(=O)n(C2CCC(=O)NC2=O)c2ccc(N3CCC(OC[C@H]4C[C@H](OC5CCN(c6cc(-c7n[nH]c8cnc(OC9(C)CC9)cc78)ncn6)CC5)C4)CC3)cc21] |
| 33 | 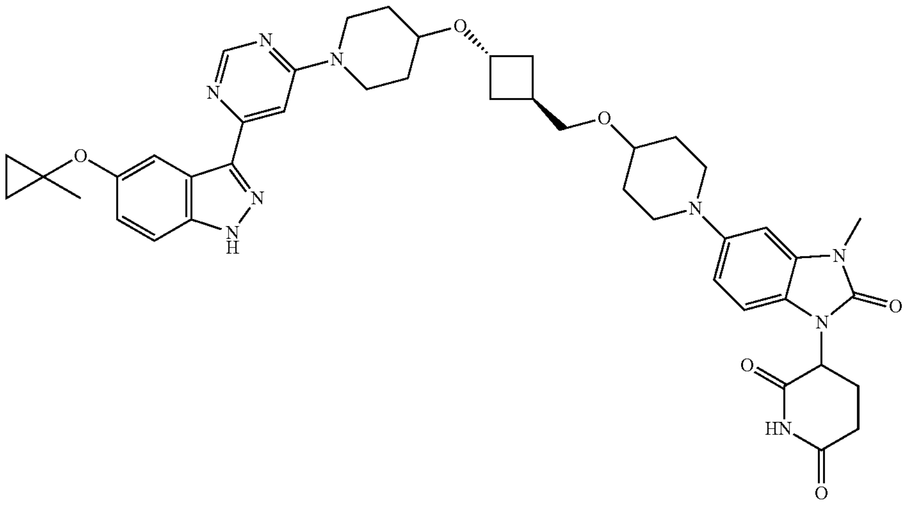 [SMILES: Cn1c(=O)n(C2CCC(=O)NC2=O)c2ccc(N3CCC(OC[C@H]4C[C@H](OC5CCN(c6cc(-c7n[nH]c8ccc(OC9(C)CC9)cc78)ncn6)CC5)C4)CC3)cc21] |

-continued
| Compound No. | Structure |
|---|---|
| 34 | 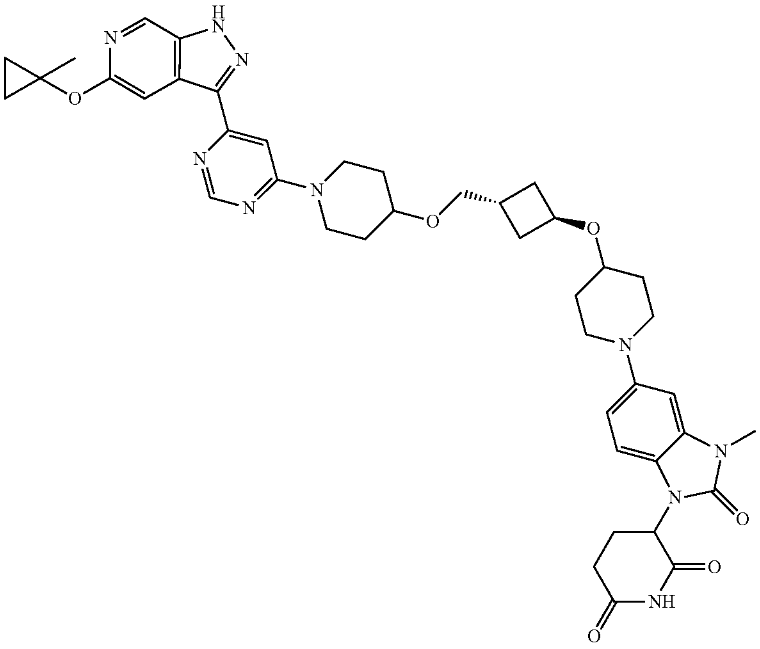 [SMILES: Cn1c(=O)n(C2CCC(=O)NC2=O)c2ccc(N3CCC(O[C@H]4C[C@H](COC5CCN(c6cc(-c7n[nH]c8cnc(OC9(C)CC9)cc78)ncn6)CC5)C4)CC3)cc21] |
| 35 | 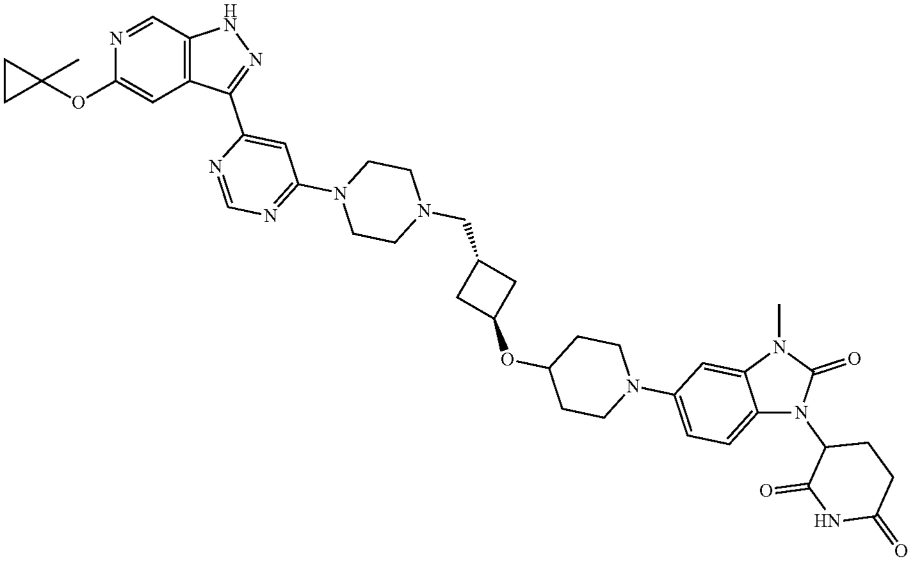 [SMILES: Cn1c(=O)n(C2CCC(=O)NC2=O)c2ccc(N3CCC(O[C@H]4C[C@H](CN5CCN(c6cc(-c7n[nH]c8cnc(OC9(C)CC9)cc78)ncn6)CC5)C4)CC3)cc21] |

-continued
| Compound No. | Structure |
|---|---|
| 36 | 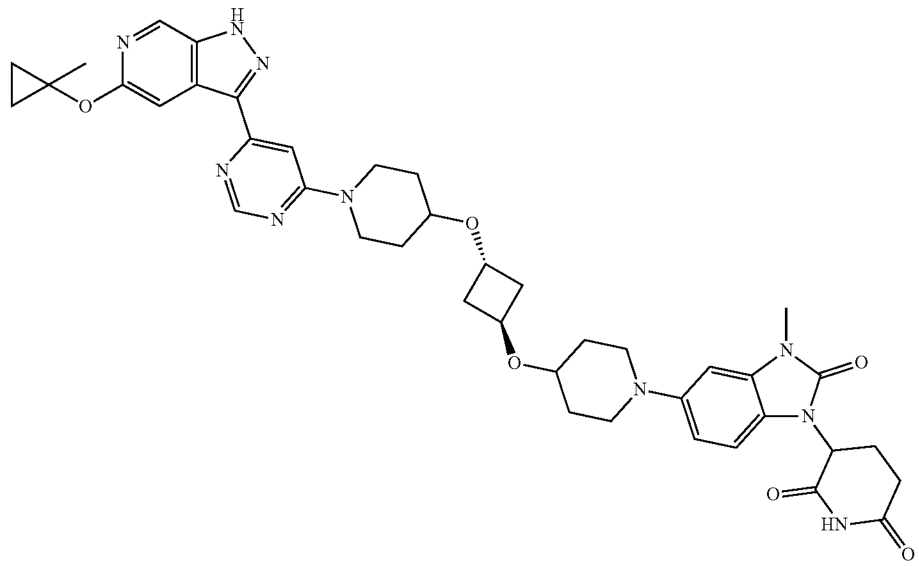 [SMILES: Cn1c(=O)n(C2CCC(=O)NC2=O)c2ccc(N3CCC(O[C@H]4C[C@H](OC5CCN(c6cc(-c7n[nH]c8cnc(OC9(C)CC9)cc78)ncn6)CC5)C4)CC3)cc21] |
| 37 | 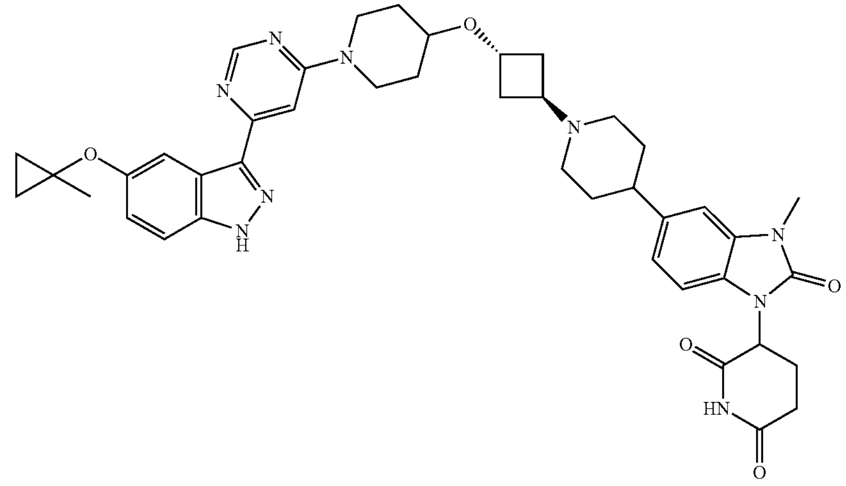 [SMILES: Cn1c(=O)n(C2CCC(=O)NC2=O)c2ccc(C3CCN([C@H]4C[C@H](OC5CCN(c6cc(-c7n[nH]c8ccc(OC9(C)CC9)cc78)ncn6)CC5)C4)CC3)cc21] |
| 38 | 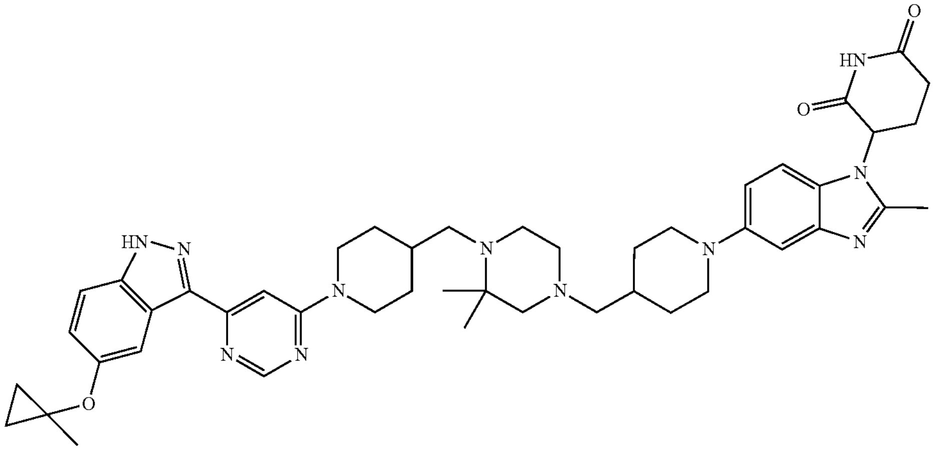 [SMILES: Cc1nc2cc(N3CCC(CN4CCN(CC5CCN(c6cc(-c7n[nH]c8ccc(OC9(C)CC9)cc78)ncn6)CC5)C(C)(C)C4)CC3)ccc2n1C1CCC(=O)NC1=O] |

-continued
| Compound No. | Structure |
|---|---|
| 39 | 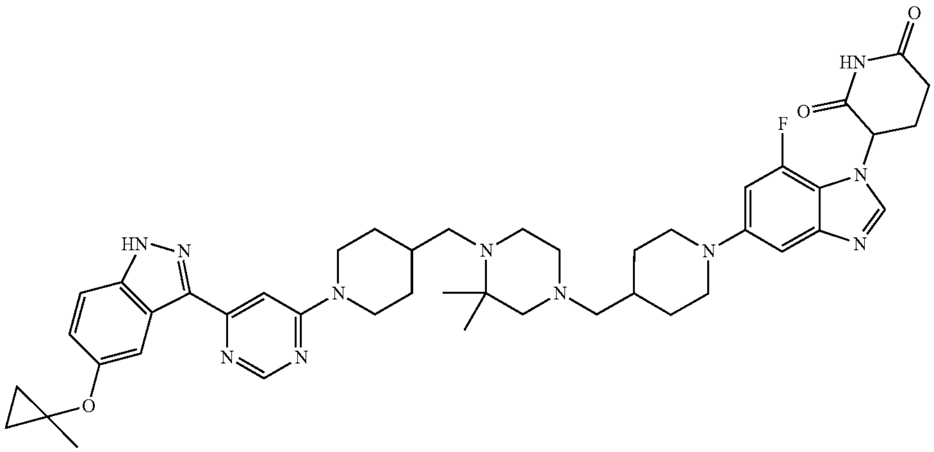 [SMILES: CC1(Oc2ccc3[nH]nc(-c4cc(N5CCC(CN6CCN(CC7CCN(c8cc(F)c9c(c8)ncn9C8CCC(=O)NC8=O)CC7)CC6(C)C)CC5)ncn4)c3c2)CC1] |
| 40 | 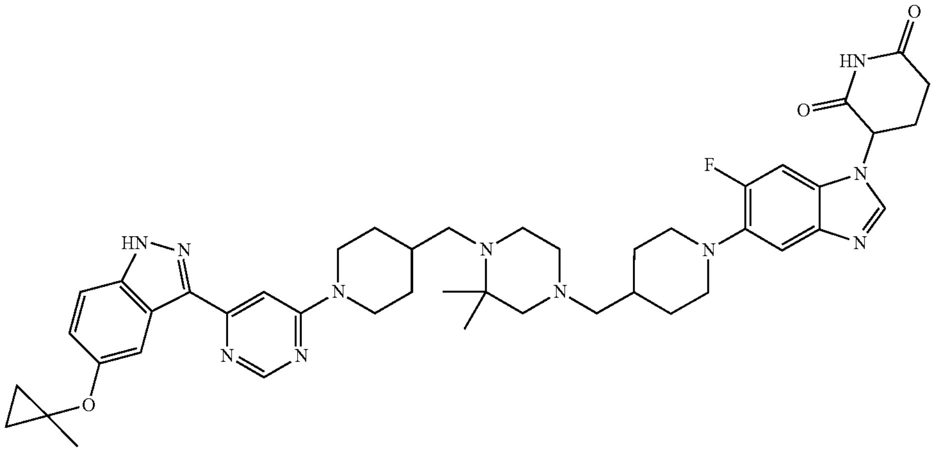 [SMILES: CC1(Oc2ccc3[nH]nc(-c4cc(N5CCC(CN6CCN(CC7CCN(c8cc9ncn(C%10CCC(=O)NC%10=O)c9cc8F)CC7)CC6(C)C)CC5)ncn4)c3c2)CC1] |
| 41 | 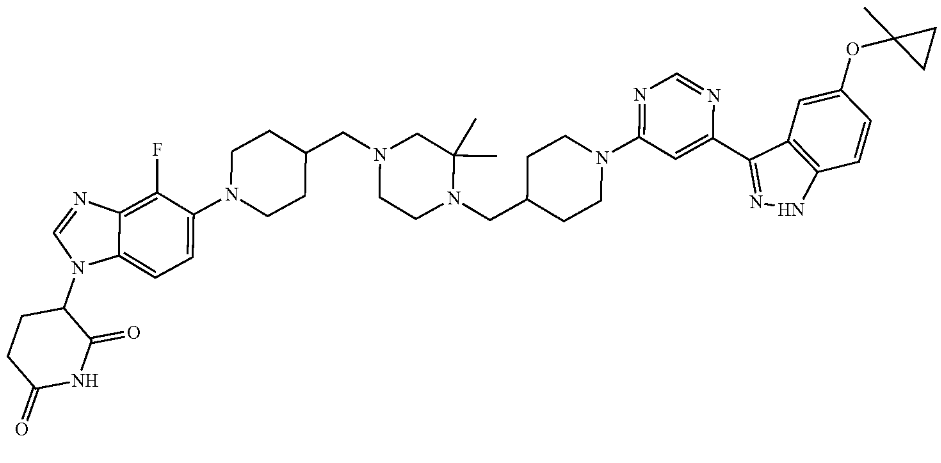 [SMILES: CC1(Oc2ccc3[nH]nc(-c4cc(N5CCC(CN6CCN(CC7CCN(c8ccc9c(ncn9C9CCC(=O)NC9=O)c8F)CC7)CC6(C)C)CC5)ncn4)c3c2)CC1] |

-continued
| Compound No. | Structure |
|---|---|
| 42 | 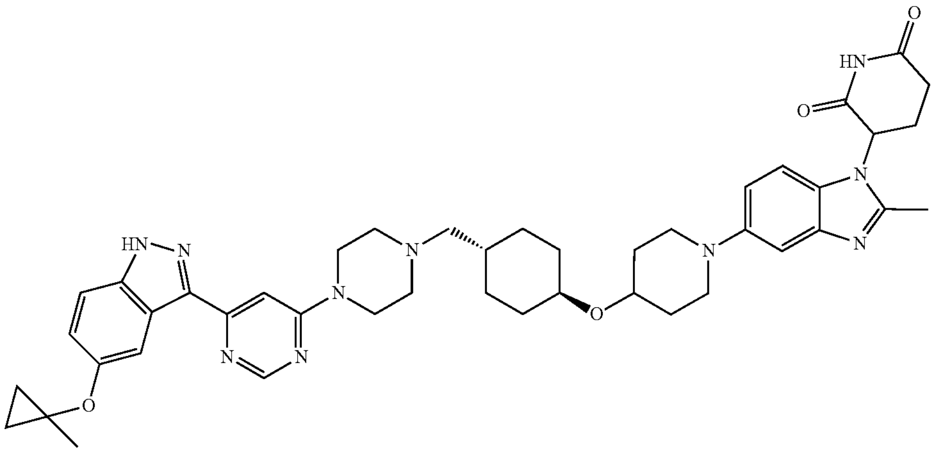 [SMILES: Cc1nc2cc(N3CCC(O[C@H]4CC[C@H](CN5CCN(c6cc(-c7n[nH]c8ccc(OC9(C)CC9)cc78)ncn6)CC5)CC4)CC3)ccc2n1C1CCC(=O)NC1=O] |
| 43 | 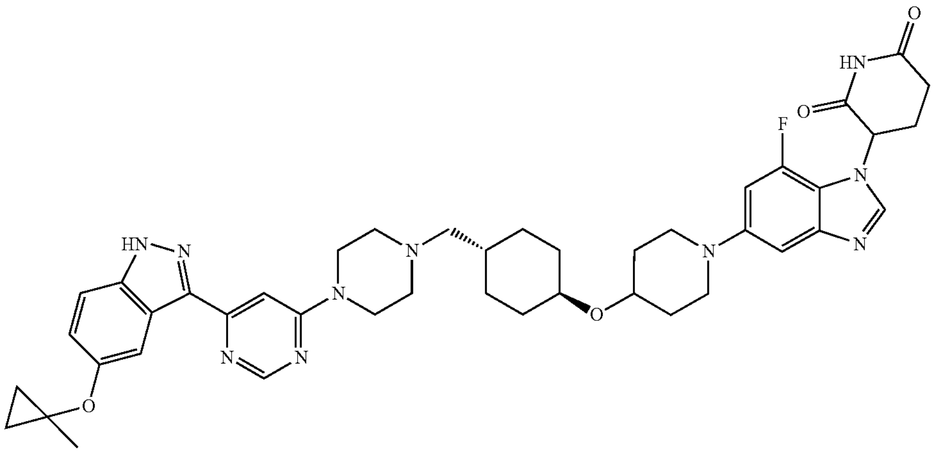 [SMILES: CC1(Oc2ccc3[nH]nc(-c4cc(N5CCN(C[C@H]6CC[C@H](OC7CCN(c8cc(F)c9c(c8)ncn9C8CCC(=O)NC8=O)CC7)CC6)CC5)ncn4)c3c2)CC1] |
| 44 | 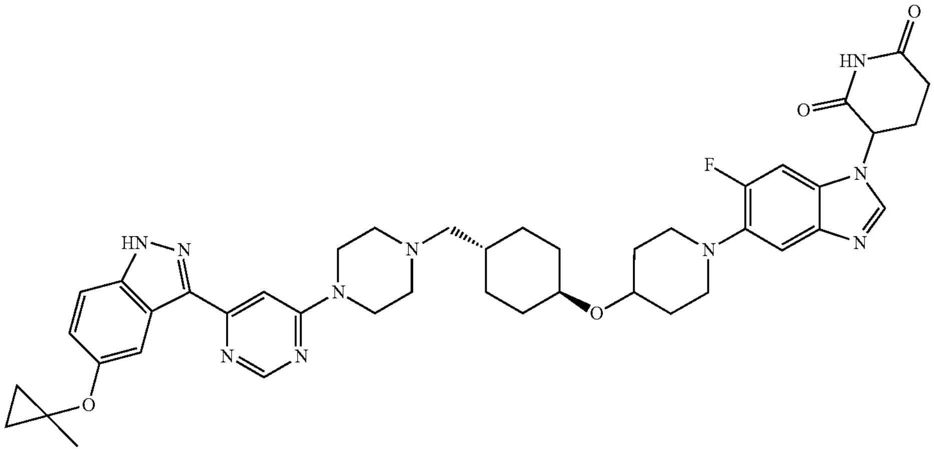 [SMILES: CC1(Oc2ccc3[nH]nc(-c4cc(N5CCN(C[C@H]6CC[C@H](OC7CCN(c8cc9ncn(C%10CCC(=O)NC%10=O)c9cc8F)CC7)CC6)CC5)ncn4)c3c2)CC1] |

-continued
| Compound No. | Structure |
| --- | --- |
| 45 | 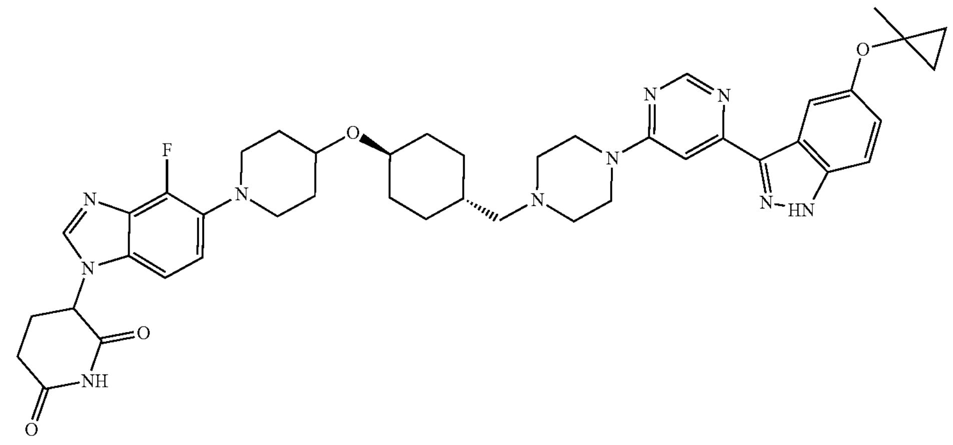 [SMILES: CC1(Oc2ccc3[nH]nc(-c4cc(N5CCN(C[C@H]6CC[C@H](OC7CCN(c8ccc9c(ncn9C9CCC(=O)NC9=O)c8F)CC7)CC6)CC5)ncn4)c3c2)CC1] |
| 46 | 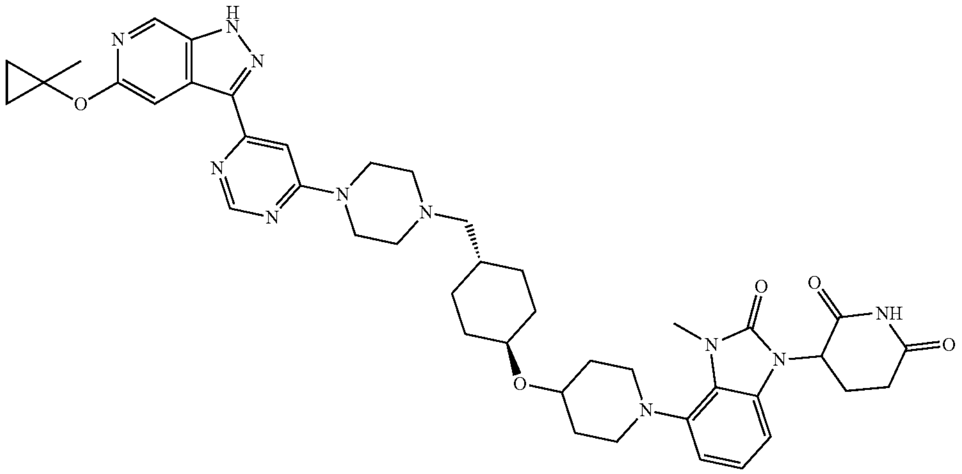 [SMILES: Cn1c(=O)n(C2CCC(=O)NC2=O)c2cccc(N3CCC(O[C@H]4CC[C@H](CN5CCN(c6cc(-c7n[nH]c8cnc(OC9(C)CC9)cc78)ncn6)CC5)CC4)CC3)c21] |
| 47 | 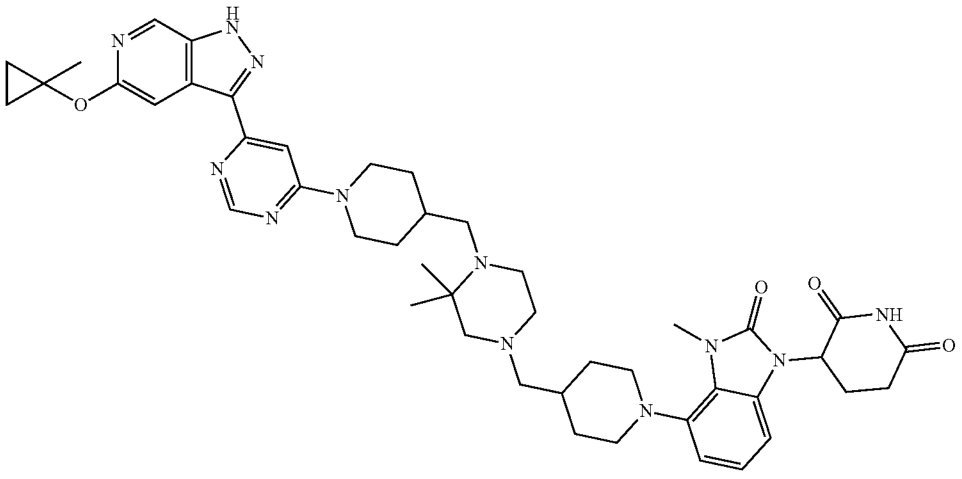 [SMILES: Cn1c(=O)n(C2CCC(=O)NC2=O)c2cccc(N3CCC(CN4CCN(CC5CCN(c6cc(-c7n[nH]c8cnc(OC9(C)CC9)cc78)ncn6)CC5)C(C)(C)C4)CC3)c21] |

-continued
| Compound No. | Structure |
|---|---|
| 48 | 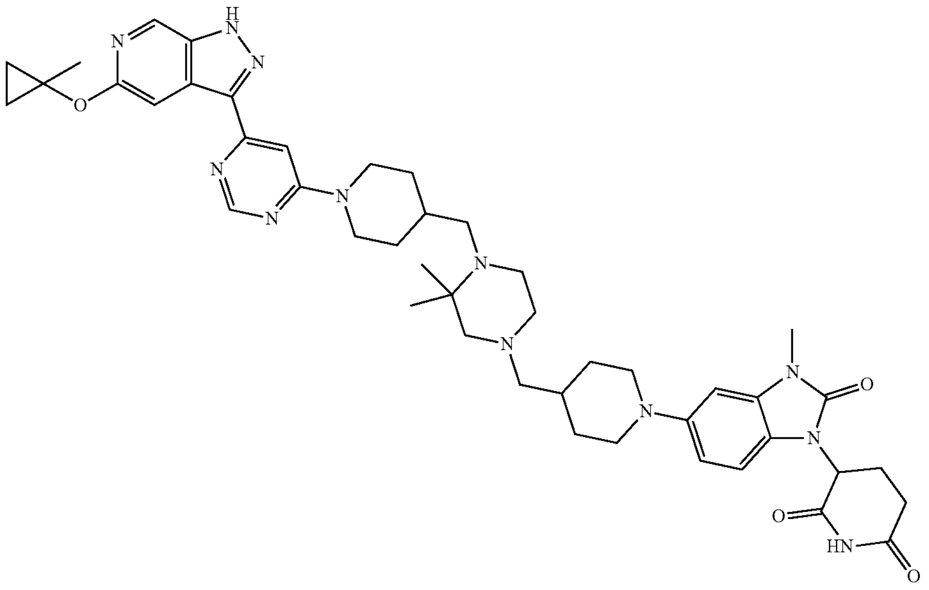 [SMILES: Cn1c(=O)n(C2CCC(=O)NC2=O)c2ccc(N3CCC(CN4CCN(CC5CCN(c6cc(-c7n[nH]c8cnc(OC9(C)CC9)cc78)ncn6)CC5)C(C)(C)C4)CC3)cc21] |
| 49 | 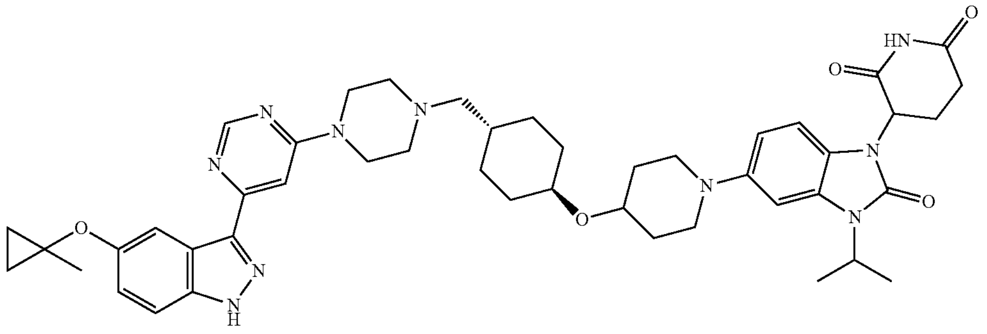 [SMILES: CC(C)n1c(=O)n(C2CCC(=O)NC2=O)c2ccc(N3CCC(O[C@H]4CC[C@H](CN5CCN(c6cc(-c7n[nH]c8ccc(OC9(C)CC9)cc78)ncn6)CC5)CC4)CC3)cc21] |
| 50 | 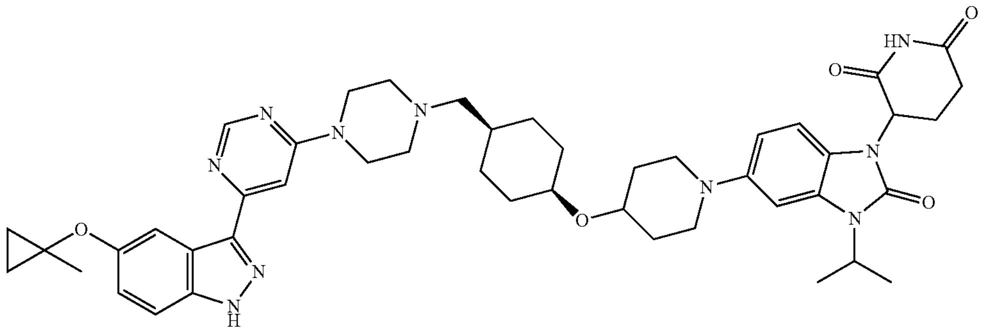 [SMILES: CC(C)n1c(=O)n(C2CCC(=O)NC2=O)c2ccc(N3CCC(O[C@H]4CC[C@@H](CN5CCN(c6cc(-c7n[nH]c8ccc(OC9(C)CC9)cc78)ncn6)CC5)CC4)CC3)cc21] |

-continued
| Compound No. | Structure |
|---|---|
| 51 | 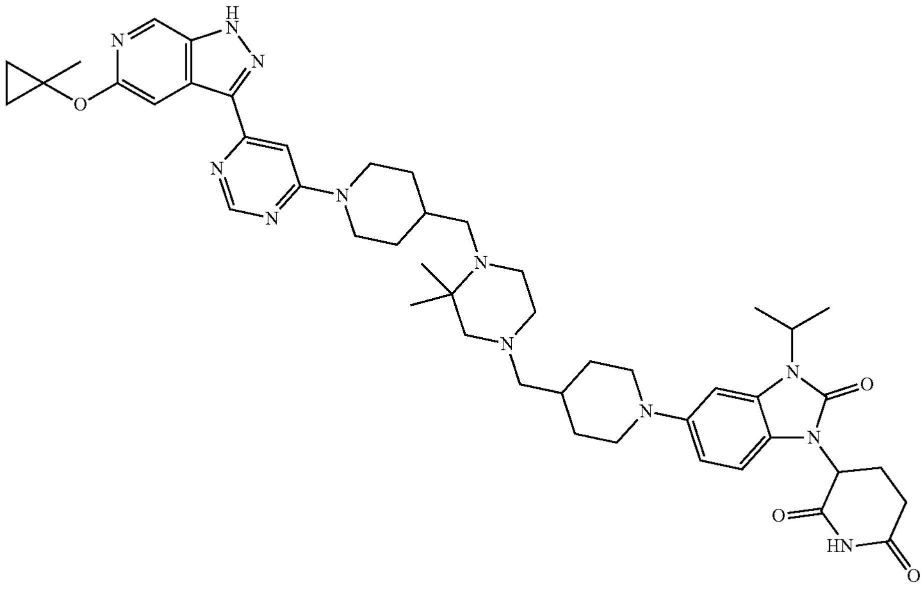 [SMILES: CC(C)n1c(=O)n(C2CCC(=O)NC2=O)c2ccc(N3CCC(CN4CCN(CC5CCN(c6cc(-c7n[nH]c8cnc(OC9(C)CC9)cc78)ncn6)CC5)C(C)(C)C4)CC3)cc21] |
| 52 | 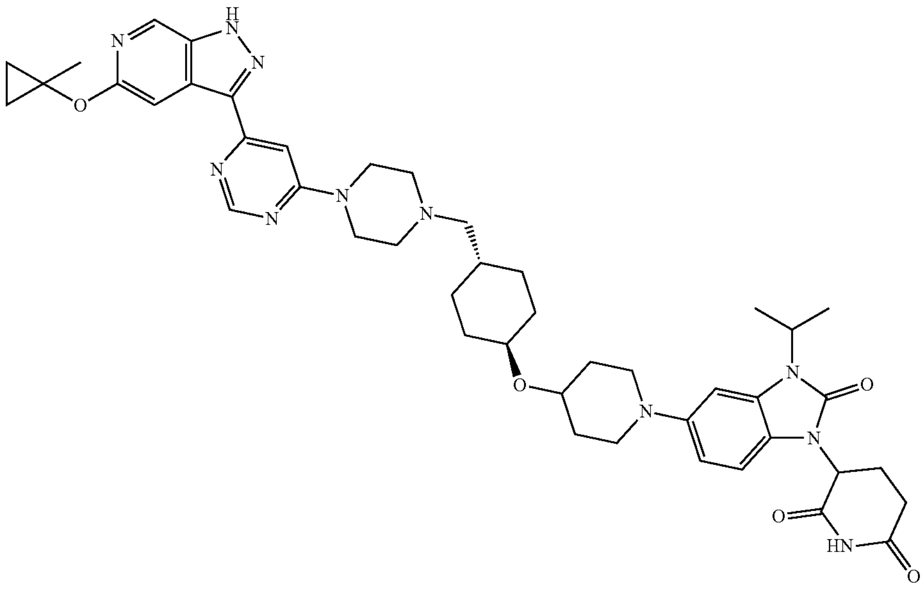 [SMILES: CC(C)n1c(=O)n(C2CCC(=O)NC2=O)c2ccc(N3CCC(O[C@H]4CC[C@H](CN5CCN(c6cc(-c7n[nH]c8cnc(OC9(C)CC9)cc78)ncn6)CC5)CC4)CC3)cc21] |

-continued
| Compound No. | Structure |
|---|---|
| 53 | 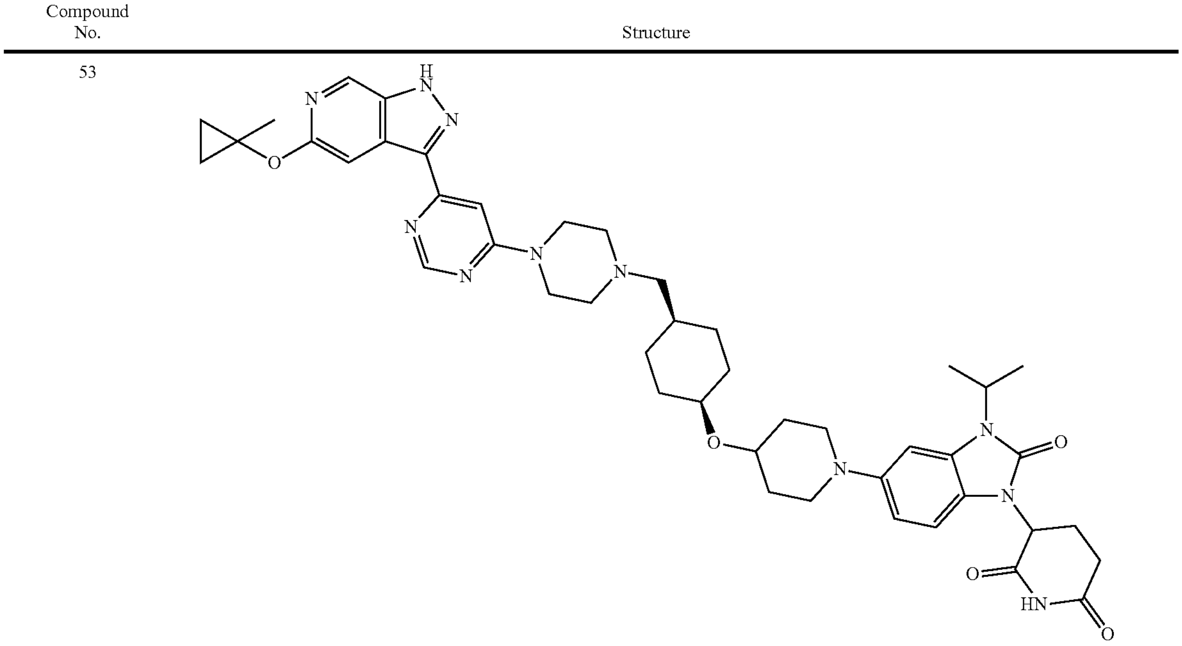 |
| 54 | 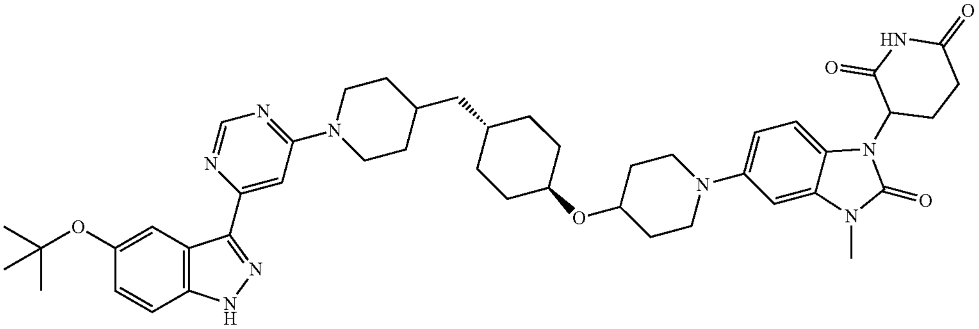 [SMILES: Cn1c(=O)n(C2CCC(=O)NC2=O)c2ccc(N3CCC(O[C@H]4CC[C@H](CC5CCN(c6cc(-c7n[nH]c8ccc(OC(C)(C)C)cc78)ncn6)CC5)CC4)CC3)cc21] |
| 55 | 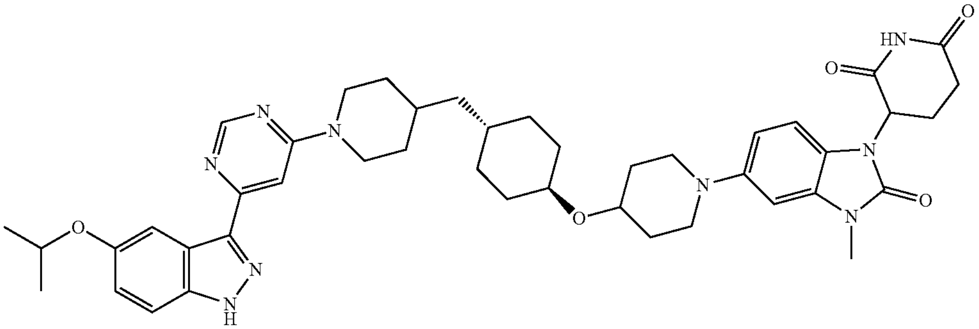 [SMILES: CC(C)Oc1ccc2[nH]nc(-c3cc(N4CCC(C[C@H]5CC[C@H](OC6CCN(c7ccc8c(c7)n(C)c(=O)n8C7CCC(=O)NC7=O)CC6)CC5)CC4)ncn3)c2c1] |
| 56 | 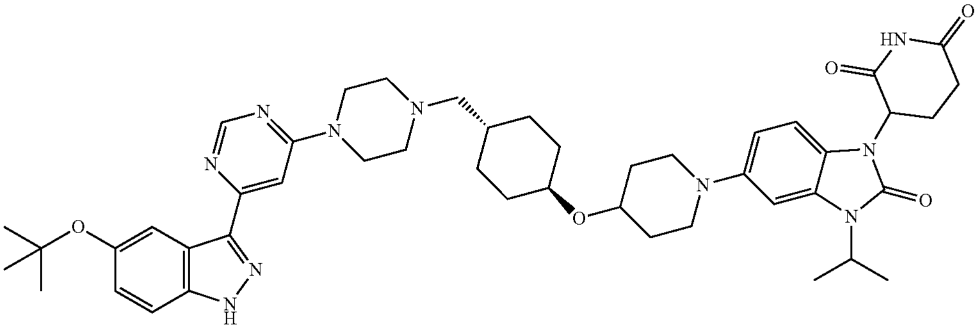 [SMILES: CC(C)n1c(=O)n(C2CCC(=O)NC2=O)c2ccc(N3CCC(O[C@H]4CC[C@H](CN5CCN(c6cc(-c7n[nH]c8ccc(OC(C)(C)C)cc78)ncn6)CC5)CC4)CC3)cc21] |

-continued
| Compound No. | Structure |
|---|---|
| 57 | 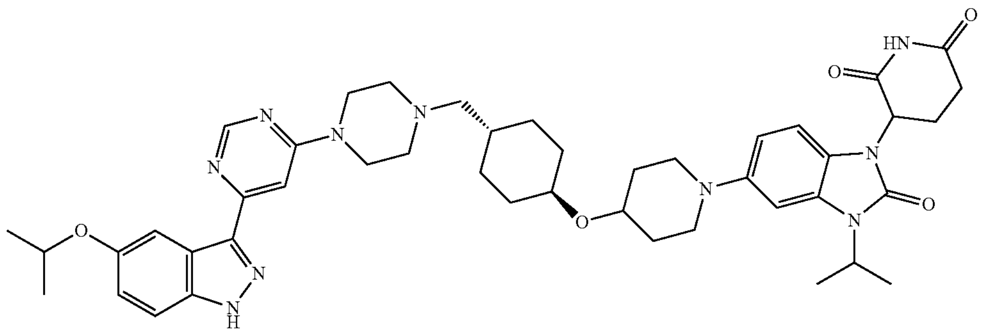 [SMILES: CC(C)Oc1ccc2[nH]nc(-c3cc(N4CCN(C[C@H]5CC[C@H](OC6CCN(c7ccc8c(c7)n(C(C)C)c(=O)n8C7CCC(=O)NC7=O)CC6)CC5)CC4)ncn3)c2c1] |
| 58 | 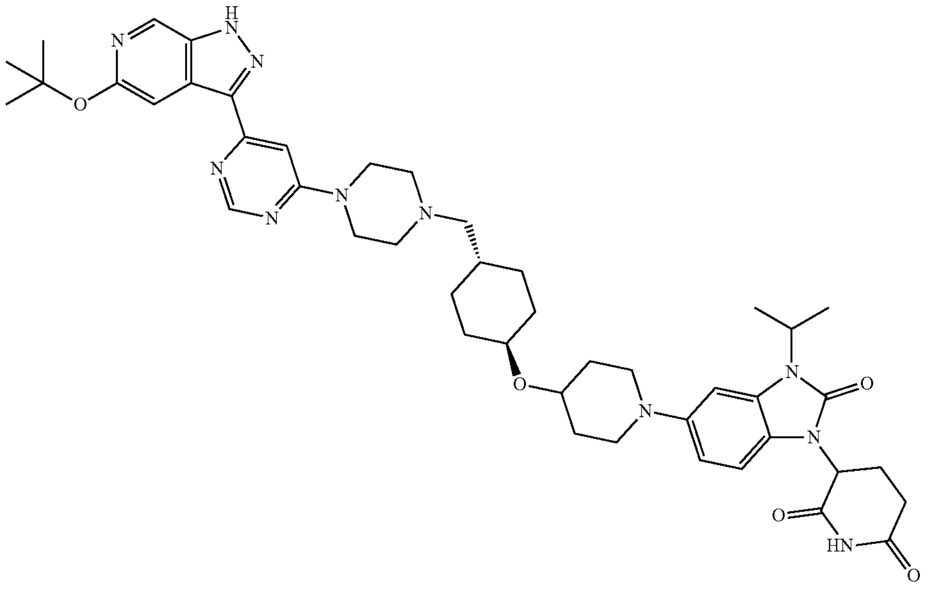 [SMILES: CC(C)n1c(=O)n(C2CCC(=O)NC2=O)c2ccc(N3CCC(O[C@H]4CC[C@H](CN5CCN(c6cc(-c7n[nH]c8cnc(OC(C)(C)C)cc78)ncn6)CC5)CC4)CC3)cc21] |
| 59 | 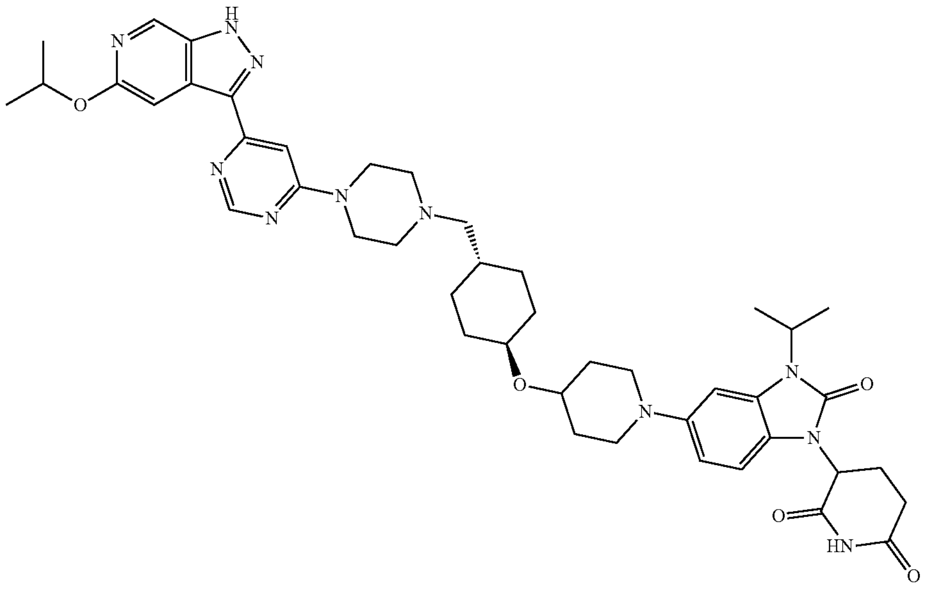 [SMILES: CC(C)Oc1cc2c(-c3cc(N4CCN(C[C@H]5CC[C@H](OC6CCN(c7ccc8c(c7)n(C(C)C)c(=O)n8C7CCC(=O)NC7=O)CC6)CC5)CC4)ncn3)n[nH]c2cn1] |

-continued
| Compound No. | Structure |
|---|---|
| 60 | 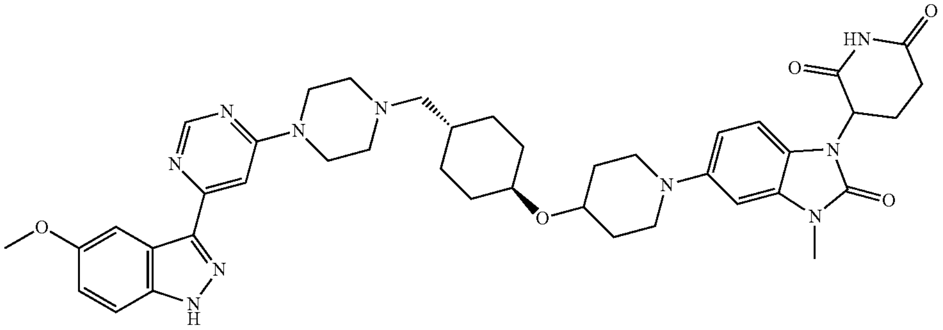 [SMILES: COc1ccc2[nH]nc(-c3cc(N4CCN(C[C@H]5CC[C@H](OC6CCN(c7ccc8c(c7)n(C)c(=O)n8C7CCC(=O)NC7=O)CC6)CC5)CC4)ncn3)c2c1] |
| 61 | 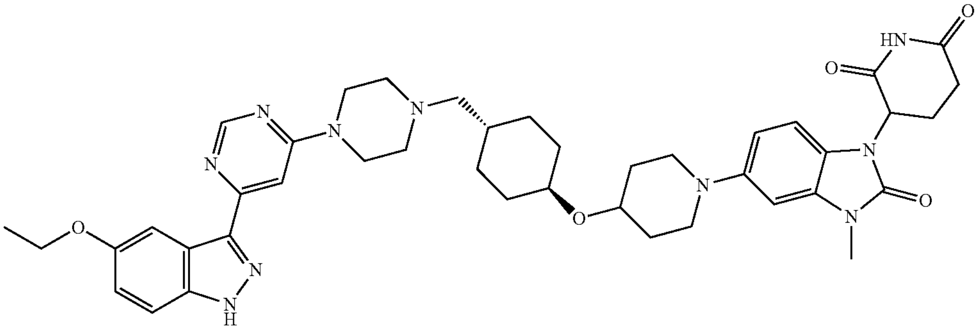 [SMILES: CCOc1ccc2[nH]nc(-c3cc(N4CCN(C[C@H]5CC[C@H](OC6CCN(c7ccc8c(c7)n(C)c(=O)n8C7CCC(=O)NC7=O)CC6)CC5)CC4)ncn3)c2c1] |
| 62 | 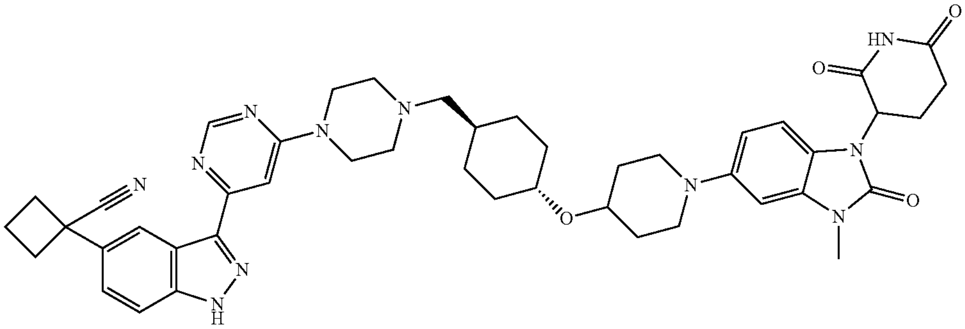 [SMILES: Cn1c(=O)n(C2CCC(=O)NC2=O)c2ccc(N3CCC(O[C@H]4CC[C@H](CN5CCN(c6cc(-c7n[nH]c8ccc(C9(C#N)CCC9)cc78)ncn6)CC5)CC4)CC3)cc21] |
| 63 | 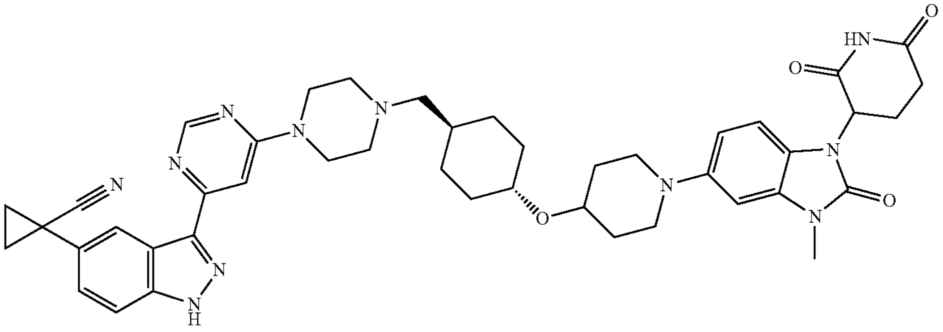 [SMILES: Cn1c(=O)n(C2CCC(=O)NC2=O)c2ccc(N3CCC(O[C@H]4CC[C@H](CN5CCN(c6cc(-c7n[nH]c8ccc(C9(C#N)CC9)cc78)ncn6)CC5)CC4)CC3)cc21] |

-continued
| Compound No. | Structure |
|---|---|
| 64 | 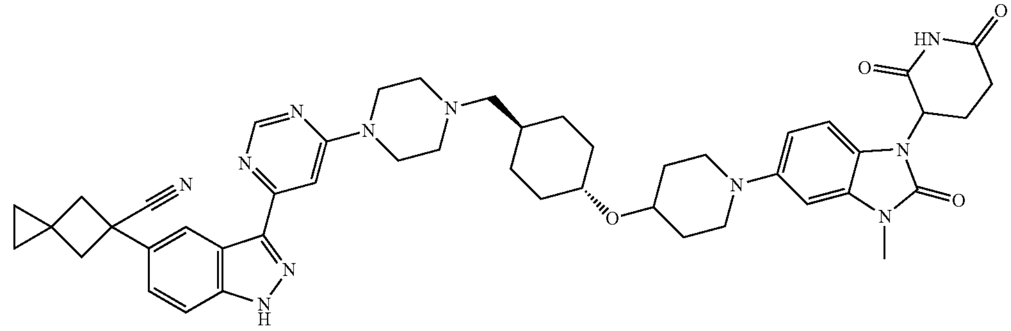 [SMILES: Cn1c(=O)n(C2CCC(=O)NC2=O)c2ccc(N3CCC(O[C@H]4CC[C@H](CN5CCN(c6cc(-c7n[nH]c8ccc(C9(C#N)CC%10(CC%10)C9)cc78)ncn6)CC5)CC4)CC3)cc21] |
| 65 | 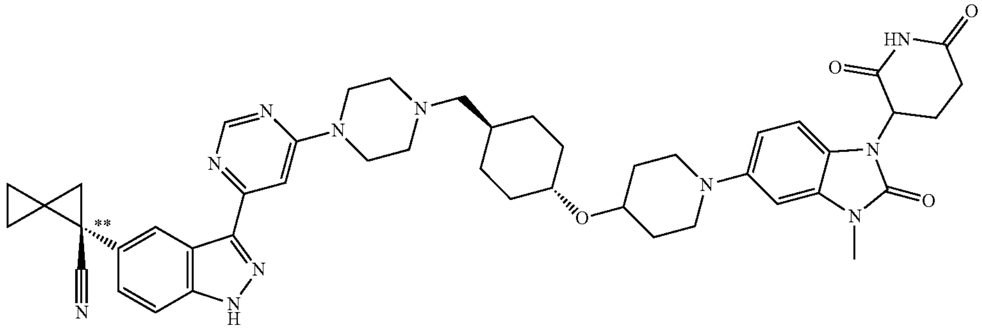 [SMILES: Cn1c(=O)n(C2CCC(=O)NC2=O)c2ccc(N3CCC(O[C@H]4CC[C@H](CN5CCN(c6cc(-c7n[nH]c8ccc([C@@]9(C#N)CC9%10CC%10)cc78)ncn6)CC5)CC4)CC3)cc21]<br>**Stereochemistry at cyano carbon is arbitrarily assigned |
| 66 | 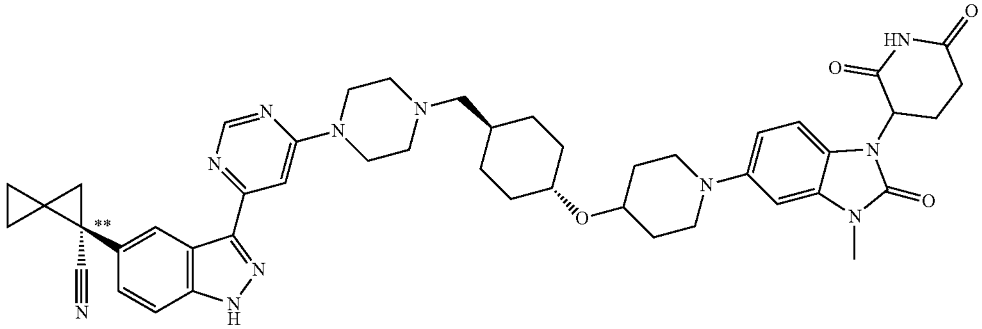 [SMILES: Cn1c(=O)n(C2CCC(=O)NC2=O)c2ccc(N3CCC(O[C@H]4CC[C@H](CN5CCN(c6cc(-c7n[nH]c8ccc([C@]9(C#N)CC9%10CC%10)cc78)ncn6)CC5)CC4)CC3)cc21]<br>**Stereochemistry at cyano carbon is arbitrarily ssigned |

-continued
| Compound No. | Structure |
|---|---|
| 67 | 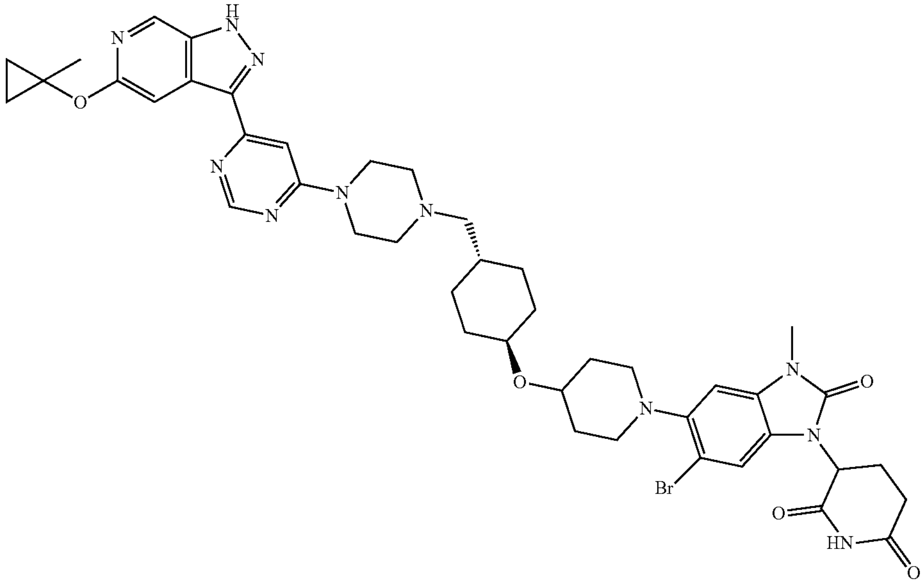 [SMILES: Cn1c(=O)n(C2CCC(=O)NC2=O)c2cc(Br)c(N3CCC(O[C@H]4CC[C@H](CN5CCN(c6cc(-c7n[nH]c8cnc(OC9(C)CC9)cc78)ncn6)CC5)CC4)CC3)cc21] |
| 68 | 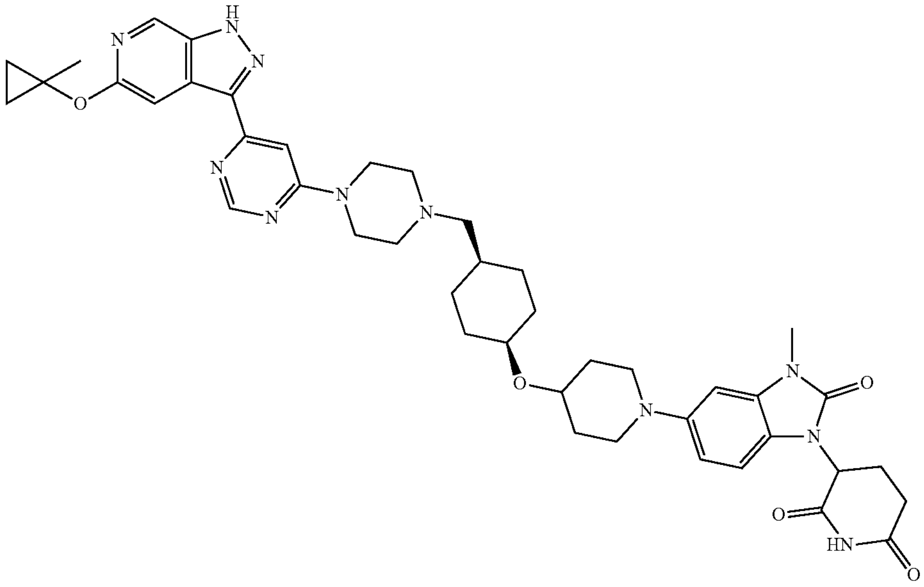 [SMILES: Cn1c(=O)n(C2CCC(=O)NC2=O)c2ccc(N3CCC(O[C@H]4CC[C@@H](CN5CCN(c6cc(-c7n[nH]c8cnc(OC9(C)CC9)cc78)ncn6)CC5)CC4)CC3)cc21] |

-continued

| Compound No. | Structure |
| --- | --- |
| 69 | 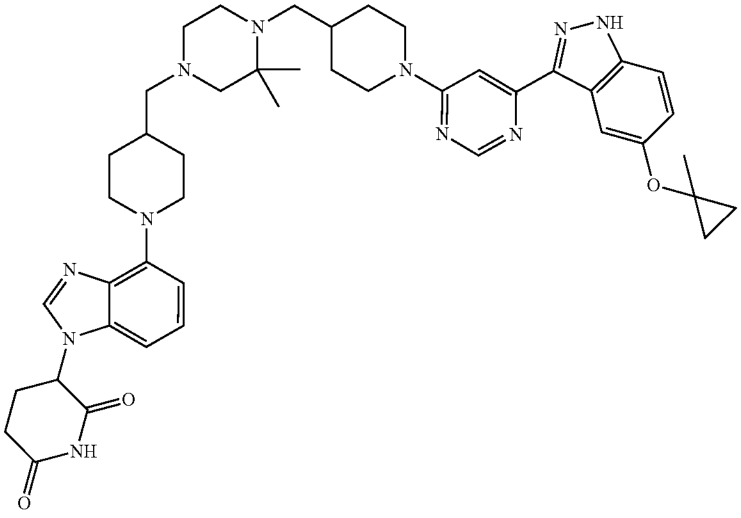 [SMILES: CC1(Oc2ccc3[nH]nc(-c4cc(N5CCC(CN6CCN(CC7CCN(c8cccc9c8ncn9C8CCC(=O)NC8=O)CC7)CC6(C)C)CC5)ncn4)c3c2)CC1] |
| 70 | 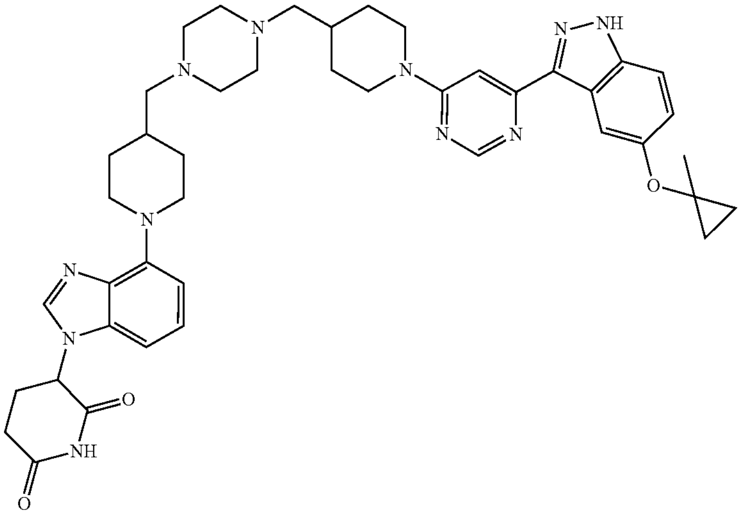 [SMILES: CC1(Oc2ccc3[nH]nc(-c4cc(N5CCC(CN6CCN(CC7CCN(c8cccc9c8ncn9C8CCC(=O)NC8=O)CC7)CC6)CC5)ncn4)c3c2)CC1] |

In embodiments, certain compounds comprising a 3-(3-methyl-2-oxo-2,3-dihydro-1H-benzo[d]imidazol-1-yl)piperidine-2,6-dione group attached to variable (L) in the described compounds had improved activity. See e.g., Table 3.

Pharmaceutical Compositions

Also provided herein are pharmaceutical compositions comprising any of the compounds described herein or a pharmaceutically acceptable salt thereof; and a pharmaceutically acceptable carrier.

In embodiments, the pharmaceutical composition further comprises an additional bioactive agent. In embodiments, the additional bioactive agent is an anti-inflammatory, a chemotherapy agent, or an immunomodulatory agent.

In one embodiment, the pharmaceutical compositions effect targeted protein degradation in a patient or subject, for example, an animal such as a human, and can be used for treating or ameliorating disease states or conditions that are modulated by degrading the target protein. In embodiments, the therapeutic compositions as described herein may be used to effectuate the degradation of protein for the treatment or amelioration of LRRK2-mediated inflammatory diseases, autoimmune diseases, or cancer. In additional embodiments, the disease is idiopathic Parkinson's Disease (PD), LRRK2 mutation-associated Parkinson's Disease (PD), progressive supranuclear palsy (PSP), corticobasal degeneration (CBD, lewy body dementia, Crohn's Disease, Leprosy with type 1 inflammatory reactions, neuroinflammation, Kennedy's disease, TDP-43 ALS, c9orf ALS, Huntington's disease, Alzheimer's disease, Picks disease, multiple systems atrophy, systemic lupus erythematosus (SLE), acute kidney injury, rhabdomyolysis, lipofusinosis, fabry's disease, batten's disease, ulcerative colitis, irritable bowel disease, Kufor-Rakeb syndrome, gaucher Disease, Frontal Temporal Dementia, spinocerebellar ataxias (SCAs) 1, 2, 3, 6, 7 and 17, and/or dentatorubral pallidoluysian atrophy (DRPLA).

In embodiments, the disease is idiopathic PD. In embodiments, the disease is LRRK2 mutation-associated PD. In embodiments, the disease is progressive supranuclear palsy (PSP). In embodiments, the disease is systemic lupus erythematosus (SLE).

Methods of Treatment

Further, disclosed herein is a method of treating a disease, a disorder, or a symptom causally related to LRRK2, comprising administering to a subject an effective amount of any of the compounds provided herein, or a pharmaceutically acceptable salt thereof, or an effective amount of any of the compounds provided herein, or a pharmaceutically acceptable salt thereof as part of a pharmaceutical composition.

Further, disclosed herein is the use of an effective amount of any of the compounds provided herein, or a pharmaceutically acceptable salt thereof, or an effective amount of any of the compounds provided herein, or a pharmaceutically acceptable salt thereof as part of a pharmaceutical composition for treating a disease, a disorder, or a symptom causally related to LRRK2.

Further, disclosed herein is the use of an effective amount of any of the compounds provided herein, or a pharmaceutically acceptable salt thereof, or an effective amount of any of the compounds provided herein, or a pharmaceutically acceptable salt thereof as part of a pharmaceutical composition for the manufacture of a medicament for treating a disease, a disorder, or a symptom causally related to LRRK2.

In embodiments, the disease or disorder is idiopathic Parkinson's Disease (PD), LRRK2 mutation-associated Parkinson's Disease (PD), progressive supranuclear palsy (PSP), corticobasal degeneration (CBD, lewy body dementia, Crohn's Disease, Leprosy with type 1 inflammatory reactions, neuroinflammation, Kennedy's disease, TDP-43 ALS, c9orf ALS, Huntington's disease, Alzheimer's disease, Picks disease, multiple systems atrophy, systemic lupus erythematosus (SLE), acute kidney injury, rhabdomyolysis, lipofusinosis, fabry's disease, batten's disease, ulcerative colitis, irritable bowel disease, Kufor-Rakeb syndrome, gaucher Disease, Frontal Temporal Dementia, spinocerebellar ataxias (SCAs) 1, 2, 3, 6, 7 and 17, and/or dentatorubral pallidoluysian atrophy (DRPLA). In embodiments, the disease is idiopathic PD. In embodiments, the disease is LRRK2 mutation-associated PD. In embodiments, the disease is progressive supranuclear palsy (PSP). In embodiments, the disease is systemic lupus crythematosus (SLE).

Also provided herein is a method of treating Parkinson's disease, comprising administering to a subject an effective amount of any of the compounds of the present disclosure, or a pharmaceutically acceptable salt thereof, or an effective amount of any of the compounds provided herein, or a pharmaceutically acceptable salt thereof as part of a pharmaceutical composition.

Further, disclosed herein is the use of an effective amount of any of the compounds provided herein, or a pharmaceutically acceptable salt thereof, or an effective amount of any of the compounds provided herein, or a pharmaceutically acceptable salt thereof as part of a pharmaceutical composition for treating Parkinson's disease.

Further, disclosed herein is the use of an effective amount of any of the compounds provided herein, or a pharmaceutically acceptable salt thereof, or an effective amount of any of the compounds provided herein, or a pharmaceutically acceptable salt thereof as part of a pharmaceutical composition for the manufacture of a medicament for treating Parkinson's discasc.

In embodiments, the Parkinson's disease is LRRK2 mutation associated Parkinson's disease.

Provided herein is a method of treating progressive supranuclear palsy (PSP) comprising administering to a subject an effective amount of any of the compounds of the present disclosure, or a pharmaceutically acceptable salt thereof, or an effective amount of any of the compounds provided herein, or a pharmaceutically acceptable salt thereof as part of a pharmaceutical composition.

Further, disclosed herein is the use of an effective amount of any of the compounds provided herein, or a pharmaceutically acceptable salt thereof, or an effective amount of any of the compounds provided herein, or a pharmaceutically acceptable salt thereof as part of a pharmaceutical composition for treating progressive supranuclear palsy (PSP).

Further, disclosed herein is the use of an effective amount of any of the compounds provided herein, or a pharmaceutically acceptable salt thereof, or an effective amount of any of the compounds provided herein, or a pharmaceutically acceptable salt thereof as part of a pharmaceutical composition for the manufacture of a medicament for treating progressive supranuclear palsy (PSP).

Also, provided herein is a method of treating systemic lupus erythematosus (SLE) comprising administering to a subject an effective amount of any of the compounds of the present disclosure, or a pharmaceutically acceptable salt thereof, or an effective amount of any of the compounds provided herein, or a pharmaceutically acceptable salt thereof as part of a pharmaceutical composition.

Further, disclosed herein is the use of an effective amount of any of the compounds provided herein, or a pharmaceutically acceptable salt thereof, or an effective amount of any of the compounds provided herein, or a pharmaceutically acceptable salt thereof as part of a pharmaceutical composition for treating systemic lupus erythematosus (SLE).

Further, disclosed herein is the use of an effective amount of any of the compounds provided herein, or a pharmaceutically acceptable salt thereof, or an effective amount of any of the compounds provided herein, or a pharmaceutically acceptable salt thereof as part of a pharmaceutical composition for the manufacture of a medicament for treating systemic lupus erythematosus (SLE).

The present disclosure further relates to a method for treating a disease state or ameliorating one or more symptoms of a disease or condition by degrading the LRRK2 protein (e.g., a wildtype LRRK2 protein or an LRRK2 mutant protein (e.g., a LRRK2 mutant protein including one or more mutation selected from G2019S, I2020T, N1437H, R1441G/C/H, and Y1699C) comprising administering to a subject an effective amount of at least one compound as described herein, or a pharmaceutically acceptable salt thereof, optionally in combination with another bioactive agent, or an effective amount of compounds provided herein, or a pharmaceutically acceptable salt thereof as part of a pharmaceutical composition, wherein the compound or pharmaceutical composition is effective for treating or ameliorating the disease or disorder or one or more symptoms thereof in the subject.

Further, disclosed herein is the use of an effective amount of any of the compounds provided herein, or a pharmaceutically acceptable salt thereof, or an effective amount of any of the compounds provided herein, or a pharmaceutically acceptable salt thereof as part of a pharmaceutical composition for treating a disease state or ameliorating one or more symptoms of a disease or condition by degrading the LRRK2 protein (e.g., a wildtype LRRK2 protein or an LRRK2 mutant protein (e.g., a LRRK2 mutant protein including one or more mutation selected from G2019S, I2020T, N1437H, R1441G/C/H, and Y1699C).

Further, disclosed herein is the use of an effective amount of any of the compounds provided herein, or a pharmaceutically acceptable salt thereof, or an effective amount of any of the compounds provided herein, or a pharmaceutically acceptable salt thereof as part of a pharmaceutical composition for the manufacture of a medicament for treating a disease state or ameliorating one or more symptoms of a disease or condition by degrading the LRRK2 protein (e.g., a wildtype LRRK2 protein or an LRRK2 mutant protein (e.g., a LRRK2 mutant protein including one or more mutation selected from G2019S, I2020T, N1437H, R1441G/C/H, and Y1699C).

The methods and uses according to the present disclosure may be used to treat certain disease states, conditions or symptoms including inflammatory disease, autoimmune disease, or cancer, by virtue of the administration of effective amounts of at least one compound described herein. For example, the method according to the present disclosure may be used to treat one or more of Parkinson's Disease (PD), idiopathic PD, LRRK2 mutation associated PD (e.g., PD associated with one or more LRRK2 activating mutations), primary tauopathies (e.g., progressive supranuclear palsy (PSP) or corticobasal degeneration (CBD)), lewy body dementia, Crohn's Disease, Leprosy (e.g., Leprosy with type 1 inflammatory reactions), and neuroinflammation (such as is observed in Alzheimer's disease, PD, multiple sclerosis, traumatic brain injury, spinal cord injury, etc.).

Also provided herein is a process for making a small molecule that can cause degradation of LRRK2 in a cell, comprising the steps of: (i) providing a small molecule that binds to the LRRK2 or a mutated form thereof; (ii) providing an E3 ubiquitin ligase binding moiety (ULM), preferably a CLM such as thalidomide, pomalidomide, lenalidomide or an analog thereof; and (iii) covalently coupling the small molecule of step (i) to the ULM of step (ii) via a chemical linking group (L), to form a compound which binds to both a cereblon E3 ubiquitin ligase and LRRK2 protein and/or mutated form in the cell, such that the cereblon E3 ubiquitin ligase is in proximity to, and ubiquitinates the LRRK2 protein bound thereto, such that the ubiquitinated LRRK2 protein is then degraded.

Further, disclosed herein is a method for detecting whether a small molecule can trigger degradation of a LRRK2 protein in a cell, the method comprising the steps of: (i) providing a small molecule for which the ability to trigger degradation of LRRK2 protein in a cell is to be detected, said small molecule comprising the structure: CLM-L-PTM, wherein CLM is a cereblon E3 ubiquitin ligase binding moiety capable of binding a cereblon E3 ubiquitin ligase in a cell, which CLM is thalidomide, pomalidomide, lenalidomide, or an analog thereof; PTM is a protein targeting moiety, which is a small molecule that binds to LRRK2 and/or mutated LRRK form thereof, said LRRK2 having at least one lysine residue available to be ubiquitinated by a cereblon E3 ubiquitin ligase bound to the CLM of the molecule; and L is a chemical linking group that covalently links the CLM to the PTM to form the small molecule; (ii) incubating a LRRK2 protein-expressing cell in the presence of the small molecule of step (i); and (iii) detecting whether the LRRK2 protein in the cell has been degraded.

In embodiments, the small molecule capable of binding LRRK2, is a small molecule that binds LRRK2. In embodiments, the small molecule that binds the LRRK2 protein is as described herein.

The present disclosure further provides a method of treating a human patient in need of said treatment of a disease state, condition, or symptom causally related to LRRK2, and/or LRRK2 mutated form, expression, overexpression, mutation, aggregation, accumulation, misfolding or dysregulation where the degradation of the LRRK2 protein will produce a therapeutic effect in the patient, the method comprising administering to the patient an effective amount of any of the compounds according to the present disclosure, optionally in combination with another bioactive agent, or an effective amount of any of the pharmaceutical compositions according to the present disclosure.

Also provided herein is a method of treating a human patient in need of said treatment of a disease state, condition, or symptom causally related to alpha-synuclein expression, over-expression, mutation, aggregation, accumulation, misfolding or dysregulation where the degradation of the LRRK2 protein and/or mutated form thereof will produce a therapeutic effect in the patient, the method comprising administering to the patient an effective amount of any of the compounds according to the present disclosure, optionally in combination with another bioactive agent, or an effective amount of any of the pharmaceutical compositions according to the present disclosure.

Further, disclosed herein is method of treating a human patient in need of said treatment of a disease state, condition, or symptom causally related to Tau over-expression, mutation, aggregation, misfolding or dysregulation where the degradation of the LRRK2 protein and/or mutated form thereof will produce a therapeutic effect in the patient, the method comprising administering to the patient an effective amount of any of the compounds according to the present disclosure, optionally in combination with another bioactive agent, or an effective amount of any of the pharmaceutical compositions according to the present disclosure.

In embodiments, the disease state, condition, or symptom may be caused by a microbial agent or other exogenous agent such as a virus, bacteria, fungus, protozoa, or other microbe, or may be a disease state, which is caused by expression, overexpression, mutation, misfolding, or dysregulation of the protein, which leads to a disease state, condition, or symptom.

In embodiments, the disease state, condition, or symptom which may be treated using compounds or pharmaceutical compositions according to the present disclosure include, for example, Parkinson's Disease (PD), idiopathic PD, LRRK2 mutation associated PD (e.g., PD associated with one or more LRRK2 activating mutations), primary tauopathies (e.g., progressive supranuclear palsy (PSP) or corticobasal degeneration (CBD)), lewy body dementia, Crohn's Disease, Leprosy (e.g., Leprosy with type 1 inflammatory reactions), and/or neuroinflammation (such as is observed in Alzheimer's disease, PD, multiple sclerosis, traumatic brain injury, spinal cord injury, etc.).

Also provided herein is a method of treating or ameliorating at least one symptom of a disease or condition in a subject, comprising the steps of:

a) providing a subject identified as having a symptom of a disease or condition causally related to expression, overexpression, mutation, misfolding, or dysregulation of the LRRK2 protein and/or mutated form thereof in the subject, and the symptom of the disease or condition is treated or ameliorated by degrading the LRRK2 protein and/or mutated form thereof in cells of the subject; and
b) administering to the subject an effective amount of a compound comprising a small molecule of the present disclosure such that the LRRK2 protein and/or mutated form thereof is degraded, thereby treating, or ameliorating at least one symptom of a disease or condition in the subject.

Administration/Dosages/Formulations

Liquid dosage forms for oral administration include pharmaceutically acceptable emulsions, microemulsions, solutions, suspensions, syrups, and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations (for example, sterile injectable aqueous or oleaginous suspensions) may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

To prolong the effect of a drug, it is often desirable to slow the absorption of the drug from subcutaneous or intramuscular injection. This may be accomplished using a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this disclosure with suitable non-irritating excipients or carriers such as cocoa butter, polyethylene glycol, or a suppository wax which are solid at ambient temperature but liquid at body temperature and therefore melt in the rectum or vaginal cavity and release the active compound.

Solid compositions of a similar type may also be employed as fillers in soft and hard filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active compound may be admixed with at least one inert diluent such as sucrose, lactose, or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents.

Dosage forms for topical or transdermal administration of a compound of this disclosure include ointments, pastes, creams, lotions, gels, powders, solutions, sprays, inhalants, or patches. The active component is admixed under sterile conditions with a pharmaceutically acceptable carrier and any needed preservatives or buffers as may be required. Ophthalmic formulation, car drops, eye ointments, powders and solutions are also contemplated as being within the scope of this disclosure.

The ointments, pastes, creams, and gels may contain, in addition to an active compound of this disclosure, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this disclosure, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Compounds of the present disclosure can be administered intratympanically, wherein a long, narrow, bore needle is passed through the car canal and through the cardrum to administer medications into the middle car space where they are absorbed by the inner car.

According to the methods of treatment of the present disclosure, disorders are treated or prevented in a subject, such as a human or other animal, by administering to the subject a therapeutically effective amount of a compound of the disclosure, in such amounts and for such time as is necessary to achieve the desired result. The term "therapeutically effective amount" of a compound of the disclosure, as used herein, means a sufficient amount of the compound so as to decrease the symptoms of a disorder in a subject. As is well understood in the medical arts a therapeutically effective amount of a compound of this disclosure will be at a reasonable benefit/risk ratio applicable to any medical treatment.

In general, compounds of the disclosure will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages from about 0.03 to 2.5 mg/kg per body weight. An indicated daily dosage in the larger mammal, e.g., humans, is in the range from about 0.5 mg to about 100 mg, conveniently administered, e.g., in divided doses up to four times a day or in retard form. Suitable unit dosage forms for oral administration comprise from ca. 1 to 50 mg active ingredient.

In embodiments, a therapeutic amount or dose of the compounds of the present disclosure may range from about 0.1 mg/Kg to about 500 mg/Kg, alternatively from about 1 to about 50 mg/Kg. In general, treatment regimens according to the present disclosure comprise administration to a patient in need of such treatment from about 10 mg to about 1000 mg of the compound(s) of this disclosure per day in single or multiple doses. Therapeutic amounts or doses will also vary depending on route of administration, as well as the possibility of co-usage with other agents.

Upon improvement of a subject's condition, a maintenance dose of a compound, composition or combination of this disclosure may be administered, if necessary. Subsequently, the dosage or frequency of administration, or both, may be reduced, as a function of the symptoms, to a level at which the improved condition is retained; when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present disclosure will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The disclosure also provides for a pharmaceutical combination, e.g., a kit, comprising a) a first agent which is a compound of the disclosure as disclosed herein, in free form or in pharmaceutically acceptable salt form, and b) at least one co-agent. The kit can comprise instructions for its administration.

Some examples of materials which can serve as pharmaceutically acceptable carriers include, but are not limited to, ion exchangers; alumina; aluminum stearate; lecithin; serum proteins, such as human serum albumin; buffer substances such as phosphates, glycine, sorbic acid, or potassium sorbate; partial glyceride mixtures of saturated vegetable fatty acids; water; salts or electrolytes, such as protamine sulfate; disodium hydrogen phosphate; potassium hydrogen phosphate; sodium chloride; zinc salts; colloidal silica; magnesium trisilicate; polyvinyl pyrrolidone; polyacrylates; waxes; polyethylenepolyoxypropylene-block polymers; wool fat; sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols, such a propylene glycol or polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; and phosphate buffer solutions. Further, non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The protein kinase inhibitors or pharmaceutical salts thereof may be formulated into pharmaceutical compositions for administration to animals or humans. These pharmaceutical compositions, which comprise an amount of the protein inhibitor effective to treat or prevent a protein kinase-mediated condition and a pharmaceutically acceptable carrier, are other embodiments of the present disclosure.

Kits

Provided herein are kits comprising a compound capable of causing the degradation of LRRK2 in a subject comprising one or more compounds described herein and instructions for use in treating a disorder associated with LRRK2.

Also provided herein are kits comprising a compound described herein for the treatment of any of the indications described herein.

Those skilled in the art will recognize or be able to ascertain using no more than routine experimentation, numerous equivalents to the specific procedures, embodiments, claims, and examples described herein. Such equivalents are considered to be within the scope of this disclosure and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present disclosure. Moreover, all values that fall within these ranges, as well as the upper or lower limits of a range of values, are also contemplated by the present application.

The following examples further illustrate aspects of the present disclosure. However, they are in no way a limitation of the teachings of the present disclosure as set forth.

EXAMPLES

The compounds and methods described herein are further illustrated by the following examples, which should not be construed as further limiting. The practice of the present disclosure will employ, unless otherwise indicated, conventional techniques of organic synthesis, cell biology, cell culture, and molecular biology, which are within the skill of the art.

| Abbreviations | |
|---|---|
| AcOH or HOAc | Acetic acid |
| CBz | Benzyl chloroformate |
| Boc | tert-butoxycarbonyl |
| $CDCl_3$ | Chloroform-d |
| $Cs_2CO_3$ | Cesium carbonate |
| DIEA | Diisopropylethylamine |
| $D_{max}$ | Maximal degradation (%) |
| DMF | N,N-Dimethylformamide |

-continued

| Abbreviations | |
|---|---|
| DMSO | Dimethyl sulfoxide |
| DMSO-$d_6$ | Deuterated dimethyl sulfoxide ($C_2D_6SO$) |
| DTT | Dithiothreitol |
| ESI | Electrospray ionization |
| EtOH | Ethanol |
| eq | Equivalent(s) |
| g | Gram(s) |
| h | Hour(s) |
| Hz | Hertz |
| HCl | Hydrochloric acid |
| HPLC | High performance liquid chromatography |
| $DC_{50}$ | Half maximal degradation concentration |
| $K_2CO_3$ | Potassium carbonate |
| $K_3PO_4$ | Potassium phosphate |
| min | Minute(s) |
| m/z | Mass/charge |
| MS | Mass spectrometry |
| MHz | Megahertz |
| MeOH | Methanol |
| MOM | Methoxymethyl |
| μL | Microliter(s) |
| μm | Micrometer(s) |
| mg | Milligram(s) |
| mm | Millimeter(s) |
| mL | Milliliter(s) |
| mmol | Millimole(s) |
| $NH_4Cl$ | Ammonium chloride |
| nM | Nanomolar |
| NMR | Nuclear magnetic resonance |
| Pd(dppf)$Cl_2$ | [1,1-Bis(diphenylphosphino)ferrocene]dichloropalladium(II), complex with dichloromethane |
| PMB | para-methoxybenzyl |
| psi | Pound(s) per square inch |
| TEA | Triethylamine |
| TFA | Trifluoroacetic acid |
| Tf | Trifluoromethanesulfonate |
| TIPS | Triisopropylsilyl ether |
| TBDPS | tert-butyldiphenylsilyl |
| THF | Tetrahydrofuran |
| TLC | Thin-layer chromatography |

Synthetic Procedures

Exemplary Synthesis of Compound 1:

Synthesis of Intermediate trans-benzyl 4-[4-(dimethoxymethyl)cyclohexoxy]piperidine-1-carboxylate Step 1

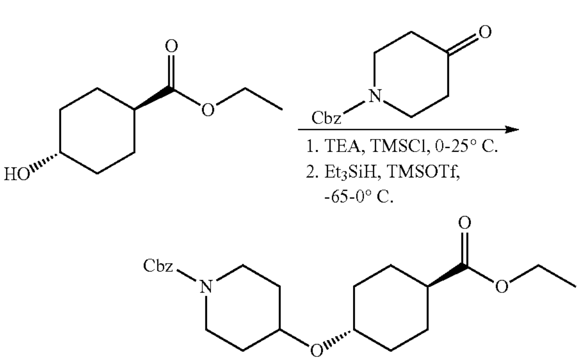

To a solution of trans-ethyl 4-hydroxycyclohexanecarboxylate (20 g, 116.13 mmol, 1 eq) in THF (200 mL) was added TMSCl (13.88 g, 127.74 mmol, 16.21 mL, 1.1 eq) and TEA (14.10 g, 139.36 mmol, 19.40 mL, 1.2 eq) at 0° C., and the reaction mixture was stirred at 25° C. for 1 hour. The reaction mixture was filtered, and the filtrate was concentrated under reduced pressure to give a residue. A stirred solution of the residue and benzyl 4-oxopiperidine-1-carboxylate (31.15 g, 133.55 mmol, 26.63 mL, 1.15 eq) in DCM (300 mL) at −65° C. under $N_2$ was added $Et_3SiH$ (20.25 g, 174.19 mmol, 27.82 mL, 1.5 eq) and TMSOTf (14.20 g, 63.87 mmol, 11.54 mL, 0.55 eq) dropwise, and the reaction mixture was stirred at 0° C. under $N_2$ for 3 hours. The reaction mixture was quenched by addition water (300 mL) and extracted with DCM (200 mL*3). The combined organic layers were washed with brine (300 mL), dried over $Na_2SO_4$, filtered, and concentrated under reduced pressure to give a residue. The residue was purified by flash silica gel chromatography (ISCO®; 120 g SepaFlash® Silica Flash Column, Eluent of 0~20% Ethyl acetate/Petroleum ether gradient @ 100 ml/min). trans-Benzyl 4-(4-ethoxycarbonylcyclohexoxy)piperidine-1-carboxylate (40.8 g, 104.75 mmol, 90.20% yield) was obtained as a colorless oil.

Step 2

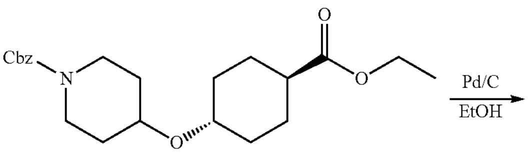

-continued

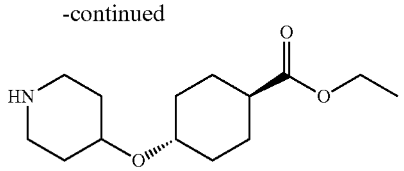

To a solution of trans-benzyl 4-(4-ethoxycarbonylcyclohexoxy)piperidine-1-carboxylate (40.8 g, 104.75 mmol, 1 eq) in EtOH (40 mL) was added Pd/C (8 g, 104.75 mmol, 10%, 1 eq), and the mixture was stirred at 25° C. under $H_2$ (15 psi) for 4 hours. TLC (Petroleum ether:Ethyl acetate=3:1, $I_2$) showed a new spot formed. The reaction mixture was filtered and concentrated under reduced pressure to give a residue. trans-Ethyl 4-(4-piperidyloxy)cyclohexanecarboxylate (26.7 g, 104.56 mmol, 99.82% yield) was obtained as a colorless solid.

Step 3

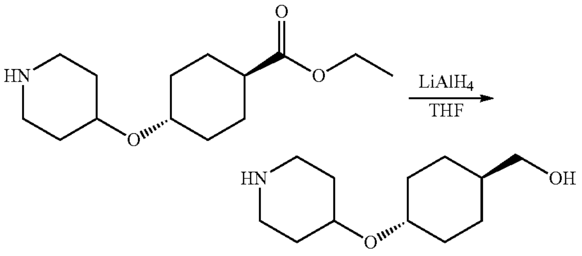

To a solution of trans-ethyl 4-(4-piperidyloxy)cyclohexanecarboxylate (10 g, 39.16 mmol, 1 eq) in THF (70 mL) was added $LiAlH_4$ (2.23 g, 58.74 mmol, 1.5 eq) at 0° C. and the solution was stirred at 0° C. under $N_2$ for 2 hours. TLC (Dichloromethane:Methanol=5:1) showed starting material was consumed completely. The reaction mixture was quenched by addition water (2 mL) and 10% NaOH (4 mL) at 0° C., and then dried over $Na_2SO_4$, filtered, and concentrated under reduced pressure to give a residue. trans-[4-(4-piperidyloxy)cyclohexyl]methanol (7.9 g, 37.03 mmol, 94.57% yield) was obtained as a light-yellow solid.

Step 4

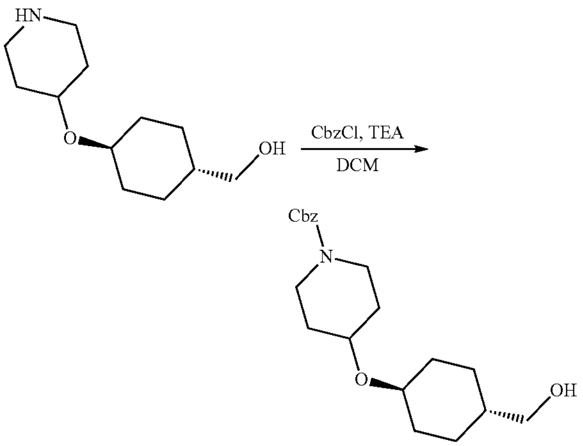

To a mixture of trans-[4-(4-piperidyloxy)cyclohexyl]methanol (30 g, 140.64 mmol, 1 eq) in DCM (300 mL) was added CbzCl (31.19 g, 182.83 mmol, 25.99 mL, 1.3 eq) and TEA (42.69 g, 421.91 mmol, 58.72 mL, 3 eq) at 0° C. under $N_2$. After addition, the reaction mixture was stirred at 25° C. for 1 hour to give light yellow suspension. The reaction was quenched by $H_2O$ (200 mL) and extracted with ethyl acetate (3×100 mL). The combined organic phases were washed with water, dried with $Na_2SO_4$, concentrated in vacuum to give a residue. The residue was purified by silica gel column chromatography (0-100% Ethyl acetate in Petroleum ether) to give trans-benzyl 4-[4-(hydroxymethyl)cyclohexoxy]piperidine-1-carboxylate (37 g, 106.49 mmol, 75.72% yield) as a colorless oil.

Step 5

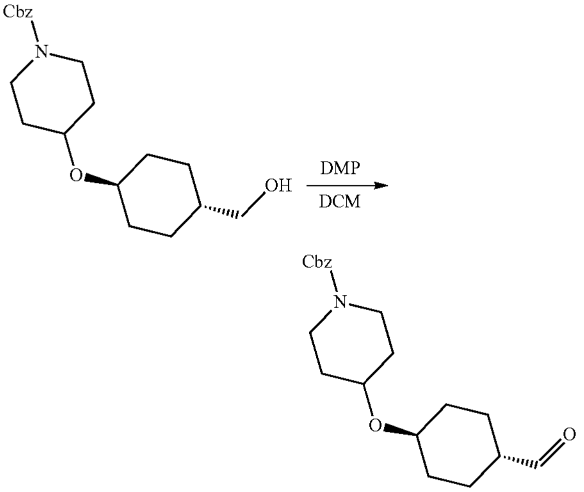

DMP (55.50 g, 130.85 mmol, 40.51 mL, 1.23 eq) was added to a solution of trans-benzyl 4-[4-(hydroxymethyl)cyclohexoxy]piperidine-1-carboxylate (37 g, 106.49 mmol, 1 eq) in DCM (200. mL) and the mixture stirred at 25° C. for 2 h to give yellow solution. The reaction mixture was quenched by addition sat.$NaHCO_3$(pH~8) at 0° C. and extracted with DCM (100 mL*3). The combined organic layers were washed with Sat. $Na_2SO_3$ (100 mL*2) and brine (60 mL*2), dried over $Na_2SO_4$, filtered, and concentrated under reduced pressure to give a residue. The residue was purified by silica gel chromatography (Petroleum ether/Ethyl acetate=100/1, 1/1) to afford trans-benzyl 4-(4-formylcyclohexoxy)piperidine-1-carboxylate (30 g, 85.98 mmol, 80.74% yield, 99% purity) as colorless oil.

Step 6

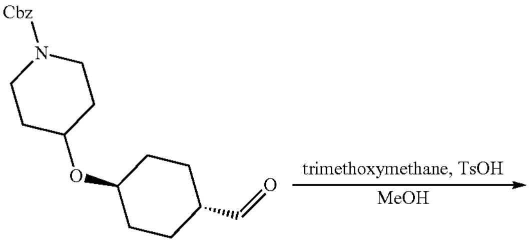

-continued

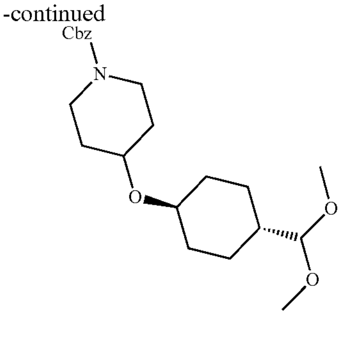

To a solution of trans-benzyl 4-(4-formylcyclohexoxy) piperidine-1-carboxylate (30 g, 86.85 mmol, 1 eq) in MeOH (200 mL) was added TosOH (747.77 mg, 4.34 mmol, 0.05 eq) and trimethoxymethane (46.08 g, 434.24 mmol, 47.60 mL, 5 eq) in one portion at 25° C. under $N_2$. The mixture was stirred at 25° C. for 2 h. The reaction was quenched with $H_2O$ (100 mL) and extracted with ethyl acetate (3*200 mL). The combined organic phases were washed with water, dried with $Na_2SO_4$, and concentrated under vacuum to give a residue. The residue was purified by silica gel column chromatography (0-30% Ethyl acetate in Petroleum ether) to give trans-benzyl 4-[4-(dimethoxymethyl)cyclohexoxy]piperidine-1-carboxylate (31 g, 75.22 mmol, 86.62% yield, 95% purity) as colorless oil.

Step 7

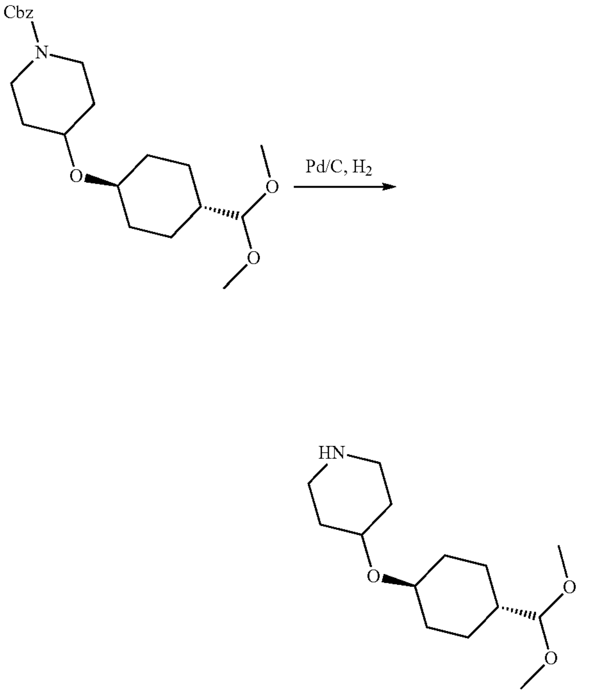

To a mixture of trans-benzyl 4-[4-(dimethoxymethyl) cyclohexoxy]piperidine-1-carboxylate (31 g, 79.18 mmol, 1 eq) in EtOH (200 mL) was added Pd/C (8 g, 79.18 mmol, 10% purity, 1 eq) at 25° C. under $H_2$ (15 PSI) for 16 h. TLC (Petroleum ether:Ethyl acetate=3:1) showed one new spot. The residue was filtered and concentrated in vacuum to give trans-4-[4-(dimethoxymethyl)cyclohexoxy]piperidine (18.6 g, 72.27 mmol, 91.27% yield) as a white solid.

Synthesis of Intermediate 5-(1-methylcyclopropoxy)-3-(6-piperazin-1-ylpyrimidin-4-yl)-1H-pyrazolo[3,4-c]pyridine Step 1

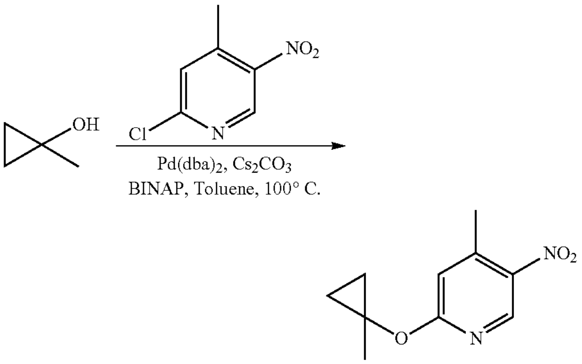

To a solution of 2-chloro-4-methyl-5-nitro-pyridine (10 g, 57.95 mmol, 1 eq), 1-methylcyclopropanol (8.36 g, 115.90 mmol, 2 eq) in toluene (100 mL) was added (+/−)-2,2-Bis (diphenylphosphino)-1,1-binaphthyl (2.16 g, 3.48 mmol, 0.06 eq), cesium carbonate (28.32 g, 86.92 mmol, 1.5 eq) and bis(dibenzylideneacetone) Palladium (0) (666 mg, 1.16 mmol, 0.02 eq) under nitrogen. The reaction mixture was stirred at 100° C. for 3 h and cooled. The mixture was filtered and the filtrate was concentrated in vacuo. The residue was purified by silica gel chromatography (petroleum ether:ethyl acetate=1:0 to 20:1). 4-methyl-2-(1-methylcyclopropoxy)-5-nitro-pyridine (7.7 g, 36.98 mmol, 63.82% yield) was obtained as colorless oil.

Step 2

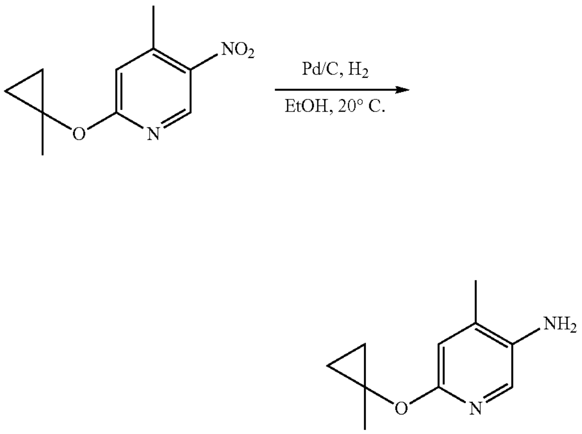

To a solution of 4-methyl-2-(1-methylcyclopropoxy)-5-nitro-pyridine (8.6 g, 41.30 mmol, 1 eq) in ethanol (100 mL) was added palladium on activated carbon (0.8 g, 10% purity) under nitrogen. The reaction was stirred at 20° C. under hydrogen (15 Psi) for 12 h. TLC (petroleum ether:ethyl acetate=3:1) showed new spot was detected. The mixture was filtered and the filtrate was concentrated in vacuum. The residue was used into next step directly. 4-methyl-6-(1-methylcyclopropoxy)pyridin-3-amine (7.1 g, 39.84 mmol, 96% yield) was obtained as a pink solid.

Step 3

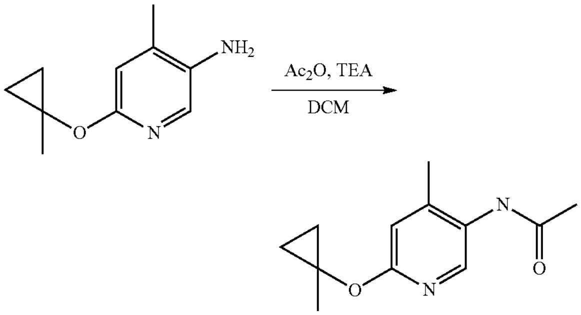

To a solution of 4-methyl-6-(1-methylcyclopropoxy)pyridin-3-amine (7.1 g, 39.84 mmol, 1 eq) in dichloromethane (100 mL) was added triethylamine (8.06 g, 79.67 mmol, 11 mL, 2 eq) and acetic anhydride (6.10 g, 59.75 mmol, 5.6 mL, 1.5 eq) at 0° C. The reaction mixture was stirred at 20° C. for 1 h. TLC (petroleum ether:ethyl acetate=1:1) showed new spot was detected. Water (100 mL) was added and the mixture was extracted with dichloromethane (50 mL*2). The combined organic phase was washed with brine (100 mL), dried over sodium sulfate, filtered, and concentrated in vacuo. The residue was purified by silica gel chromatography (petroleum ether:ethyl acetate=10:1 to 0:1). N-[4-methyl-6-(1-methylcyclopropoxy)-3-pyridyl]acetamide (8.3 g, 37.68 mmol, 94.59% yield, 100% purity) was obtained as a brown oil.

Step 4

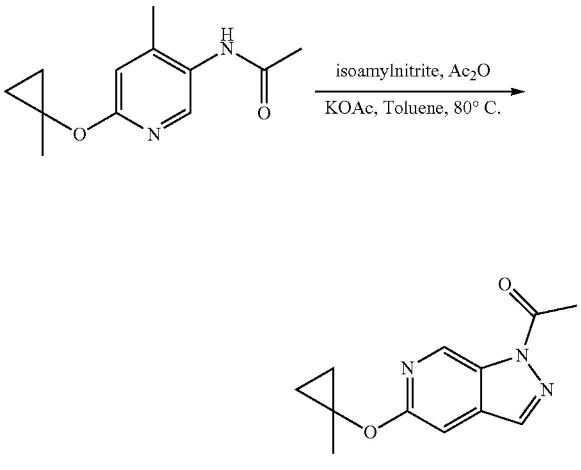

A mixture of N-[4-methyl-6-(1-methylcyclopropoxy)-3-pyridyl]acetamide (7.3 g, 33.14 mmol, 1 eq), potassium acetate (4.88 g, 49.71 mmol, 1.5 eq) and acetic anhydride (15.56 g, 152.45 mmol, 14.28 mL, 4.6 eq) in toluene (150 mL) was heated to 80° C. Isoamylnitrite (15.53 g, 132.57 mmol, 17.8 mL, 4 eq) was added dropwise. The reaction was stirred at 80° C. for 12 h. LCMS showed desired MS was detected. The mixture was filtered, and the filtrate was concentrated in vacuo. The residue was purified by silica gel chromatography (petroleum ether:ethyl acetate=1:0 to 20:1). 1-[5-(1-methylcyclopropoxy) pyrazolo[3,4-c]pyridin-1-yl] ethanone (4.9 g, 21.19 mmol, 63.94% yield) was obtained as a yellow solid.

Step 5

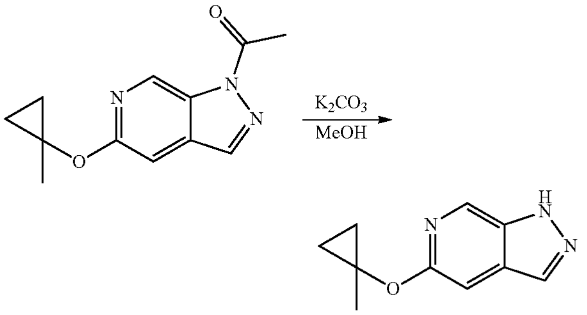

To a solution of 1-[5-(1-methylcyclopropoxy) pyrazolo [3,4-c]pyridin-1-yl]ethanone (4.9 g, 21.19 mmol, 1 eq) in methanol (50 mL) was added potassium carbonate (4.39 g, 31.78 mmol, 1.5 eq). The reaction was stirred at 20° C. for 1 h. Ethyl acetate (100 mL) was added and HCl solution (1M) was added to adjust the pH to 7. Water (100 mL) was added to the mixture, the aqueous phase was extracted with ethyl acetate (100 mL*2). The combined organic phase was washed with brine (100 mL), dried over sodium sulfate, filtered, and concentrated under vacuum. The residue was used into next step directly. 5-(1-methylcyclopropoxy)-1H-pyrazolo[3,4-c]pyridine (3.9 g, 20.61 mmol, 97% yield) was obtained as a yellow solid.

Step 6

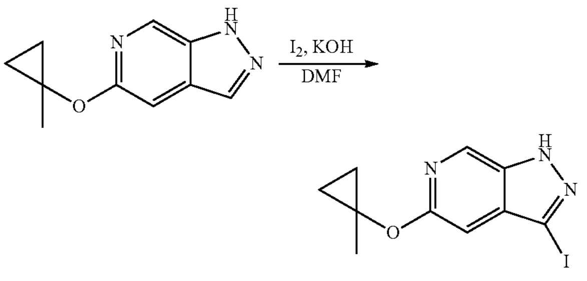

To a solution of 5-(1-methylcyclopropoxy)-1H-pyrazolo [3,4-c]pyridine (2.5 g, 13.21 mmol, 1 eq) in N,N-dimethyl formamide (25 mL) was added potassium hydroxide (1.85 g, 33.03 mmol, 2.5 eq) and iodine (3.69 g, 14.53 mmol, 2.93 mL, 1.1 eq). The reaction mixture was stirred at 20° C. for 12 h. The mixture was quenched by addition of saturated sodium sulfite. Water (100 mL) was added to the mixture, HCl solution (1M) was added to the mixture to adjust the pH to 4. The solid was filtered and dried under vacuum. The mixture was used into next step directly. 3-iodo-5-(1-methylcyclopropoxy)-1H-pyrazolo[3,4-c]pyridine (3.9 g, 12.38 mmol, 94% yield) was obtained as a light-yellow solid.

Step 7

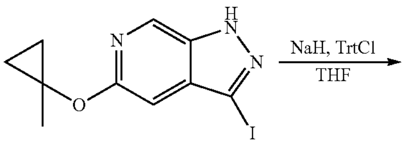

-continued

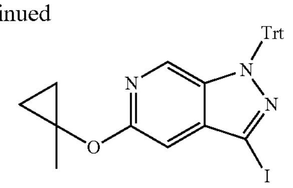

To a solution of 3-iodo-5-(1-methylcyclopropoxy)-1H-pyrazolo[3,4-c]pyridine (3.9 g, 12.38 mmol, 1 eq) in tetrahydrofuran (40 mL) was added sodium hydride (594 mg, 14.85 mmol, 60% purity in mineral oil, 1.2 eq) at 0° C., the mixture was stirred at 0° C. for 0.5 h. Then tritylchloride (3.80 g, 13.61 mmol, 1.1 eq) was added to the mixture at 0° C., the reaction mixture was stirred at 20° C. for 10 h. Saturated ammonium chloride (100 mL) was added to the mixture, the aqueous phase was extracted with ethyl acetate (100 mL*3). The combined organic phase was washed with brine (100 mL), dried over sodium sulfate, filtered, and concentrated under vacuum. The residue was purified by silica gel chromatography (petroleum ether:ethyl acetate=1:0 to 20:1). 3-iodo-5-(1-methylcyclopropoxy)-1-trityl-pyrazolo[3,4-c]pyridine (5.9 g, 10.58 mmol, 85% yield) was confirmed as a light yellow solid.

Step 8

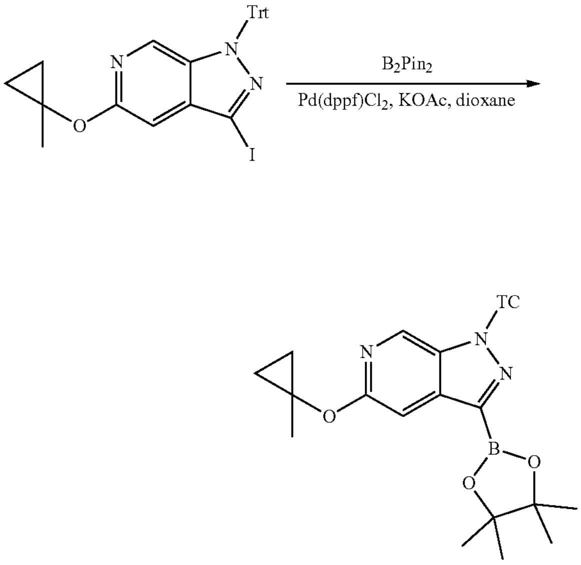

To a solution of 3-iodo-5-(1-methylcyclopropoxy)-1-trityl-pyrazolo[3,4-c]pyridine (2.3 g, 4.13 mmol, 1 eq) and 4,4,5,5-tetramethyl-2-(4,4,5,5-tetramethyl-1,3,2-dioxaborolan-2-yl)-1,3,2-dioxaborolane (2.10 g, 8.25 mmol, 2. eq) in dioxane (20 mL) was added Pd(dppf)$Cl_2$ (301.91 mg, 412.61 umol, 0.1 eq) and KOAc (1.21 g, 12.38 mmol, 3 eq). Then the mixture was stirred at 100° C. for 16 hr under $N_2$ and cooled. The reaction mixture was filtered and concentrated under reduced pressure to afford 5-(1-methylcyclopropoxy)-3-(4,4,5,5-tetramethyl-1,3,2-dioxaborolan-2-yl)-1-trityl-pyrazolo[3,4-c]pyridine (2.3 g, crude) as a gray gum.

Step 9

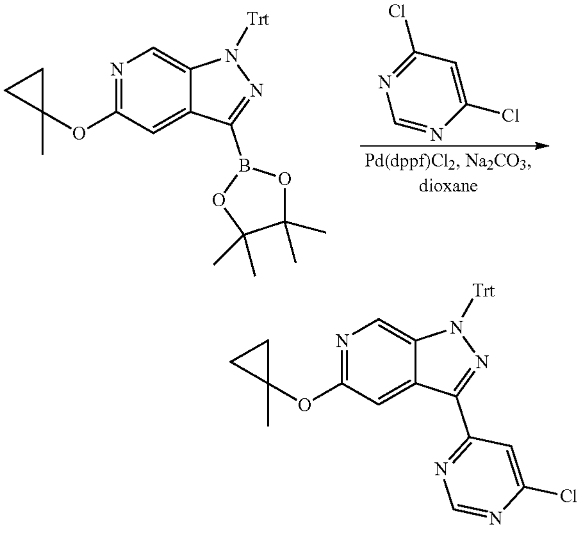

To a solution of 5-(1-methylcyclopropoxy)-3-(4,4,5,5-tetramethyl-1,3,2-dioxaborolan-2-yl)-1-trityl-pyrazolo[3,4-c]pyridine (2.3 g, 4.13 mmol, 1 eq) and 4,6-dichloropyrimidine (921.95 mg, 6.19 mmol, 1.5 eq) in dioxane (20 mL) and $H_2O$ (4 mL) was added $Na_2CO_3$ (1.31 g, 12.38 mmol, 3 eq) and Pd(dppf)$Cl_2$ (301.88 mg, 412.56 umol, 0.1 eq). Then the mixture was stirred at 100° C. for 1 hr under $N_2$. TLC (Petroleum ether:Ethyl acetate=5:1, Rf=0.7) showed no start material and one major new spot was detected. The reaction mixture was filtered and concentrated under reduced pressure. $H_2O$ (20 mL) was added and the mixture was extracted with ethyl acetate (3*20 mL). The combined organic phases were washed with water, dried with $Na_2SO_4$, concentrated under vacuum to give a residue. The residue was purified by silica gel column chromatography (0 to 30% Ethyl acetate in Petroleum ether) to give 3-(6-chloropyrimidin-4-yl)-5-(1-methylcyclopropoxy)-1-trityl-pyrazolo[3,4-c]pyridine (1.73 g, 2.54 mmol, 61.66% yield, 80% purity) as a off-white solid.

Step 10

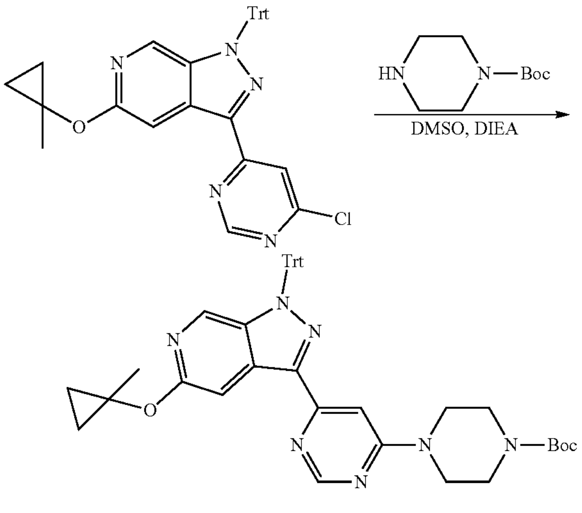

To a solution of 3-(6-chloropyrimidin-4-yl)-5-(1-methylcyclopropoxy)-1-trityl-pyrazolo[3,4-c]pyridine (0.9 g, 1.65 mmol, 1 eq) and tert-butyl piperazine-1-carboxylate (462.17 mg, 2.48 mmol, 1.5 eq) in DMSO (10 mL) was added DIEA (641.40 mg, 4.96 mmol, 864.42 μL, 3 eq) and the reaction was stirred at 80° C. for 16 h under $N_2$ and cooled. $NH_4Cl$ (80 mL) solution was added and the mixture was extracted with ethyl acetate (3*60 mL). The combined organic phases were washed with water, dried with $Na_2SO_4$, and concentrated under vacuum to give a residue. The residue was purified by silica gel chromatography (Petroleum ether/Ethyl acetate=100/1, 1/1) to give tert-butyl 4-[6-[5-(1-methylcyclopropoxy)-1-trityl-pyrazolo[3,4-c]pyridin-3-yl]pyrimidin-4-yl]piperazine-1-carboxylate (1 g, 1.35 mmol, 81.90% yield, 94% purity) as a white solid.

Step 11

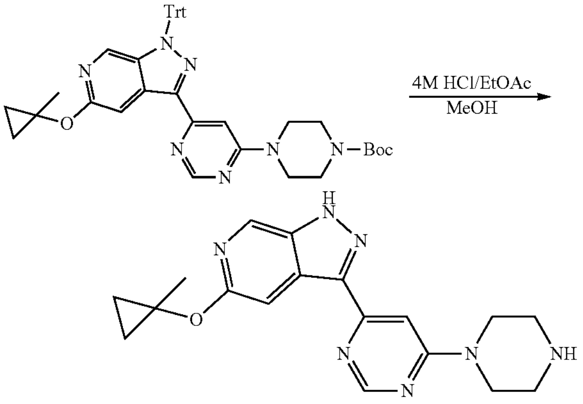

To a solution of tert-butyl 4-[6-[5-(1-methylcyclopropoxy)-1-trityl-pyrazolo[3,4-c]pyridin-3-yl]pyrimidin-4-yl]piperazine-1-carboxylate (1 g, 1.44 mmol, 1 eq) in DCM (6 mL) was added HCl/dioxane (4 M, 6 mL, 16.65 eq) and the reaction was stirred at 40° C. for 4 h under $N_2$. After cooling, the reaction mixture was filtered and the filter cake was collected. The solid was dissolved in water (50 mL), the solution basified to PH~13 with NaOH and extracted with ethyl acetate (50 mL*3). The organic layer was dried over sodium sulfate and concentrated under reduced pressure to give 5-(1-methylcyclopropoxy)-3-(6-piperazin-1-ylpyrimidin-4-yl)-1H-pyrazolo[3,4-c]pyridine (490 mg, 1.39 mmol, 96.75% yield) as a red solid.

Exemplary Final Synthesis of Compound 1:

Step 1

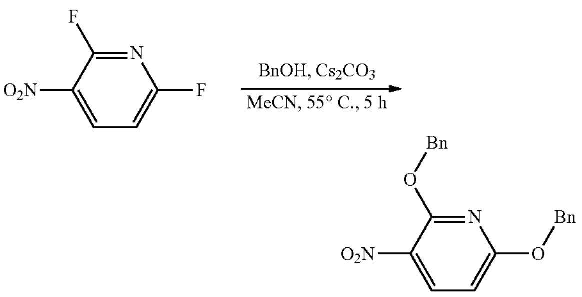

To a stirring solution of 2,6-difluoro-3-nitro-pyridine (7.0 g, 43.73 mmol, 1.0 eq) in acetonitrile (140 mL) were added BnOH (13.6 mL, 131.19 mmol, 3.0 eq) and $Cs_2CO_3$ (57.0 g, 174.91 mmol, 4.0 eq). The resulting mixture was heated to 55° C. for 5 hours and cooled. The reaction mixture was filtered and concentrated under vacuum. The residue was purified by Biotage® combi flash (Column: 120 g Biotage® Silica Flash column; Eluent: gradient 0~3% ethyl acetate in petroleum ether; Gradient time: 20 min; Hold time: 100 min; Flow rate: 100 mL/min). Pure fractions were combined and concentrated under reduced pressure to afford 2,6-dibenzyloxy-3-nitro-pyridine (16.5 g, 39.74 mmol, 90.87% yield, 81% purity) as a yellow solid.

Step 2

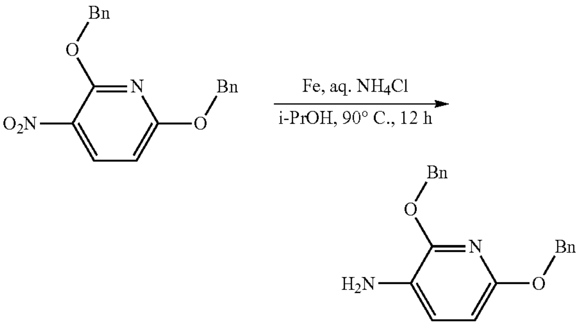

To a stirred solution of 2,6-dibenzyloxy-3-nitro-pyridine (8.25 g, 19.87 mmol, 81% purity, 1.0 eq) in i-PrOH (160 mL) and $H_2O$ (80 mL) was added Fe (8.9 g, 158.95 mmol, 8.0 eq) and $NH_4Cl$ (15.9 g, 298.02 mmol, 15.0 eq). The resulting mixture was heated to 90° C. for 12 hours (2 parallel reactions). The reaction mixture was cooled to ambient temperature and ethyl acetate (200 mL) was added. The mixture was filtered to remove insoluble solid, and the filter cake was washed with ethyl acetate (75 mL×2). The combined organic extracts were washed with brine (150 mL), dried over anhydrous $Na_2SO_4$, filtered, and concentrated under vacuum. The residue was purified by Biotage® combi flash (Column: 120 g Biotage® Silica Flash column; Eluent: gradient 0~5% ethyl acetate in petroleum ether; Gradient time: 30 min; Hold time: 120 min; Flow rate: 100 mL/min). Pure fractions were combined and concentrated under reduced pressure to afford 2,6-dibenzyloxypyridin-3-amine (11.5 g, 29.95 mmol, 75.38% yield, 80% purity) as a yellow oil.

Step 3

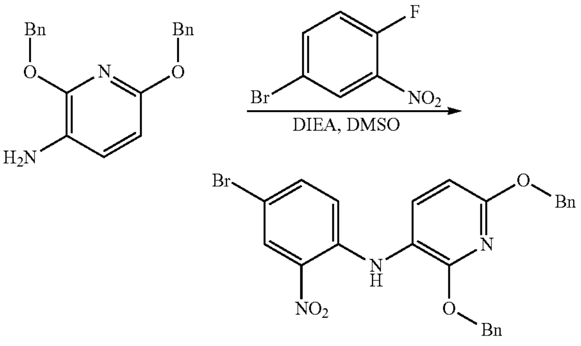

To a solution of 2,6-dibenzyloxypyridin-3-amine (4.0 g, 13.06 mmol, 1.0 eq) and 4-bromo-1-fluoro-2-nitro-benzene (2.9 g, 13.06 mmol, 1.0 eq) in DMSO (45 mL) was added DIEA (5.7 mL, 32.64 mmol, 2.5 eq). The reaction mixture was stirred at 100° C. for 16 hours and cooled. The reaction mixture was quenched with water (50 mL) and extracted with ethyl acetate (100 mL×3). The combined organic layers were washed with brine (50 mL×2), dried over $Na_2SO_4$, filtered, and concentrated under reduced pressure to give a residue which was purified by Biotage® combi flash (Column: 80 g Biotage® Silica Flash column; Eluent: gradient 0~5% tetrahydrofuran in petroleum ether; Gradient time: 15 min; Hold time: 30 min; Flow rate: 70 mL/min). Pure fraction was concentrated under reduced pressure to afford 2,6-dibenzyloxy-N-(4-bromo-2-nitro-phenyl)pyridin-3-amine (3.47 g, 6.85 mmol, 52% yield) as a brown solid.

Step 4

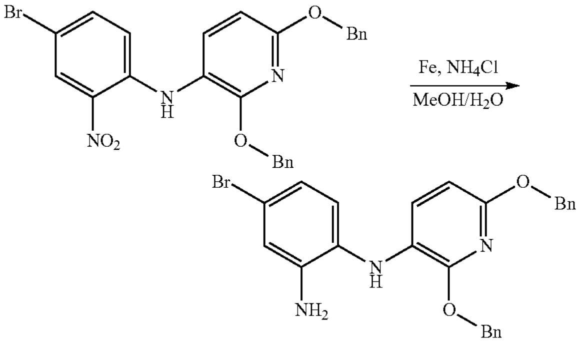

To a solution of 2,6-dibenzyloxy-N-(4-bromo-2-nitro-phenyl)pyridin-3-amine (3.47 g, 6.85 mmol, 1.0 eq) in methanol (50 mL) and water (5 mL) were added $NH_4Cl$ (5.50 g, 102.80 mmol, 15.0 eq) and Fe (1.91 g, 34.27 mmol, 5.0 eq). The mixture was stirred at 90° C. for 1 hour and allowed to cool. The mixture was filtered and the filtrate was concentrated under reduced pressure. The mixture was diluted with water (50 mL) and extracted with ethyl acetate (50 mL×3). The combined organic layer was washed with brine (50 mL), dried over $Na_2SO_4$, filtered and concentrated under reduced pressure to afford 4-bromo-$N_1$-(2,6-dibenzyloxy-3-pyridyl)benzene-1,2-diamine (2.97 g, 6.23 mmol, 90% yield) as colorless liquid.

Step 5

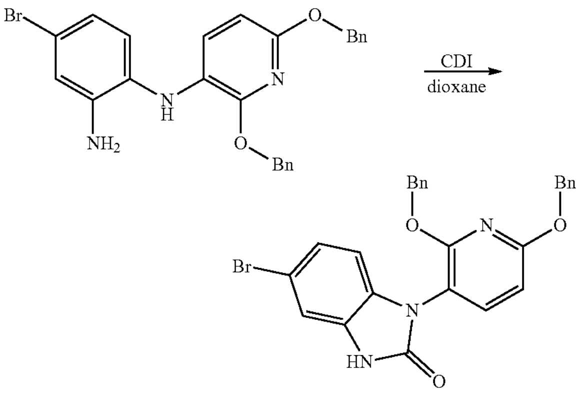

To a solution of 4-bromo-$N_1$-(2,6-dibenzyloxy-3-pyridyl) benzene-1,2-diamine (2.77 g, 1.84 mmol, 1.0 eq) in 1,4-dioxane (90 mL) was added CDI (9.43 g, 58.15 mmol, 10.0 eq). The mixture was stirred at 120° C. for 12 hours and cooled. The mixture was concentrated to remove most solvent and diluted with water (50 mL). The aqueous phase was extracted with ethyl acetate (50 mL×3). The combined organic layers were washed with water (15 mL×6), brine (15 mL), dried over $Na_2SO_4$, filtered, and concentrated under reduced pressure. The residue was purified by Biotage® combi flash (Column: 80 g Biotage® Silica Flash column; Eluent: gradient 0~30% ethyl acetate in petroleum ether; Gradient time: 20 min; Hold time: 10 min; Flow rate: 70 mL/min). Pure fractions were collected and concentrated under reduced pressure to afford 6-bromo-3-(2,6-dibenzyloxy-3-pyridyl)-1H-benzimidazol-2-one (2.7 g, 5.37 mmol, 92% yield) as a white solid.

Step 6

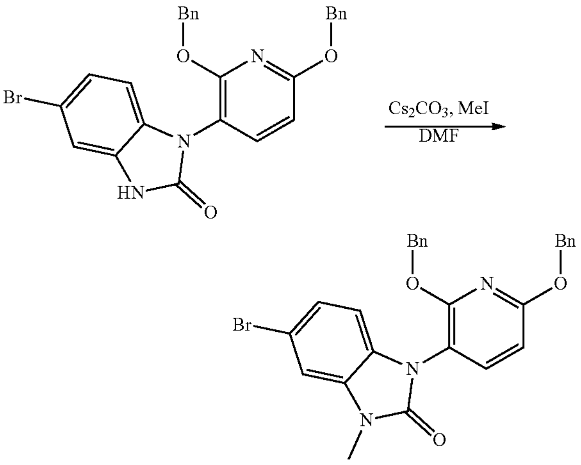

To a solution of 6-bromo-3-(2,6-dibenzyloxy-3-pyridyl)-1H-benzimidazol-2-one (1.0 g, 1.99 mmol, 1.0 eq) in DMF (10 mL) was added $Cs_2CO_3$ (1.62 g, 4.98 mmol, 2.5 eq) and iodomethane (0.37 mL, 5.97 mmol, 3.0 eq). The mixture was stirred at 25° C. for 16 hours. The reaction mixture was quenched with water (15 mL) and extracted with ethyl acetate (30 mL×3). The combined organic layers were washed with water (10 mL×3) and brine (15 mL), dried over $Na_2SO_4$, filtered, and concentrated under reduced pressure. The residue was purified by Biotage® combi flash (Column: 40 g Biotage® Silica Flash column; Eluent: gradient 0~23% ethyl acetate in petroleum ether; Gradient time: 30 min; Hold time: 5 min; Flow rate: 35 mL/min). Pure fractions were collected and concentrated under reduced pressure to afford 5-bromo-1-(2,6-dibenzyloxy-3-pyridyl)-3-methyl-benzimidazol-2-one (1.03 g, 1.99 mmol, 91% yield) as a white foam.

Step 7

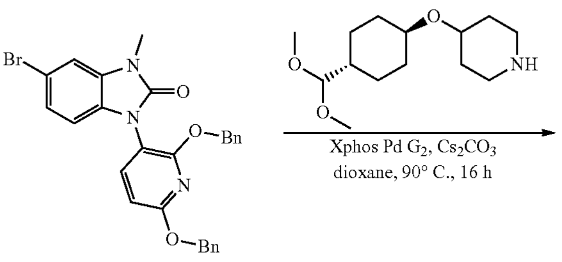

-continued

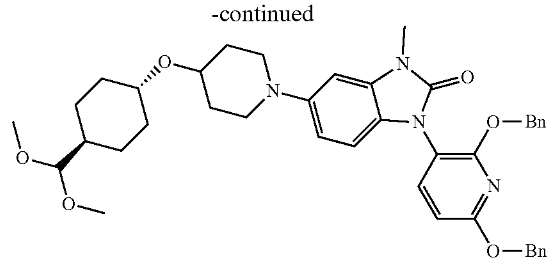

To a solution of 5-bromo-1-(2,6-dibenzyloxy-3-pyridyl)-3-methyl-benzimidazol-2-one (500 mg, 968.27 umol, 1 eq) and trans-4-[4-(dimethoxymethyl)cyclohexoxy]piperidine (299.04 mg, 1.16 mmol, 1.2 eq) in dioxane (10 mL) was added XPHOS-PD-G2 (76.18 mg, 96.83 μmol, 0.1 eq) and $Cs_2CO_3$ (946.44 mg, 2.90 mmol, 3 eq). The mixture was stirred at 90° C. for 16 hr under $N_2$ and then cooled. The reaction mixture was diluted with water (20 mL) and extracted with ethyl acetate (30 mL×2). The combined organic layers were washed with brine (20 mL), dried over $Na_2SO_4$, filtered, and concentrated under reduced pressure to give a residue. The residue was purified by silica gel chromatography (column height: 20 g, 100-200 mesh silica gel, 0-30% (5 min) of Ethyl acetate in Petroleum ether, 30-100% (15 min) of Ethyl acetate in Petroleum ether, 50-100% (5 min) of Ethyl acetate in Petroleum ether) to give trans-1-(2,6-dibenzyloxy-3-pyridyl)-5-[4-[4-(dimethoxymethyl)cyclohexoxy]-1-piperidyl]-3-methyl-benzimidazol-2-one (520 mg, 750.53 umol, 77.51% yield, N/A purity) as a yellow solid.

Step 8

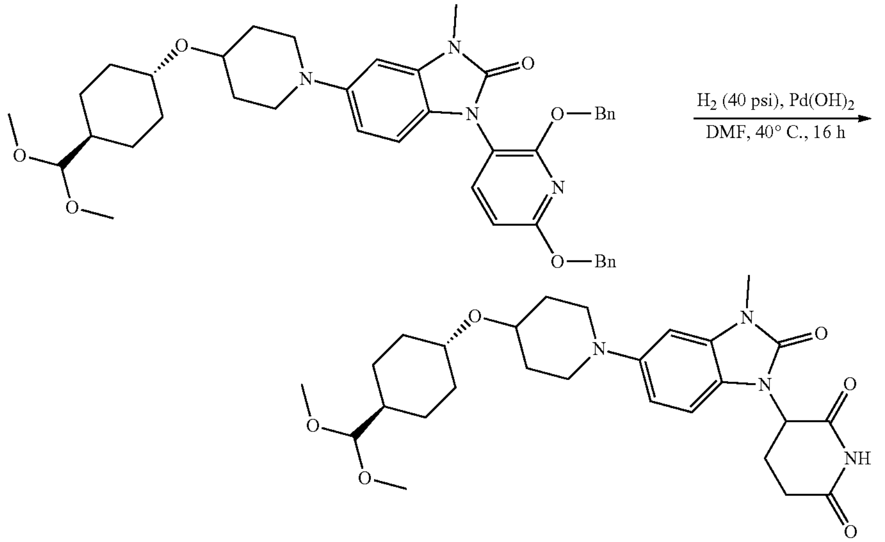

To a solution of trans-1-(2,6-dibenzyloxy-3-pyridyl)-5-[4-[4-(dimethoxymethyl)cyclohexoxy]-1-piperidyl]-3-methyl-benzimidazol-2-one (520 mg, 750.53 umol, 1 eq) in DMF (20 mL) was added Pd/C (300 mg, 10% purity) and $Pd(OH)_2$ (200 mg, 10% purity). The mixture was stirred under a $H_2$ atmosphere (40 psi) at 40° C. for 16 hrs. The mixture was filtered and extracted with EtOAc (30 mL×2). The combined organic layers were washed with brine 20 mL, dried over $Na_2SO_4$, filtered, and concentrated under reduced pressure to give a residue. The residue was purified by silica gel chromatography (column height: 4 g, 100-200 mesh silica gel, 0-30% (5 min) of Ethyl acetate in Petroleum ether, 30-85% (15 min) of Ethyl acetate in Petroleum ether, 50-100% (5 min) of Ethyl acetate in Petroleum ether) to give trans-3-[5-[4-[4-(dimethoxymethyl)cyclohexoxy]-1-piperidyl]-3-methyl-2-oxo-benzimidazol-1-yl]piperidine-2,6-dione (182 mg, 353.66 μmol, 47.12% yield, N/A purity) as a yellow solid.

Step 9

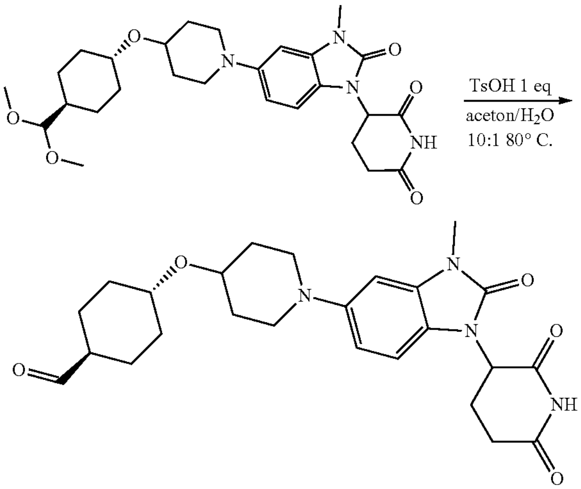

To a solution of trans-3-[5-[4-[4-(dimethoxymethyl)cyclohexoxy]-1-piperidyl]-3-methyl-2-oxo-benzimidazol-1-yl]piperidine-2,6-dione (182 mg, 353.66 μmol, 1 eq) in acetone (4 mL) and $H_2O$ (0.4 mL) was added TsOH (24.36 mg, 141.47 μmol, 0.4 eq). Then the mixture was stirred at 80° C. for 16 hrs and then cooled. Sat. $NaHCO_3$ (30 mL) was added to adjust the pH to 8 and the mixture was filtered to give trans-4-[[1-[1-(2,6-dioxo-3-piperidyl)-3-methyl-2-oxo-benzimidazol-5-yl]-4-piperidyl]oxy]cyclohexanecarbaldehyde (212 mg, crude) as an off-white solid.

Step 10

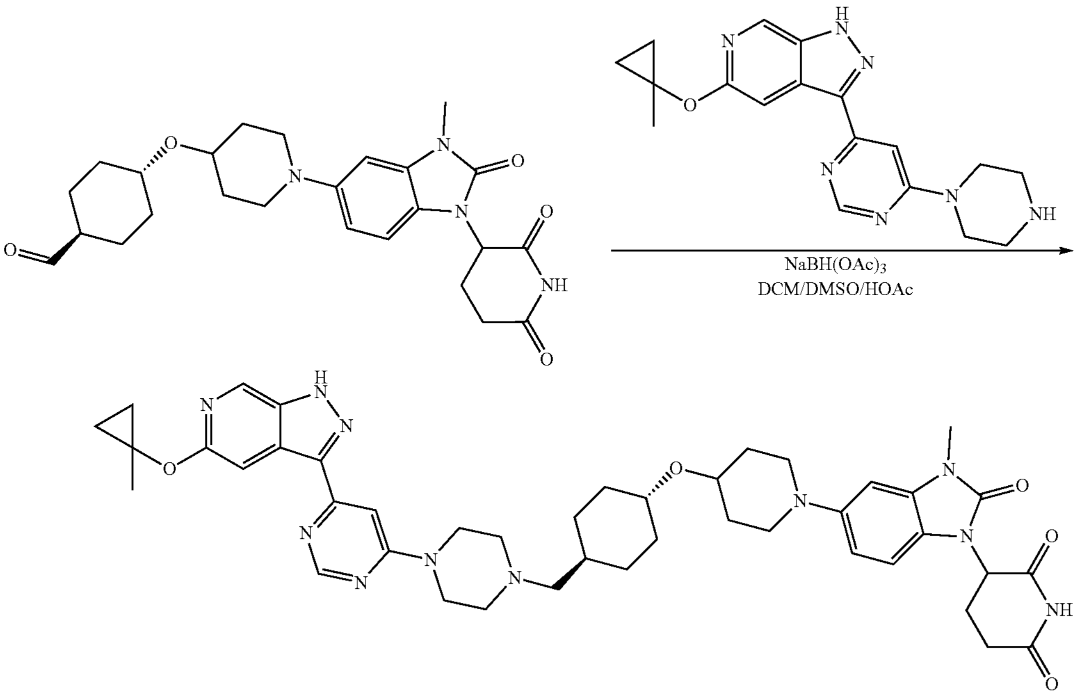

To a solution of trans-4-[[1-[1-(2,6-dioxo-3-piperidyl)-3-methyl-2-oxo-benzimidazol-5-yl]-4-piperidyl]oxy]cyclohexanecarbaldehyde (66.67 mg, 142.29 μmol, 1 eq), 5-(1-methylcyclopropoxy)-3-(6-piperazin-1-ylpyrimidin-4-yl)-1H-pyrazolo[3,4-c]pyridine (50 mg, 142.29 μmol, 1 eq) in DCM (5 mL) and DMSO (3 mL) was added HOAc (8.54 mg, 142.29 μmol, 8.15 μL, 1 eq) stirred at 20° C. for 0.5 h. Then $NaBH(OAc)_3$ (75.39 mg, 355.72 μmol, 2.5 eq) was added. After addition, the reaction mixture was stirred at 20° C. for 3 h. The reaction mixture was filtered and concentrated in vacuo. The impure product was purified by Prep-HPLC (column: Xtimate C18 150*40 mm*10 um; mobile phase: [water ($NH_4HCO_3$)-ACN]; gradient: 28%-68% B over 32 min) to get Compound 1 (51.4 mg, 63.58 μmol, 44.69% yield, 99.45% purity) as a white solid.

Exemplary Synthesis of Compound 2:

Synthesis of intermediate 3-[6-[4-[(2,2-dimethylpiperazin-1-yl)methyl]-1-piperidyl]pyrimidin-4-yl]-5-(1-methylcyclopropoxy)-1H-indazole Step 1

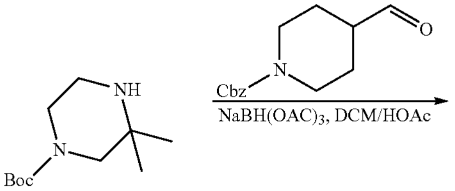

-continued

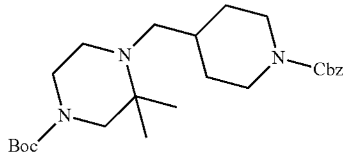

To a solution of benzyl 4-formylpiperidine-1-carboxylate (1.78 g, 7.21 mmol, 1 eq) and HOAc (25.98 mg, 432.69 μmol, 24.75 μL, 0.06 eq) in DCM (10 mL) was added tert-butyl 3,3-dimethylpiperazine-1-carboxylate (1.70 g, 7.93 mmol, 1.1 eq) and the mixture was stirred at 25° C. under $N_2$ for 20 hours. $NaBH(OAc)_3$ (2.29 g, 10.80 mmol, 1.50 eq) was added and the mixture was stirred at 25° C. for 2 hours. The reaction mixture was quenched by addition sat. $NaHCO_3$ to pH=8-9 and extracted with DCM (20 mL*3). The combined organic layers were washed with brine (50 mL*2), dried over $Na_2SO_4$, filtered, and concentrated under reduced pressure to give a residue. The residue was purified by flash silica gel chromatograph (0~25% ethyl acetate in petroleum) to give tert-butyl4-((1-((benzyloxy) carbonyl) piperidin-4-yl)methyl)-3,3-dimethylpiperazine-1-carboxylate (2.11 g, 4.73 mmol, 65.57% yield) as colorless oil.

Step 2

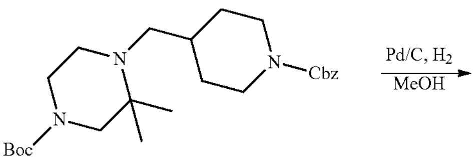

-continued

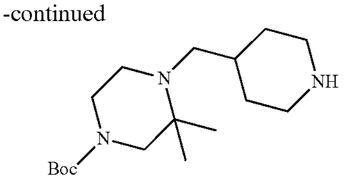

To a solution of tert-butyl 4-[(1-benzyloxycarbonyl-4-piperidyl)methyl]-3,3-dimethyl-piperazine-1-carboxylate (2.1 g, 4.71 mmol, 1 eq) in MeOH (20 mL) was added Pd/C (500 mg, 10%) under $N_2$. The suspension was degassed under vacuum and purged with $H_2$ several times. The mixture was stirred under $H_2$ (15 psi) at 25° C. for 1 hour. TLC (petroleum ether:ethyl acetate=1:1) showed the reaction completed. The reaction mixture was filtered and filtrate was concentrated under reduced pressure to give tert-butyl 3,3-dimethyl-4-(4-piperidylmethyl) piperazine-1-carboxylate (1.39 g, 4.46 mmol, 94.70% yield) as a white gum.

Step 3

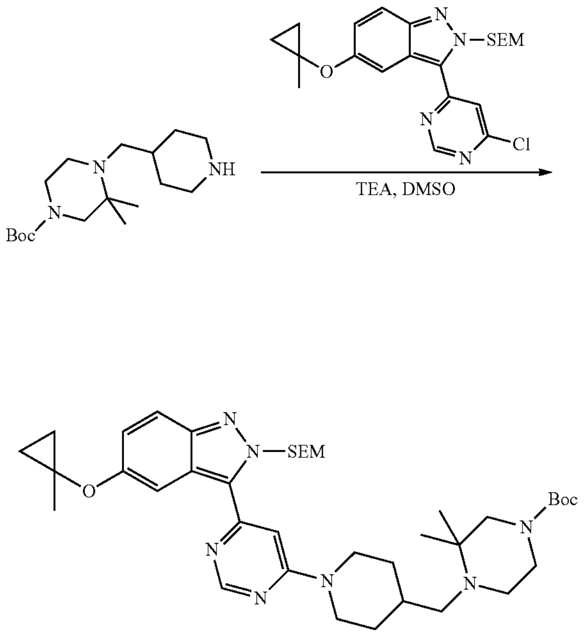

To a solution of 2-[[3-(6-chloropyrimidin-4-yl)-5-(1-methylcyclopropoxy)indazol-2-yl]methoxy]ethyl-trimethyl-silane (synthesis described below, 0.15 g, 348.03 μmol, 1 eq) in DMSO (3 mL) was added TEA (176.08 mg, 1.74 mmol, 242.20 μL, 5 eq) and tert-butyl 3,3-dimethyl-4-(4-piperidylmethyl) piperazine-1-carboxylate (216.79 mg, 696.05 μmol, 2 eq). The mixture was stirred at 100° C. for 1 hr and cooled. The reaction mixture was quenched by addition EtOAc (50 mL) and water (50 ml) at 25° C. The organic layer was washed with water (30 mL*3), dried over $Na_2SO_4$, filtered, and concentrated under reduced pressure to give a residue. The residue was purified by flash silica gel chromatography (ISCO®; 4 g SepaFlash® Silica Flash Column, Eluent of 0~20% ethyl acetate/petroleum ether gradient @ 50 mL/min) to give tert-butyl 3,3-dimethyl-4-[[1-[6-[5-(1-methylcyclopropoxy)-2-(2-trimethylsilylethoxymethyl) indazol-3-yl]pyrimidin-4-yl]-4-piperidyl]methyl]piperazine-1-carboxylate (0.19 g, 266.99 μmol, 76.72% yield, 99.210% purity) as a light yellow solid.

Step 4

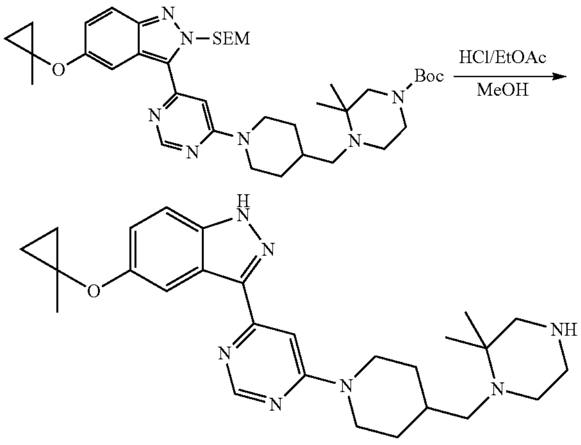

To a solution of tert-butyl 3,3-dimethyl-4-[[1-[6-[5-(1-methylcyclopropoxy)-2-(2-trimethylsilylethoxymethyl) indazol-3-yl]pyrimidin-4-yl]-4-piperidyl]methyl]piperazine-1-carboxylate (0.18 g, 254.96 μmol, 1 eq) in MeOH (3 mL) was added HCl/EtOAc (4 M, 127.48 μL, 2 eq). The mixture was stirred at 25° C. for 4 hr. The reaction mixture was concentrated under reduced pressure to remove solvent to give 3-[6-[4-[(2,2-dimethylpiperazin-1-yl)methyl]-1-piperidyl]pyrimidin-4-yl]-5-(1-methylcyclopropoxy)-1H-indazole (0.13 g, crude, HCl salt) as a white solid.

Synthesis of intermediate 2-[[3-(6-chloropyrimidin-4-yl)-5-(1-methylcyclopropoxy)indazol-2-yl]methoxy]ethyl-trimethyl-silane Step 1

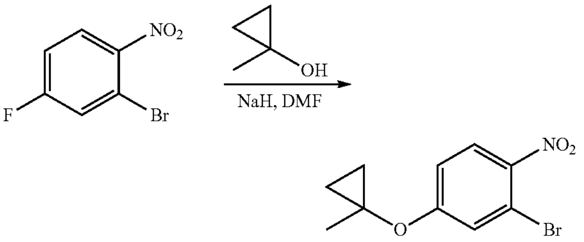

To a solution of 2-bromo-4-fluoro-1-nitro-benzene (16.78 g, 76.28 mmol, 1.1 eq) and 1-methylcyclopropanol (5 g, 69.34 mmol, 1 eq) in DMF (160 mL) was added NaH (4.16 g, 104.01 mmol, 60% in mineral oil, 1.5 eq) in one portion at 0° C. under $N_2$. Then the mixture was heated to 20° C. and stirred for 4 hours. The residue was poured into water (200 mL) and stirred for 10 min. The aqueous phase was extracted with ethyl acetate (3×300 mL). The combined organic phase was washed with brine (2×200 mL), dried with anhydrous $Na_2SO_4$, filtered, and concentrated in vacuum. The residue was purified by silica gel column chromatography (100-200 mesh silica gel, 0-2% of Ethyl acetate in Petroleum ether) to afford 2-bromo-4-(1-methylcyclopropoxy)-1-nitro-benzene (14.3 g, 52.56 mmol, 75.79% yield) as a yellow oil.

Step 2

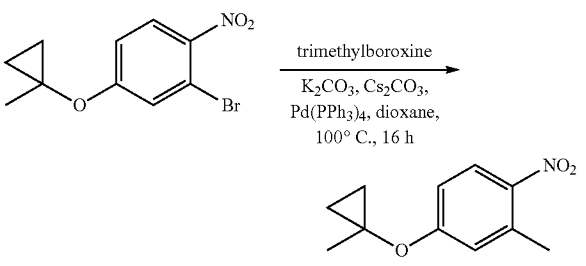

To a mixture of 2-bromo-4-(1-methylcyclopropoxy)-1-nitro-benzene (14.3 g, 52.56 mmol, 1 eq), $K_2CO_3$ (14.53 g, 105.11 mmol, 2 eq) and $Cs_2CO_3$ (17.12 g, 52.56 mmol, 1 eq) in 1,4-dioxane (100 mL) was added 2,4,6-trimethyl-1,3,5,2,4,6-trioxatriborinane (32.99 g, 131.39 mmol, 36.73 mL, 50% in EtOAc, 2.5 eq) and $Pd(PPh_3)_4$ (6.07 g, 5.26 mmol, 0.1 eq)) at 20° C., then heated to 100° C. and stirred for 16 hours to give yellow solution. TLC showed the reaction was completed. The reaction was cooled to 20° C. and concentrated under vacuum. To this residue was added PE:EtOAc (10:1, 100 mL), and the mixture was filtered through a pad of silica. The filter pad was washed with petroleum ether: EtOAc (10:1, 1000 mL) solvent. The residue was purified by silica gel chromatography (100-200 mesh silica gel, 0-1% of Ethyl acetate in Petroleum ether) to afford 2-methyl-4-(1-methylcyclopropoxy)-1-nitro-benzene (11 g, crude) as a yellow oil.

Step 3

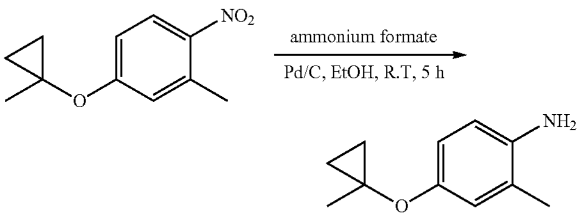

To a mixture of 2-methyl-4-(1-methylcyclopropoxy)-1-nitro-benzene (11 g, 53.08 mmol, 1 eq) in EtOH (100 mL) was added 10% of Pd/C (4 g, 5.31 mmol, 0.1 eq) and ammonium formate (40.17 g, 636.99 mmol, 12 eq) in one portion at 20° C. under $N_2$. The mixture was stirred at 20° C. for 2 h to give a black mixture. TLC showed the reaction was completed. The mixture was filtered through a pad of silica gel, washed with EtOAc (3×200 mL) and concentrated in vacuum. The residue was purified by silica gel chromatography (0-10% of Ethyl acetate in Petroleum ether) to afford 2-methyl-4-(1-methylcyclopropoxy) aniline (9.8 g, crude) as a red oil.

Step 4

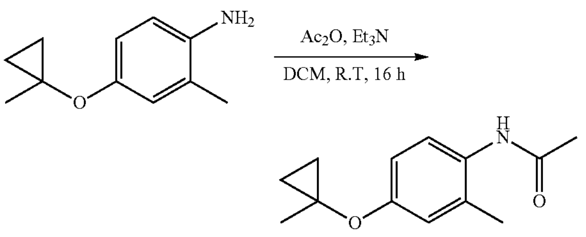

To a mixture of 2-methyl-4-(1-methylcyclopropoxy) aniline (9.8 g, 55.29 mmol, 1 eq) and $Et_3N$ (13.99 g, 138.23 mmol, 19.24 mL, 2.5 eq) in DCM (100 mL) was added $Ac_2O$ (11.29 g, 110.58 mmol, 10.36 mL, 2 eq) in one portion at 0° C. under $N_2$. The mixture was stirred at 0° C. for 30 min, then heated to 20° C. and stirred for 16 hours. TLC showed the reaction was completed. The reaction was quenched with a saturated solution of aqueous $NaHCO_3$ (30 mL) to adjusted pH=7-8 and extracted with DCM (3×50 mL). The combined organic phase was washed with brine (3×50 mL), dried with anhydrous $Na_2SO_4$, filtered and concentrated in vacuum. The residue was purified by silica gel chromatography (20-40% Ethyl acetate in Petroleum ether) to afford N-[2-methyl-4-(1-methylcyclopropoxy)phenyl]acetamide (9.3 g, 42.41 mmol, 76.71% yield) as a yellow oil.

Step 5

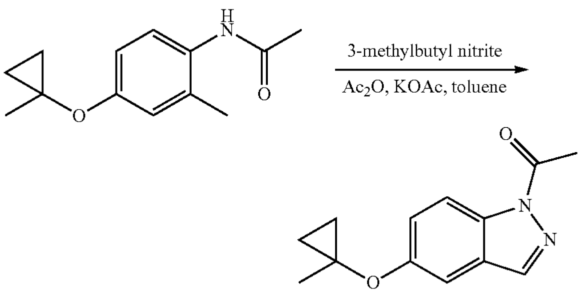

To a solution of N-[2-methyl-4-(1-methylcyclopropoxy) phenyl]acetamide (9.3 g, 42.41 mmol, 1 eq) in toluene (100 mL) was added KOAc (6.24 g, 63.62 mmol, 1.5 eq) and $Ac_2O$ (19.92 g, 195.09 mmol, 18.27 mL, 4.6 eq) at 20° C., the solution was heated to 80° C., then 3-methylbutyl nitrite (19.87 g, 169.65 mmol, 22.84 mL, 4 eq) was added drop-wise. After addition, the mixture was stirred at 80° C. for 2h. TLC showed the reaction was completed. The reaction was then filtered, the wet cake was washed with EtOAc (70 mL), and the filtrate was concentrated in vacuum. The residue was purified by silica gel chromatography (100-200 mesh silica gel, 0-10% Ethyl acetate in Petroleum ether) to afford 1-[5-(1-methylcyclopropoxy) indazol-1-yl]ethanone (8 g, crude) as a yellow solid.

Step 6

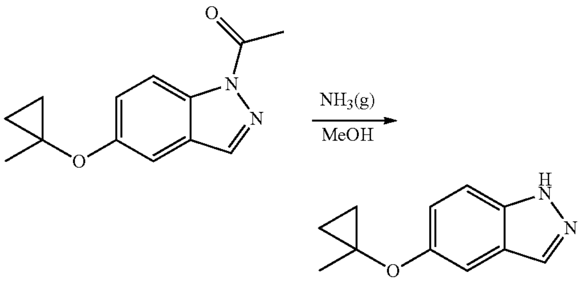

To a mixture of 1-[5-(1-methylcyclopropoxy)indazol-1-yl]ethanone (8 g, 34.74 mmol, 1 eq) in MeOH (80 mL) was added $NH_3$ (g/) MeOH (7 M, 24.82 mL, 5 eq) in one portion at 20° C. The mixture was stirred at 20° C. for 2 hours to give a yellow solution. TLC showed the reaction was completed. The solution was concentrated in vacuum to afford 5-(1-methylcyclopropoxy)-1H-indazole (7.8 g, crude) as a yellow solid.

Step 7

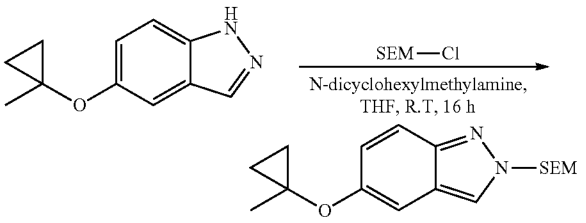

To a mixture of 5-(1-methylcyclopropoxy)-1H-indazole (7.8 g, 41.44 mmol, 1 eq) in THF (80 mL) was added N-dicyclohexylmethylamine (10.52 g, 53.87 mmol, 1.3 eq) and SEM-Cl (8.29 g, 49.73 mmol, 8.80 mL, 1.2 eq) in one portion at 20° C. The mixture was stirred at 20° C. for 16 hours to give an orange solution. TLC showed the reaction was completed. The residue was poured into water (60 mL). The aqueous phase was extracted with ethyl acetate (3×50 mL). The combined organic phase was washed with brine (2×50 mL), dried with anhydrous $Na_2SO_4$, filtered and concentrated in vacuum. The residue was purified by silica gel chromatography (100-200 mesh silica gel, 0-10% of ethyl acetate in Petroleum ether) to afford trimethyl-[2-[[5-(1-methylcyclopropoxy)indazol-2-yl]methoxy]ethyl]silane (5.4 g, 16.96 mmol, 40.92% yield) as a yellow oil.

Step 8

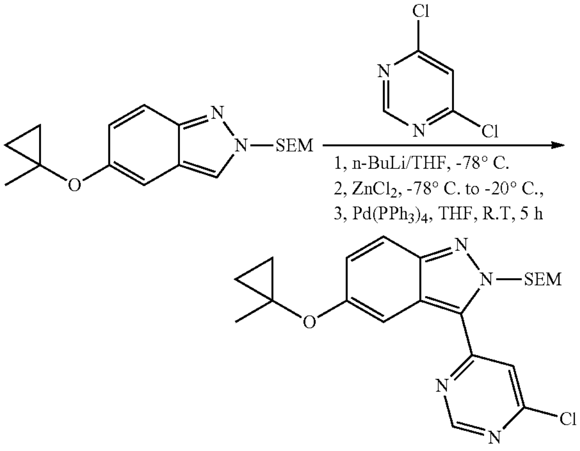

To a mixture of trimethyl-[2-[[5-(1-methylcyclopropoxy) indazol-2-yl]methoxy]ethyl]silane (4.36 g, 13.70 mmol, 5.32e-1 eq) in THF (6 mL) was dropwise added n-BuLi (2.5 M, 13.40 mL, 1.3 eq) dropwise at −70° C. under $N_2$. The mixture was then stirred at −78° C. for 1h, and a solution of $ZnCl_2$ (0.7 M, 55.20 mL, 1.5 eq) was dropwise added at −20° C. The mixture was stirred for 1 h at −20° C. A mixture of 4,6-dichloropyrimidine (4.22 g, 28.34 mmol, 1.1 eq) and $Pd(PPh_3)_4$ (1.49 g, 1.29 mmol, 0.05 eq) in THF (4 mL) was stirred at 20° C. for 1 h and was added to that solution. The cold bath was removed, and the mixture was stirred at 20° C. for 16 h to give a yellow solution. The residue was poured into water (10 mL). The aqueous phase was extracted with ethyl acetate (3×20 mL). The combined organic phase was washed with brine (2×20 mL), dried with anhydrous $Na_2SO_4$, filtered and concentrated in vacuum. The residue was purified by silica gel chromatography (100-200 mesh silica gel, 0-10% of Ethyl acetate in Petroleum ether) to afford 2-[[3-(6-chloropyrimidin-4-yl)-5-(1-methylcyclopropoxy)indazol-2-yl]methoxy]ethyl-trimethyl-silane (2.9 g, crude) as a yellow oil.

Exemplary Final Synthesis of Compound 2:

Step 1

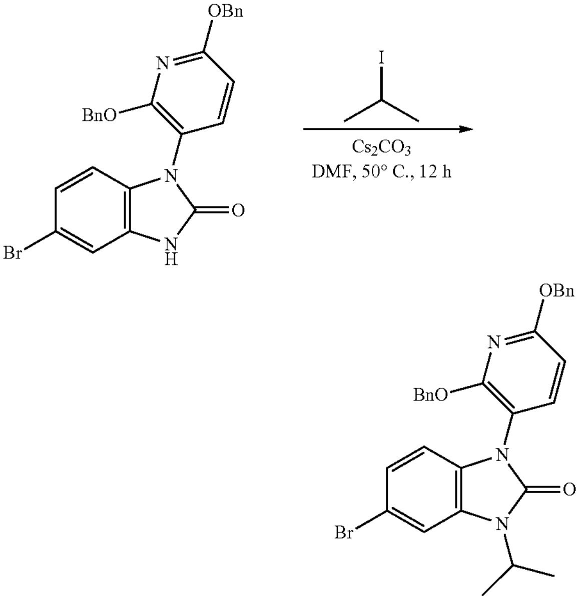

To a mixture of 6-bromo-3-(2,6-dibenzyloxy-3-pyridyl)-1H-benzimidazol-2-one (4.3 g, 8.56 mmol, 1 eq) and 2-iodopropane (2.18 g, 12.84 mmol, 1.28 mL, 1.5 eq) in N,N-dimethylformamide (40 mL) was added cesium carbonate (8.37 g, 25.68 mmol, 3 eq). The mixture was stirred at 50° C. for 12 hours. Thin layer chromatography (petroleum ether:ethyl acetate=2:1) showed the reaction was completed. The mixture was cooled to 20° C. and poured into water (w/w=1/1) (100 mL) and extracted with ethyl acetate (100 mL*2). The combined organic phase was washed with brine (100 mL*3), dried with anhydrous sodium sulfate, filtered, and concentrated under vacuum. The residue was purified by flash silica gel chromatography (ISCO®; 80 g SepaFlash® Silica Flash Column, Eluent of 0~20% Ethyl acetate/Petroleum ether gradient @ 80 mL/min). 5-bromo-1-(2,6-dibenzyloxy-3-pyridyl)-3-isopropyl-benzimidazol-2-one (4 g, 7.35 mmol, 86% yield) was obtained as red solid.

Step 2

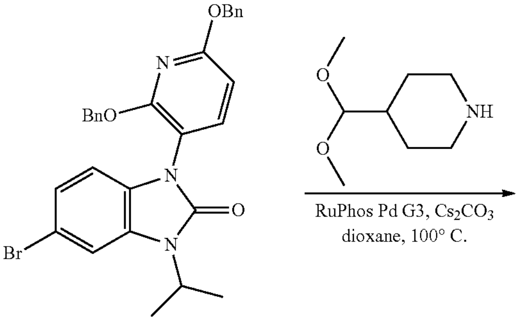

-continued

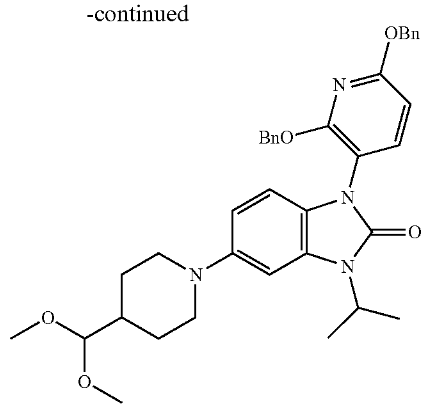

To a mixture of 5-bromo-1-(2,6-dibenzyloxy-3-pyridyl)-3-isopropyl-benzimidazol-2-one (1 g, 1.84 mmol, 1 eq) and 4-(dimethoxymethyl)piperidine (351 mg, 2.20 mmol, 1.2 eq) in dioxane (10 mL) was added cesium carbonate (1.50 g, 4.59 mmol, 2.5 eq), [2-(2-aminophenyl)phenyl]-methylsulfonyloxy-palladium; dicyclohexyl-[2-(2,6-diisopropoxyphenyl)phenyl]phosphane (154 mg, 0.18 mmol, 0.1 eq) and 1,3-bis[2,6-bis(1-propylbutyl)phenyl]-4,5-dichloro-2H-imidazol-1-ium-2-ide; 3-chloropyridine; dichloropalladium (179 mg, 0.18 mmol, 0.1 eq). The mixture was stirred at 100° C. for 12 h and then cooled to 20° C., filtered, and concentrated under reduced pressure. The residue was purified by flash silica gel chromatography (ISCO®; 20 g SepaFlash® Silica Flash Column, Eluent of 0~30% Ethyl acetate/Petroleum ether gradient @ 70 mL/min). 1-(2,6-dibenzyloxy-3-pyridyl)-5-[4-(dimethoxymethyl)-1-piperidyl]-3-isopropyl-benzimidazol-2-one (600 mg, 0.85 mmol, 46% yield, 88% purity) was obtained as yellow oil.

Step 3

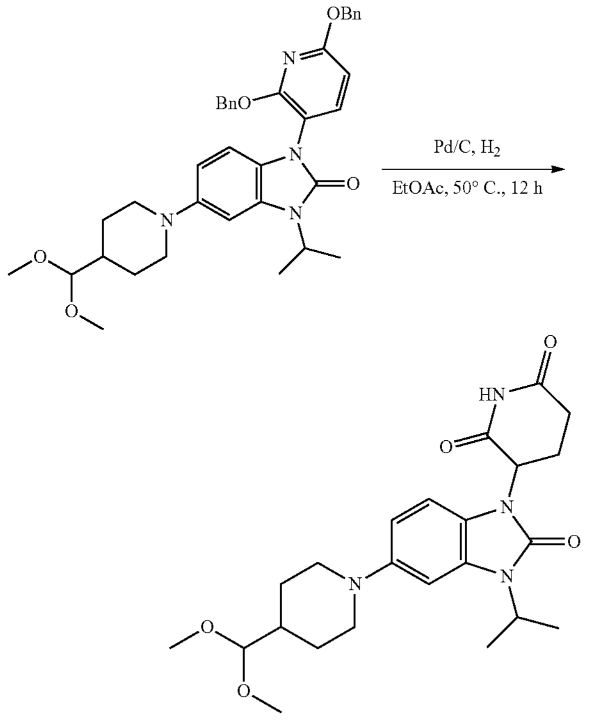

To a solution of 1-(2,6-dibenzyloxy-3-pyridyl)-5-[4-(dimethoxymethyl)-1-piperidyl]-3-isopropyl-benzimidazol-2-one (600 mg, 0.96 mmol, 1 eq) in ethyl acetate (10 mL) was added palladium on carbon (100 mg, 10% purity) and hydroxide palladium (100 mg, 10%) under nitrogen. The mixture was stirred at 50° C. for 12 h under hydrogen (50 psi) and then cooled to 20° C., filtered, and concentrated in reduced pressure. The residue was purified by preparative thin layer chromatography (dichloromethane:methanol=15:1). 3-[5-[4-(dimethoxymethyl)-1-piperidyl]-3-isopropyl-2-oxo-benzimidazol-1-yl]piperidine-2,6-dione (320 mg, 0.71 mmol, 74% yield, 99% purity) was obtained as white solid.

Step 4

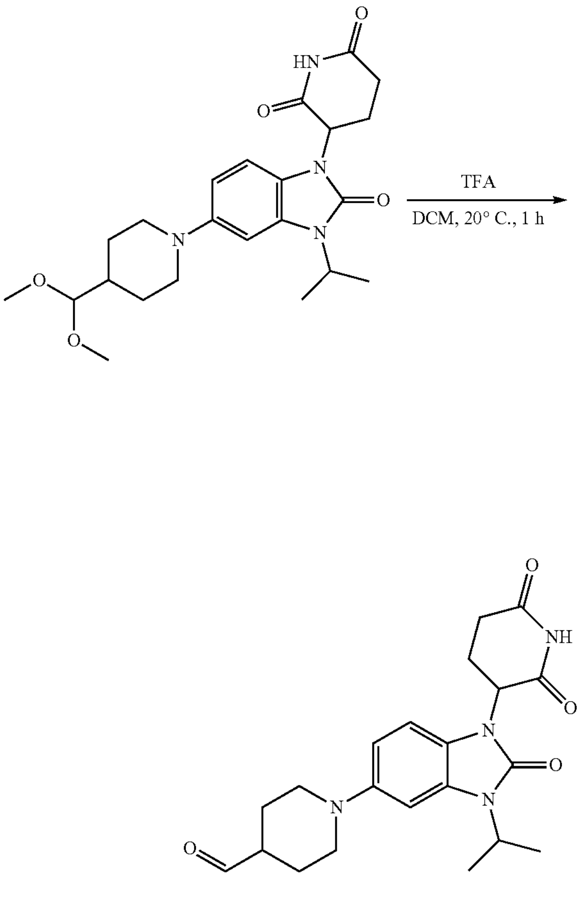

To a mixture of 3-[5-[4-(dimethoxymethyl)-1-piperidyl]-3-isopropyl-2-oxo-benzimidazol-1-yl]piperidine-2,6-dione (65 mg, 0.15 mmol, 1 eq) in dichloromethane (2 mL) was added trifluoroacetic acid (665 mg, 5.83 mmol, 0.43 mL, 39.90 eq). The mixture was stirred at 20° C. for 1 h and then concentrated under reduced pressure. 1-[1-(2,6-dioxo-3-piperidyl)-3-isopropyl-2-oxo-benzimidazol-4-yl]piperidine-4-carbaldehyde (58 mg, 0.15 mmol, 99.55% yield) was obtained as yellow oil.

Step 5

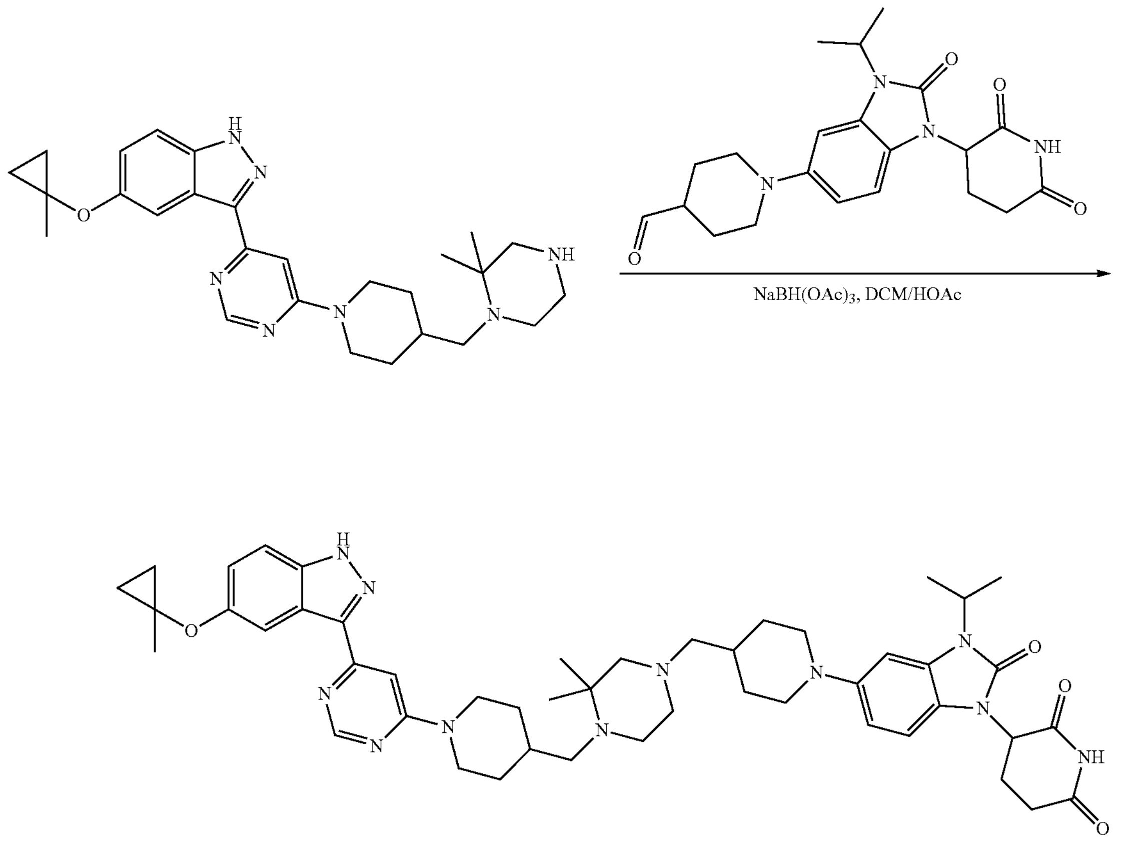 [SMILES: CC1(Oc2ccc3[nH]nc(-c4cc(N5CCC(CN6CCNCC6(C)C)CC5)ncn4)c3c2)CC1 ; CC(C)n1c(=O)n(C2CCC(=O)NC2=O)c2ccc(N3CCC(C=O)CC3)cc21 ; CC(C)n1c(=O)n(C2CCC(=O)NC2=O)c2ccc(N3CCC(CN4CCN(CC5CCN(c6cc(-c7n[nH]c8ccc(OC9(C)CC9)cc78)ncn6)CC5)C(C)(C)C4)CC3)cc21]

To a mixture of 1-[1-(2,6-dioxo-3-piperidyl)-3-isopropyl-2-oxo-benzimidazol-5-yl]piperidine-4-carbaldehyde (60 mg, 137.96 μmol, 1 eq) and 3-[6-[4-[(2,2-dimethylpiperazin-1-yl)methyl]-1-piperidyl]pyrimidin-4-yl]-5-(1-methylcyclopropoxy)-1H-indazole (65.62 mg, 137.96 μmol, 1 eq) in DCM (5 mL) was added HOAc (24.85 mg, 413.87 μmol, 23.69 μL, 3 eq) at 25° C. for 1 hour, then $NaBH(OAc)_3$ (58.48 mg, 275.92 μmol, 2 eq) was added at 25° C. for 15 hours. The residue was filtered and concentrated in vacuum. The residue was purified by prep-HPLC (column: Xtimate C18 150*40 mm*10 um; mobile phase: [water (FA)-ACN]; gradient: 0%-36% B over 36 min) to give Compound 2 (58 mg, 67.27 μmol, 48.76% yield, 99.52% purity) as white solid.

Exemplary Synthesis of Compound 3:

Synthesis of Intermediate 4-[[1-[1-(2,6-dioxo-3-piperidyl)benzimidazol-4-yl]-4-piperidyl]oxy]cyclohexanecarbaldehyde Step 1

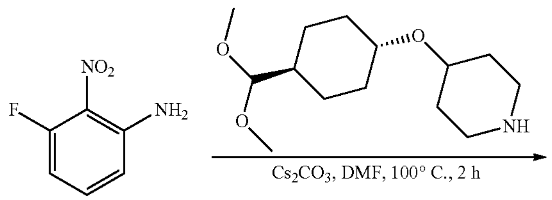

-continued

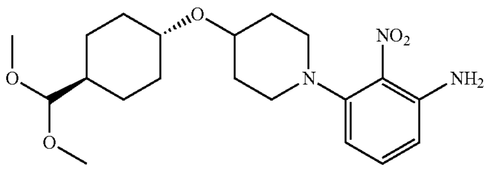

To a stirred solution of 3-fluoro-2-nitro-aniline (1 g, 6.41 mmol, 1 eq) in N,N-dimethylformamide (20 mL) was added 4-[4-(dimethoxymethyl)cyclohexoxy]piperidine (1.81 g, 7.05 mmol, 1.1 eq) and cesium carbonate (4.17 g, 12.81 mmol, 2 eq). The reaction mixture was stirred at 100° C. for 2 h and cooled. Water (200 mL) was added to the mixture and the aqueous phase was extracted with ethyl acetate (100 mL×2). The combined organic layer was washed with brine (200 mL), dried over anhydrous sodium sulfate, filtered and the filtrate was concentrated under vacuum. The residue was purified by silica gel chromatography (petroleum ether:ethyl acetate=100:1-3:1) to obtain 3-[4-[4-(dimethoxymethyl)cyclohexoxy]-1-piperidyl]2-nitro-aniline (1.5 g, 3.81 mmol, 59% yield) as a yellow oil.

Step 2

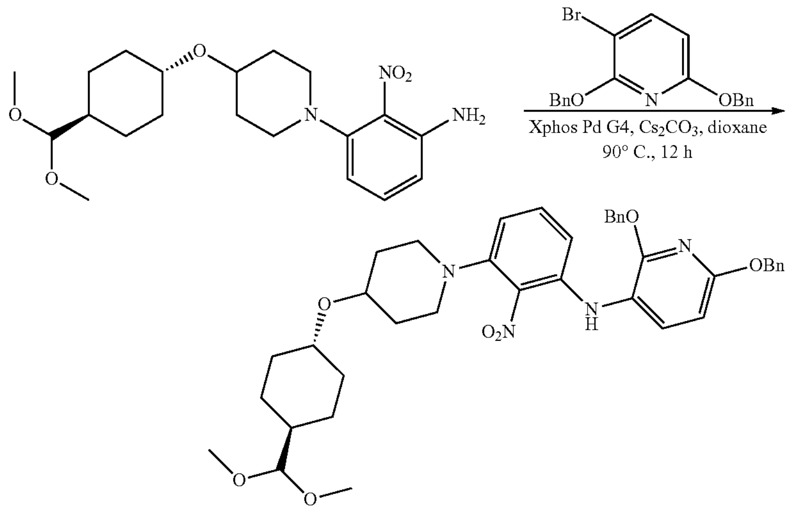

To a stirred solution of 3-[4-[4-(dimethoxymethyl)cyclohexoxy]-1-piperidyl]-2-nitro-aniline (1.5 g, 3.81 mmol, 1 eq) and 2,6-dibenzyloxy-3-bromo-pyridine (1.69 g, 4.57 mmol, 1.2 eq) in dioxane (20 mL) was added methanesulfonato (2-dicyclohexylphosphino-2,4,6-tri-i-propyl-1,1-biphenyl) (2-methylamino-1,1-biphenyl-2-yl) palladium (II) (328 mg, 0.38 mmol, 0.1 eq) and cesium carbonate (2.48 g, 7.62 mmol, 2 eq). The reaction mixture was stirred at 100° C. for 12 h and cooled. The mixture was filtered and the filtrate was concentrated under vacuum. The residue was purified by silica gel chromatography (petroleum ether:ethyl acetate=100:1-3:1) to obtain 2,6-dibenzyloxy-N-[3-[4-[4-(dimethoxymethyl)cyclohexoxy]-1-piperidyl]-2-nitro-phenyl]pyridin-3-amine (2.2 g, 3.22 mmol, 84% yield) as a yellow solid.

Step 3

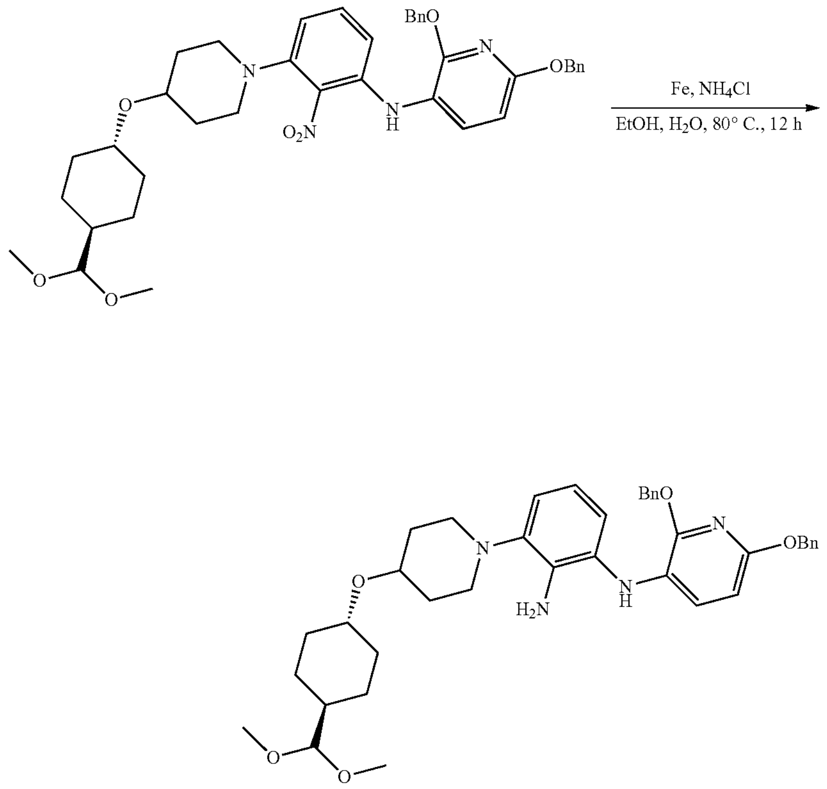

To a stirred solution of 2,6-dibenzyloxy-N-[3-[4-[4-(dimethoxymethyl)cyclohexoxy]-1-piperidyl]-2-nitro-phenyl]pyridin-3-amine (2.2 g, 3.22 mmol, 1 eq) in ethanol (20 mL) and water (5 mL) was added ammonium chloride (1.72 g, 32.22 mmol, 10 eq) and iron (900 mg, 16.11 mmol, 5 eq). The reaction mixture was stirred at 80° C. for 12 h and cooled. The mixture was filtered and the filtrate was concentrated under vacuum. The residue was purified by silica gel chromatography (petroleum ether:ethyl acetate=100:1-1:1) to obtain $N_1$-(2,6-dibenzyloxy-3-pyridyl)-3-[4-[4-(dimethoxymethyl)cyclohexoxy]-1-piperidyl]benzene-1,2-diamine (1.2 g, 1.84 mmol, 57% yield) as a yellow oil.

Step 4

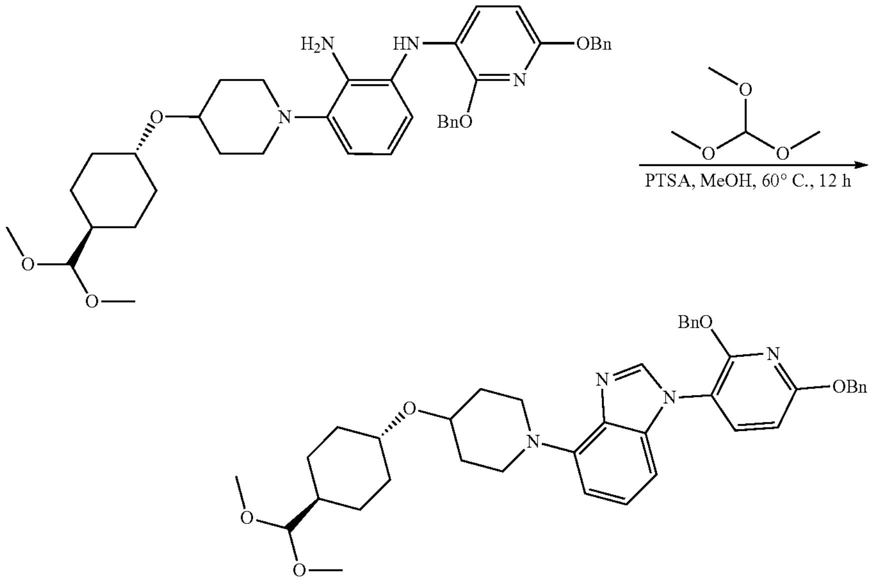

To a solution of $N_1$-(2,6-dibenzyloxy-3-pyridyl)-3-[4-[4-(dimethoxymethyl)cyclohexoxy]-1-piperidyl]benzene-1,2-diamine (1 g, 1.53 mmol, 1 eq) in methanol (10 mL) was added p-toluenesulfonic acid (26 mg, 0.15 mmol, 0.1 eq) and trimethoxymethane (488 mg, 4.60 mmol, 3 eq). The mixture was stirred at 60° C. for 2 h and cooled. The mixture was concentrated under vacuum. 1-(2,6-dibenzyloxy-3-pyridyl)-4-[4-[4-(dimethoxymethyl)cyclohexoxy]-1-piperidyl]benzimidazole (18 mg, 0.03 mmol, 88% yield) was obtained as yellow oil without further purification.

Step 5

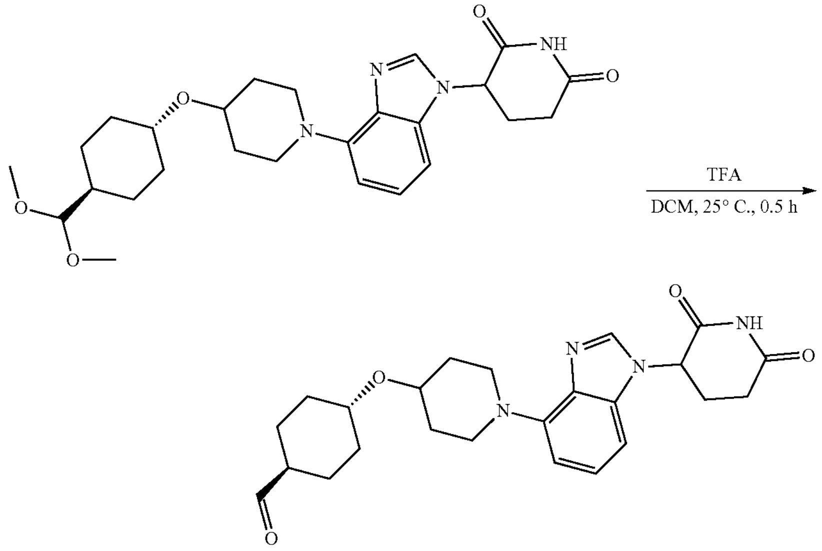

To a solution of 3-[4-[4-[4-(dimethoxymethyl)cyclohexoxy]-1-piperidyl]benzimidazol-1-yl]piperidine-2,6-dione (100 mg, 0.21 mmol, 1 eq) in dichloromethane (2.5 mL) was added trifluoroacetic acid (770 mg, 6.75 mmol, 0.5 mL, 32.72 eq). The mixture was stirred at 25° C. for 0.5 h and then concentrated under vacuum. 4-[[1-[1-(2,6-dioxo-3-piperidyl)benzimidazol-4-yl]-4-piperidyl]oxy]cyclohexanecarbaldehyde (90 mg, 0.21 mmol, 99% yield) was obtained as a white solid without purification.

Synthesis of Intermediate 5-(1-methylcyclopropoxy)-3-(6-piperazin-1-ylpyrimidin-4-yl)-1H-indazole Step 1

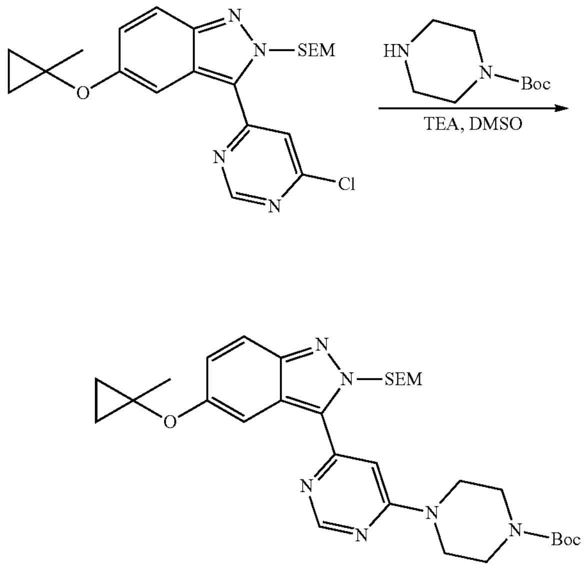

To a solution of 2-[[3-(6-chloropyrimidin-4-yl)-5-(1-methylcyclopropoxy)indazol-2-yl]methoxy]ethyl-trimethyl-silane (1 g, 2.32 mmol, 1 eq) and tert-butyl piperazine-1-carboxylate (648.20 mg, 3.48 mmol, 1.5 eq) in DMSO (5 mL) was added $Et_3N$ (704.34 mg, 6.96 mmol, 968.82 μL, 3 eq). After addition, the reaction mixture was stirred at 100° C. for 1 h. After cooling, the reaction mixture was diluted with water (10 mL) and extracted with ethyl acetate (3×10 mL). The organic layer was dried over sodium sulfate and concentrated under reduced pressure. The residue was purified by silica gel column chromatography (0 to 50% ethyl acetate in petroleum ether) to afford tert-butyl 4-[6-[5-(1-methylcyclopropoxy)-2-(2-trimethylsilylethoxymethyl) indazol-3-yl]pyrimidin-4-yl]piperazine-1-carboxylate (1.2 g, 1.96 mmol, 84.60% yield, 95% purity) as a light-yellow solid.

Step 2

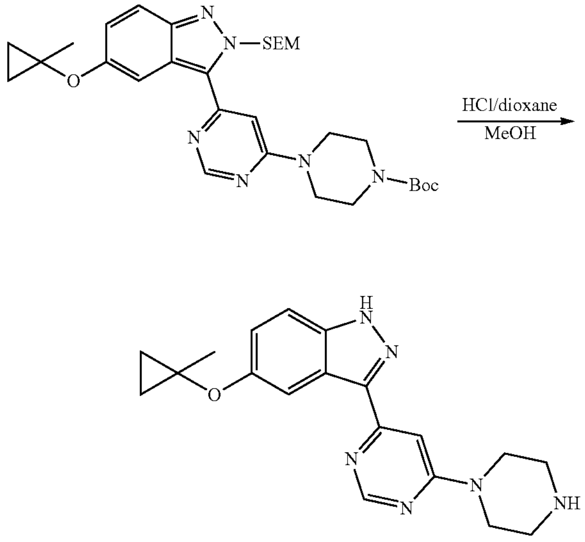

To a solution of tert-butyl 4-[6-[5-(1-methylcyclopropoxy)-2-(2-trimethylsilylethoxymethyl) indazol-3-yl]pyrimidin-4-yl]piperazine-1-carboxylate (1.2 g, 2.07 mmol, 1 eq) in MeOH (5 mL) was added HCl/dioxane (4 M, 5 mL, 9.68 eq). After addition, the reaction solution was stirred at 65° C. for 1 h. After cooling, the reaction mixture was concentrated under reduced pressure to afford 5-(1-methylcyclopropoxy)-3-(6-piperazin-1-ylpyrimidin-4-yl)-1H-indazole (770 mg, 1.81 mmol, 87.37% yield, 90.7% purity, HCl) as a yellow solid. The crude product was used for next step directly.

Exemplary Final Synthesis of Compound 3:

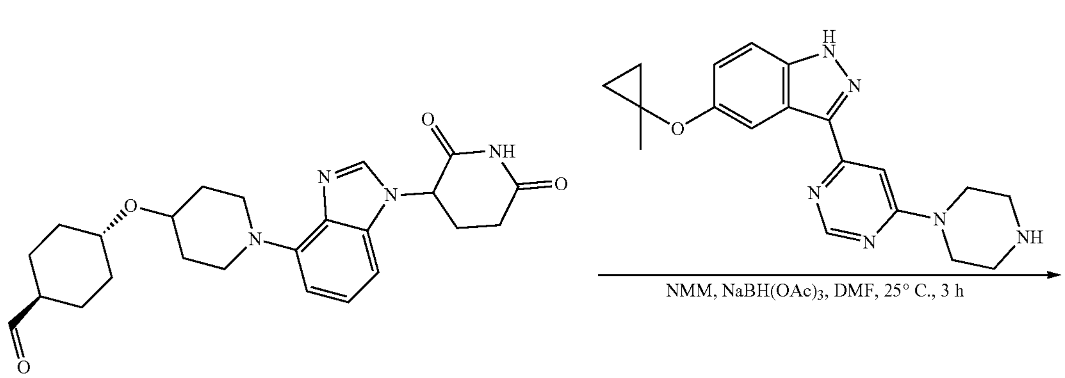

-continued

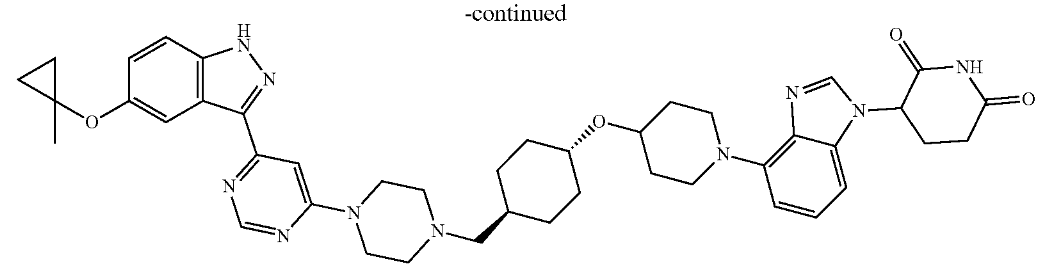

To a solution of 4-[[1-[1-(2,6-dioxo-3-piperidyl)benzimidazol-4-yl]-4-piperidyl]oxy]cyclohexanecarbaldehyde (90 mg, 0.21 mmol, 1 eq) in N,N-dimethylformamide (3 mL) was added sodium triacetoxyborohydride (87 mg, 0.41 mmol, 2 eq) and 5-(1-methylcyclopropoxy)-3-(6-piperazin-1-ylpyrimidin-4-yl)-1H-indazole (71 mg, 0.18 mmol, 0.9 eq, hydrochloric acid), followed by N-methyl morpholine (62 mg, 0.62 mmol, 0.09 ml, 3 eq). The mixture was stirred at 25° C. for 3 h and then filtered. The mixture was purified by prep-HPLC: (column: Phenomenex luna C18 150*25 mm*10 um; mobile phase: [water (FA)-ACN]; B %: 12%-42%, 7 min.). Compound 3 (27 mg, 0.03 mmol, 17% yield, 96% purity) was obtained as a white solid.

Exemplary Synthesis of Compound 4:

Synthesis of Intermediate of 2,6-dibenzyloxy-N-[5-[4-[4-(dimethoxymethyl)cyclohexoxy]-1-piperidyl]-2-nitro-phenyl]pyridin-3-amine Step 1

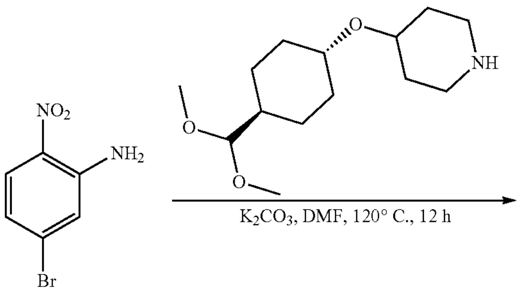

-continued

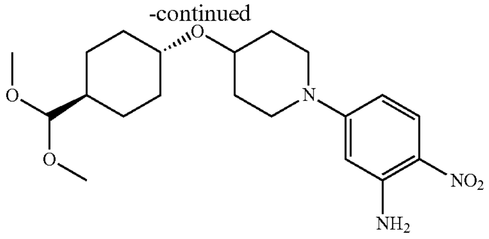

To a solution of 5-bromo-2-nitro-aniline (1.07 g, 4.92 mmol, 1.1 eq) in N,N-dimethylformamide (10 mL) was added potassium carbonate (1.24 g, 8.94 mmol, 2 eq) and 4-[4-(dimethoxymethyl)cyclohexoxy]piperidine (1.15 g, 4.47 mmol, 1 eq). The mixture was stirred at 120° C. for 12 h and cooled. The reaction mixture was partitioned between ethyl acetate (100 mL) and water (80 mL). The organic phase was separated, washed with saturated sodium chloride (30 mL), dried over anhydrous sodium sulfate, filtered, and concentrated under reduced pressure to give a residue. The residue was purified by column chromatography (silicon dioxide, Petroleum ether/Ethyl acetate=10:1 to 1:1). 5-[4-[4-(dimethoxymethyl)cyclohexoxy]-1-piperidyl]-2-nitro-aniline (0.694 g, 1.76 mmol, 39.44% yield, 5-[4-[4-(dimethoxymethyl)cyclohexoxy]-1-piperidyl]-2-nitro-aniline (0.694 g, 1.76 mmol, 39.44% yield, was obtained as a yellow solid.

Step 2

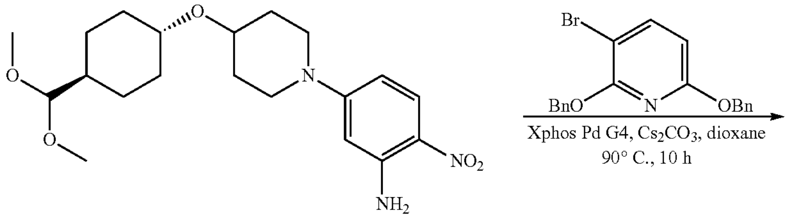

-continued

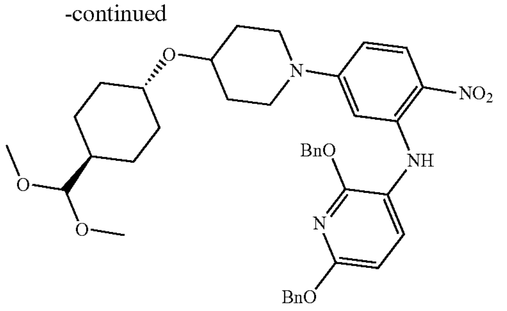

A mixture of 5-[4-[4-(dimethoxymethyl)cyclohexoxy]-1-piperidyl]-2-nitro-aniline (690 mg, 1.75 mmol, 1 eq), 2,6-dibenzyloxy-3-bromo-pyridine (779.10 mg, 2.10 mmol, 1.2 eq), dicyclohexyl-[2-(2,4,6-triisopropylphenyl)phenyl]phosphane; methanesulfonate; [2-[2-(methylamino)phenyl]phenyl]palladium (1+) (150.89 mg, 0.17 mmol, 0.1 eq), and cesium carbonate (1.14 g, 3.51 mmol, 2 eq) in dioxane (10 mL) was degassed and purged with nitrogen for 3 cycles. The mixture was then heated at 90° C. for 10 h under a $N_2$ atmosphere and cooled. The reaction mixture was partitioned between ethyl acetate (50 mL) and water (30 mL). The organic phase was separated, washed with brine (15 mL), dried over anhydrous $Na_2SO_4$, filtered, and concentrated under reduced pressure to give a residue. The residue was purified by column chromatography (silicon dioxide, Petroleum ether/Ethyl acetate=5/1). 2,6-dibenzyloxy-N-[5-[4-[4-(dimethoxymethyl)cyclohexoxy]-1-piperidyl]-2-nitro-phenyl]pyridin-3-amine (1.12 g, 1.64 mmol, 93.5% yield) was obtained as a red solid.

Compound 4 was made in a manner analogous to Compound 3 using intermediate 2,6-dibenzyloxy-N-[5-[4-[4-(dimethoxymethyl)cyclohexoxy]-1-piperidyl]-2-nitro-phenyl]pyridin-3-amine in place of 2,6-dibenzyloxy-N-[3-[4-[4-(dimethoxymethyl)cyclohexoxy]-1-piperidyl]-2-nitro-phenyl]pyridin-3-amine.

Exemplary Synthesis of Compound 5:

Synthesis of intermediate 3-(2,6-bis(benzyloxy)pyridin-3-yl)-5-(4-(((1r,4r)-4-(dimethoxymethyl)cyclohexyl)-oxy)piperidin-1-yl)-1-methyl-1,3-dihydro-2H-benzo[d]imidazol-2-one Step 1

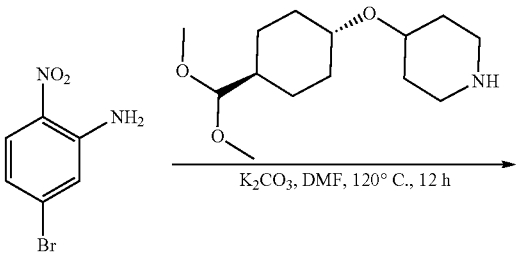

-continued

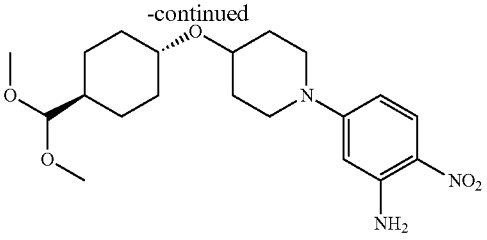

To a stirred solution of 5-bromo-2-nitro-aniline (1.69 g, 7.77 mmol, 1 eq) and 4-[4-(dimethoxymethyl)cyclohexoxy]piperidine (2 g, 7.77 mmol, 1 eq) in N,N-dimethylformamide (20 mL) was added potassium carbonate (2.36 g, 17.10 mmol, 2.2 eq). The reaction mixture was stirred at 120° C. for 12 h and cooled. Water (200 mL) was added to the mixture and the mixture was extracted with ethyl acetate (150 mL×2). The combined organic layer was washed with brine (200 mL×2), dried over anhydrous sodium sulfate, filtered, and the residue was concentrated under vacuum. The residue was purified by silica gel chromatography (petroleum ether:ethyl acetate=100:1-2:1) to obtain 5-[4-[4-(dimethoxymethyl)cyclohexoxy]-1-piperidyl]-2-nitro-aniline (1.5 g, 3.81 mmol, 49% yield) as a yellow oil.

Step 2

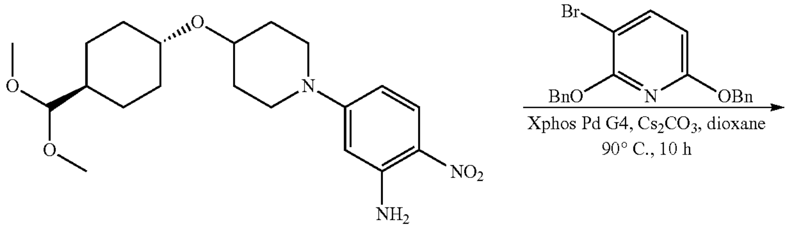

-continued

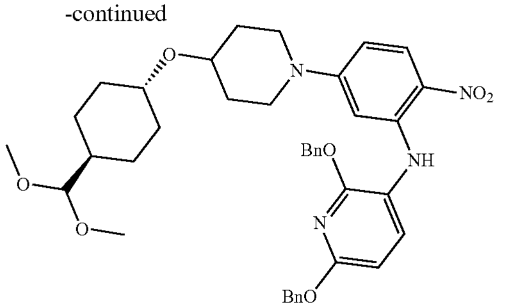

To a stirred solution of 5-(4-(((1r,4r)-4-(dimethoxymethyl)cyclohexyl)oxy)piperidin-1-yl)-2-nitroaniline (1.5 g, 3.81 mmol, 1 eq) and 2,6-dibenzyloxy-3-bromo-pyridine (1.69 g, 4.57 mmol, 1.2 eq) in dioxane (20 mL) was added methanesulfonato (2-dicyclohexylphosphino-2',4',6'-tri-i-propyl-1,1'-biphenyl) (2'-methylamino-1,1'-biphenyl-2-yl) palladium (II) (328 mg, 0.38 mmol, 0.1 eq) and cesium carbonate (2.48 g, 7.62 mmol, 2 eq). The reaction mixture was stirred at 100° C. for 12 h and cooled. The mixture was filtered, and the filtrate was concentrated under vacuum. The residue was purified by silica gel chromatography (petroleum ether:ethyl acetate=100:1-3:1) to obtain 2,6-bis(benzyloxy)-N-(5-(4-(((1r,4r)-4-(dimethoxymethyl)cyclohexyl)oxy)piperidin-1-yl)-2-nitrophenyl)pyridin-3-amine (2.2 g, 3.22 mmol, 84% yield) as a yellow solid.

Step 3

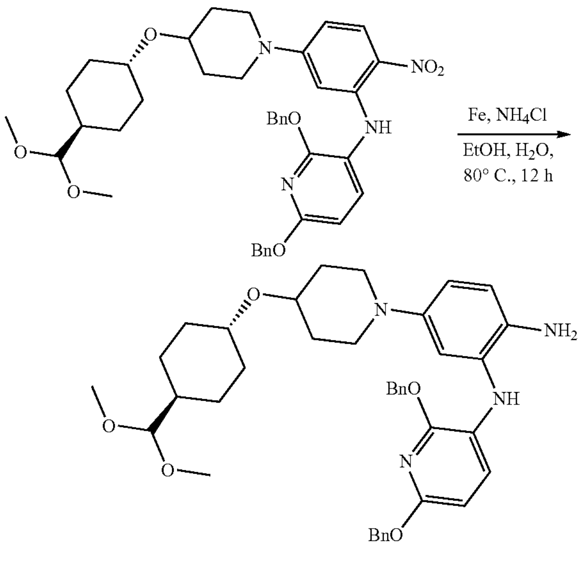

To a stirred solution of 2,6-bis(benzyloxy)-N-(5-(4-(((1r,4r)-4-(dimethoxymethyl)cyclohexyl)oxy)piperidin-1-yl)-2-nitrophenyl)pyridin-3-amine (2.2 g, 3.22 mmol, 1 eq) in ethanol (20 mL) and water (5 mL) was added ammonium chloride (1.72 g, 32.22 mmol, 10 eq) and iron (899 mg, 16.11 mmol, 5 eq). The reaction mixture was stirred at 80° C. for 12 h and cooled. The mixture was filtered and the filtrate was concentrated under vacuum. The residue was purified by silica gel chromatography (petroleum ether:ethyl acetate=100:1-1:1) to obtain $N_1$-(2,6-bis(benzyloxy)pyridin-3-yl)-5-(4-(((1r,4r)-4-(dimethoxymethyl)cyclohexyl)oxy)piperidin-1-yl)benzene-1,2-diamine (1.2 g, 1.84 mmol, 57% yield) as a yellow oil.

Step 4

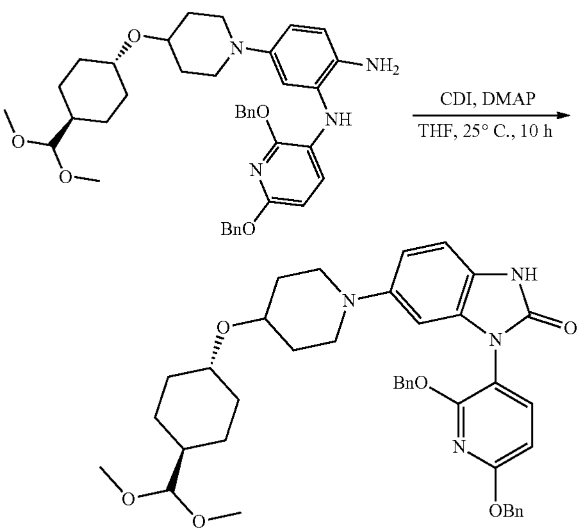

To a stirred solution of $N_1$-(2,6-bis(benzyloxy)pyridin-3-yl)-5-(4-(((1r,4r)-4-(dimethoxymethyl)cyclohexyl)oxy)piperidin-1-yl)benzene-1,2-diamine (1.2 g, 1.84 mmol, 1 eq) in tetrahydrofuran (12 mL) was added 4-dimethylaminopyridine (22 mg, 0.18 mmol, 0.1 eq) and 1,1-carbonyldiimidazole (596 mg, 3.68 mmol, 2 eq). The reaction mixture was stirred at 20° C. for 12 h. The mixture was concentrated under vacuum. The residue was purified by silica gel chromatography (petroleum ether:ethyl acetate=100:1-2:1) to obtain 1-(2,6-bis(benzyloxy)pyridin-3-yl)-6-(4-(((1r,4r)-4-(dimethoxymethyl)cyclohexyl)oxy)piperidin-1-yl)-1,3-dihydro-2H-benzo[d]imidazol-2-one (1 g, 1.47 mmol, 80% yield) as a yellow solid.

Step 5

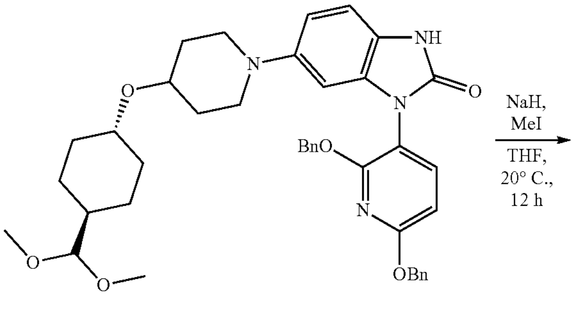

-continued

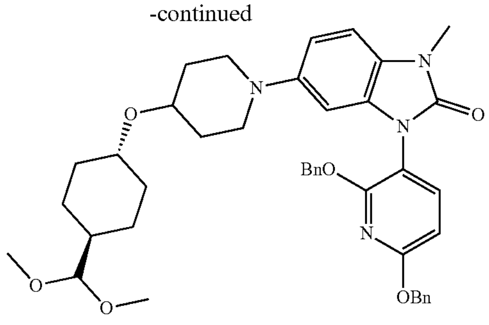

To a stirred solution of 1-(2,6-bis(benzyloxy)pyridin-3-yl)-6-(4-(((1r,4r)-4-(dimethoxymethyl)cyclohexyl)oxy)piperidin-1-yl)-1,3-dihydro-2H-benzo[d]imidazol-2-one (1 g, 1.47 mmol, 1 eq) in tetrahydrofuran (10 mL) was added sodium hydride (88 mg, 2.21 mmol, 60% purity, 1.5 eq) at 0° C. The mixture was stirred at this temperature for 0.5 h and iodomethane (313 mg, 2.21 mmol, 0.14 mL, 1.5 eq) was added to the mixture. The resulting mixture was stirred at 20° C. for 12 h. The mixture was cooled to 0° C., quenched with sat. ammonium chloride (150 mL) and extracted with ethyl acetate (100 mL*2). The combined organic phase dried with anhydrous sodium sulfate, filtered, and concentrated under vacuum. The residue was purified by silica gel chromatography (petroleum ether:ethyl acetate=100:1-1:1) to obtain 3-(2,6-bis(benzyloxy)pyridin-3-yl)-5-(4-(((1r,4r)-4-(dimethoxymethyl)cyclohexyl)-oxy)piperidin-1-yl)-1-methyl-1,3-dihydro-2H-benzo[d]imidazol-2-one (900 mg, 1.30 mmol, 88% yield) as a yellow solid.

Compound 5 was prepared in a manner analogous to Compound 1, utilizing intermediates 5-(1-methylcyclopropoxy)-3-(6-piperazin-1-ylpyrimidin-4-yl)-1H-indazole and 3-(2,6-bis(benzyloxy)pyridin-3-yl)-5-(4-(((1r,4r)-4-(dimethoxymethyl)cyclohexyl)-oxy)piperidin-1-yl)-1-methyl-1,3-dihydro-2H-benzo[d]imidazol-2-one in place of 5-(1-methylcyclopropoxy)-3-(6-piperazin-1-ylpyrimidin-4-yl)-1H-pyrazolo[3,4-c]pyridine and trans-1-(2,6-dibenzyloxy-3-pyridyl)-5-[4-[4-(dimethoxymethyl)cyclohexoxy]-1-piperidyl]-3-methyl-benzimidazol-2-one Exemplary Synthesis of Compound 6, which was prepared in a manner analogous to Compound 1 using intermediate 5-(1-methylcyclopropoxy)-3-(6-piperazin-1-ylpyrimidin-4-yl)-1H-indazole in place of 5-(1-methylcyclopropoxy)-3-(6-piperazin-1-ylpyrimidin-4-yl)-1H-pyrazolo[3,4-c]pyridine:

Step 1

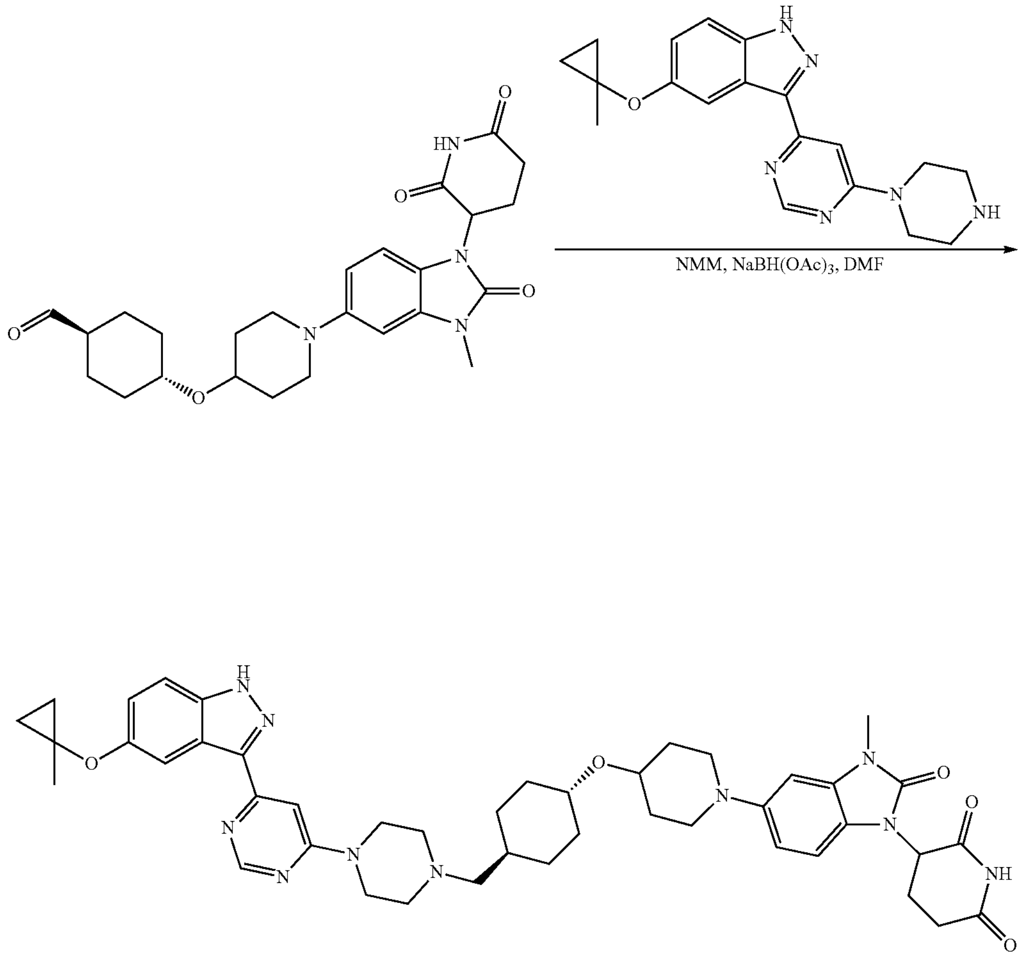

To a mixture of 4-[[1-[1-(2,6-dioxo-3-piperidyl)-3-methyl-2-oxo-benzimidazol-5-yl]-4-piperidyl]oxy]cyclohexanecarbaldehyde (109 mg, 0.23 mmol, 1 eq) and 5-(1-methylcyclopropoxy)-3-(6-piperazin-1-ylpyrimidin-4-yl)-1H-indazole (107 mg, 0.23 mmol, 1 eq, 3 hydrochloride acid) in N,N-dimethylformamide (3 mL) was added 4-methylmorpholine (71 mg, 0.70 mmol, 0.077 mL, 3 eq) and sodium triacetoxyborohydride (99 mmg, 0.47 mmol, 2 eq) at 0° C. The mixture was stirred at 20° C. for 12 h and then concentrated under reduced pressure. The residue was purified by semi-preparative reverse phase (column: YMC Triart C18 150*25 mm*5 um; mobile phase: [water (TFA)-ACN]; B %: 20%-40%, 10 min) and (column: YMC Triart C18 150*25 mm*5 um; mobile phase: [water (TFA)-ACN]; B %: 23%-43%, 10 min). Compound 6 (60.7 mg, 0.072 mmol, 31% yield, 95.59% purity) was obtained as off-white solid.

Exemplary Synthesis of Compound 7:

Step 1

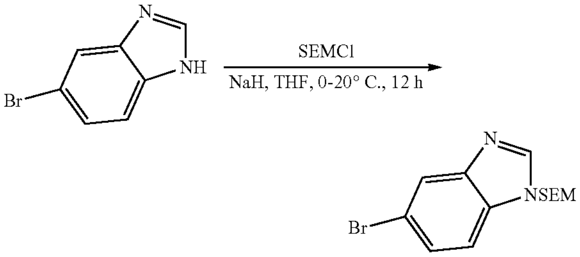

To a stirred, cooled (0° C.) solution of 5-bromo-1H-benzimidazole (8 g, 40.60 mmol, 1 eq) in tetrahydrofuran (80 mL) was added sodium hydride (2.44 g, 60.90 mmol, 60% purity, 1.5 eq) portions. The mixture was stirred at 0° C. for 0.5 h and SEM-$C_1$ (8.12 g, 48.72 mmol, 8.62 mL, 1.2 eq) was added to the mixture. The reaction was stirred at 20° C. for 2 h and then quenched by addition of saturated ammonium chloride aqueous (250 mL) and the mixture was extracted with ethyl acetate (150 mL×2). The combined organic layer was dried over anhydrous sodium sulfate, filtered, and the filtrate was concentrated under vacuum. The residue was purified by silica gel chromatography (petroleum ether:ethyl acetate=5:1-0:1) to afford 2-[(5-bromobenzimidazol-1-yl)methoxy]ethyl-trimethyl-silane (10 g, 30.55 mmol, 75% yield) was obtained as a yellow oil.

Step 2

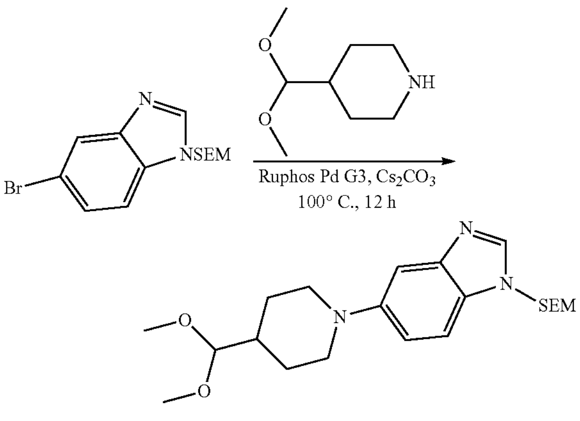

To a stirred solution of 2-[(5-bromobenzimidazol-1-yl)methoxy]ethyl-trimethyl-silane (10 g, 30.55 mmol, 1 eq) and 4-(dimethoxymethyl)piperidine (5.35 g, 33.61 mmol, 1.1 eq) in dioxane (100 mL) was added RuPhos Pd G3 (1.28 g, 1.53 mmol, 0.05 eq) and cesium carbonate (21.90 g, 67.22 mmol, 2.2 eq). The reaction mixture was stirred at 100° C. under nitrogen for 12 h and cooled. The mixture was filtered, and the filtrate was concentrated under vacuum. The residue was purified by silica gel chromatography (petroleum ether: ethyl acetate=10:1-1:1) to afford 2-[[5-[4-(dimethoxymethyl)-1-piperidyl]benzimidazol-1-yl]methoxy]ethyl-trimethyl-silane (6.5 g, 16.03 mmol, 52% yield) as a yellow oil.

Step 3

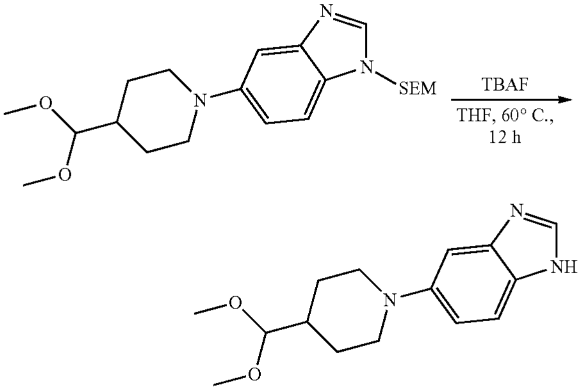

To a stirred solution of 2-[[5-[4-(dimethoxymethyl)-1-piperidyl]benzimidazol-1-yl]methoxy]ethyl-trimethyl-silane (4.50 g, 11.09 mmol, 1 eq) in tetrahydrofuran (50 mL) was added the solution of tetrabutylammonium fluoride (1 M, 13.31 mL, 1.2 eq). The reaction mixture was stirred at 60° C. for 12 h and cooled. Water (300 mL) was added, and the mixture was extracted with ethyl acetate (150 mL×3). The combined organic layer was dried over anhydrous sodium sulfate, filtered, and the filtrate was concentrated under vacuum. The residue was purified by prep-HPLC (column: Kromasil Eternity XT 250*80 mm*10 um; mobile phase: [water (ammonia hydroxide v/v)-ACN]; B %: 18%-48%, 20 min) to obtain 5-[4-(dimethoxymethyl)-1-piperidyl]-1H-benzimidazole (2.6 g, 9.44 mmol, 85% yield) was obtained as a yellow solid.

Step 4

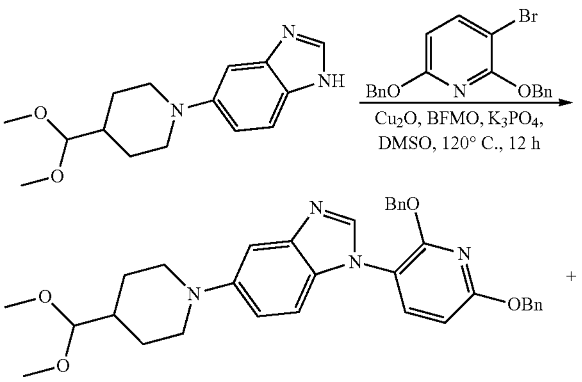

-continued

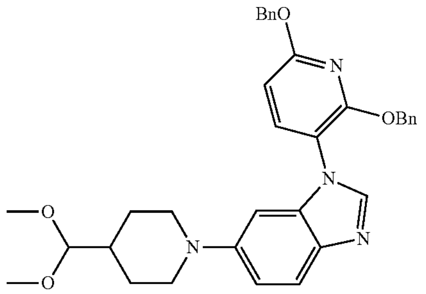

To a stirred solution of 5-[4-(dimethoxymethyl)-1-piperidyl]-1H-benzimidazole (300 mg, 1.09 mmol, 1 eq) and 2,6-dibenzyloxy-3-bromo-pyridine (484.07 mg, 1.31 mmol, 1.2 eq) in dimethyl sulfoxide (5 mL) was added N,N'-bis (2-furylmethyl) oxamide (108.19 mg, 435.82 μmol, 0.4 eq), potassium phosphate (231.28 mg, 1.09 mmol, 1 eq) and cuprous oxide (31.18 mg, 217.91 μmol, 22.27 μL, 0.2 eq). The reaction mixture was stirred at 120° C. for 12 h and cooled. The mixture was filtered, and the filtrate was diluted with water (300 mL). The mixture was extracted with ethyl acetate (150 mL×2) and the combined organic layer was washed with brine (100 mL×2), dried over anhydrous sodium sulfate, filtered, and the filtrate was concentrated under vacuum. The residue was purified by prep-HPLC (column: Waters Xbridge C18 150*50 mm*10 um; mobile phase: [water (ammonium hydrogen carbonate)-ACN]; B %: 51%-81%, 10 min) to afford the mixture (900 mg). The crude was further purified by SFC (column: DAICEL CHIRALPAK AD (250 mm*30 mm, 10 um); mobile phase: [0.1% ammonium hydroxide IPA]; B %: 50%-50%, 3.6 min) to obtain 1-(2,6-dibenzyloxy-3-pyridyl)-5-[4-(dimethoxymethyl)-1-piperidyl]benzimidazole (500 mg, 885.47 μmol, 55% yield) and 1-(2,6-dibenzyloxy-3-pyridyl)-6-[4-(dimethoxymethyl)-1-piperidyl]benzimidazole (400 mg, 708.38 μmol, 44.44% yield) as a yellow oil.

Step 5

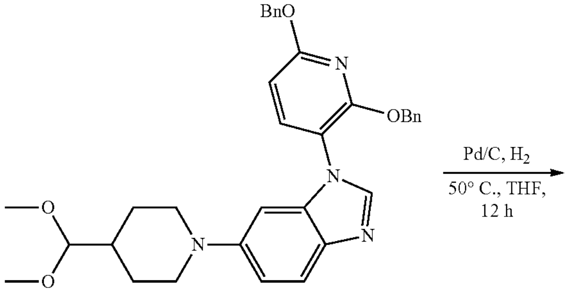

-continued

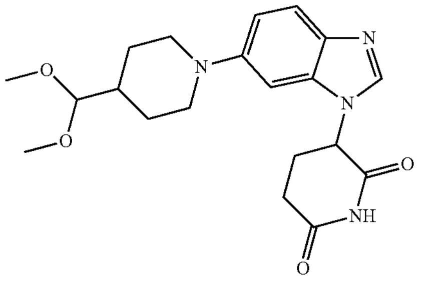

To a stirred solution of 1-(2,6-dibenzyloxy-3-pyridyl)-6-[4-(dimethoxymethyl)-1-piperidyl]benzimidazole (400 mg, 0.71 mmol, 1 eq) in tetrahydrofuran (10 mL) was added Pd/C showed desired product was detected. The mixture was filtered and the filtrate was concentrated under vacuum. The residue was triturated with N,N-dimethylformamide (6 mL) at 20° C. for 10 min to obtain 3-[6-[4-(dimethoxymethyl)-1-piperidyl]benzimidazol-1-yl]piperidine-2,6-dione (170 mg, 0.44 mmol, 62% yield) as a white solid.

Step 6

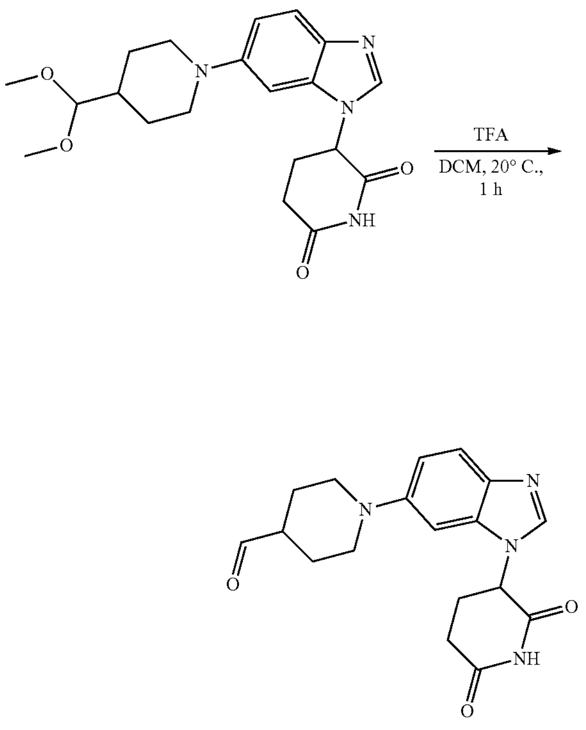

To a stirred solution of 3-[6-[4-(dimethoxymethyl)-1-piperidyl]benzimidazol-1-yl]piperidine-2,6-dione (160 mg, 0.41 mmol, 1 eq) in dichloromethane (3 mL) was added trifluoroacetic acid (2.46 g, 21.61 mmol, 1.60 mL, 52.19 eq). The reaction mixture was stirred at 20° C. for 1 h. LCMS showed desired MS was detected. The mixture was concentrated under vacuum. The residue was used directly for next step to obtain 1-[3-(2,6-dioxo-3-piperidyl)benzimidazol-5-yl]piperidine-4-carbaldehyde (140 mg, 0.41 mmol, 99% yield) as a yellow oil.

Step 7

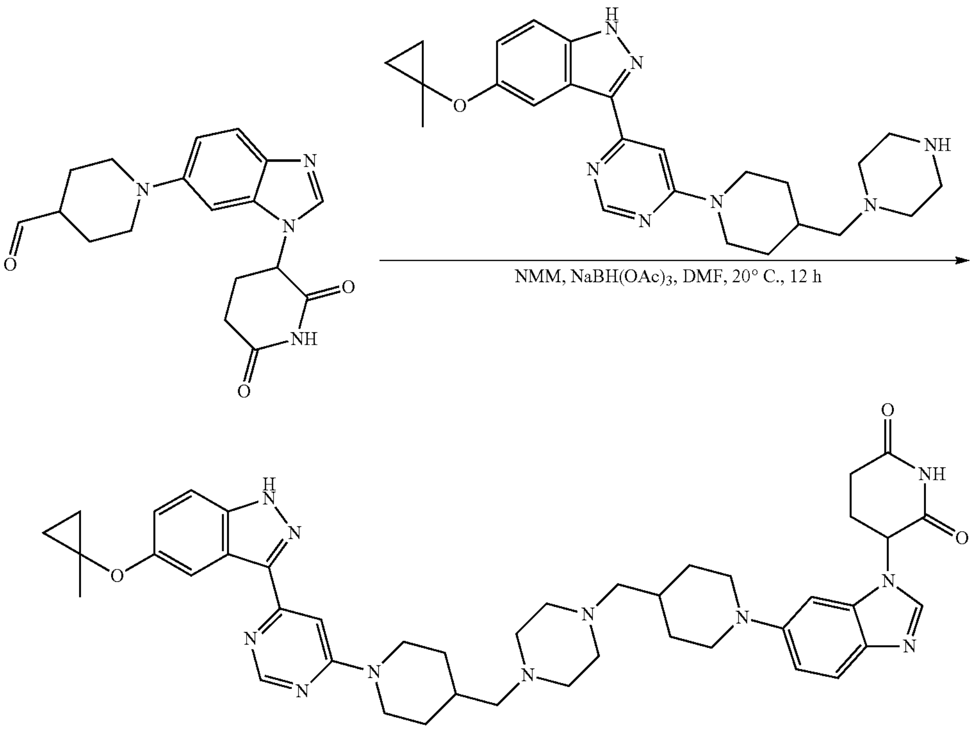

To a stirred solution of 1-[3-(2,6-dioxo-3-piperidyl)benzimidazol-5-yl]piperidine-4-carbaldehyde (70 mg, 0.21 mmol, 1 eq) in N,N-dimethylformamide (2 mL) was added 5-(1-methylcyclopropoxy)-3-[6-[4-(piperazin-1-ylmethyl)-1-piperidyl]pyrimidin-4-yl]-1H-indazole (made in a manner analogous to intermediate 3-[6-[4-[(2,2-dimethylpiperazin-1-yl)methyl]-1-piperidyl]pyrimidin-4-yl]-5-(1-methylcyclopropoxy)-1H-indazole, 82 mg, 0.15 mmol, 0.72 eq, 3hydrochloride) and N-methylmorpholine (41 mg, 0.41 mmol, 2 eq). Sodium triacetoxyborohydride (87 mg, 411.31 μmol, 2 eq) was added and the mixture was stirred at 20° C. for 12 h. The mixture was concentrated under vacuum and the residue was purified by prep-HPLC (column: Phenomenex luna C18 150*25 mm*10 um; mobile phase: [water (FA)-ACN]; B %: 2%-32%, 9 min) to obtain Compound 7 (51.82 mg, 67.13 μmol, 32% yield) as a purple solid.

Exemplary Synthesis of Compound 8:

Step 1

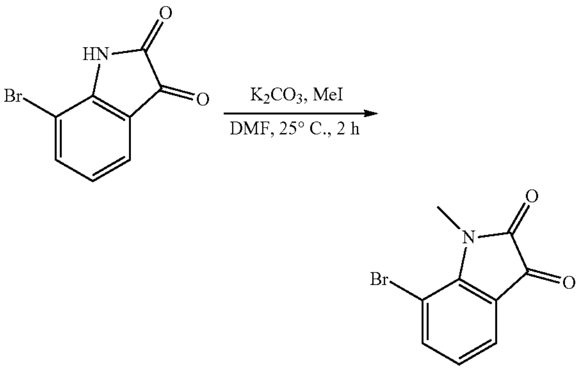

To a mixture of 7-bromoindoline-2,3-dione (12 g, 53.09 mmol, 1 eq), potassium carbonate (11.01 g, 79.64 mmol, 1.5 eq) and water (1.2 mL) in N,N-dimethylformamide (60 mL) was added dropwise methyl iodide (8.44 g, 59.43 mmol, 3.7 mL, 1.12 eq) in N,N-dimethylformamide (24 mL) The mixture was stirred at 25° C. for 2 h. Water (120 mL) was added and the mixture was stirred at 0° C. for 1 h. The resultant precipitate was collected by filtration, washed with water (50 mL×2), and dried in vacuo to give a residue. The residue was used for the next step without further purification. 7-bromo-1-methylindoline-2,3-dione (8 g, 33.33 mmol, 62% yield) was obtained as a red solid.

Step 2

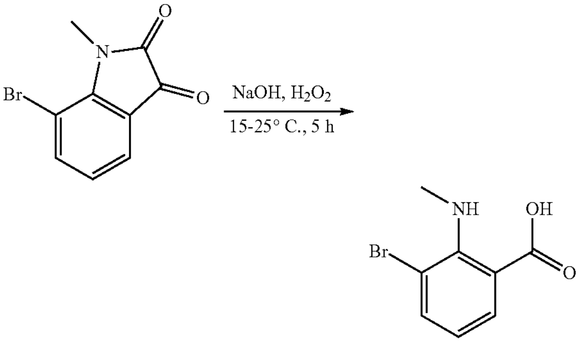

Hydrogen peroxide (38 g, 335.15 mmol, 32.20 mL, 30% in $H_2O$, 10.06 eq) was added dropwise to a mixture of 7-bromo-1-methylindoline-2,3-dione (8 g, 33.33 mmol, 1 eq) and sodium hydroxide (2 M, 199.96 mL, 12 eq) while maintaining the reaction temperature below 15° C. The mixture was stirred at 25° C. for 5 h. The pH of the reaction mixture was adjusted to 4.0 with hydrochloric acid (1 M) and the mixture was stirred at 10° C. for 1 h. The mixture was then extracted with ethyl acetate (80 mL×3). The combined organic phase was washed with water (60 mL), dried with anhydrous sodium sulfate, filtered, and concentrated under vacuum. The residue was used for the next step without further purification. 3-bromo-2-(methylamino)benzoic acid (6.0 g, crude) was obtained as a brown oil.

Step 3

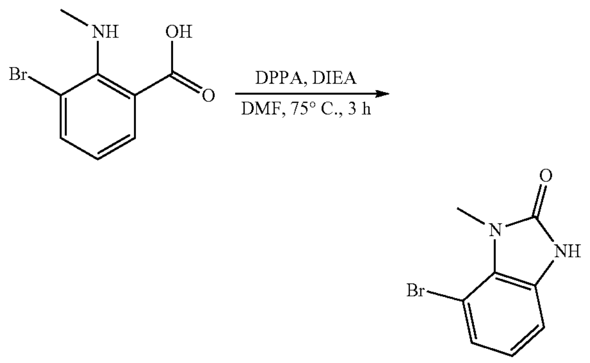

To a solution of 3-bromo-2-(methylamino)benzoic acid (6 g, 26.08 mmol, 1 eq, crude) and N,N-diisopropylethylamine (5.04 g, 39.01 mmol, 6.80 mL, 1.50 eq) in N,N-dimethylformamide (40 mL) was added dropwise diphenylphosphoryl azide (10.76 g, 39.10 mmol, 8.47 mL, 1.50 eq) at 75° C. The reaction mixture was stirred at 75° C. for 3 h and cooled. Water (30 mL) was added at 25° C. and the mixture was stirred at 0° C. for 0.5 h. The resultant precipitate was collected by filtration, washed with water (30 mL) and diisopropylether (15 mL), and dried in vacuo at 50° C. to give a residue. The residue was used for the next step without further purification. 7-bromo-1-methyl-1H-benzo[d]imidazol-2 (3H)-one (4 g, 17.62 mmol, 67% yield) was obtained as an off-white solid.

Step 4

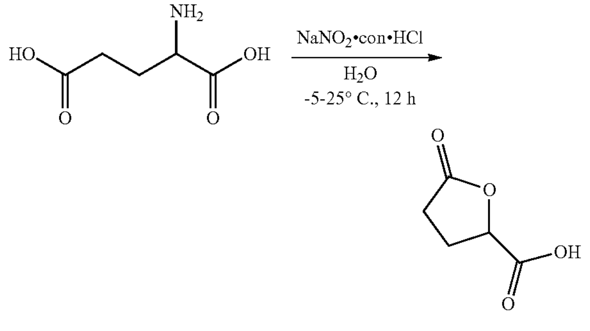

To a solution of 2-aminopentanedioic acid (50 g, 339.84 mmol, 1 eq) in water (300 mL) and hydrochloric acid (37%, 50 mL) was added sodium nitrite (35.17 g, 509.76 mmol, 1.5 eq) at −5° C. The mixture was stirred at 25° C. for 12 h. The reaction was filtered and the filtrate was concentrated in vacuo to give the crude product. The residue was used for the next step without further purification. 5-oxotetrahydrofuran-2-carboxylic acid (34 g, crude) was obtained as a colorless oil.

Step 5

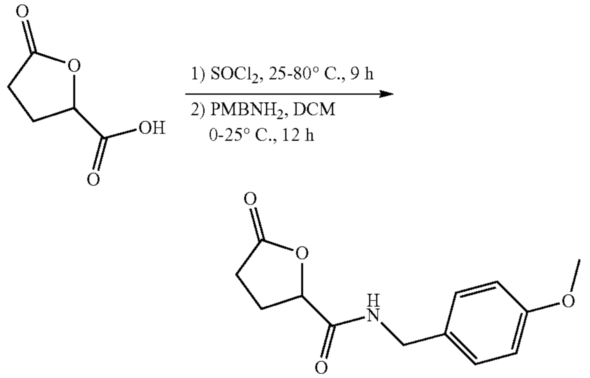

To a solution of 5-oxotetrahydrofuran-2-carboxylic acid (67 g, 514.99 mmol, 1 eq, crude) in dichloromethane (400 mL) was added thionyl chloride (135 g, 1.13 mol, 82.32 mL, 2.20 eq) at 0° C. The mixture was stirred at 85° C. for 3 h and then at 25° C. for 6 h. The reaction mixture was concentrated in vacuo to give the crude product. The residue was dissolved in dichloromethane (400 mL) and p-methoxyaniline (56.52 g, 411.99 mmol, 53.32 mL, 0.8 eq) and triethylamine (104.22 g, 1.03 mol, 143.36 mL, 2 eq) were added to the solution at 0° C. The mixture was stirred at 25° C. for 12 h. Water (500 mL) was added, and the mixture was extracted with ethyl acetate (500 mL×3). The combined organic phase was washed with brine (200 mL), dried, filtered, and concentrated in vacuo. The residue was purified by column chromatography (petroleum ether/ethyl acetate=3/1 to 1/1), desired product (Rf=0.20). N-(4-methoxybenzyl)-5-oxotetrahydrofuran-2-carboxamide (59 g, 236.70 mmol, 45% yield) was obtained as a yellow solid.

Step 6

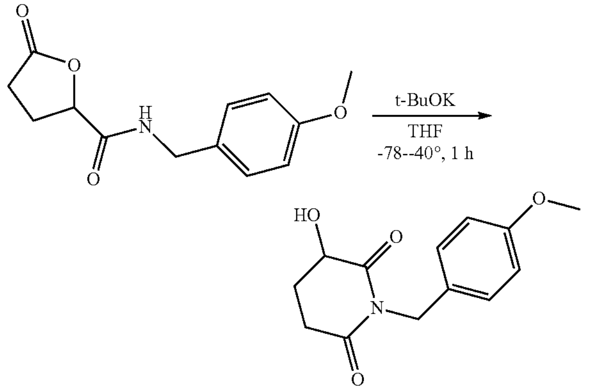

To a solution of N-(4-methoxybenzyl)-5-oxotetrahydrofuran-2-carboxamide (10 g, 40.12 mmol, 1 eq) in tetrahydrofuran (120 mL) was added dropwise potassium 2-methylpropan-2-olate (1 M, 40.52 mL, 1.01 eq) at −78° C. under nitrogen. The resulting reaction mixture was stirred at −40° C. for 1 h. The reaction mixture was quenched by addition ammonium chloride (50 mL) at −40° C., and then diluted with water (150 mL) and extracted with ethyl acetate (100 mL×3). The combined organic layers were washed with brine (100 mL), dried over anhydrous sodium sulfate, filtered, and concentrated under reduced pressure to give a residue. The residue was purified by silica gel column chromatography (petroleum ether/ethyl acetate=5/1 to 2/1).

3-hydroxy-1-[(4-methoxyphenyl)methyl]piperidine-2,6-dione (7.5 g, 30.09 mmol, 75% yield) was obtained as a light yellow solid.

Step 7

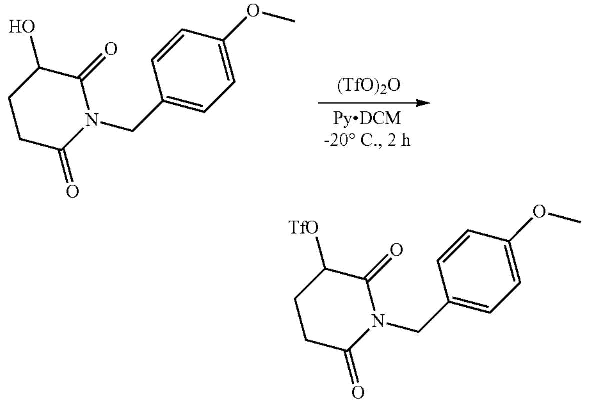

To a solution of 3-hydroxy-1-(4-methoxybenzyl)piperidine-2,6-dione (3 g, 12.04 mmol, 1 eq) and pyridine (1.90 g, 24.02 mmol, 1.94 mL, 2.00 eq) in dichloromethane (100 mL) was added 1,3-bis((trifluoromethyl) sulfonyl)trioxidane (5.67 g, 18.05 mmol, 1.5 eq) at −20° C. The mixture was stirred at −20° C. for 2 h. The reaction mixture was loaded directly onto a silica gel column and eluted petroleum ether/ethyl acetate (10/1 to 2/1). 1-(4-methoxybenzyl)-2,6-dioxopiperidin-3-yl trifluoromethanesulfonate (4.2 g, 11.01 mmol, 92% yield) was obtained as a colorless oil.

Step 8

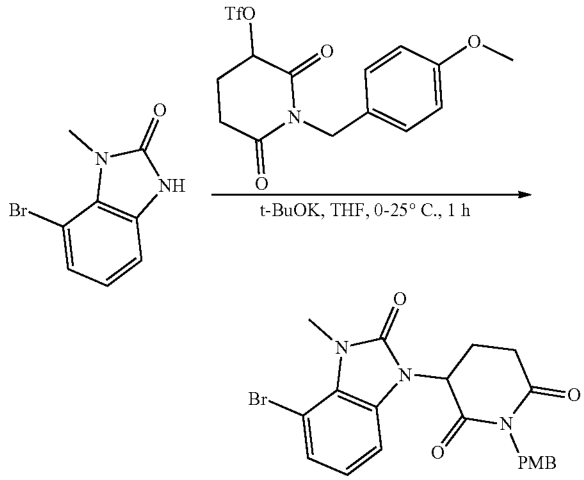

To a solution of 7-bromo-1-methyl-1H-benzo[d]imidazol-2 (3H)-one (2.00 g, 8.81 mmol, 1 eq) in tetrahydrofuran (40 mL) was added potassium 2-methylpropan-2-olate (1 M, 10.67 mL, 1.21 eq) and the mixture was stirred at 0° C. for 0.5 h. 1-(4-Methoxybenzyl)-2,6-dioxopiperidin-3-yl trifluoromethanesulfonate (4.2 g, 11.01 mmol, 1.25 eq) in tetrahydrofuran (20 mL) was added dropwise. The mixture was stirred at 0-25° C. for 0.5 h. The reaction mixture was quenched by addition 10% ammonium chloride solution 10 mL at 0° C. and stirred at 0° C. for 1 h, extracted with ethyl acetate (50 mL×3). The combined organic layers were washed with brine (50 mL), dried over anhydrous sodium sulfate, filtered, and concentrated under reduced pressure to give a solid. The solid was purified by silica gel column chromatography (Petroleum ether/Ethyl acetate=6/1 to 1/1). 3-(4-bromo-3-methyl-2-oxo-2,3-dihydro-1H-benzo[d]imidazol-1-yl)-1-(4-methoxybenzyl)piperidine-2,6-dione (3.5 g, 7.64 mmol, 87% yield) was obtained as a white solid.

Step 9

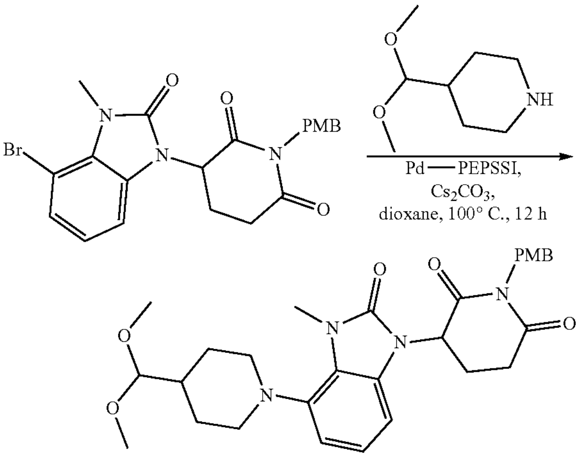

To a stirred solution of 3-(4-bromo-3-methyl-2-oxo-benzimidazol-1-yl)-1-[(4-methoxyphenyl)methyl]piperidine-2,6-dione (2 g, 4.36 mmol, 1 eq) and 4-(dimethoxymethyl) piperidine (1.04 g, 6.55 mmol, 1.5 eq) in dioxane (20 mL) was added 1,3-bis[2,6-bis(1-propylbutyl)phenyl]-4,5-dichloro-2H-imidazol-1-ium-2-ide; 3-chloropyridine; dichloropalladium (424.51 mg, 436.39 μmol, 0.1 eq) and cesium carbonate (2.84 g, 8.73 mmol, 2 eq). The resulting mixture was stirred at 100° C. under $N_2$ for 2 h and cooled. The mixture was slowly poured into 1M HCl (150 mL) at 0° C. and the pH of the mixture was adjusted to 8 with aqueous sodium bicarbonate solution. The mixture was extracted with dichloromethane (100 mL×2) and the combined organic layer was dried over anhydrous sodium sulfate, filtered, and the filtrate was concentrated under vacuum. The residue was purified by silica gel chromatography (PE: EA=10:1-1:2) to afford 3-[4-[4-(dimethoxymethyl)-1-piperidyl]-3-methyl-2-oxo-benzimidazol-1-yl]-1-[(4-methoxyphenyl)methyl]piperidine-2,6-dione (900 mg, 1.68 mmol, 38% yield) as a white solid.

Step 10

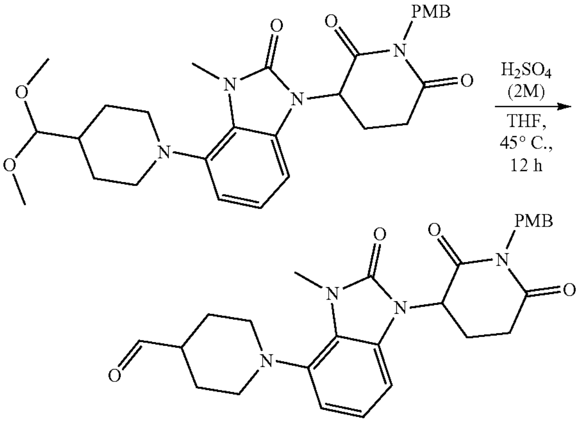

To a stirred solution of 3-[4-[4-(dimethoxymethyl)-1-piperidyl]-3-methyl-2-oxo-benzimidazol-1-yl]-1-[(4-methoxyphenyl)methyl]piperidine-2,6-dione (900 mg, 1.68 mmol, 1 eq) in tetrahydrofuran (5 mL) was added the solution of $H_2SO_4$ (2 M, 4.50 mL, 5.37 eq). The reaction mixture was stirred at 45° C. for 12 h and cooled. The pH value of the mixture was adjusted to 8 by addition of a sodium bicarbonate solution and the aqueous layer was then extracted with ethyl acetate (100 mL×2). The combined organic layer was dried over anhydrous sodium sulfate, filtered, and the filtrate was concentrated under vacuum. This afforded 1-[1-[1-[(4-methoxyphenyl)methyl]-2,6-dioxo-3-piperidyl]-3-methyl-2-oxo-benzimidazol-4-yl]piperidine-4-carbaldehyde (700 mg, 1.43 mmol, 85% yield) as a yellow solid, which was used directly without further purification.

Compound 8 was prepared in a manner analogous to Compound 7 utilizing intermediate 1-[1-[1-[(4-methoxyphenyl)methyl]-2,6-dioxo-3-piperidyl]-3-methyl-2-oxo-benzimidazol-4-yl]piperidine-4-carbaldehyde in place of 1-[1-(2,6-dioxo-3-piperidyl)-3-isopropyl-2-oxo-benzimidazol-4-yl]piperidine-4-carbaldehyde.

Exemplary Synthesis of Compound 9:

Synthesis of Intermediate trans-1-(2,6-dibenzyloxy-3-pyridyl)-4-[4-[4-(dimethoxymethyl)cyclohexoxy]-1-piperidyl]-3-methyl-benzimidazol-2-one Step 1

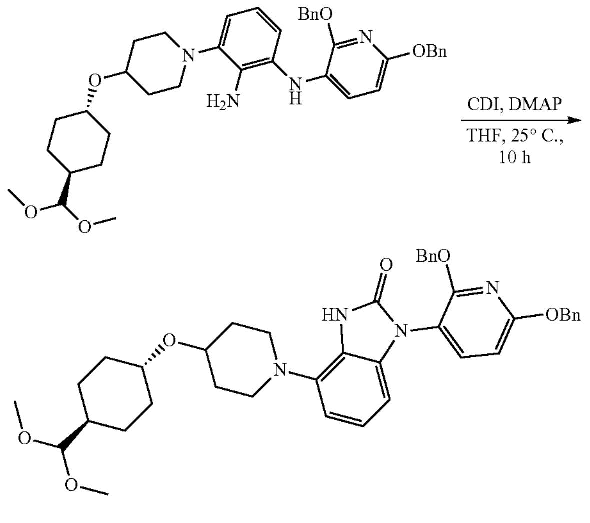

To a stirred solution of $N_1$-(2,6-dibenzyloxy-3-pyridyl)-3-[4-[4-(dimethoxymethyl)cyclohexoxy]-1-piperidyl]benzene-1,2-diamine (1.2 g, 1.84 mmol, 1 eq) in tetrahydrofuran (12 mL) was added 4-dimethylaminopyridine (22 mg, 0.18 mmol, 0.1 eq) and 1,1-carbonyldiimidazole (596 mg, 3.68 mmol, 2 eq). The reaction mixture was stirred at 20° C. for 12 h and then concentrated under vacuum. The residue was purified by silica gel chromatography (petroleum ether: ethyl acetate=100:1-2:1) to obtain trans-3-(2,6-dibenzyloxy-3-pyridyl)-7-[4-[4-(dimethoxymethyl)cyclohexoxy]-1-piperidyl]-1H-benzimidazol-2-one (1 g, 1.47 mmol, 80% yield) as a yellow solid.

Step 2

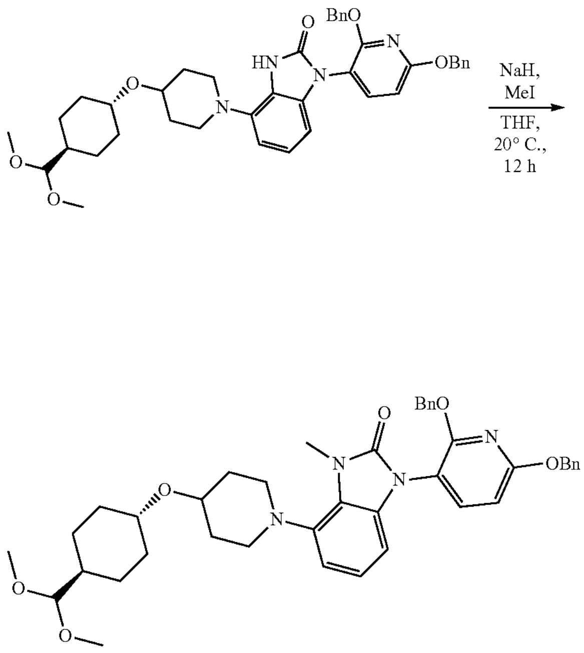

To a stirred solution of trans-3-(2,6-dibenzyloxy-3-pyridyl)-7-[4-[4-(dimethoxymethyl)cyclohexoxy]-1-piperidyl]-1H-benzimidazol-2-one (1 g, 1.47 mmol, 1 eq) in tetrahydrofuran (10 mL) was added sodium hydride (88 mg, 2.21 mmol, 60% purity, 1.5 eq) at 0° C. The mixture was stirred at this temperature for 0.5 h and iodomethane (313 mg, 2.21 mmol, 137.56 μL, 1.5 eq) was then added. The resulting mixture was stirred at 20° C. for 12 h. The mixture was cooled to 0° C., quenched with sat. ammonium chloride (150 mL) and extracted with ethyl acetate (100 mL*2). The combined organic phase was dried with anhydrous sodium sulfate, filtered, and concentrated under vacuum. The residue was purified by silica gel chromatography (petroleum ether:ethyl acetate=100:1-1:1) to obtain 1-(2,6-dibenzyloxy-3-pyridyl)-4-[4-[4-(dimethoxymethyl)cyclohexoxy]-1-piperidyl]-3-methyl-benzimidazol-2-one (900 mg, 1.30 mmol, 88% yield) as a yellow solid.

Compound 9 was prepared in a manner analogous to Compound 1 using intermediate trans-1-(2,6-dibenzyloxy-3-pyridyl)-4-[4-[4-(dimethoxymethyl)cyclohexoxy]-1-piperidyl]-3-methyl-benzimidazol-2-one in place of trans-1-(2,6-dibenzyloxy-3-pyridyl)-5-[4-[4-(dimethoxymethyl)cyclohexoxy]-1-piperidyl]-3-methyl-benzimidazol-2-one Exemplary Synthesis of Compound 12, which was prepared in a manner analogous t Compound 2.

Step 1

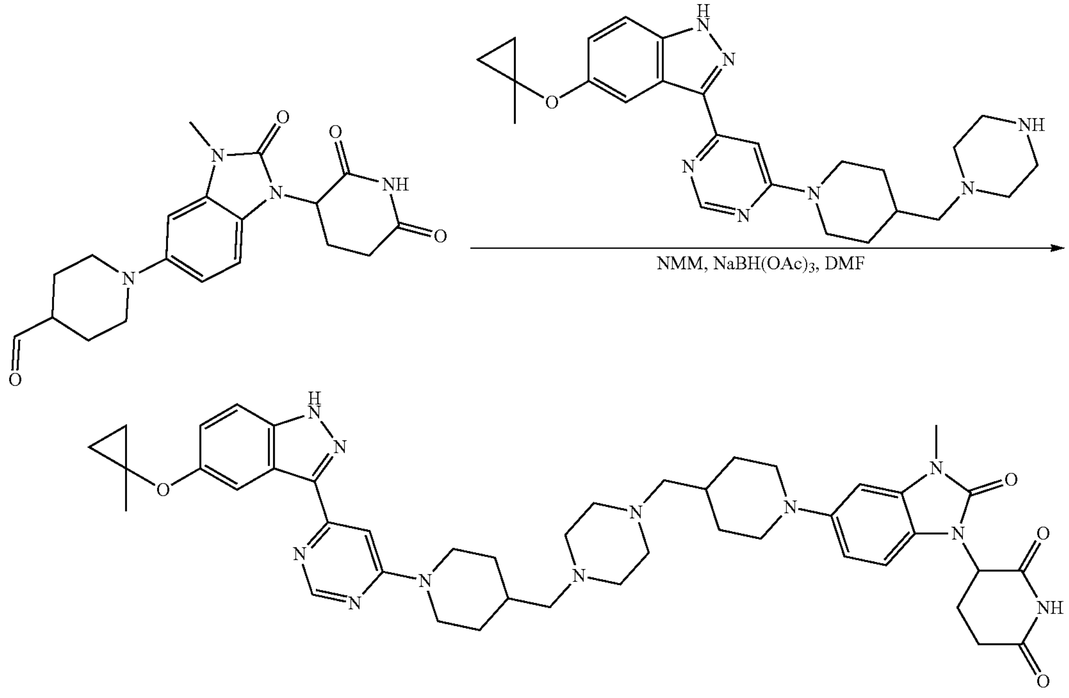

To a solution of 5-(1-methylcyclopropoxy)-3-[6-[4-(piperazin-1-ylmethyl)-1-piperidyl]pyrimidin-4-yl]-1H-indazole (135 mg, 0.24 mmol, 1 eq, 3 hydrochloride acid) in N,N-dimethylformamide (2 mL) was added 4-methylmorpholine (74 mg, 0.73 mmol, 0.080 mL, 3 eq). The solution was stirred at 20° C. for 30 min, and then 1-[1-(2,6-dioxo-3-piperidyl)-3-methyl-2-oxo-benzimidazol-5-yl]piperidine-4-carbaldehyde (90 mg, 0.24 mmol, 1 eq) was added. The mixture was stirred at 20° C. for 30 min and sodium then triacetoxyborohydride (103 mg, 0.49 mmol, 2 eq) was added and the mixture was stirred at 20° C. for another 12 h. The mixture was concentrated in reduced pressure and the resulting residue was purified by semi-preparative reverse phase (column: Phenomenex luna C18 150*25 mm*10 um; mobile phase: [water (FA)-ACN]; B %: 2%-32%, 10 min). Compound 12 (63.7 mg, 0.079 mmol, 32% yield, 99.15% purity) was obtained as orange solid.

Exemplary Synthesis of Compound 16:

Synthesis of Intermediate 3-(2,6-dibenzyloxy-3-pyridyl)-5-[4-(dimethoxymethyl)-1-piperidyl]-1-methyl-benzimidazol-2-one Step 1

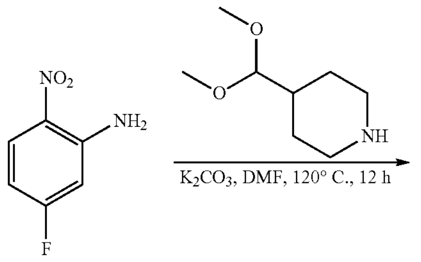

-continued

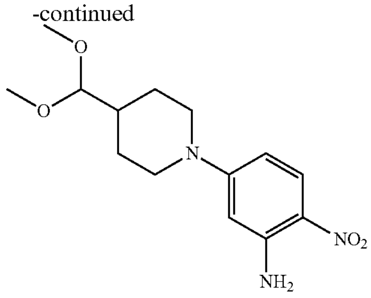

To a mixture of 5-fluoro-2-nitro-aniline (6 g, 38.43 mmol, 1 eq) and 4-(dimethoxymethyl)piperidine (12.24 g, 76.87 mmol, 2 eq) in N,N-dimethylformamide (80 mL) was added potassium carbonate (15.94 g, 115.30 mmol, 3 eq). The mixture was stirred at 120° C. for 12 h and then cooled to 0° C. Water (100 mL) was added which resulted in the formation of solid. The mixture was filtered and the filtrate cake was washed with water (5 mL*3) and dried to provide 5-[4-(dimethoxymethyl)-1-piperidyl]-2-nitro-aniline (10.5 g, 35.55 mmol, 92.51% yield) was obtained as yellow solid.

Step 2

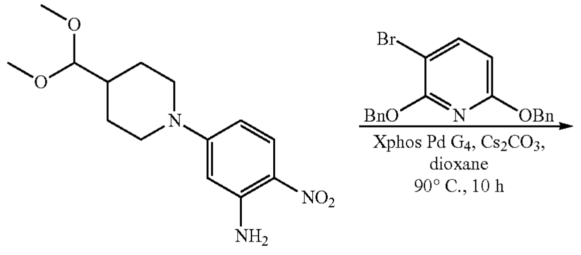

-continued

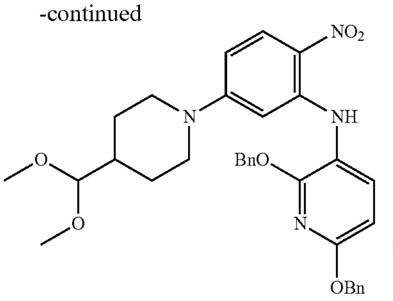

To a mixture of 5-[4-(dimethoxymethyl)-1-piperidyl]-2-nitro-aniline (2.63 g, 8.91 mmol, 1.1 eq) and 2,6-dibenzyloxy-3-bromo-pyridine (3 g, 8.10 mmol, 1 eq) in dioxane (50 mL) was added dicyclohexyl-[2-(2,4,6-triisopropylphenyl)phenyl]phosphane; methanesulfonate; [2-[2-(methylamino)phenyl]phenyl]palladium (1+) (697 mg, 0.81 mmol, 0.1 eq) and cesium carbonate (7.92 g, 24.31 mmol, 3 eq) under nitrogen. The mixture was stirred at 90° C. for 12 h and then cooled to 20° C. Ethyl acetate (50 mL) was added and the mixture was stirred at 20° C. for 30 min, filtered, and the filtrate was concentrated under vacuum. The residue was purified by silica gel chromatography (column height: 250 mm, diameter: 100 mm, 100-200 mesh silica gel, dichloromethane/Ethyl acetate=100/1, 1/1). 2,6-dibenzyloxy-N-[5-[4-(dimethoxymethyl)-1-piperidyl]-2-nitro-phenyl]pyridin-3-amine (4.9 g, 7.21 mmol, 89% yield, 86% purity) was obtained as yellow solid.

Step 3

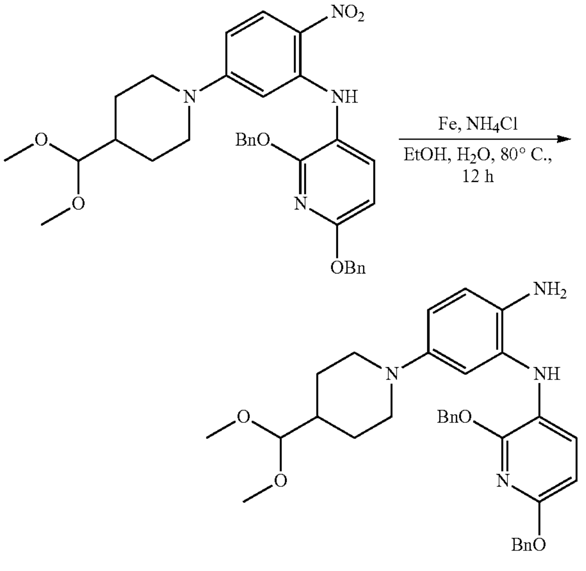

To a mixture of 2,6-dibenzyloxy-N-[5-[4-(dimethoxymethyl)-1-piperidyl]-2-nitro-phenyl]pyridin-3-amine (4.2 g, 7.18 mmol, 1 eq) in ethanol (90 mL) and water (30 mL) was added reduced iron powder (2.01 g, 35.92 mmol, 5 eq) and ammonium chloride (3.84 g, 71.84 mmol, 10 eq). The mixture was stirred at 80° C. for 12 h and then cooled to 20° C. Ethyl acetate (100 mL) was added and the mixture was stirred at 20° C. for 30 min, filtered, the filtrate was concentrated in reduced pressure. The residue was poured into ice-water (w/w=1/1) (100 mL) and extracted with ethyl acetate (100 mL*2). The combined organic phase was washed with brine (100 mL), dried with anhydrous sodium sulfate, filtered, and concentrated under vacuum. The residue was purified by silica gel chromatography (column height: 250 mm, diameter: 100 mm, 100-200 mesh silica gel, dichloromethane/Ethyl acetate=100/1, 1/1). $N_2$-(2,6-dibenzyloxy-3-pyridyl)-4-[4-(dimethoxymethyl)-1-piperidyl]benzene-1,2-diamine (3.8 g, 6.85 mmol, 95% yield) was obtained as brown oil.

Step 4

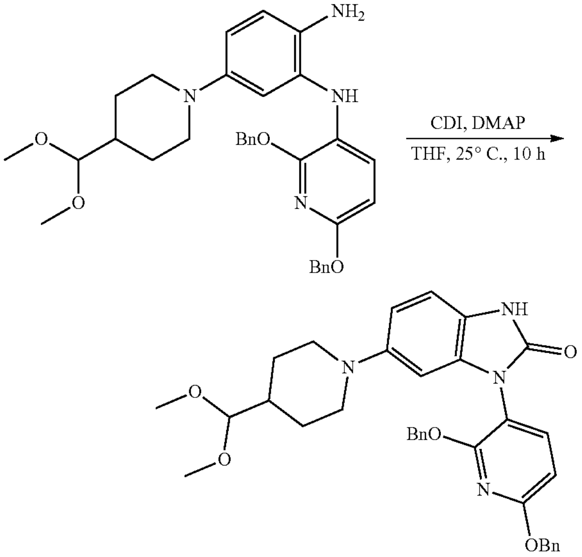

To a solution of $N_2$-(2,6-dibenzyloxy-3-pyridyl)-4-[4-(dimethoxymethyl)-1-piperidyl]benzene-1,2-diamine (3.8 g, 6.85 mmol, 1 eq) in tetrahydrofuran (50 mL) was added 4-dimethylaminopyridine (84 mg, 0.69 mmol, 0.1 eq) and di(1H-imidazol-1-yl) methanone (2.22 g, 13.70 mmol, 2 eq) at 0° C. The mixture was stirred at 20° C. for 12 h and poured into ice-water (w/w=1/1) (50 mL) and extracted with ethyl acetate (50 mL*2). The combined organic phase was washed with brine (50 mL), dried with anhydrous sodium sulfate, filtered, and concentrated under vacuum. The residue was purified by silica gel chromatography (column height: 250 mm, diameter: 100 mm, 100-200 mesh silica gel, Petroleum ether/Ethyl acetate=100/1, 1/2). 3-(2,6-dibenzyloxy-3-pyridyl)-5-[4-(dimethoxymethyl)-1-piperidyl]-1H-benzimidazol-2-one (3.2 g, 5.51 mmol, 80% yield) was obtained as brown solid.

Step 5

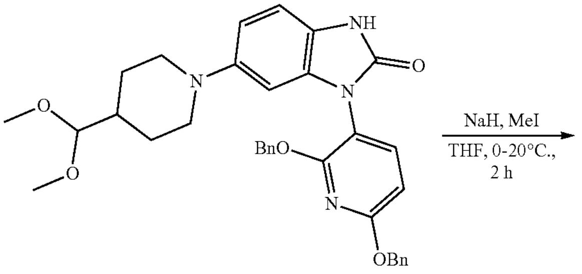

-continued

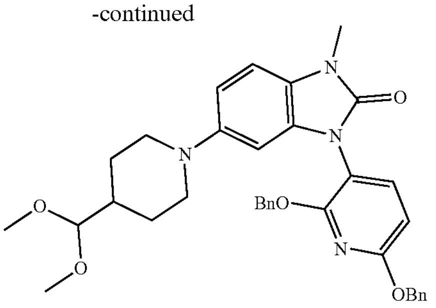

To a mixture of 3-(2,6-dibenzyloxy-3-pyridyl)-5-[4-(dimethoxymethyl)-1-piperidyl]-1H-benzimidazol-2-one (2.9 g, 4.99 mmol, 1 eq) in tetrahydrofuran (60 mL) was added sodium hydride (299 mg, 7.49 mmol, 60% purity, 1.5 eq) at 0° C. The mixture was stirred at 0° C. for 30 min, then the solution of iodomethane (780 mg, 5.49 mmol, 0.34 mL, 1.1 eq) in tetrahydrofuran (20 mL) was added. The mixture was stirred at 20° C. for 2 hours. The mixture was quenched by addition of sat. Ammonium chloride (50 mL) and extracted with ethyl acetate (100 mL*2), and the organic phase was concentrated under reduced pressure. The residue was purified by silica gel chromatography (column height: 250 mm, diameter: 100 mm, 100-200 mesh silica gel, petroleum ether/ethyl acetate=100/1, 1/1). 3-(2,6-dibenzyloxy-3-pyridyl)-5-[4-(dimethoxymethyl)-1-piperidyl]-1-methyl-benzimidazol-2-one (2.7 g, 4.36 mmol, 87% yield, 96% purity) was obtained as yellow solid.

Compound 16, was prepared in a manner analogous to Compound 7, using 3-(2,6-dibenzyloxy-3-pyridyl)-5-[4-(dimethoxymethyl)-1-piperidyl]-1-methyl-benzimidazol-2-one in place of 1-(2,6-dibenzyloxy-3-pyridyl)-5-[4-(dimethoxymethyl)-1-piperidyl]benzimidazole.

Exemplary Synthesis of Compound 18:

Step 1

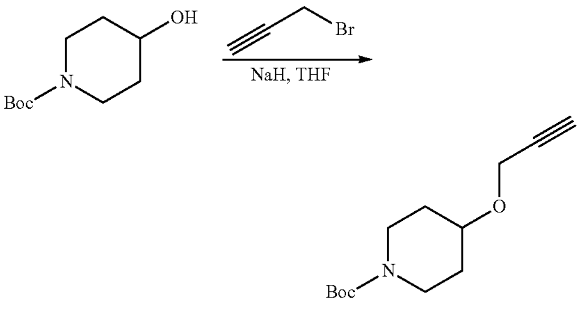

To a solution of tert-butyl 4-hydroxypiperidine-1-carboxylate (2 g, 9.94 mmol, 1 eq) in THF (20 mL) was cooled to 0° C. and NaH (794.91 mg, 19.87 mmol, 60% purity, 2 eq) was added. The reaction mixture was stirred at 0° C. for 0.5 h and then 3-bromoprop-1-yne (1.77 g, 14.91 mmol, 1.28 mL, 1.5 eq) was added and the reaction was stirred at 25° C. for 16 h under $N_2$. The reaction mixture was quenched by addition $H_2O$ (10 mL×2) at 0° C. and extracted with EtOAc (10 mL*3). The combined organic layers were washed with brine (10 mL*3), dried over $Na_2SO_4$, filtered, and concentrated under reduced pressure to give a residue. The residue was purified by flash silica gel chromatography (ISCO®; 12 g SepaFlash® Silica Flash Column, Eluent of 0~10% Ethyl acetate/Petroleum ether gradient @ 60 mL/min) to give tert-butyl 4-prop-2-ynoxypiperidine-1-carboxylate (720 mg, 3.01 mmol, 30.28% yield) as a yellow liquid.

Step 2

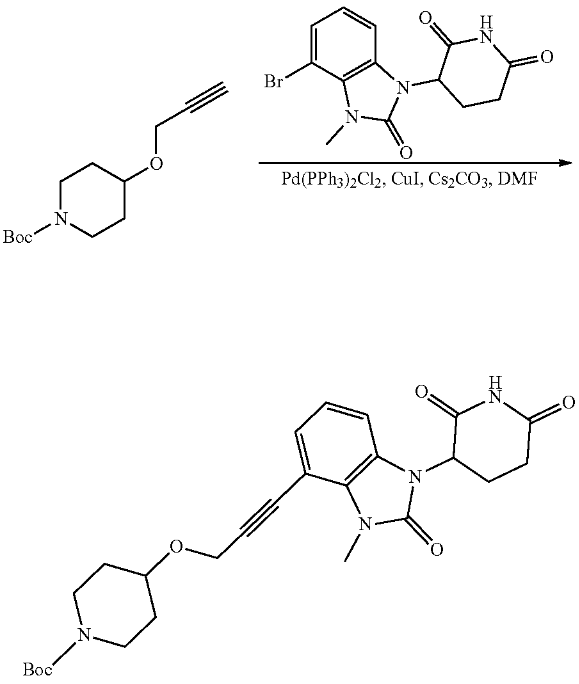

A mixture of tert-butyl 4-prop-2-ynoxypiperidine-1-carboxylate (318 mg, 1.33 mmol, 1.33 eq) and 3-(4-bromo-3-methyl-2-oxo-benzimidazol-1-yl)piperidine-2,6-dione (300 mg, 887.16 μmol, 8.88e-1 eq) in DMF (5 mL) was added $Cs_2CO_3$ (1.16 g, 3.56 mmol, 3.56 eq), CuI (33.8 mg, 177.47 μmol, 1.78e-1 eq) and $Pd(PPh_3)_2Cl_2$ (124 mg, 176.66 μmol, 1.77e-1 eq). The mixture was stirred at 80° C. for 16 h and allowed to cool. The mixture was filtered and concentrated under vacuum. The residue was purified by Biotage® combi flash (column 20 g SepaFlash® Silica Flash column; Eluted: gradient 0~100% Ethyl acetate in petroleum ether; Gradient time: 25 min; Hold time: 20 min; Flow rate: 35 mL/min). Pure fractions were combined and concentrated under reduced pressure to afford tert-butyl 4-[3-[1-(2,6-dioxo-3-piperidyl)-3-methyl-2-oxo-benzimidazol-4-yl]prop-2-ynoxy]piperidine-1-carboxylate (265 mg, 405.60 μmol, 40.60% yield, 76% purity) as a brown oil.

Step 3

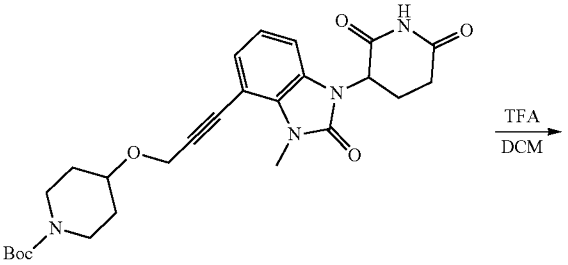

-continued

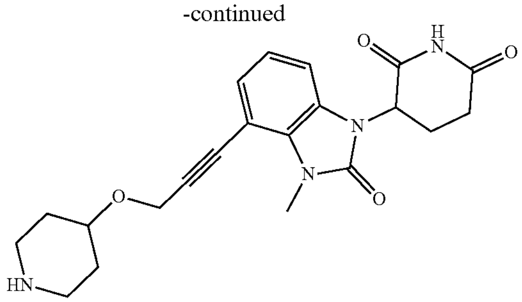

A mixture of tert-butyl 4-[3-[1-(2,6-dioxo-3-piperidyl)-3-methyl-2-oxo-benzimidazol-4-yl]prop-2-ynoxy]piperidine-1-carboxylate (265 mg, 533.68 μmol, 1 eq) in DCM (5 mL) was added TFA (15 M, 1.35 mL, 37.96 eq), then the mixture was stirred at 25° C. for 2 h. TLC (Petroleum ether:Ethyl acetate=3:1) showed one new spot. The residue was filtered and concentrated in vacuum to give 3-[3-methyl-2-oxo-4-[3-(4-piperidyloxy) prop-1-ynyl]benzimidazol-1-yl]piperidine-2,6-dione (200 mg, crude, TFA) was obtained as a brown oil.

Step 4

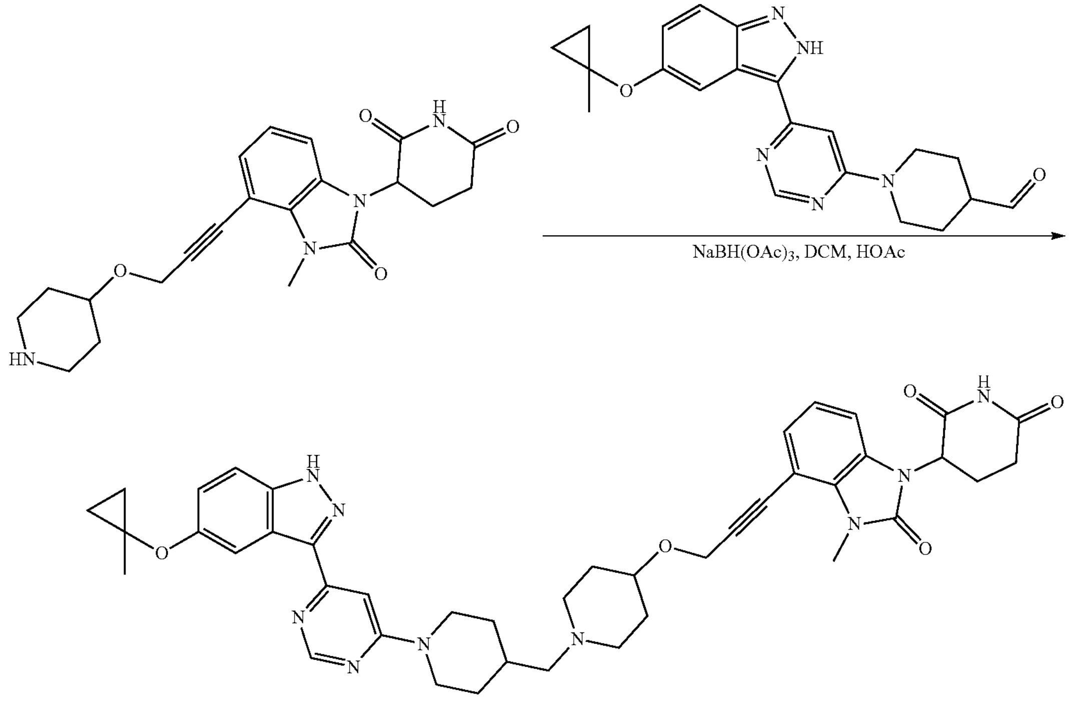

A mixture of 3-[3-methyl-2-oxo-4-[3-(4-piperidyloxy) prop-1-ynyl]benzimidazol-1-yl]piperidine-2,6-dione (200 mg, 391.80 μmol, 1 eq, TFA) and 1-[6-[5-(1-methylcyclopropoxy)-2H-indazol-3-yl]pyrimidin-4-yl]piperidine-4-carbaldehyde (50.48 mg, 133.75 μmol, 3.41e-1 eq) in DCM (10 mL) and DMSO (0.5 mL) was added HOAc (407.73 mg, 6.79 mmol, 388.31 μL, 17.33 eq). The mixture was stirred at 0° C. for 1 h, then $NaBH(OAc)_3$ (83.04 mg, 391.80 μmol, 1 eq) was added and the mixture was stirred at 0° C. for 12 h. The mixture was then filtered and concentrated under vacuum. The resulting residue was purified by prep-HPLC (column: Phenomenex C18 75*30 mm*3 um; mobile phase: [water (FA)-ACN], B %: 8%-38%, 25 min). Compound 18 (16.1 mg, 20.90 μmol, 5.34% yield, 98.4% purity) was obtained as a white solid.

Exemplary Synthesis of Compound 19:

Step 1

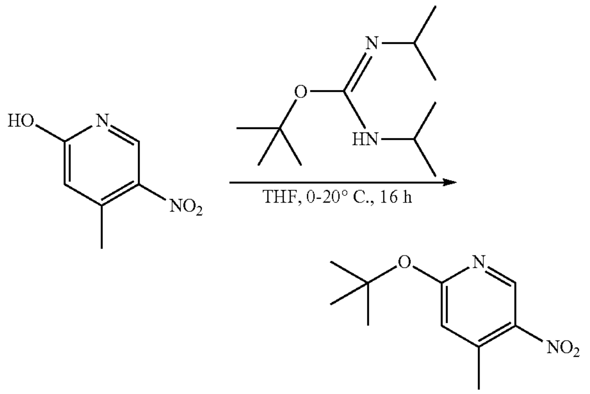

To a stirred solution of 4-methyl-5-nitro-pyridin-2-ol (10 g, 65 mmol) in THF (300 mL) was added 2-tert-butyl-1,3-diisopropyl-isourea (25.99 g, 130 mmol) dropwise at 0° C. under nitrogen atmosphere. Then reaction mixture was stirred for 16 h at 20° C. under nitrogen atmosphere. The mixture was diluted with water (100 mL) and extracted with ethyl acetate (150 mL×3). The combined organic phase was washed with brine (80 mL×2), dried over anhydrous sodium sulfate, filtered and concentrated under reduced pressure. The residue was purified by silica gel chromatography (0-50% ethyl acetate/petroleum ether) to afford 2-tert-butoxy-4-methyl-5-nitro-pyridine (7.7 g, 56%) as colorless oil.

Step 2

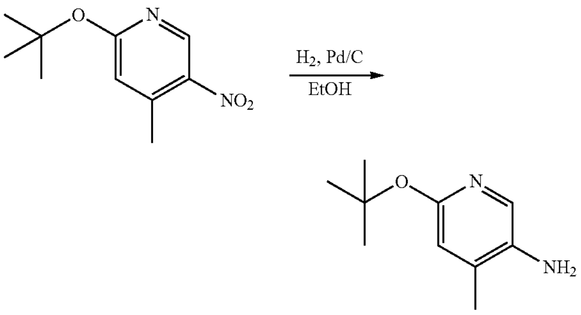

To a stirred solution of 2-tert-butoxy-4-methyl-5-nitro-pyridine (7.7 g, 37 mmol) in THF (100 mL) and EtOH (100 mL) was added 10% palladium over carbon (1 g, 4 mmol). The suspension was degassed and purged with hydrogen several times. The mixture was stirred under hydrogen (50 psi.) at 50° C. for 16 h. The reaction mixture was filtered through celite, washed with THF (100 mL×3) and ethyl acetate (100 mL×3) to afford 6-tert-butoxy-4-methyl-pyridin-3-amine (5.6 g, 85%) as a yellow solid.

Step 3

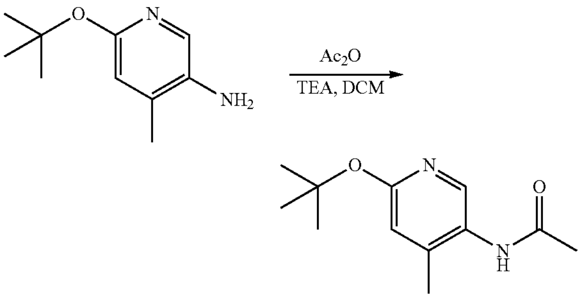

To a solution of 6-tert-butoxy-4-methyl-pyridin-3-amine (2.5 g, 14 mmol) in dichloromethane (30 mL) was added triethylamine (5.23 mL, 38 mmol), followed by the drop-wise addition of acetic anhydride (2.83 mL, 30 mmol) at 0° C. under nitrogen atmosphere. The mixture was stirred at 0° C. for 30 min, then 25° C. for 1 h. The reaction was diluted with water (50 mL) and extracted with ethyl acetate (3×40 mL). The combined organic phases were washed with water (40 mL), dried over sodium sulfate, concentrated under reduced pressure. The residue was purified by silica gel chromatography (0-50% ethyl acetate in petroleum ether) to afford N-(6-tert-butoxy-4-methyl-3-pyridyl) acetamide (3.5 g, 89%, 85% purity) as a yellow solid.

Step 4

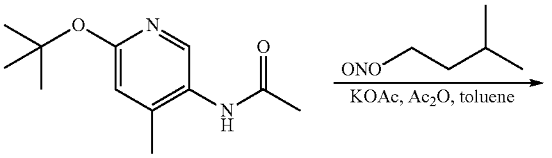

-continued

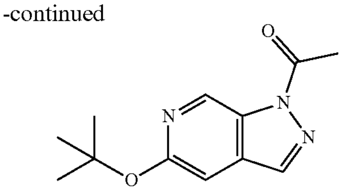

To a solution of N-(6-tert-butoxy-4-methyl-3-pyridyl) acetamide (0.50 g, 2 mmol) in toluene (10 mL) were added acetic anhydride (0.98 mL, 10 mmol) and potassium acetate (331 mg, 3 mmol), the solution was heated to 80° C., and isopentyl nitrite (0.91 mL, 6.8 mmol) was added dropwise. The mixture was stirred at 80° C. for 16 h. The reaction mixture was filtered through celite, the filtrate was diluted with water (50 mL) and extracted with ethyl acetate (3×40 mL). The combined organic phases were washed with water (40 mL), dried over sodium sulfate, filtered and concentrated under reduced pressure. The residue was purified by silica gel chromatography (0-30% ethyl acetate/petroleum ether) to afford 1-(5-tert-butoxypyrazolo[3,4-c]pyridin-1-yl) ethanone (0.3 g, 57%) as a yellow solid.

Step 5

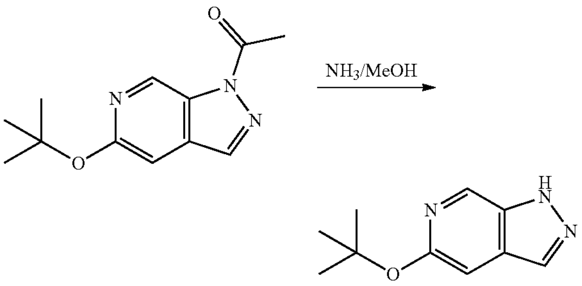

To a mixture of 1-(5-tert-butoxypyrazolo[3,4-c]pyridin-1-yl) ethanone (2.7 g, 12 mmol) in MeOH (10 mL) was added $NH_3$/MeOH (7 M, 2.5 mL) in one portion. The reaction mixture was stirred at 25° C. for 1 h, then concentrated under reduced pressure. The residue was purified by silica gel chromatography (0-50% ethyl acetate/petroleum ether) to afford 5-tert-butoxy-1H-pyrazolo[3,4-c]pyridine (1.57 g, 71%) as a yellow solid.

Step 6

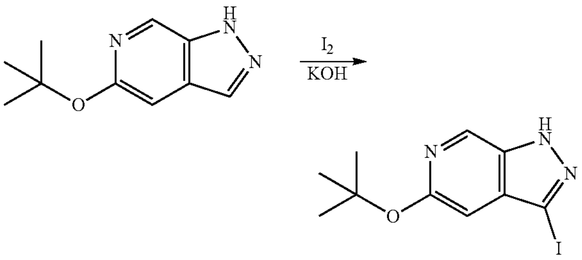

To a solution of 5-tert-butoxy-1H-pyrazolo[3,4-c]pyridine (1.57 g, 8 mmol) in DMF (20 mL) were added potassium hydroxide (1.84 g, 33 mmol) and iodine (3.31 mL, 16 mmol), the solution was stirred at 25° C. for 1 h. The reaction mixture was diluted with saturated sodium thiosulfate solution (50 mL) and extracted with ethyl acetate (2×30 mL). The organic layer was dried over sodium sulfate, filtered and concentrated under reduced pressure. The residue was purified by silica gel chromatography (0-30% ethyl acetate/petroleum ether) to afford 5-tert-butoxy-3-iodo-1H-pyrazolo[3,4-c]pyridine (2.3 g, 88%) as a yellow solid.

Step 7

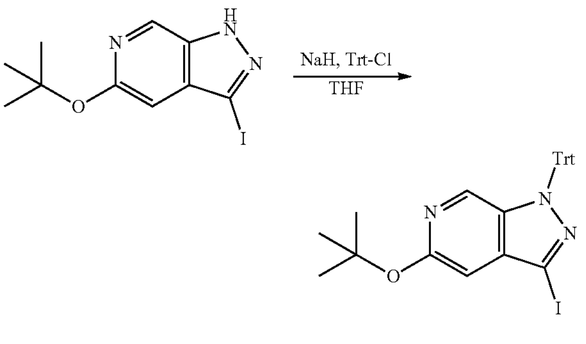

To a solution of 5-tert-butoxy-3-iodo-1H-pyrazolo[3,4-c]pyridine (2.3 g, 7 mmol) in DMF (10 mL) was added NaH (435 mg, 11 mmol, 60%) at 0° C. under nitrogen atmosphere. The solution was stirred at 0° C. for 0.5 h, followed by the addition of trityl chloride (2.43 g, 9 mmol). The reaction mixture was stirred at 25° C. for 2 h under nitrogen atmosphere. The mixture was diluted with water (30 mL) and extracted with ethyl acetate (30 mL×3). The combined organic layers were washed with brine (30 mL×3), dried over sodium sulfate, filtered and concentrated under reduced pressure. The residue was purified by silica gel chromatography (0-6% ethyl acetate/petroleum ether) to afford 5-tert-butoxy-3-iodo-1-trityl-pyrazolo[3,4-c]pyridine (3.6 g, 89%) as a yellow solid.

Step 8

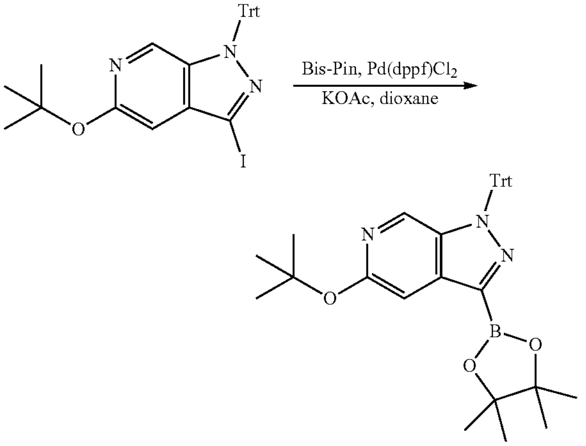

To a solution of 5-tert-butoxy-3-iodo-1-trityl-pyrazolo[3,4-c]pyridine (1 g, 2 mmol) and 4,4,5,5-tetramethyl-2-(4,4,5,5-tetramethyl-1,3,2-dioxaborolan-2-yl)-1,3,2-dioxaborolane (908 mg, 3 mmol) in dioxane (20 mL) were added Pd(dppf)$Cl_2$ (131 mg, 0.2 mmol) and potassium acetate (526 mg, 5 mmol). The mixture was stirred at 100° C. for 16 h under nitrogen atmosphere. The reaction mixture was filtered and the filtrate was concentrated under reduced pressure to afford 5-tert-butoxy-3-(4,4,5,5-tetramethyl-1,3,2-dioxaborolan-2-yl)-1-trityl-pyrazolo[3,4-c]pyridine (1.5 g, crude) as a gray gum, which was used in the next step directly. MS (ESI) m/z: 478.1 $[M-81]^+$.

Step 9

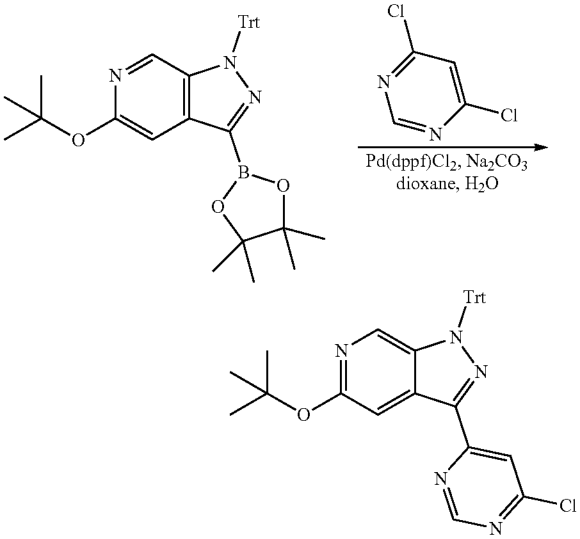

To a solution of 5-tert-butoxy-3-(4,4,5,5-tetramethyl-1,3,2-dioxaborolan-2-yl)-1-trityl-pyrazolo[3,4-c]pyridine (1 g, 2 mmol) and 4,6-dichloropyrimidine (399 mg, 3 mmol) in dioxane (10 mL) and water (2 mL) were added sodium carbonate (568 mg, 5 mmol) and Pd(dppf)$Cl_2$ (131 mg, 0.2 mmol). The mixture was stirred at 100° C. for 1 h under nitrogen atmosphere. The reaction mixture was diluted with water (30 mL) and extracted with ethyl acetate (30 mL×3). The combined organic layers were washed with brine (30 mL×3), dried over sodium sulfate, filtered and concentrated under reduced pressure. The residue was purified by silica gel column chromatography (0 to 30% ethyl acetate in petroleum ether) to afford 5-tert-butoxy-3-(6-chloropyrimidin-4-yl)-1-trityl-pyrazolo[3,4-c]pyridine (0.9 g, 52%, 56% purity) as a yellow solid. MS (ESI) m/z: 546.2 $[M+H]^+$.

Step 10

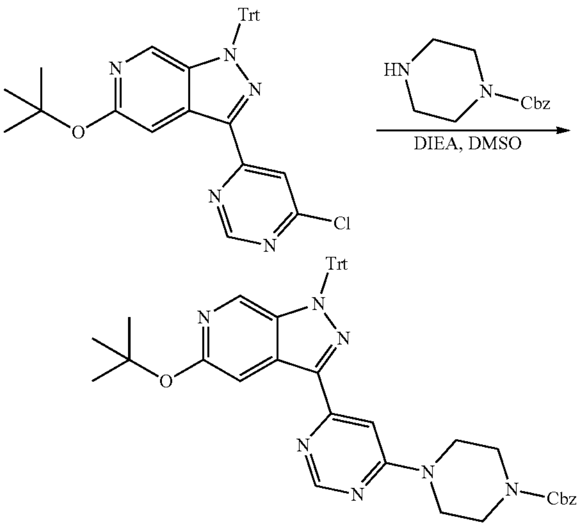

To a solution of benzyl piperazine-1-carboxylate (472 mg, 2 mmol) and 5-tert-butoxy-3-(6-chloropyrimidin-4-yl)-1-trityl-pyrazolo[3,4-c]pyridine (0.9 g, 2 mmol) in DMSO (10 mL) was added DIEA (0.86 mL, 5 mmol). The mixture was stirred at 100° C. for 1 h under nitrogen atmosphere. The reaction was diluted with water (40 mL) and extracted with ethyl acetate (3×40 mL). The combined organic phases were washed with brine (40 mL), dried over sodium sulfate, filtered and concentrated under reduced pressure. The residue was purified by silica gel column chromatography (0 to 30% ethyl acetate in petroleum ether) to afford benzyl 4-[6-(5-tert-butoxy-1-trityl-pyrazolo[3,4-c]pyridin-3-yl)pyrimidin-4-yl]piperazine-1-carboxylate (0.9 g, 75%) as a yellow solid.

Step 11

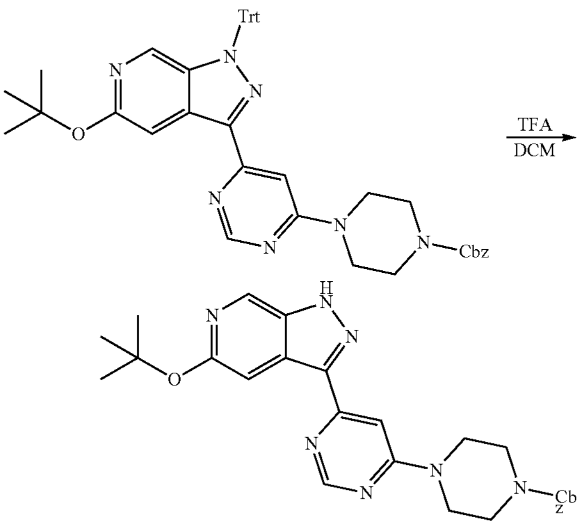

To a solution of benzyl 4-[6-(5-tert-butoxy-1-trityl-pyrazolo[3,4-c]pyridin-3-yl)pyrimidin-4-yl]piperazine-1-carboxylate (1 g, 1 mmol) in dichloromethane (20 mL) was added TFA (4 mL). The mixture was stirred at 0° C. for 3 h. The reaction mixture was diluted with water (10 mL), then sodium bicarbonate was added to adjust the pH to 8, the resulting mixture was extracted with dichloromethane (40 mL×3). The combined organic layer was dried over sodium sulfate, filtered and concentrated under reduced pressure. The residue was purified by silica gel column chromatography (0 to 100% ethyl acetate in petroleum ether) to afford 800 mg crude product as a yellow oil. The material was further purified by prep-HPLC (38%-78% acetonitrile in water (ammonium bicarbonate) over 20 min) to afford benzyl 4-[6-(5-tert-butoxy-1H-pyrazolo[3,4-c]pyridin-3-yl)pyrimidin-4-yl]piperazine-1-carboxylate (230 mg, 34%) as a yellow solid. MS (ESI) m/z: 488.3 $[M+H]^+$.

Step 12

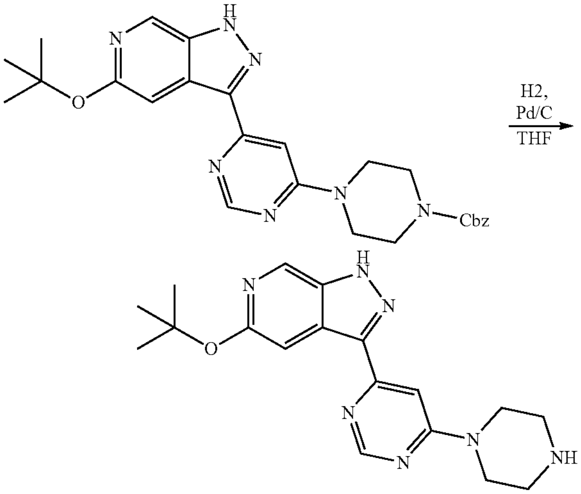

To a stirred solution of benzyl 4-[6-(5-tert-butoxy-1H-pyrazolo[3,4-c]pyridin-3-yl)pyrimidin-4-yl]piperazine-1-carboxylate (230 mg, 0.5 mmol) in EtOH (10 mL) and ethyl acetate (10 mL) was added 10% palladium over carbon (70 mg). The suspension was degassed and purged with hydrogen several times. The reaction mixture was stirred under hydrogen (15 psi.) at 40° C. for 16 h, then filtered through celite. The celite was rinsed with THF (30 mL×3) and ethyl acetate (20 mL×3) and the combined filtrates were concentrated under reduced pressure to afford 5-tert-butoxy-3-(6-piperazin-1-ylpyrimidin-4-yl)-1H-pyrazolo[3,4-c]pyridine (160 mg, 96%) as a yellow solid.

Step 13

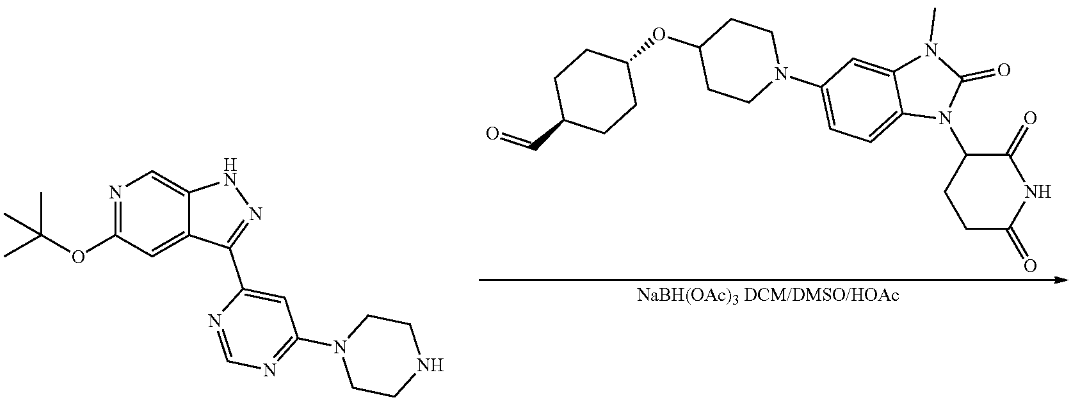

-continued

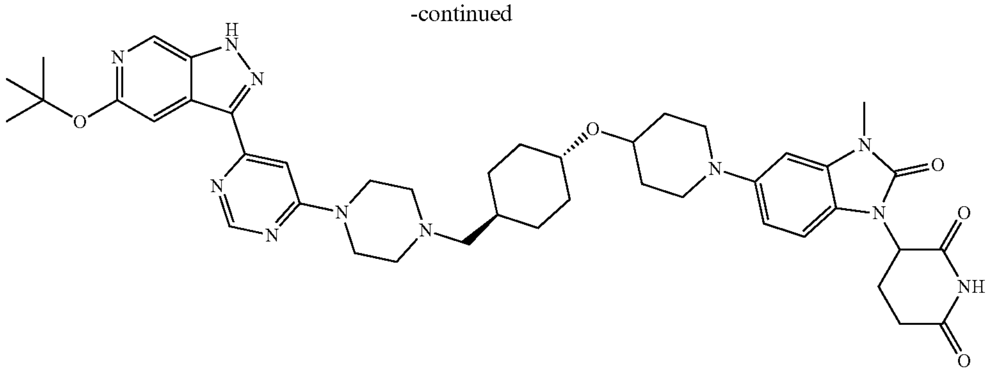

To a solution of 5-tert-butoxy-3-(6-piperazin-1-ylpyrimidin-4-yl)-1H-pyrazolo[3,4-c]pyridine (25 mg, 71 μmol) in dichloromethanedichloromethanme (10 mL) and DMSO (2 mL) was added 4-[[1-[1-(2,6-dioxo-3-piperidyl)-3-methyl-2-oxo-benzimidazol-5-yl]-4-piperidyl]oxy]cyclohexanecarbaldehyde (33.1 mg, 71 μmol) at 0° C., the mixture was stirred for 0.5 h at 0° C. acetic acid before the addition of acetic acid (2.02 μL, 35 μmol). The mixture was stirred at 0° C. for 2 h, followed by adding sodium triacetoxyborohydride (29.98 mg, 141 μmol,). The reaction mixture was stirred at 0° C. for 2 h, then diluted with water (40 mL) and extracted with dichloromethane (30 mL×3). The organic phase was washed with brine (30 mL), dried over anhydrous sodium sulfate and concentrated under reduced pressure. The residue was purified by prep-HPLC (36%-76% acetonitrile in water (ammonium bicarbonate) over 20 min) to give Compound 19 (22.4 mg, 39%) as off-white solid. MS (ESI) m/z: 806.5 $[M+H]^+$.

Exemplary Synthesis of Compound 20:

Step 1

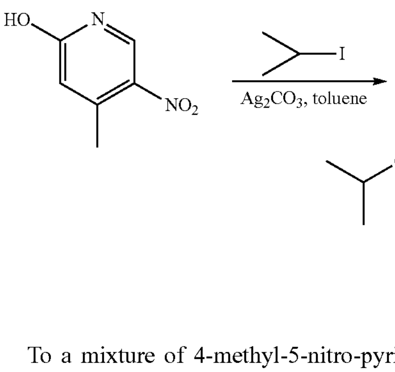

To a mixture of 4-methyl-5-nitro-pyridin-2-ol (10 g, 65 mmol) and 2-iodopropane (19.4 mL, 195 mmol) in toluene (240 mL) was added silver carbonate (3.42 mL, 75 mmol). The mixture was stirred at 60° C. for 16 h under nitrogen atmosphere. The reaction mixture was filtered through celite, the filtrate was diluted with water (50 mL) and extracted with ethyl acetate (3×200 mL). The combined organic phases were washed with brine (100 mL), dried over sodium sulfate, filtered and concentrated under reduced pressure. The residue was purified by silica gel chromatography (0-15% ethyl acetate/petroleum ether) to afford 2-isopropoxy-4-methyl-5-nitro-pyridine (12 g, 94%) as a yellow solid.

Step 2

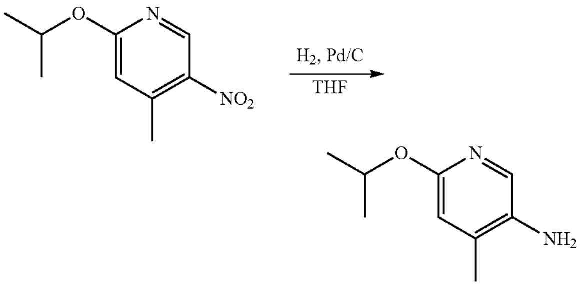

To a mixture of 2-isopropoxy-4-methyl-5-nitro-pyridine (12 g, 61 mmol) in THF (200 mL) was added 10% palladium over carbon (1.4 g). The suspension was degassed and purged with hydrogen several times, then stirred at 25° C. for 16 h under hydrogen (40 psi). The reaction mixture was filtered through celite, washed with MeOH (500 mL) and concentrated under reduced pressure to afford 6-isopropoxy-4-methyl-pyridin-3-amine (10.1 g, 99%) as a yellow gum.

Step 3

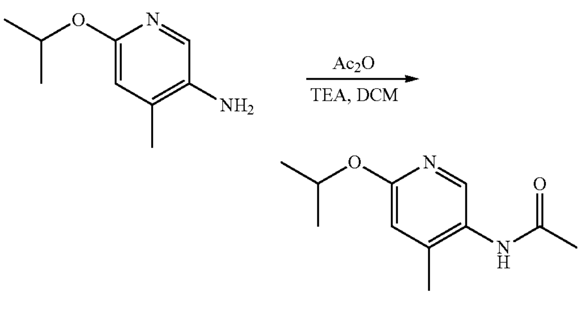

To a solution of 6-isopropoxy-4-methyl-pyridin-3-amine (10 g, 60 mmol) in dichloromethane (100 mL) was added triethylamine (21 mL, 0.15 mol), followed by the dropwise addition of acetic anhydride (11.3 mL, 0.12 mol) at 0° C. under nitrogen atmosphere. The mixture was stirred at 0° C. for 30 min, then 25° C. for 1 h. The reaction mixture was diluted with water (50 mL) and extracted with ethyl acetate (3×50 mL). The combined organic phases were washed with brine (50 mL), dried over sodium sulfate, filtered and concentrated under reduced pressure. The residue was purified by silica gel chromatography (0-50% ethyl acetate/petroleum ether) to afford N-(6-isopropoxy-4-methyl-3-pyridyl) acetamide (12 g, 96%) as a yellow solid.

Step 4

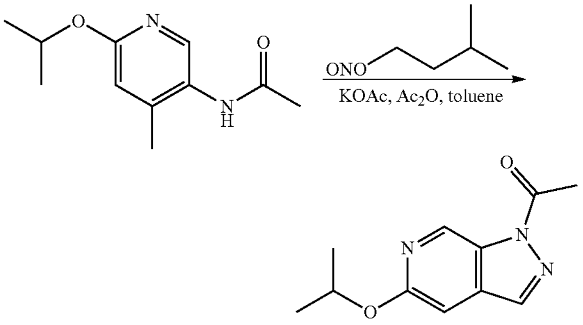

To a solution of N-(6-isopropoxy-4-methyl-3-pyridyl) acetamide (12 g, 58 mmol) in toluene (80 mL) were added acetic anhydride (25 mL, 0.27 mol) and potassium acetate (8.48 g, 86 mmol), the solution was heated to 80° C. and isopentyl nitrite (31 mL, 0.23 mol) was dropwise added. The reaction mixture was stirred at 80° C. for 16 h, then filtered through celite. The filtrate solution was diluted with water (50 mL) and extracted with ethyl acetate (3×200 mL). The combined organic phases were washed with brine (100 mL), dried over sodium sulfate, filtered and concentrated under reduced pressure. The residue was purified by silica gel chromatography (0-30% ethyl acetate/petroleum ether) to afford 1-(5-isopropoxypyrazolo[3,4-c]pyridin-1-yl) ethanone (7.5 g, 59%) as a yellow solid.

Step 5

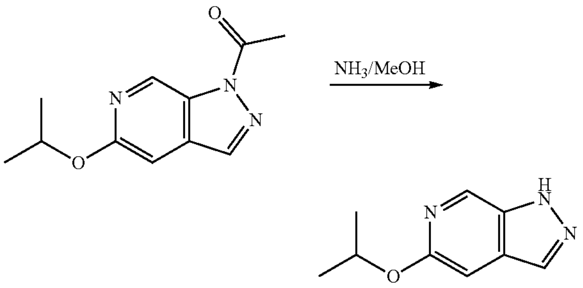

To a mixture of 1-(5-isopropoxypyrazolo[3,4-c]pyridin-1-yl) ethanone (7.5 g, 34 mmol) in MeOH (100 mL) was added $NH_3$/MeOH (7 M, 7.33 mL). The mixture was stirred at 25° C. for 16 h, then concentrated under reduced pressure. The residue was purified by silica gel chromatography (0-50% ethyl acetate/petroleum ether) to afford 5-isopropoxy-1H-pyrazolo[3,4-c]pyridine (5.3 g, 87%) as a yellow solid.

Step 6

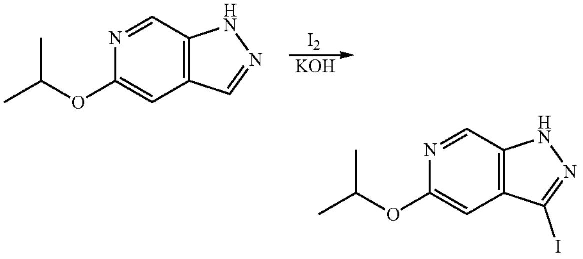

To a solution of 5-isopropoxy-1H-pyrazolo[3,4-c]pyridine (5.3 g, 30 mmol) in DMF (50 mL) were added potassium hydroxide (6.71 g, 0.12 mol) and iodine (12 mL, 60 mmol), the solution was stirred at 25° C. for 1 h. The reaction mixture was diluted with saturated sodium thiosulfate solution (50 mL) and extracted with ethyl acetate (2×30 mL). The organic layer was dried over sodium sulfate, filtered and concentrated under reduced pressure. The residue was purified by silica gel chromatography (0-30% ethyl acetate/petroleum ether) to afford 3-iodo-5-isopropoxy-1H-pyrazolo[3,4-c]pyridine (7 g, 77%) as a yellow solid.

Step 7

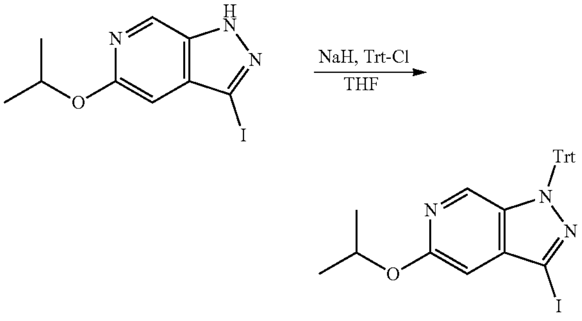

To a solution of 3-iodo-5-isopropoxy-1H-pyrazolo[3,4-c]pyridine (7.0 g, 23 mmol) in DMF (50 mL) was added sodium hydride (1.39 g, 35 mmol, 60%). The solution was stirred at 0° C. for 0.5 h before the addition of trityl chloride (7.73 g, 28 mmol). The reaction mixture was stirred at 25° C. for 2 h, then diluted with water (50 mL) and extracted with ethyl acetate (30 mL×3). The combined organic layers were washed with brine (20 mL×3), dried over sodium sulfate, filtered and concentrated under reduced pressure. The residue was purified by silica gel chromatography (0-6% ethyl acetate/petroleum ether) to afford 3-iodo-5-isopropoxy-1-trityl-pyrazolo[3,4-c]pyridine (7 g, 56%) as an off-white solid.

Step 8

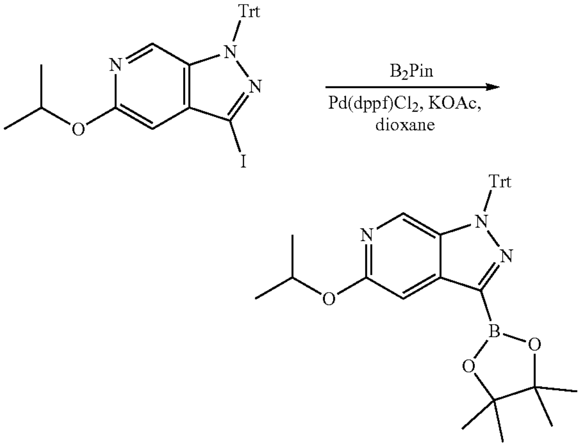

To a solution of 3-iodo-5-isopropoxy-1-trityl-pyrazolo[3,4-c]pyridine (2 g, 4 mmol) and 4,4,5,5-tetramethyl-2-(4,4,5,5-tetramethyl-1,3,2-dioxaborolan-2-yl)-1,3,2-dioxaborolane (1.86 g, 7 mmol) in dioxane (20 mL) were added Pd(dppf)$Cl_2$ (268.3 mg, 0.4 mmol) and potassium acetate (1.08 g, 11 mmol). The mixture was stirred at 100° C. for 16 h under nitrogen atmosphere. The reaction mixture was filtered and concentrated under reduced pressure to afford 5-isopropoxy-3-(4,4,5,5-tetramethyl-1,3,2-dioxaborolan-2-yl)-1-trityl-pyrazolo[3,4-c]pyridine (2. g, crude) as a gray gum, which was used in the next step directly. MS (ESI) m/z: 464.1 [M−81]$^+$.

Step 9

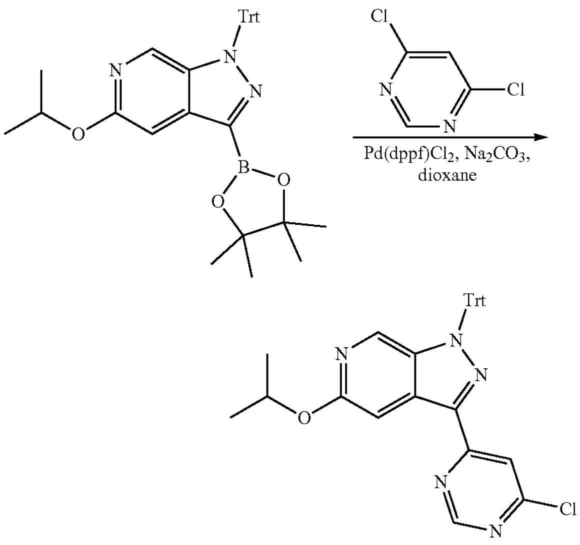

To a solution of 5-isopropoxy-3-(4,4,5,5-tetramethyl-1,3,2-dioxaborolan-2-yl)-1-trityl-pyrazolo[3,4-c]pyridine (2 g, 4 mmol) and 4,6-dichloropyrimidine (819 mg, 6 mmol) in dioxane (20 mL) and water (4 mL) were added sodium carbonate (1.17 g, 11 mmol) and Pd(dppf)$Cl_2$ (268.3 mg, 0.4 mmol). The mixture was stirred at 100° C. for 1 h under nitrogen atmosphere, then filtered and concentrated under reduced pressure. The residue was diluted with water (20 mL) and extracted with ethyl acetate (3×20 mL). The combined organic phases were washed with water, dried over sodium sulfate, filtered and concentrated under reduced pressure. The residue was purified by silica gel column chromatography (0 to 30% ethyl acetate in petroleum ether) to afford 3-(6-chloropyrimidin-4-yl)-5-isopropoxy-1-trityl-pyrazolo[3,4-c]pyridine (1.1 g, 56%) as an off-white solid.

Step 10

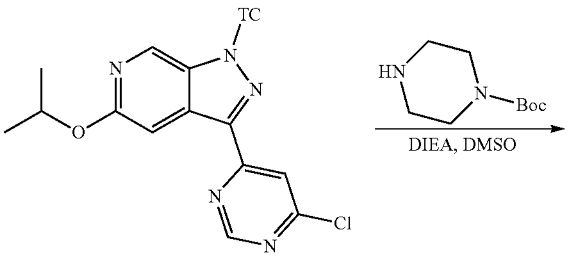

-continued

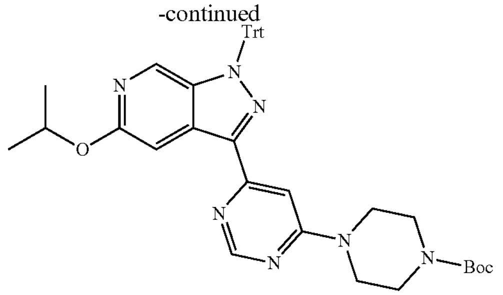

To a solution of tert-butyl piperazine-1-carboxylate (578 mg, 3 mmol) and 3-(6-chloropyrimidin-4-yl)-5-isopropoxy-1-trityl-pyrazolo[3,4-c]pyridine (1.1 g, 2 mmol) in DMSO (10 mL) was added DIEA (1.08 mL, 6 mmol). The mixture was stirred at 100° C. for 1 h under nitrogen atmosphere, then diluted with water (40 mL) and extracted with ethyl acetate (3×40 mL). The combined organic phases were washed with brine (50 mL), dried over sodium sulfate, filtered and concentrated under reduced pressure. The residue was purified by silica gel column chromatography (0 to 30% ethyl acetate in petroleum ether) to afford tert-butyl 4-[6-(5-isopropoxy-1-trityl-pyrazolo[3,4-c]pyridin-3-yl)pyrimidin-4-yl]piperazine-1-carboxylate (1.3 g, 92%) as a yellow solid.

Step 11

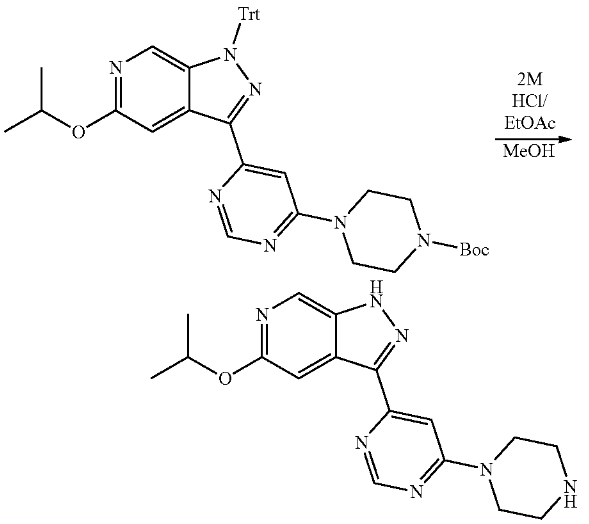

To a solution of tert-butyl 4-[6-(5-isopropoxy-1-trityl-pyrazolo[3,4-c]pyridin-3-yl)pyrimidin-4-yl]piperazine-1-carboxylate (1.22 g, 1.8 mmol) in MeOH (8 mL) was added HCl/dioxane (2 M, 10 mL). The mixture was stirred at 40° C. for 16 h under nitrogen atmosphere, then diluted with water (10 mL). The pH of the mixture was adjusted to 13 with sodium hydroxide, then extracted with ethyl acetate (40 mL×3). The organic layer was dried over sodium sulfate, filtered and concentrated under reduced pressure to afford 5-isopropoxy-3-(6-piperazin-1-ylpyrimidin-4-yl)-1H-pyrazolo[3,4-c]pyridine (0.6 g, 99%) as a red solid, which was used in the next step directly.

Step 12

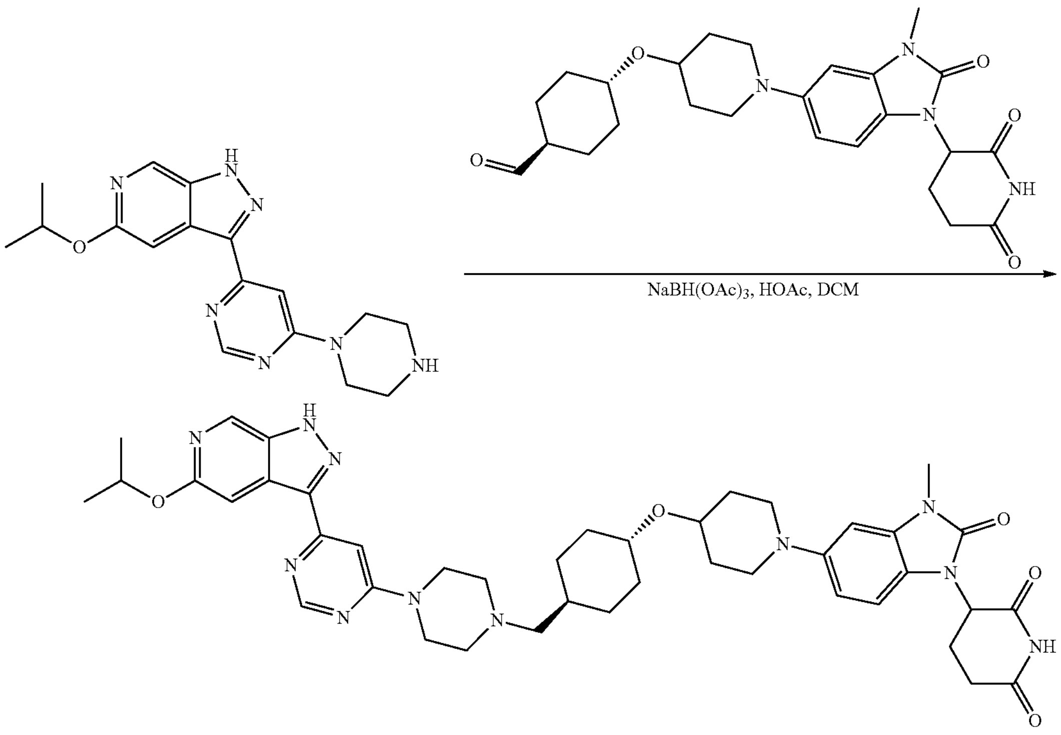

To a solution of 5-isopropoxy-3-(6-piperazin-1-ylpyrimidin-4-yl)-1H-pyrazolo[3,4-c]pyridine (100 mg, 0.29 mmol) and 4-[[1-[1-(2,6-dioxo-3-piperidyl)-3-methyl-2-oxo-benzimidazol-5-yl]-4-piperidyl]oxy]cyclohexanecarbaldehyde (138 mg, 0.29 mmol) in dichloromethanedichloromethane (10 mL) was added acetic acid (16.9 μL 0.29 mmol) at 0° C. under nitrogen atmosphere. The mixture was stirred at 0° C. for 30 min and then sodium triacetoxyborohydridesodium triacetoxyborohydride (156.1 mg, 0.74 mmol) was added. The mixture was stirred at 0° C. for 12 h and filtered. The filtrate solution was concentrated. The residue was purified by prep-HPLC (0%-34% acetonitrile in water (TFA) over 20 min), the crude product was further purified by prep-HPLC (0%-32% acetonitrile in water (formic acid) over 20.5 min) to afford Compound 20 (104.7 mg, 45%) as an off-white solid. MS (ESI) m/z: 792.4 $[M+H]^+$.

Exemplary Synthesis of Compound 21:

Step 1

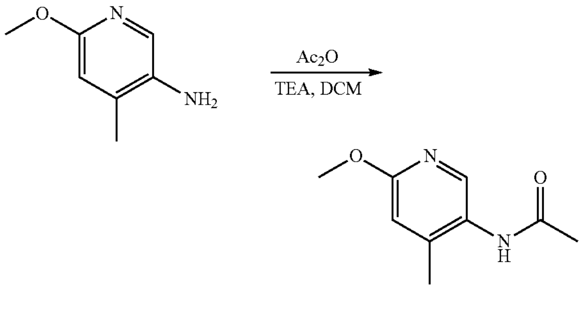

To a mixture of 6-methoxy-4-methyl-pyridin-3-amine (10 g, 72 mmol) and triethylamine (25.18 mL, 181 mmol) in dichloromethane (100 mL) was added acetic anhydride (13.6 mL, 145 mmol). The mixture was stirred at 25° C. for 16 h, then diluted with water (60 mL) and extracted with ethyl acetate (60 mL×3). The combined organic phase was washed with brine (60 mL×2), dried over anhydrous sodium sulfate, filtered and concentrated under reduced pressure. The residue was purified by silica gel chromatography (0-100% ethyl acetate in petroleum ether) to afford N-(6-methoxy-4-methyl-3-pyridyl) acetamide (12 g, 92%) as a yellow gum. MS (ESI) m/z: 180.9 $[M+H]^+$.

Step 2

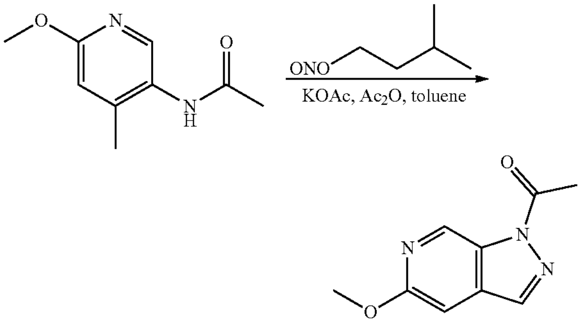

To a solution of N-(6-methoxy-4-methyl-3-pyridyl) acetamide (12.0 g, 66 mmol) in toluene (20 mL) were added acetic anhydride (28.8 mL, 306 mmol) and potassium acetate (9.80 g, 100 mmol), the solution was heated to 80° C., followed by the dropwise addition of isopentyl nitrite (35.9 mL, 266 mmol). The reaction mixture was stirred at 80° C. for 16 h, then filtered and concentrated under reduced pressure. The residue was purified by silica gel chromatography (0-13% ethyl acetate in petroleum ether) to afford 1-(5-methoxypyrazolo[3,4-c]pyridin-1-yl) ethanone (8.2 g, 64%) as a yellow solid. MS (ESI) m/z: 192.0 $[M+H]^+$.

Step 3

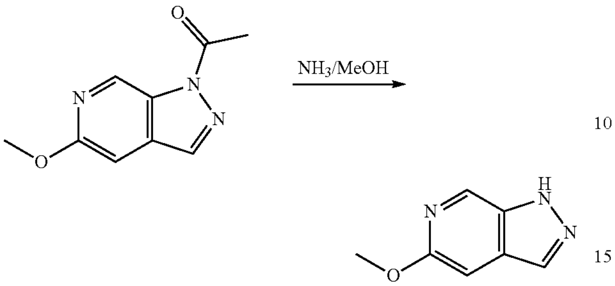

To a mixture of 1-(5-methoxypyrazolo[3,4-c]pyridin-1-yl) ethanone (8.2 g, 43 mmol) in MeOH (100 mL) was added $NH_3$/MeOH (7 M, 12.3 mL). The mixture was stirred at 25° C. for 16 h, then concentrated under reduced pressure. The residue was triturated with methyl tert-butyl ether:petroleum ether (1:1) to afford 5-methoxy-1H-pyrazolo[3,4-c]pyridine (6.3 g, 98%) as a yellow solid. MS (ESI) m/z: 150.0 $[M+H]^+$.

Step 4

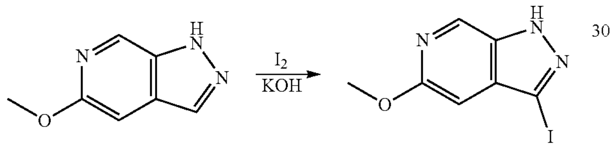

To a mixture of 5-methoxy-1H-pyrazolo[3,4-c]pyridine (6.2 g, 41 mmol) and potassium hydroxide (9.33 g, 166 mmol) in DMF (50 mL) was added iodine (16.8 mL, 83 mmol). The mixture was stirred at 25° C. for 16 h. The reaction mixture was diluted with saturated sodium thiosulfate solution (50 mL) and extracted with ethyl acetate (3×50 mL). The combined organic layers were washed with brine (3×40 mL), dried over anhydrous sodium sulfate, filtered and concentrated under reduced pressure. The residue was triturated with methyl tert-butyl ether:acetonitrile (5:1) to afford 3-iodo-5-methoxy-1H-pyrazolo[3,4-c]pyridine (8.2 g, 72%) as a yellow solid. MS (ESI) m/z: 275.8 $[M+H]^+$.

Step 5

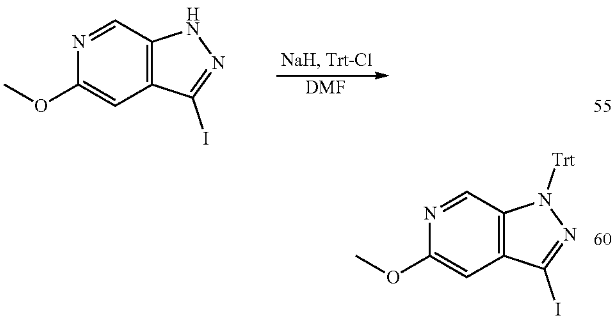

To a mixture of 3-iodo-5-methoxy-1H-pyrazolo[3,4-c]pyridine (7.5 g, 27 mmol) in DMF (30 mL) was added sodium hydride (1.64 g, 41 mmol, 60%) at 0° C., the mixture was stirred at 25° C. for 1 h under nitrogen atmosphere, followed by the addition of trityl chloride (9.12 g, 33 mmol) at 0° C. The reaction mixture was stirred at 25° C. for 15 h, then diluted with water (50 mL) and extracted with ethyl acetate (60 mL×3). The combined organic phase was washed with brine (50 mL), dried over anhydrous sodium sulfate, filtered and concentrated under reduced pressure. The residue was purified by silica gel chromatography (0-14% ethyl acetate in petroleum ether) to afford 3-iodo-5-methoxy-1-trityl-pyrazolo[3,4-c]pyridine (7.2 g, 51%) as a yellow solid.

Step 6

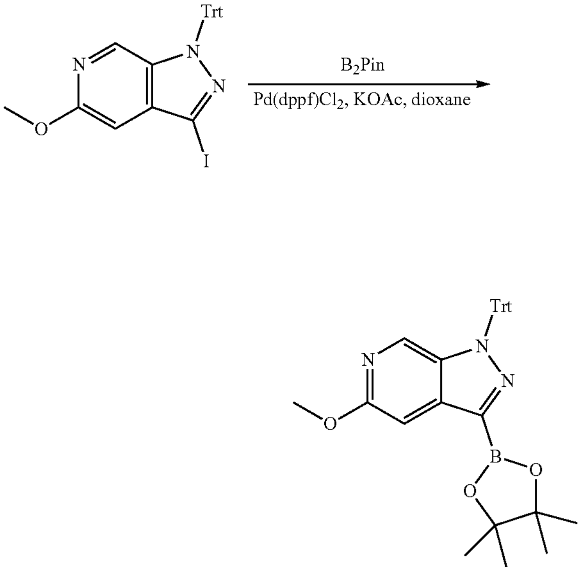

To a mixture of 3-iodo-5-methoxy-1-trityl-pyrazolo[3,4-c]pyridine (2 g, 4 mmol) and 4,4,5,5-tetramethyl-2-(4,4,5,5-tetramethyl-1,3,2-dioxaborolan-2-yl)-1,3,2-dioxaborolane (1.47 g, 6 mmol) in dioxane (10 mL) were added Pd(dppf)$Cl_2$ (282.9 mg, 0.4 mmol) and potassium acetate (1.14 g, 12 mmol) under nitrogen atmosphere. The mixture was stirred at 100° C. for 16 h under nitrogen atmosphere, then filtered and concentrated under reduced pressure to afford 5-methoxy-3-(4,4,5,5-tetramethyl-1,3,2-dioxaborolan-2-yl)-1-trityl-pyrazolo[3,4-c]pyridine (2 g, 75%, 75% purity) as black solid, which was used in the next step directly. MS (ESI) m/z: 436.2 $[M-81+H]^+$.

Step 7

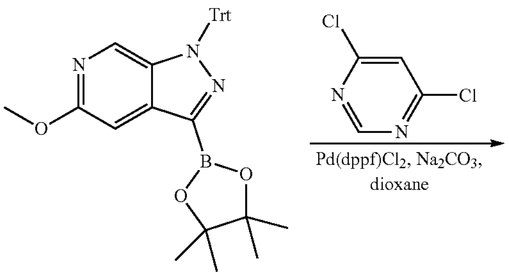

-continued

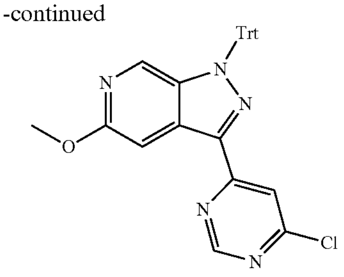

To a mixture of 5-methoxy-3-(4,4,5,5-tetramethyl-1,3,2-dioxaborolan-2-yl)-1-trityl-pyrazolo[3,4-c]pyridine (2 g, 4 mmol) and 4,6-dichloropyrimidine (748.6 mg, 5 mmol) in dioxane (50 mL) and water (5 mL) were added Pd(dppf)$Cl_2$ (282.8 mg, 0.4 mmol) and sodium carbonate (1.23 g, 12 mmol) under nitrogen atmosphere. The mixture was stirred at 100° C. for 2 h under nitrogen, then filtered and concentrated under reduced pressure. The residue was purified by silica gel chromatography (0-17% ethyl acetate in petroleum ether) to afford 3-(6-chloropyrimidin-4-yl)-5-methoxy-1-trityl-pyrazolo[3,4-c]pyridine (680 mg, 35%) as a yellow solid. MS (ESI) m/z: 504.1 $[M+H]^+$.

Step 8

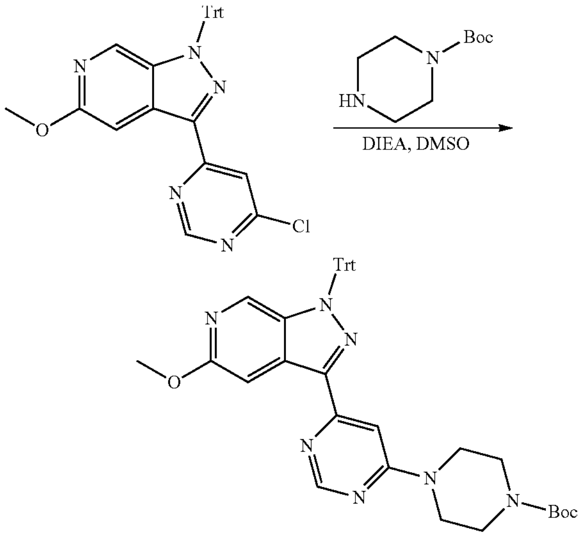

To a mixture of 3-(6-chloropyrimidin-4-yl)-5-methoxy-1-trityl-pyrazolo[3,4-c]pyridine (250 mg, 0.5 mmol) and tert-butyl piperazine-1-carboxylate (120 mg, 0.6 mmol) in DMSO (5 mL) was added DIEA (260 μL, 1.5 mmol). The mixture was stirred at 100° C. for 1 h, then diluted with water (60 mL) and extracted with ethyl acetate (60 mL×3). The combined organic phase was washed with brine (60 mL×2), dried over anhydrous sodium sulfate, filtered and concentrated under reduced pressure. The residue was purified by silica gel chromatography (0-23% ethyl acetate in petroleum ether) to afford tert-butyl 4-[6-(5-methoxy-1-trityl-pyrazolo[3,4-c]pyridin-3-yl)pyrimidin-4-yl]piperazine-1-carboxylate (250 mg, 77%) as a yellow solid. MS (ESI) m/z: 654.4 $[M+H]^+$.

Step 9

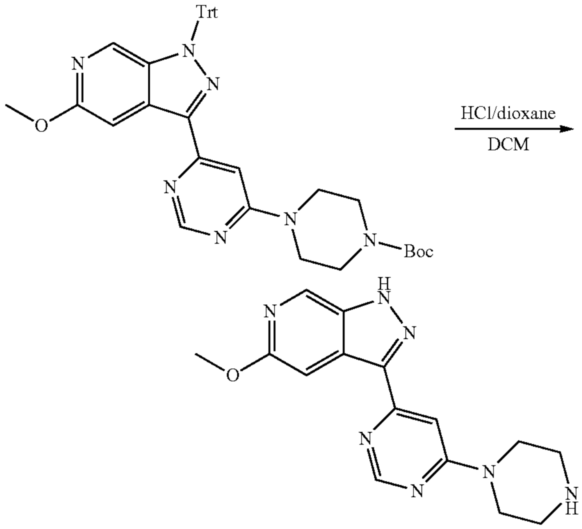

To a mixture of tert-butyl 4-[6-(5-methoxy-1-trityl-pyrazolo[3,4-c]pyridin-3-yl)pyrimidin-4-yl]piperazine-1-carboxylate (250 mg, 0.4 mmol) in MeOH (5 mL) was added HCl/dioxane (2 M, 10 mL). The mixture was stirred at 40° C. for 1 h, then sodium hydroxide was added to adjust the pH to 14, the resulting mixture was concentrated under reduced pressure. The residue was suspended in dichloromethane:MeOH (10:1), filtered and the filtrate solution was concentrated under reduced pressure to afford 5-methoxy-3-(6-piperazin-1-ylpyrimidin-4-yl)-1H-pyrazolo[3,4-c]pyridine (110 mg, 83%) as pink solid. MS (ESI) m/z: 312.2 $[M+H]^+$.

Step 10

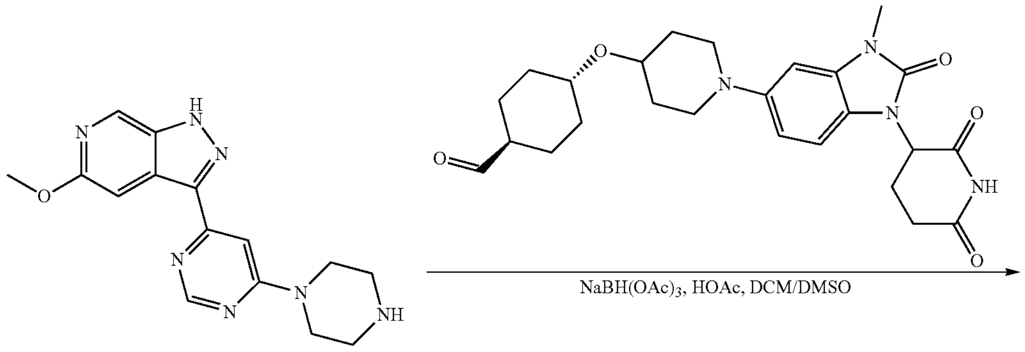

-continued

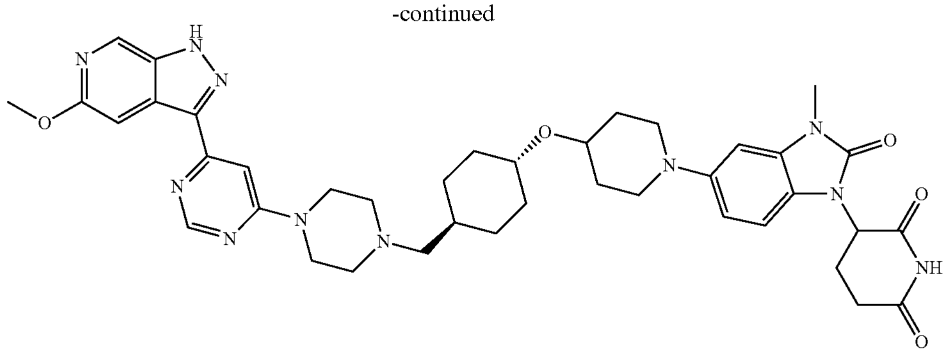

To a mixture of 5-methoxy-3-(6-piperazin-1-ylpyrimidin-4-yl)-1H-pyrazolo[3,4-c]pyridine (110 mg, 0.35 mmol) and 4-[[1-[1-(2,6-dioxo-3-piperidyl)-3-methyl-2-oxo-benzimidazol-5-yl]-4-piperidyl]oxy]cyclohexanecarbaldehyde (165.5 mg, 0.35 mmol) in dichloromethanedichloromethane (5 mL) was added acetic acid (60.68 μL, 1.1 mmol) in one portion at 0° C. under nitrogen atmosphere. The mixture was stirred for 1 h before the addition of sodium triacetoxyborohydride sodium triacetoxyborohydride (149.8 mg, 0.7 mmol). The reaction mixture was stirred for 3 h, then filtered and concentrated under reduced pressure. The residue was purified by prep-HPLC (0%-30% acetonitrile in water (formic acid) over 20.5 min) to give Compound 21 (93.7 mg, 33%, formic acid salt) as white solid. MS (ESI) m/z: 764.6 $[M+H]^+$.

Exemplary Synthesis of Compound 22:

Step 1

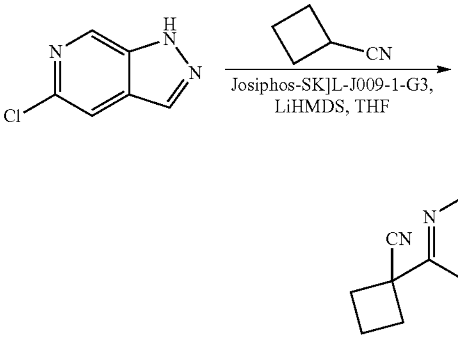

To a solution of 5-chloro-1H-pyrazolo[3,4-c]pyridine (1.0 g, 7 mmol), cyclobutanecarbonitrile (1.58 g, 19 mmol) and {(R)-1-[(sp)-2-(dicyclohexylphosphino) ferrocenyl]ethyldi-tert-butylphosphine}[2-(2'-amino-1,1'-biphenyl)]palladium (II) methanesulfonate (602 mg, 0.7 mmol) in THF (20 mL) was added lithium bis(trimethylsilyl)amide (1 M, 16.3 mL). The mixture was stirred at 80° C. for 12 h, then slowly diluted with saturated ammonium chloride solution (100 mL) at 0° C. and extracted with ethyl acetate (100 mL×2). The combined organic phase was washed with brine (100 mL), dried over anhydrous sodium sulfate, filtered and concentrated under reduced pressure. The residue was purified by silica gel chromatography (0-30% ethyl acetate/petroleum ether) to afford 1-(1H-pyrazolo[3,4-c]pyridin-5-yl)cyclobutanecarbonitrile (1.2 g, 93%) as a yellow solid. MS (ESI) m/z: 199.1 $[M+H]^+$.

Step 2

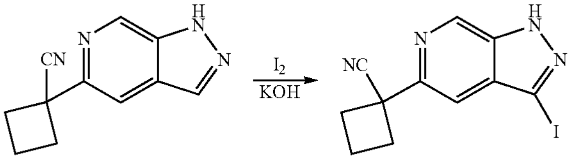

To a solution of 1-(1H-pyrazolo[3,4-c]pyridin-5-yl)cyclobutanecarbonitrile (0.5 g, 2 mmol) and potassium hydroxide (566 mg, 10 mmol) and in DMF (10 mL) was added iodine (1 mL, 5 mmol). The mixture was stirred at 25° C. for 2 h, then slowly diluted with saturated ammonium chloride solution (100 mL) and extracted with ethyl acetate (100 mL×2). The combined organic phase was washed with brine (100 mL×3), dried over anhydrous sodium sulfate, filtered and concentrated under reduced pressure. The residue was purified by silica gel chromatography (0-30% THF in petroleum ether) to afford 1-(3-iodo-1H-pyrazolo[3,4-c]pyridin-5-yl)cyclobutanecarbonitrile (0.55 g, 67%) as a brown solid. MS (ESI) m/z: 325.0 $[M+H]^+$.

Step 3

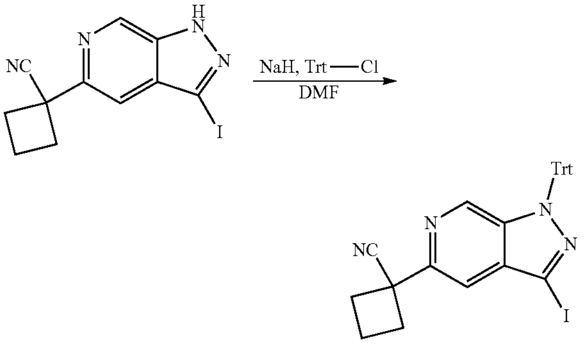

To a solution of 1-(3-iodo-1H-pyrazolo[3,4-c]pyridin-5-yl)cyclobutanecarbonitrile (0.55 g, 1.7 mmol) in DMF (10 mL) was added sodium hydride (81.4 mg, 2 mmol, 60%) at 0° C. under nitrogen atmosphere. The mixture was stirred for 30 min before the addition of trityl chloride (567.7 mg, 2 mmol) at 0° C., the mixture was warmed to 25° C. and stirred for 3 h under nitrogen atmosphere. The reaction mixture was slowly diluted with saturated ammonium chloride solution (100 mL) and extracted with ethyl acetate (100 mL×2). The combined organic phase was washed with brine (100 mL×3), dried over anhydrous sodium sulfate, filtered and concentrated under reduced pressure. The residue was triturated with petroleum ether/methyl tert-butyl ether (10 mL/1 mL) to afford 1-(3-iodo-1-trityl-pyrazolo[3,4-c]pyridin-5-yl)cyclobutanecarbonitrile (0.8 g, 77%) as a brown solid. MS (ESI) m/z: 567.1 $[M+H]^+$.

Step 4

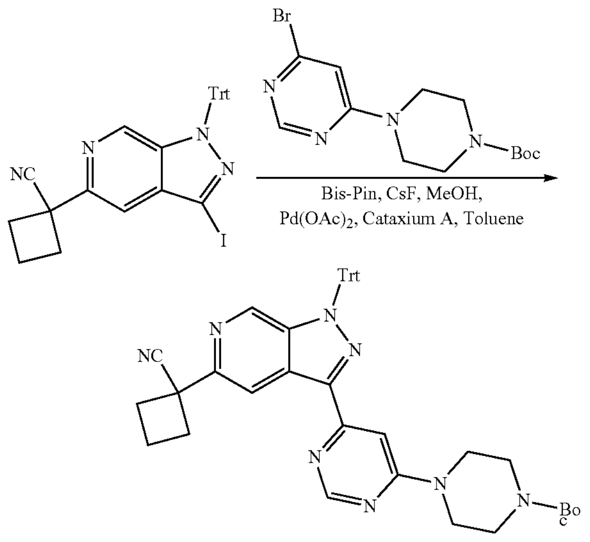

A mixture of 1-(3-iodo-1-trityl-pyrazolo[3,4-c]pyridin-5-yl)cyclobutanecarbonitrile (0.4 g, 0.7 mmol), tert-butyl 4-(6-bromopyrimidin-4-yl) piperazine-1-carboxylate (218 mg, 0.6 mmol), 4,4,5,5-tetramethyl-2-(4,4,5,5-tetramethyl-1,3,2-dioxaborolan-2-yl)-1,3,2-dioxaborolane (179.3 mg, 0.7 mmol) and cesium fluoride (536 mg, 3.5 mmol) in MeOH (10 mL) was degassed and purged with nitrogen several times. Then a solution of palladium (II) acetate (15.9 mg, 71 μmol) and bis(1-adamantyl)-butyl-phosphane (50.6 mg, 0.1 mmol) in toluene (5 mL) was added to the mixture and the mixture was further degassed and purged with nitrogen. The reaction mixture was stirred at 70° C. under nitrogen atmosphere for 2 h, then filtered and concentrated under reduced pressure. The residue was diluted with water (100 mL) and extracted with ethyl acetate (100 mL×3). The combined organic phase was washed with brine (150 mL×3), dried over anhydrous sodium sulfate, filtered and concentrated under reduced pressure. The residue was purified by silica gel chromatography (0-20% THF in petroleum ether) to afford tert-butyl 4-[6-[5-(1-cyanocyclobutyl)-1-trityl-pyrazolo[3,4-c]pyridin-3-yl]pyrimidin-4-yl]piperazine-1-carboxylate (220 mg, 39%, 88% purity) as light yellow solid. MS (ESI) m/z: 703.4 $[M+H]^+$.

Step 5

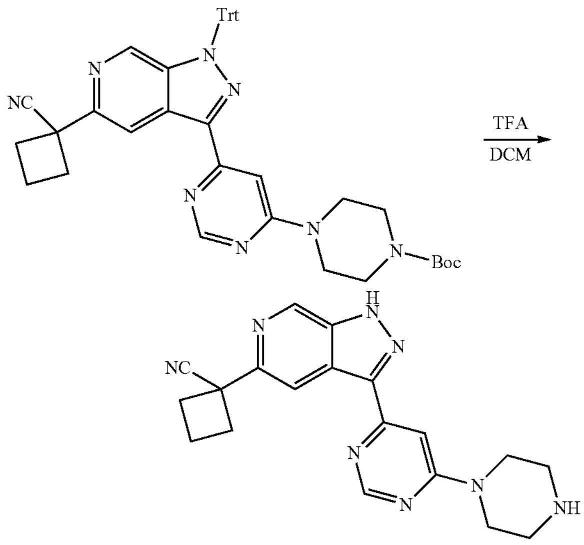

To a solution of tert-butyl 4-[6-[5-(1-cyanocyclobutyl)-1-trityl-pyrazolo[3,4-c]pyridin-3-yl]pyrimidin-4-yl]piperazine-1-carboxylate (200 mg, 0.3 mmol) in dichloromethane (3 mL) was added TFA (4 mL). The mixture was stirred at 25° C. for 2 h, then concentrated under reduced pressure to afford 1-[3-(6-piperazin-1-ylpyrimidin-4-yl)-1H-pyrazolo[3,4-c]pyridin-5-yl]cyclobutanecarbonitrile (200 mg, crude, 3TFA salt) as a brown oil. MS (ESI) m/z: 361.2 $[M+H]^+$.

Step 6

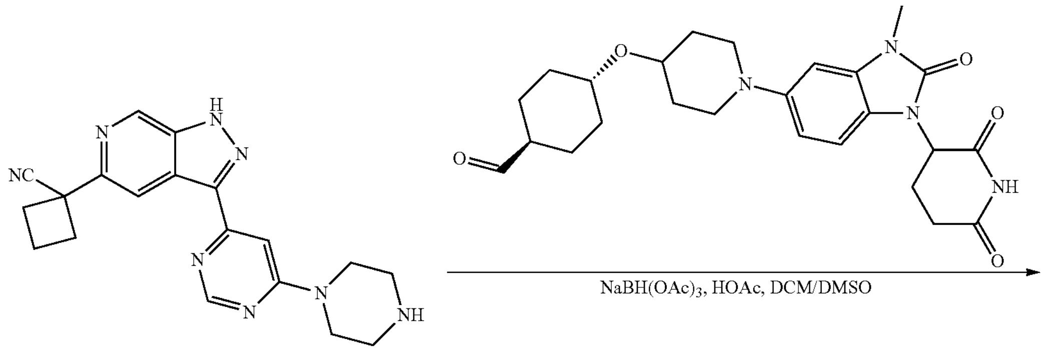

-continued

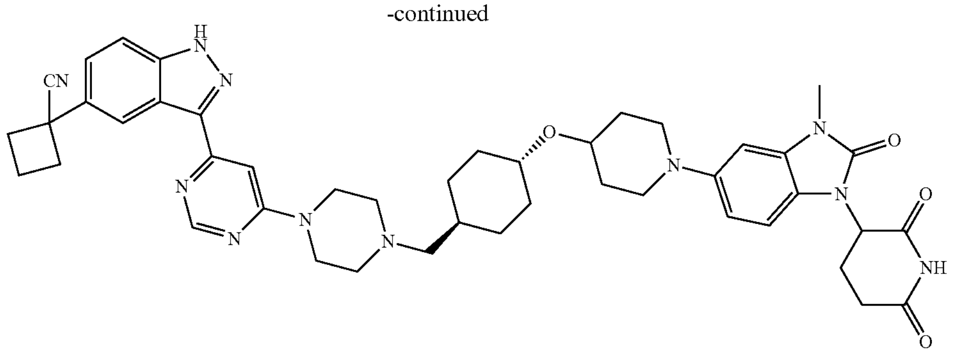

To a solution of 1-[3-(6-piperazin-1-ylpyrimidin-4-yl)-1H-pyrazolo[3,4-c]pyridin-5-yl]cyclobutanecarbonitrile (100 mg, 0.28 mmol) and 4-[[1-[1-(2,6-dioxo-3-piperidyl)-3-methyl-2-oxo-benzimidazol-5-yl]-4-piperidyl]oxy]cyclohexanecarbaldehyde (65.0 mg, 0.14 mmol) in dichloromethanedichloromethane (10 mL) was added acetic acid (0.5 mL, 9 mmol) at 0° C. under nitrogen atmosphere, followed by the addition of sodium triacetoxyborohydride (88.2 mg, 0.42 mmol). The reaction mixture was stirred for 12 h at 0° C., then filtered and concentrated under reduced pressure. The residue was purified by prep-HPLC (0%-36% acetonitrile in water (TFA) over 20.5 min) to give a light yellow solid (60 mg, 94% purity), which was further purified by prep-HPLC (30%-70% acetonitrile in water (ammonium bicarbonate) over 25 min) to afford Compound 22 (32.2 mg, 13% formic acid salt) as a white solid. MS (ESI) m/z: 813.4 $[M+H]^+$.

Exemplary Synthesis of Compound 23:

Step 1

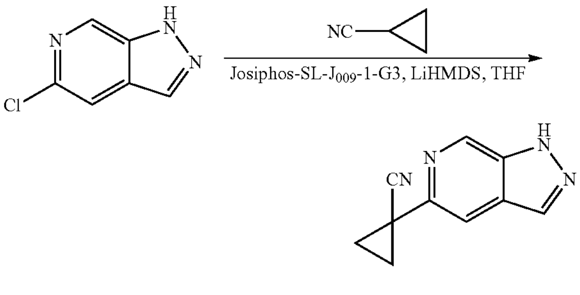

To a solution of 5-chloro-1H-pyrazolo[3,4-c]pyridine (1.8 g, 12 mmol) and cyclopropanecarbonitrile (2.6 mL, 35 mmol) in THF (30 mL) were added lithium bis(trimethylsilyl)amide (1 M, 29.3 mL) and {(R)-1-[(sp)-2-(dicyclohexylphosphino) ferrocenyl]ethyldi-tert-butylphosphine}[2-(2'-amino-1,1'-biphenyl)]palladium (II) methanesulfonate (1.08 g, 1 mmol) under argon atmosphere, the mixture was stirred at 80° C. under argon atmosphere for 12 h. The reaction mixture was diluted with saturated ammonium chloride solution at 0° C. and extracted with ethyl acetate (60 mL×3). The combined organic layers were washed with brine (50 mL), dried over sodium sulfate, filtered and concentrated under reduced pressure. The residue was purified by silica gel chromatography (0-30% ethyl acetate in petroleum ether) to afford 1-(1H-pyrazolo[3,4-c]pyridin-5-yl) cyclopropanecarbonitrile (1.9 g, 88%) as a light yellow solid. MS (ESI) m/z: 185.1 $[M+H]^+$.

Step 2

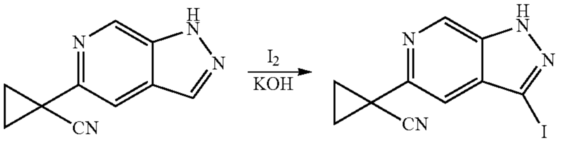

To a solution of 1-(1H-pyrazolo[3,4-c]pyridin-5-yl) cyclopropanecarbonitrile (1.9 g, 10 mmol) in DMSO (20 mL) were added potassium hydroxide (2.31 g, 41 mmol) and iodine (3.1 mL, 15 mmol). The mixture was stirred at 25° C. for 2 h, then diluted with water (50 mL) and extracted with ethyl acetate (40 mL×3). The combined organic layers were washed with brine (30 mL×3), dried over sodium sulfate, filtered and concentrated under reduced pressure. The residue was purified by silica gel chromatography (0-100% ethyl acetate in petroleum ether) to afford 1-(3-iodo-1H-pyrazolo[3,4-c]pyridin-5-yl) cyclopropanecarbonitrile (3 g, 94%) as a light yellow solid.

Step 3

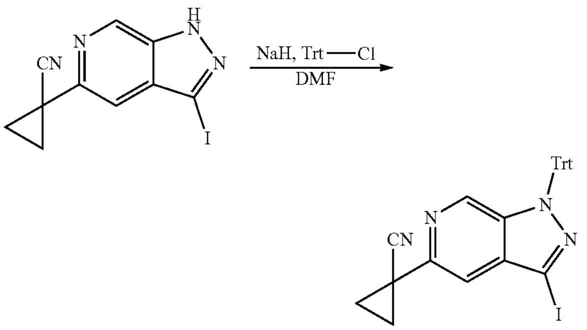

To a solution of 1-(3-iodo-1H-pyrazolo[3,4-c]pyridin-5-yl) cyclopropanecarbonitrile (3.0 g, 10 mmol) in DMF (70 mL) was added sodium hydride (464 mg, 12 mmol, 60%) at 0° C. under nitrogen atmosphere. The mixture was stirred at 0° C. under nitrogen atmosphere for 0.5 h before the addition of trityl chloride (3.24 g, 12 mmol). The reaction mixture was stirred at 25° C. under nitrogen atmosphere for 2 h, then diluted with water (100 mL) and extracted with ethyl acetate (80 mL×3). The combined organic layers were washed with brine (70 mL×3), dried over sodium sulfate, filtered and concentrated under reduced pressure. The residue was triturated with petroleum ether (30 mL) and methyl tert-butyl ether (30 mL) to afford 1-(3-iodo-1-trityl-pyrazolo[3,4-c]pyridin-5-yl) cyclopropanecarbonitrile (3 g, 50%) as a light yellow solid. MS (ESI) m/z: 553.1 $[M+H]^+$.

Step 4

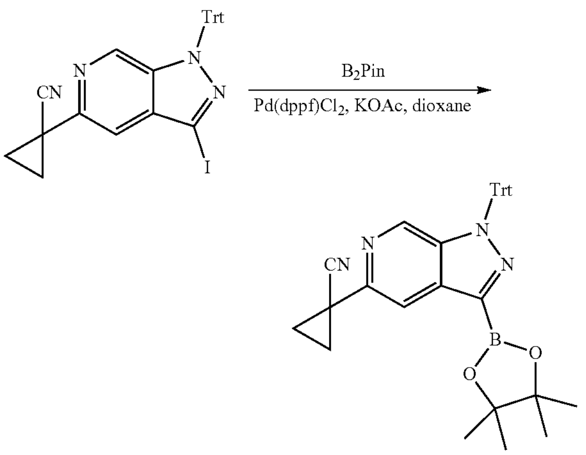

To a solution of 1-(3-iodo-1-trityl-pyrazolo[3,4-c]pyridin-5-yl) cyclopropanecarbonitrile (1.3 g, 2 mmol) and 4,4,5,5-tetramethyl-2-(4,4,5,5-tetramethyl-1,3,2-dioxaborolan-2-yl)-1,3,2-dioxaborolane (956 mg, 4 mmol) in dioxane (50 mL) were added potassium acetate (693 mg, 7 mmol) and Pd(dppf)$Cl_2$ (137.8 mg, 0.2 mmol), the mixture was stirred at 110° C. under nitrogen atmosphere for 12 h. The reaction mixture was filtered and concentrated under reduced pressure to afford 1-[3-(4,4,5,5-tetramethyl-1,3,2-dioxaborolan-2-yl)-1-trityl-pyrazolo[3,4-c]pyridin-5-yl]cyclopropanecarbonitrile (3 g, crude) as a brown solid, which was used in the next step directly. MS (ESI) m/z: 471.2 $[M-81+H]^+$.

Step 5

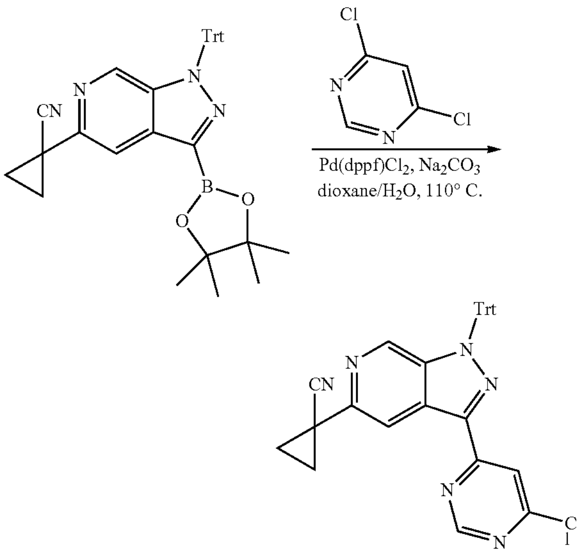

To a solution of 1-[3-(4,4,5,5-tetramethyl-1,3,2-dioxaborolan-2-yl)-1-trityl-pyrazolo[3,4-c]pyridin-5-yl]cyclopropanecarbonitrile (1.5 g, 3 mmol) and 4,6-dichloropyrimidine (445 mg, 3 mmol) in dioxane (50 mL) and water (10 mL) were added sodium carbonate (719 mg, 7 mmol) and Pd(dppf)$Cl_2$ (139 mg, 0.2 mmol), the mixture was stirred at 100° C. under nitrogen atmosphere for 4 h. The reaction mixture was diluted with water (50 mL) and extracted with ethyl acetate (40 mL×3). The combined organic layers were washed with brine (30 mL), dried over sodium sulfate, filtered and concentrated under reduced pressure. The residue was purified by silica gel chromatography (0-20% ethyl acetate in petroleum ether) to afford 1-[3-(6-chloropyrimidin-4-yl)-1-trityl-pyrazolo[3,4-c]pyridin-5-yl]cyclopropanecarbonitrile (1.5 g, 54%, 53% purity) as a colorless oil. MS (ESI) m/z: 539.3 $[M+H]^+$.

Step 6

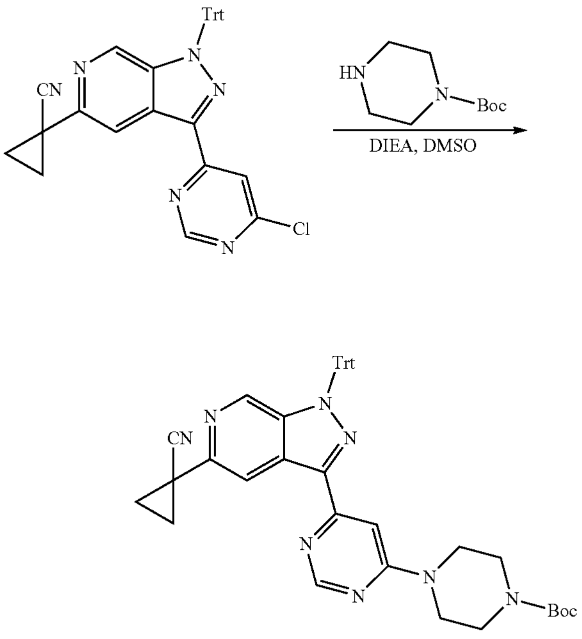

To a solution of 1-[3-(6-chloropyrimidin-4-yl)-1-trityl-pyrazolo[3,4-c]pyridin-5-yl]cyclopropanecarbonitrile (1.5 g, 3 mmol) and tert-butyl piperazine-1-carboxylate (777 mg, 4 mmol) in DMSO (30 mL) was added DIEA (1.5 mL, 8 mmol), and the mixture was stirred at 90° C. for 8 h. The reaction mixture was diluted with water (50 mL) and extracted with ethyl acetate (40 mL×3). The combined organic layers were washed with brine (40 mL×3), dried over sodium sulfate, filtered and concentrated under reduced pressure. The residue was purified by silica gel chromatography (0-28% ethyl acetate in petroleum ether) to afford tert-butyl 4-[6-[5-(1-cyanocyclopropyl)-1-trityl-pyrazolo[3,4-c]pyridin-3-yl]pyrimidin-4-yl]piperazine-1-carboxylate (0.8 g, 38%) as a white solid.

Step 7

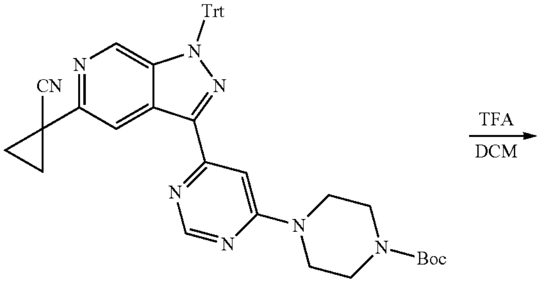

-continued

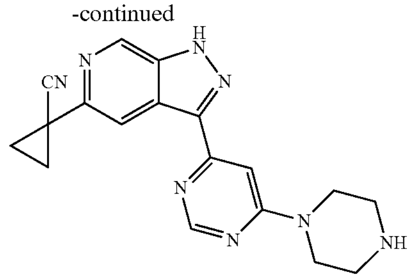

To a solution of tert-butyl 4-[6-[5-(1-cyanocyclopropyl)-1-trityl-pyrazolo[3,4-c]pyridin-3-yl]pyrimidin-4-yl]piperazine-1-carboxylate (250 mg, 0.4 mmol) in dichloromethane (3 mL) was added TFA (3.8 mL). The reaction solution was stirred at 25° C. for 4 h, then concentrated under reduced pressure to afford 1-[3-(6-piperazin-1-ylpyrimidin-4-yl)-1H-pyrazolo[3,4-c]pyridin-5-yl]cyclopropanecarbonitrile (210 mg, 70%, 56% purity, TFA salt) as a yellow gum, which was used in the next step without further purification. MS (ESI) m/z: 347.1 $[M+H]^+$.

Step 8

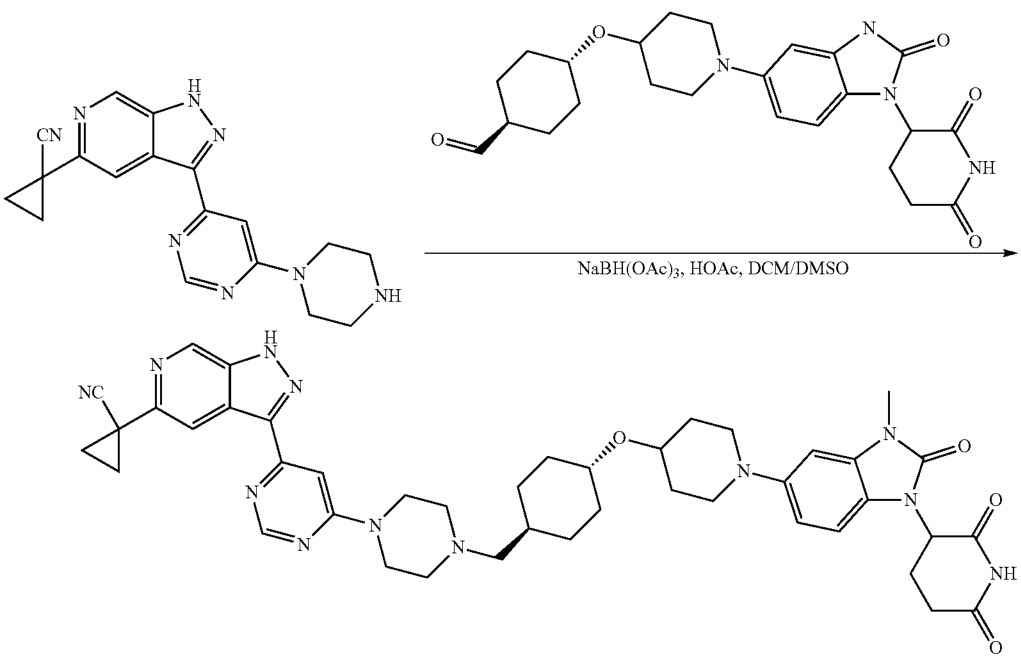

To a solution of 1-[3-(6-piperazin-1-ylpyrimidin-4-yl)-1H-pyrazolo[3,4-c]pyridin-5-yl]cyclopropanecarbonitrile (77.63 mg, 0.22 mmol) in dichloromethane (15 mL) were added acetic acid (8.55 μL, 0.15 mmol) and 4-[[1-[1-(2,6-dioxo-3-piperidyl)-3-methyl-2-oxo-benzimidazol-5-yl]-4-piperidyl]oxy]cyclohexanecarbaldehyde (70 mg, 0.15 mmol) in dichloromethane (15 mL) at −10° C. The mixture was stirred for 1 h, followed by the addition of sodium triacetoxyborohydride (79.16 mg, 0.37 mmol,). The reaction mixture was stirred for 4 h at −10° C., then filtered and concentrated under reduced pressure. The resulting residue was purified by prep-HPLC (26%-66% acetonitrile in water (ammonium bicarbonate) over 25 min) to afford Compound 23 (81.3 mg, 68%) as a white solid. MS (ESI) m/z: 799.4 $[M/2+H]^+$.

Exemplary Synthesis of Compound 24:

Step 1

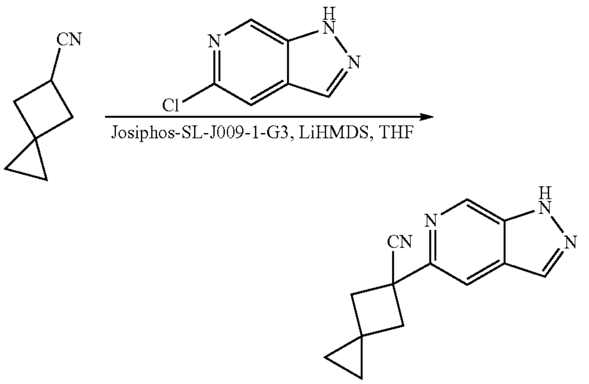

To a solution of spiro[2.3]hexane-5-carbonitrile (1 g, 9 mmol) and 5-chloro-1H-pyrazolo[3,4-c]pyridine (1.58 g, 10 mmol) in THF (30 mL) was added [bis(trimethylsilyl)amino]lithium (1 M, 23 mL) and {(R)-1-[(sp)-2-(dicyclohexylphosphino) ferrocenyl]ethyldi-tert-butylphosphine}[2-(2'-amino-1,1'-biphenyl)]palladium (II) methanesulfonate (863 mg, 0.9 mmol) at 25° C. under argon atmosphere. The mixture was stirred at 80° C. under argon atmosphere for 12 h. The reaction mixture was diluted with saturated ammonium chloride solution (60 mL) at 0° C. and extracted with ethyl acetate (60 mL×3). The combined organic layers were washed with brine (50 mL), dried over sodium sulfate, filtered and concentrated under reduced pressure. The residue was purified by silica gel chromatography (0-30% ethyl acetate in petroleum ether) to afford a crude product (1.7 g). The above material was triturated with methyl tert-butyl ether (20 mL) to afford 5-(1H-pyrazolo[3,4-c]pyridin-5-yl)spiro[2.3]hexane-5-carbonitrile (750 mg, 36%) as a light yellow solid. MS (ESI) m/z: 225.1 $[M+H]^+$.

Step 2

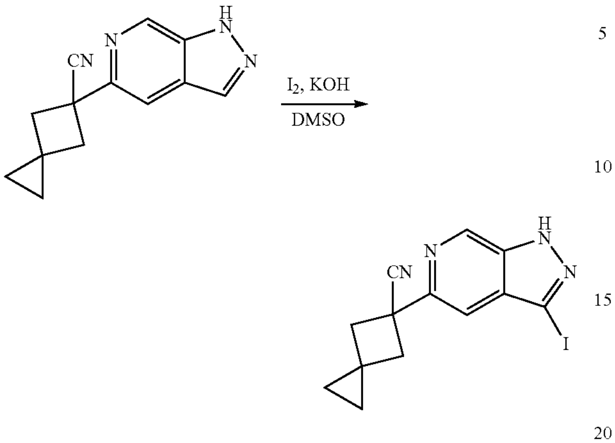

To a solution of 5-(1H-pyrazolo[3,4-c]pyridin-5-yl)spiro[2.3]hexane-5-carbonitrile (0.75 g, 3 mmol) in DMSO (15 mL) were added potassium hydroxide (562.9 mg, 10 mmol) and iodine (1 mL, 5 mmol). The reaction mixture was stirred at 25° C. for 2 h, then diluted with water (50 mL) and extracted with ethyl acetate (40 mL×3). The combined organic layers were washed with brine (40 mL×3), dried over sodium sulfate, filtered and concentrated under reduced pressure. The residue was triturated with methyl tert-butyl ether (20 mL) to afford 5-(3-iodo-1H-pyrazolo[3,4-c]pyridin-5-yl)spiro[2.3]hexane-5-carbonitrile (1.1 g, 94%) as a white solid. MS (ESI) m/z: 351.0 $[M+H]^+$.

Step 3

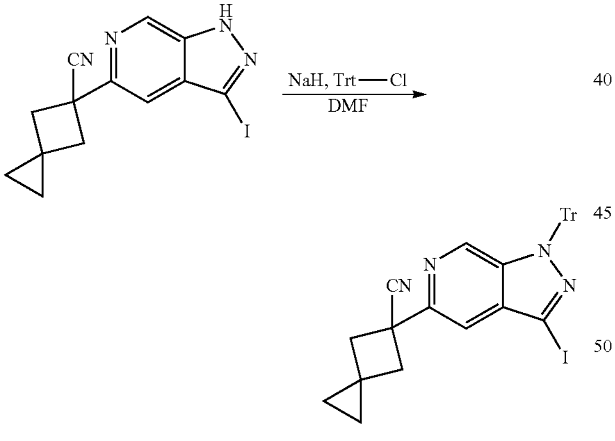

To a solution of 5-(3-iodo-1H-pyrazolo[3,4-c]pyridin-5-yl)spiro[2.3]hexane-5-carbonitrile (1.1 g, 3 mmol) in DMF (30 mL) was added NaH (188.5 mg, 5 mmol, 60%) at 0° C. under nitrogen atmosphere. The mixture was stirred at 0° C. for 0.5 h, followed by the addition of trityl chloride (1.14 g, 4 mmol). The reaction mixture was stirred at 25° C. under nitrogen atmosphere for 2 h, then suspended in water (100 mL). The mixture was filtered and the filter cake was washed with methyl tert-butyl ether (70 mL), dried to afford 5-(3-iodo-1-trityl-pyrazolo[3,4-c]pyridin-5-yl)spiro[2.3]hexane-5-carbonitrile (1.8 g, 97%) as a white solid. MS (ESI) m/z: 593.1 $[M+H]^+$.

Step 4

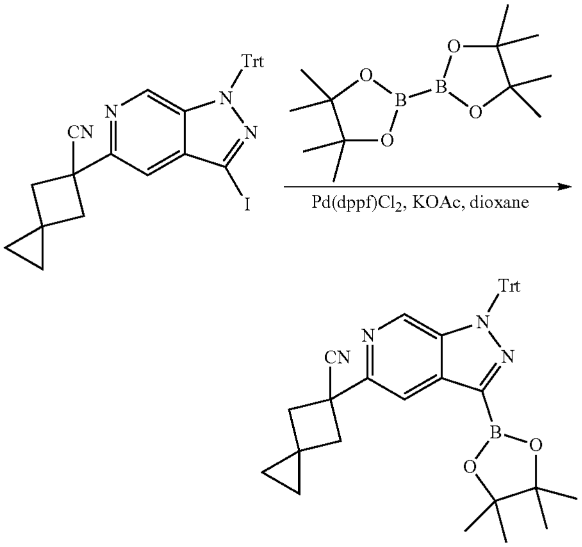

To a solution of 5-(3-iodo-1-trityl-pyrazolo[3,4-c]pyridin-5-yl)spiro[2.3]hexane-5-carbonitrile (1.8 g, 3 mmol) and 4,4,5,5-tetramethyl-2-(4,4,5,5-tetramethyl-1,3,2-dioxaborolan-2-yl)-1,3,2-dioxaborolane (1.16 g, 5 mmol) in dioxane (30 mL) were added Pd (dppf) $C_{12}$ (178 mg, 0.2 mmol) and potassium acetate (894.51 mg, 9 mmol). The reaction mixture was stirred at 110° C. under nitrogen atmosphere for 12 h, then filtered and concentrated under reduced pressure to afford 5-[3-(4,4,5,5-tetramethyl-1,3,2-dioxaborolan-2-yl)-1-trityl-pyrazolo[3,4-c]pyridin-5-yl]spiro[2.3]hexane-5-carbonitrile (2.1 g, 85%, 73% purity) as a brown solid. MS (ESI) m/z: 511.2 $[M-81+H]^+$.

Step 5

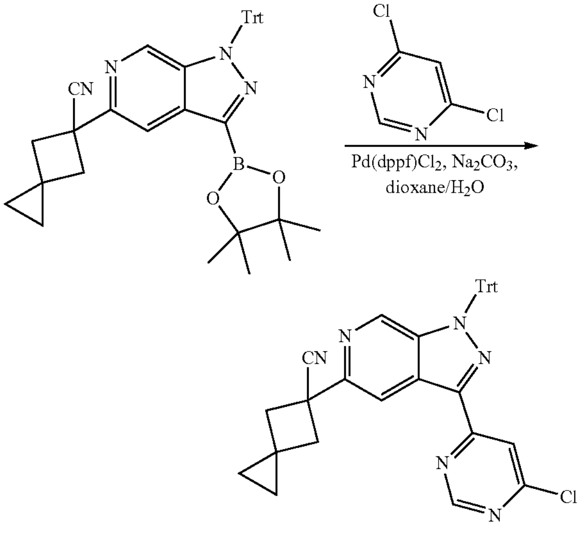

To a solution of 4,6-dichloropyrimidine (452.6 mg, 3 mmol) and 5-[3-(4,4,5,5-tetramethyl-1,3,2-dioxaborolan-2-yl)-1-trityl-pyrazolo[3,4-c]pyridin-5-yl]spiro[2.3]hexane-5-carbonitrile (1.8 g, 3 mmol) in dioxane (30 mL) and water (5 mL) were added Pd(dppf)$Cl_2$ (178 mg, 0.2 mmol) and sodium carbonate (708 mg, 7 mmol), the mixture was stirred at 90° C. under nitrogen atmosphere for 4 h. The reaction mixture was diluted with water (80 mL) and extracted with ethyl acetate (60 mL×3). The combined organic layers were washed with brine (60 mL), dried over sodium sulfate, filtered and concentrated under reduced pressure. The residue was purified by silica gel chromatography (0-12% ethyl acetate in petroleum ether) to afford 5-[3-(6-chloropyrimidin-4-yl)-1-trityl-pyrazolo[3,4-c]pyridin-5-yl]spiro[2.3]hexane-5-carbonitrile (1.2 g, 68%) as a light yellow solid. MS (ESI) m/z: 579.2 [M+H]$^+$.

Step 6

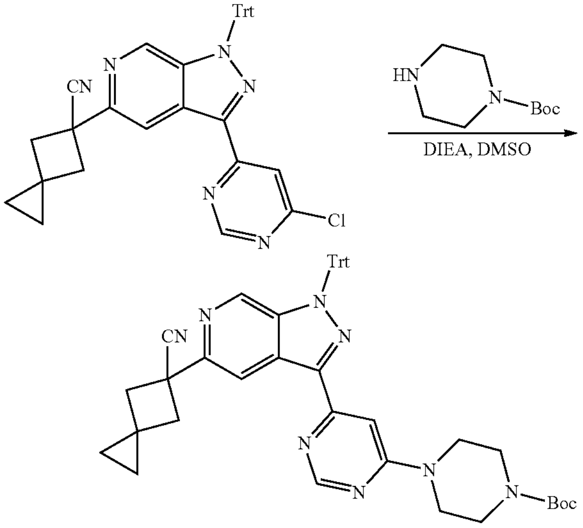

To a solution of 5-[3-(6-chloropyrimidin-4-yl)-1-trityl-pyrazolo[3,4-c]pyridin-5-yl]spiro[2.3]hexane-5-carbonitrile (1.2 g, 2 mmol) and tert-butyl piperazine-1-carboxylate (579 mg, 3 mmol) in DMSO (30 mL) was added DIEA (1.8 mL, 10 mmol), and the mixture was stirred at 90° C. for 6 h. The reaction mixture was diluted with water (100 mL) and extracted with ethyl acetate (50 mL×3). The combined organic layers were washed with brine (40 mL×4), dried over sodium sulfate, filtered and concentrated under reduced pressure. The residue was purified by silica gel chromatography (0-17% ethyl acetate in petroleum ether) to afford tert-butyl 4-[6-[5-(5-cyanospiro[2.3]hexan-5-yl)-1-trityl-pyrazolo[3,4-c]pyridin-3-yl]pyrimidin-4-yl]piperazine-1-carboxylate (1.2 g, 79%) as a light yellow solid.

Step 7

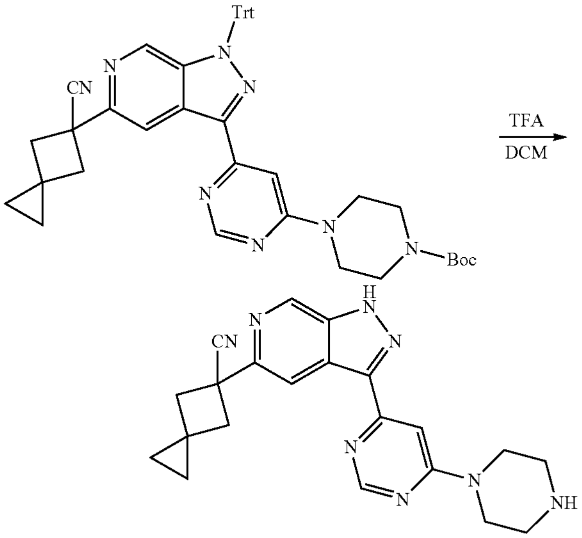

To a solution of tert-butyl 4-[6-[5-(5-cyanospiro[2.3]hexan-5-yl)-1-trityl-pyrazolo[3,4-c]pyridin-3-yl]pyrimidin-4-yl]piperazine-1-carboxylate (0.5 g, 0.7 mmol) in dichloromethane (3 mL) was added TFA (6 mL). The reaction solution was stirred at 25° C. for 2 h, then concentrated under reduced pressure to afford 5-[3-(6-piperazin-1-ylpyrimidin-4-yl)-1H-pyrazolo[3,4-c]pyridin-5-yl]spiro[2.3]hexane-5-carbonitrile (0.52 g, 78%, 75% purity, 3 TFA salt) as a white solid, which was used in the next step without further purification. MS (ESI) m/z: 387.2 [M+H]$^+$.

Step 8

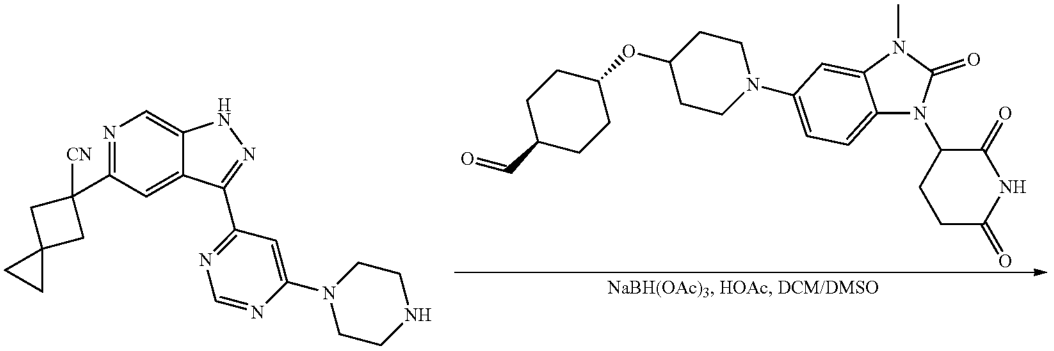

-continued

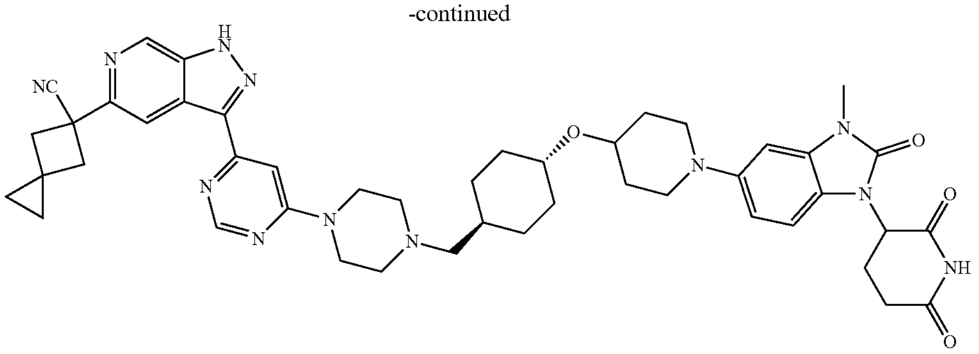

To a solution of 5-[3-(6-piperazin-1-ylpyrimidin-4-yl)-1H-pyrazolo[3,4-c]pyridin-5-yl]spiro[2.3]hexane-5-carbonitrile (123.7 mg, 320 μmol) in dichloromethane (15 mL) were added acetic acid (12.2 μL, 213 μmol) and 4-[[1-[1-(2,6-dioxo-3-piperidyl)-3-methyl-2-oxo-benzimidazol-5-yl]-4-piperidyl]oxy]cyclohexanecarbaldehyde (0.1 g, 0.2 mmol) in dichloromethane (5 mL) at −10° C. The mixture was stirred for 1 h, then sodium triacetoxyborohydride (90.47 mg, 0.43 mmol) was added. The reaction mixture was stirred for 4 h, then filtered and concentrated under reduced pressure. The residue was purified by prep-HPLC (0%-38% acetonitrile in water (TFA) over 20 min), the crude product was further purified by prep-HPLC (38%-78% acetonitrile in water (ammonium bicarbonate) over 25 min) to afford Compound 24 (61.1 mg, 34%) as a white solid. MS (ESI) m/z: 420.4 $[M/2+H]^+$.

Exemplary Synthesis of Compound 25:

Step 1

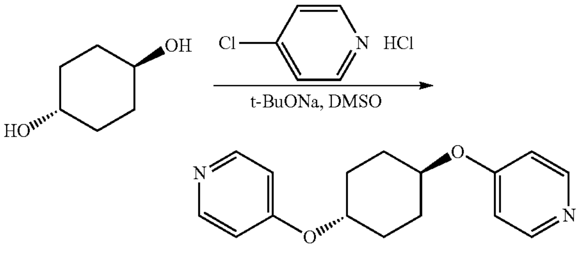

To a solution of cyclohexane-1,4-diol (5.0 g, 43 mmol) and 4-chloropyridine (14.2 g, 95 mmol, HCl salt) in DMSO (150 mL) was added sodium tert-butoxide (20.7 g, 215 mmol), and the reaction mixture was stirred at 80° C. for 10 h. The mixture was cooled to 25° C., diluted with water (100 mL) and extracted with ethyl acetate (200 mL×3). The combined organic phase was washed with brine (200 mL×2), dried over anhydrous sodium sulfate, filtered and concentrated under reduced pressure. The residue was purified by silica gel column chromatography (0-4% methanol in dichloromethane) to afford 4-[4-(4-pyridyloxy)cyclohexoxy]pyridine (8.73 g, 75%) as a brown solid. MS (ESI) m/z: 271.2 $[M+H]^+$.

Step 2

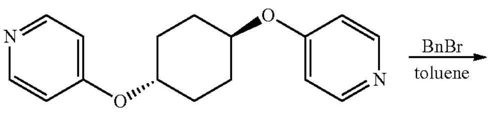

-continued

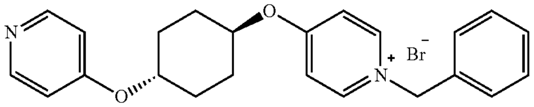

To a solution of 4-[4-(4-pyridyloxy)cyclohexoxy]pyridine (7.73 g, 29 mmol) in toluene (400 mL) was dropwise added bromomethylbenzene (5.1 mL, 43 mmol) in toluene (40 mL) over 15 h. The mixture was stirred at 80° C. for 36 h. The reaction mixture was filtered, the filter cake was washed with petroleum ether (500 mL) and dried to afford 1-benzyl-4-[4-(4-pyridyloxy)cyclohexoxy]pyridin-1-ium (11.52 g, crude) as a white solid, which was used directly in the next step. MS (ESI) m/z: 361.1 $[M+H]^+$.

Step 3

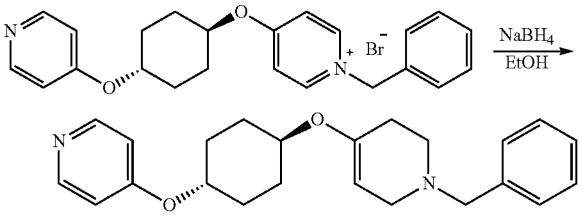

To a solution of 4-[4-[(1-benzyl-4-pyridyl)oxy]cyclohexoxy]pyridine (11.52 g, 28 mmol, 89% purity) in EtOH (120 mL) was added sodium borohydride (3.8 g, 0.1 mol) at 0° C. under nitrogen atmosphere. The mixture was stirred at 0° C. for 1 h, then diluted with water (200 mL) and extracted with ethyl acetate (300 mL×3). The combined organic phase was washed with brine (100 mL), dried over anhydrous sodium sulfate, filtered and concentrated under reduced pressure to afford 4-[4-[(1-benzyl-3,6-dihydro-2H-pyridin-4-yl)oxy]cyclohexoxy]pyridine (9.97 g, 68%, 71% purity) as a yellow oil, which was used directly in the next step. MS (ESI) m/z: 365.1 $[M+H]^+$.

Step 4

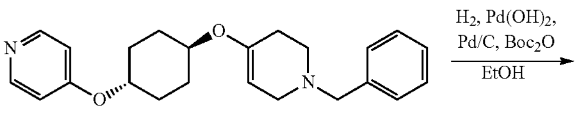

-continued

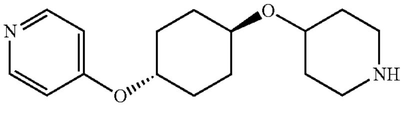

To a solution of 4-[4-[(1-benzyl-3,6-dihydro-2H-pyridin-4-yl)oxy]cyclohexoxy]pyridine (9.97 g, 24 mmol) in EtOH (200 mL) were added 10% palladium on carbon (2.5 g), 20% palladium hydroxide (2.5 g) and di-tert-butyl dicarbonate (10.9 mL, 48 mmol). The suspension was degassed and purged with hydrogen several times. The mixture was stirred under hydrogen (50 psi) at 60° C. for 12 h. The reaction mixture was filtered and concentrated to afford 4-[4-(4-piperidyloxy)cyclohexoxy]pyridine (7.09 g, crude) as a white gum, which was used directly in the next step. MS (ESI) m/z: 277.1 [M+H]$^+$.

Step 5

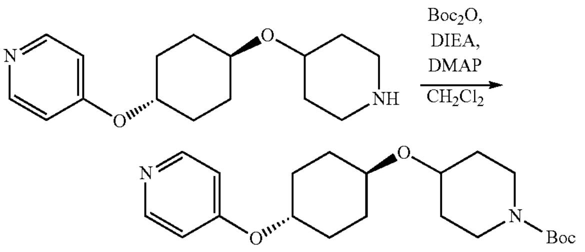

To a solution of 4-[4-(4-piperidyloxy)cyclohexoxy]pyridine (7.09 g, 26 mmol), DIEA (4.5 mL, 26 mmol) and DMAP (313 mg, 2.6 mmol) in dichloromethane (140 mL) was added di-tert-butyl dicarbonate (8.8 mL, 38 mmol). The mixture was stirred at 25° C. for 12 h, then concentrated under reduced pressure. The residue was purified by flash column chromotography (0-52% ethyl acetate in petroleum ether) to afford tert-butyl 4-[4-(4-pyridyloxy)cyclohexoxy] piperidine-1-carboxylate (4.37 g, 37%, 82% purity) as a yellow solid. MS (ESI) m/z: 377.2 [M+H]$^+$.

Step 6

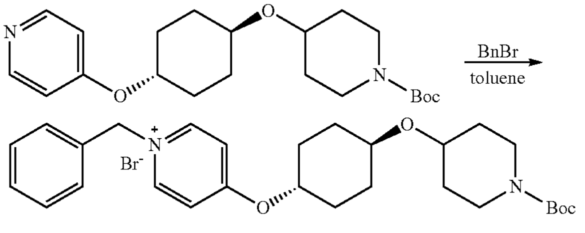

To a solution of tert-butyl 4-[4-(4-pyridyloxy)cyclohexoxy]piperidine-1-carboxylate (4.37 g, 12 mmol) in toluene (160 mL) was added benzyl bromide (1.8 mL, 15 mmol). The mixture was stirred at 80° C. for 12 h. The reaction mixture was filtered, the filter cake was washed with petroleum ether (250 mL) and dried to afford tert-butyl 4-[4-(1-benzylpyridin-1-ium-4-yl)oxycyclohexoxy]piperidine-1-carboxylate (5.27 g, 78%) as a white solid. MS (ESI) m/z: 467.2 [M+H]$^+$.

Step 7

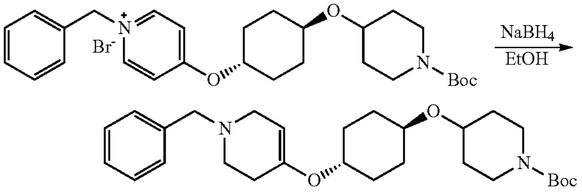

To a solution of tert-butyl 4-[4-(1-benzylpyridin-1-ium-4-yl)oxycyclohexoxy]piperidine-1-carboxylate (5.27 g, 9 mmol, 89% purity) in EtOH (50 mL) was added sodium borohydride (1.18 g, 31 mmol) at 0° C. under nitrogen atmosphere. The mixture was stirred at 0° C. for 1 h, then diluted with water (50 mL) and extracted with ethyl acetate (70 mL×3). The combined organic phase was washed with brine (20 mL), dried over anhydrous sodium sulfate, filtered and concentrated under reduced pressure. The residue was purified by prep-HPLC (5%-43% acetonitrile in water (formic acid) over 22 min). The collected fractions were combined, sodium carbonate was added to adjust the pH to 9, the mixture was extracted with dichloromethane/MeOH (10/1). The organic phase was concentrated under reduced pressure to afford tert-butyl 4-[4-[(1-benzyl-3,6-dihydro-2H-pyridin-4-yl)oxy]cyclohexoxy]piperidine-1-carboxylate (2.92 g, 70%) as a white solid. MS (ESI) m/z: 471.7 [M+H]$^+$.

Step 8

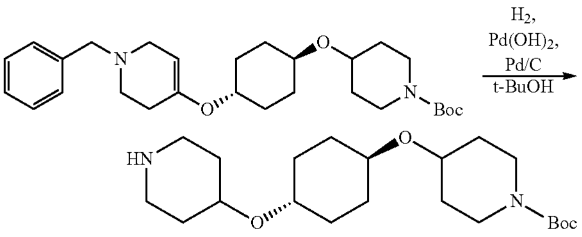

To a solution of tert-butyl 4-[4-[(1-benzyl-3,6-dihydro-2H-pyridin-4-yl)oxy]cyclohexoxy]piperidine-1-carboxylate (200 mg, 0.4 mmol) in tert-butanol (10 mL) were added 10% palladium on carbon (40 mg) and 20% palladium hydroxide (40 mg) under nitrogen atmosphere. The suspension was degassed and purged with hydrogen several times. The mixture was stirred under hydrogen (50 psi) at 60° C. for 36 h, then filtered and concentrated to afford tert-butyl 4-[4-(4-piperidyloxy)cyclohexoxy]piperidine-1-carboxylate (116.2 mg, 71%) as a white solid. MS (ESI) m/z: 383.5 [M+H]$^+$.

Step 9

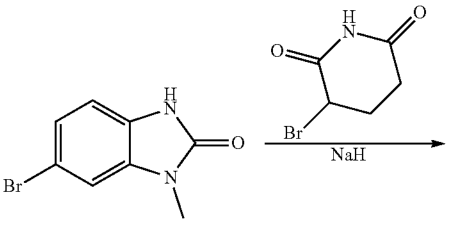

-continued

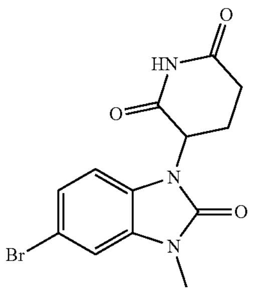

To a solution of 5-bromo-3-methyl-1H-benzimidazol-2-one (15 g, 66 mmol) in THF (400 mL) was added sodium hydride (15.85 g, 0.4 mol, 60%) at 0° C. and stirred for 0.5 h, the mixture was heated to 65° C. Then a solution of 3-bromopiperidine-2,6-dione (38.05 g, 0.2 mol) in THF (200 mL) was dropwise added, the resulting mixture was stirred for 2 h at 65° C. The reaction mixture was poured into 1 M aqueous sulfuric acid (400 mL) at 0° C., then diluted with saturated aqueous sodium bicarbonate solution (150 mL) and extracted with dichloromethane (500 mL×2). The combined organic layers were washed with brine (300 mL×2), dried over sodium sulfate, filtered and concentrated under reduced pressure. The residue was triturated with MeOH/THF (300 mL/30 mL) at 25° C. for 12 h, filtered to afford 3-(5-bromo-3-methyl-2-oxo-benzimidazol-1-yl)piperidine-2,6-dione (14 g, 63%) as a gray solid. MS (ESI) m/z: 339.9 $[M+H]^+$.

Step 10

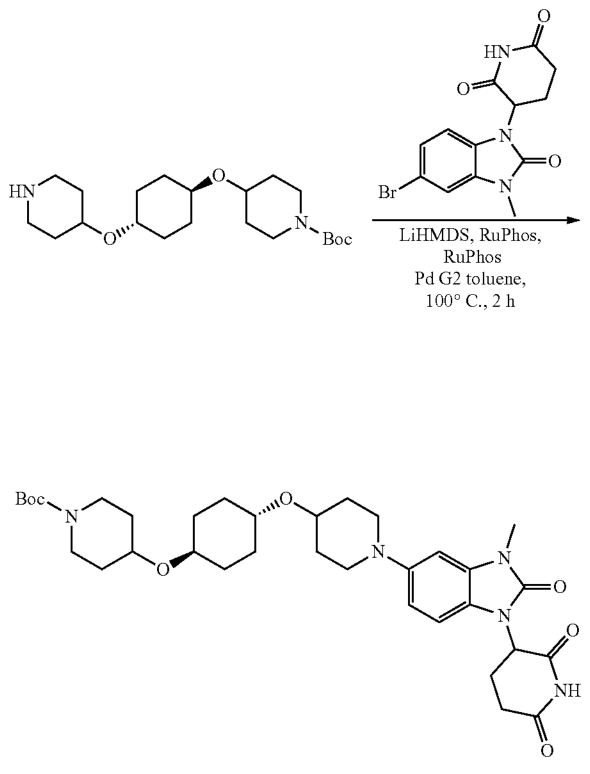

To a mixture of tert-butyl 4-[4-(4-piperidyloxy)cyclohexoxy]piperidine-1-carboxylate (0.5 g, 1 mmol), 3-(5-bromo-3-methyl-2-oxo-benzimidazol-1-yl)piperidine-2,6-dione (663 mg, 2 mmol) and RuPhos (30.5 mg, 65 μmol) in toluene (7 mL) were added Ruphos Pd G2 (50.8 mg, 65 μmol) and lithium bis(trimethylsilyl)amide (1 M, 6.5 mL) dropwise at 0° C. The mixture was stirred at 100° C. for 3 h under nitrogen atmosphere. The reaction solution was cooled to 25° C. and poured into aqueous acetic acid solution (acetic acid/water=2 mL/20 mL) at 0° C., the mixture was diluted with saturated aqueous sodium bicarbonate solution to adjust the pH to 8-9. The mixture was extracted with ethyl acetate (100 mL×2). The combined organic layers were washed with brine (100 mL) and dried over anhydrous sodium sulfate, filtered and concentrated. The residue was purified by silica gel chromatography (0-80% THF/petroleum ether) to afford tert-butyl 4-[4-[[1-[1-(2,6-dioxo-3-piperidyl)-3-methyl-2-oxo-benzimidazol-5-yl]-4-piperidyl]oxy]cyclohexoxy]piperidine-1-carboxylate (300 mg, 36%) as a white solid. MS (ESI) m/z: 640.4 $[M+H]^+$.

Step 11

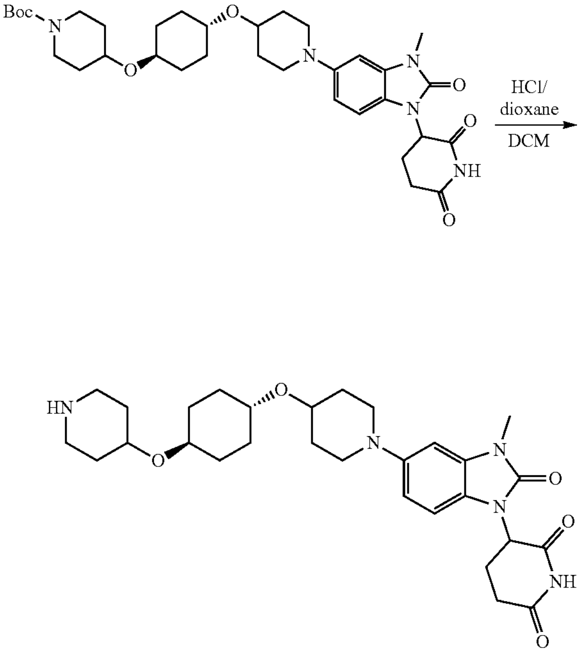

To a solution of tert-butyl 4-[4-[[1-[1-(2,6-dioxo-3-piperidyl)-3-methyl-2-oxo-benzimidazol-5-yl]-4-piperidyl]oxy]cyclohexoxy]piperidine-1-carboxylate (0.3 g, 0.5 mmol) in dichloromethane (5 mL) was added HCl/dioxane (2 M, 10 mL). The reaction solution was stirred at 25° C. for 2 h, then concentrated under reduced pressure to afford 3-[3-methyl-2-oxo-5-[4-[4-(4-piperidyloxy)cyclohexoxy]-1-piperidyl]benzimidazol-1-yl]piperidine-2,6-dione (300 mg, crude, 2HCl salt) as a gray solid. MS (ESI) m/z: 540.3 $[M+H]^+$.

Step 12

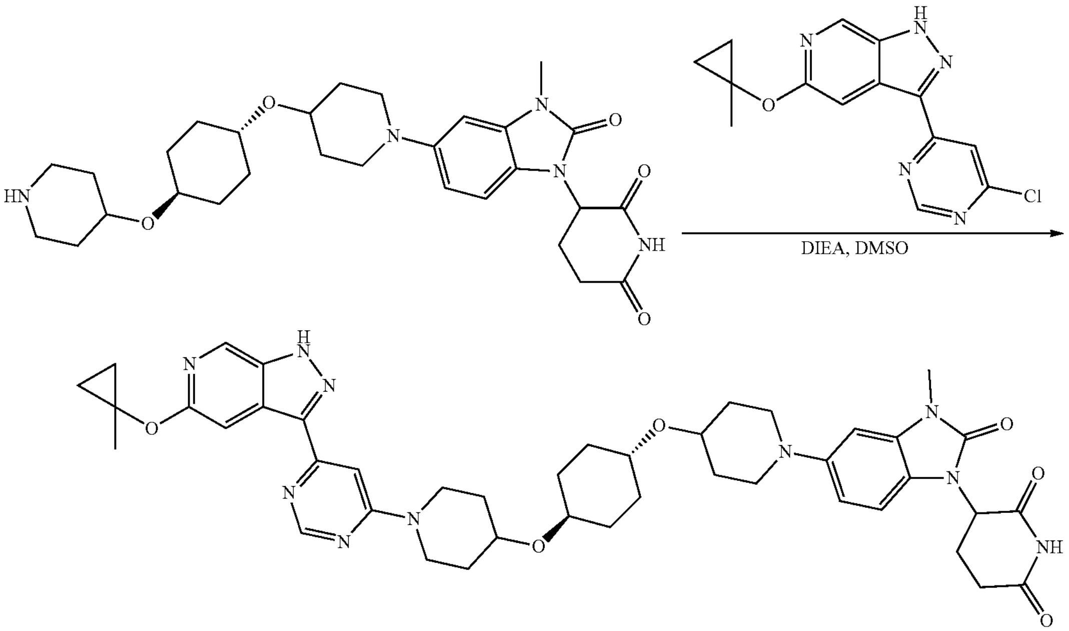

To a solution of 3-(6-chloropyrimidin-4-yl)-5-(1-methylcyclopropoxy)-1H-pyrazolo[3,4-c]pyridine (50 mg, 0.17 mmol) and 3-[3-methyl-2-oxo-5-[4-[4-(4-piperidyloxy)cyclohexoxy]-1-piperidyl]benzimidazol-1-yl]piperidine-2,6-dione (89.4 mg, 0.17 mmol) in DMSO (5 mL) was added DIEA (144 μL, 0.83 mmol), the resulting mixture was heated to 80° C. and stirred for 2 h. The reaction mixture was allowed to cool to 25° C., filtered, and the filtrate solution was purified by prep-HPLC (0%-40% acetonitrile in water (formic acid) over 25 min), the crude product was further purified by prep-HPLC (28%-68% acetonitrile in water (sodium bicarbonate) over 25 min) to afford Compound 25 (57.1 mg, 42%) as a white solid. MS (ESI) m/z: 805.3 $[M+H]^+$.

Exemplary Synthesis of Compound 26:

Step 1

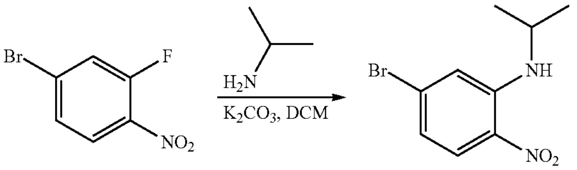

To a solution of 4-bromo-2-fluoro-1-nitro-benzene (10 g, 45 mmol) in DMF (100 mL) were added propan-2-amine (3.91 mL, 45 mmol) and potassium carbonate (12.56 g, 91 mmol). The mixture was stirred at 25° C. for 12 h, then diluted with water (100 mL) and extracted with ethyl acetate (150 mL×2). The combined organic phase was washed with brine (150 mL×3), dried over anhydrous sodium sulfate, filtered and concentrated under reduced pressure. The residue was purified by silica gel chromatography (0-1% ethyl acetate/petroleum ether) to afford 5-bromo-N-isopropyl-2-nitro-aniline (11.3 g, 96%) as an orange solid. MS (ESI) m/z: 259.0 $[M+H]^+$.

Step 2

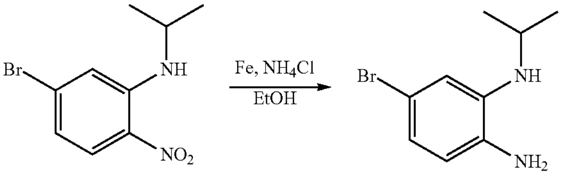

To a solution of 5-bromo-N-isopropyl-2-nitro-aniline (11.3 g, 44 mmol) in EtOH (100 mL) and water (100 mL) were added iron (12.18 g, 0.2 mol) and ammonium chloride (23.33 g, 0.4 mol). The mixture was stirred at 80° C. for 5 h, then filtered and washed with MeOH. The filtrate solution was concentrated under reduced pressure. The residue was diluted with water (200 mL) and extracted with ethyl acetate (200 mL×2). The combined organic phase was washed with brine (400 mL), dried over anhydrous sodium sulfate, filtered and concentrated under reduced pressure. The residue was purified by silica gel chromatography (0-20% ethyl acetate/petroleum ether) to afford 4-bromo-nitrogen atmosphere-isopropyl-benzene-1,2-diamine (9.8 g, 98%) as a purple solid. MS (ESI) m/z: 229.0 $[M+H]^+$.

Step 3

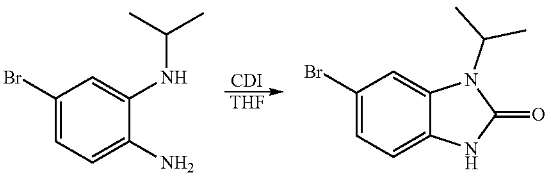

To a solution of 4-bromo-nitrogen atmosphere-isopropyl-benzene-1,2-diamine (9.8 g, 43 mmol) in THF (100 mL) was added carbonyldiimidazole (10.4 g, 64 mmol). The mixture was stirred at 60° C. for 12 h, then diluted with water (100 mL) and extracted with ethyl acetate (150 mL×2). The combined organic phase was washed with brine (150 mL×3), dried over anhydrous sodium sulfate, filtered and concentrated under reduced pressure. The residue was purified by silica gel chromatography (0-40% ethyl acetate/petroleum ether) to afford 5-bromo-3-isopropyl-1H-benzimidazol-2-one (10.5 g, 96%) as a gray solid. MS (ESI) m/z: 257.0 [M+H]$^+$.

Step 4

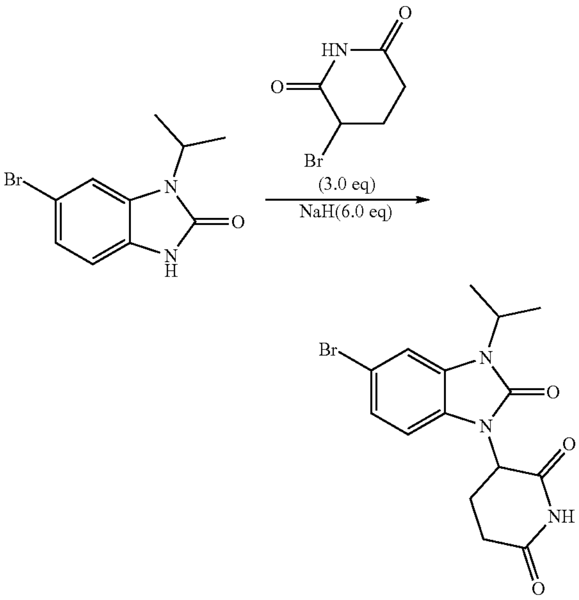

To a solution of 5-bromo-3-isopropyl-1H-benzimidazol-2-one (10.5 g, 41 mmol) in THF (200 mL) was added sodium hydride (9.88 g, 0.2 mol, 60%) at 0° C. and stirred for 0.5 h. The mixture was heated to 65° C. and a solution of 3-bromopiperidine-2,6-dione (23.71 g, 0.1 mol) in THF (200 mL) was added dropwise. The mixture was stirred for 3 h at 65° C. The reaction mixture was poured into 1 M aqueous sulfuric acid solution (250 mL) at 0° C. and diluted with saturated aqueous sodium bicarbonate solution (150 mL), the mixture was extracted with dichloromethane (500 mL×2). The combined organic layers were washed with brine (300 mL×2), dried over sodium sulfate, filtered and concentrated under reduced pressure. The residue was triturated with isopropyl alcohol/THF (200 mL/20 mL) to afford 3-(5-bromo-3-isopropyl-2-oxo-benzimidazol-1-yl)piperidine-2,6-dione (9.7 g, 54%, 84% purity) as an off-white solid. MS (ESI) m/z: 368.3 [M+H]$^+$.

Step 5

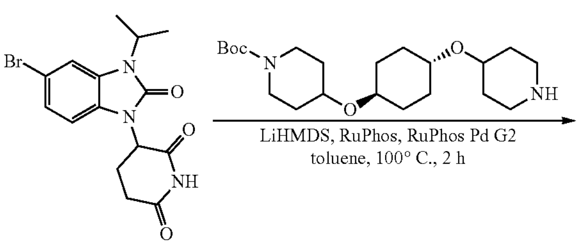

-continued

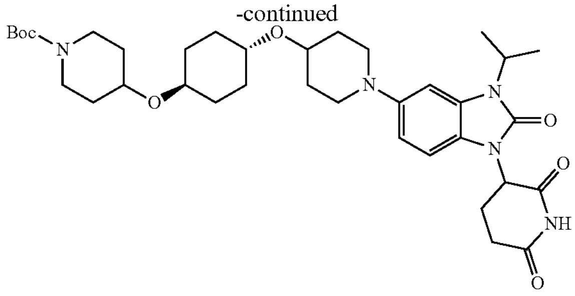

To a mixture of tert-butyl 4-[4-(4-piperidyloxy)cyclohexoxy]piperidine-1-carboxylate (200 mg, 0.5 mmol), 3-(5-bromo-3-isopropyl-2-oxo-benzimidazol-1-yl)piperidine-2,6-dione (287.2 mg, 0.8 mmol) and RuPhos (12.2 mg, 26 μmol) in toluene (5 mL) were added Ruphos Pd $G_2$ (20.3 mg, 26 μmol) and lithium bis(trimethylsilyl)amide (1 M, 2.6 mL) dropwise at 0° C. The mixture was stirred at 100° C. for 3 h under nitrogen atmosphere. The reaction mixture was cooled to 25° C. and poured into aqueous acetic acid solution (acetic acid/water=2 mL/20 mL) at 0° C., then saturated aqueous sodium bicarbonate solution was added to adjust the pH to 8-9. The above mixture was extracted with ethyl acetate (100 mL×2). The combined organic layers were washed with brine (100 mL) and dried over anhydrous sodium sulfate, filtered and concentrated. The residue was purified by silica gel chromatography (0-60% THF/petroleum ether) to afford tert-butyl 4-[4-[[1-[1-(2,6-dioxo-3-piperidyl)-3-isopropyl-2-oxo-benzimidazol-5-yl]-4-piperidyl]oxy]cyclohexoxy]piperidine-1-carboxylate (110 mg, 20%, 65% purity) as a light yellow solid. MS (ESI) m/z: 668.3 [M+H]$^+$.

Step 6

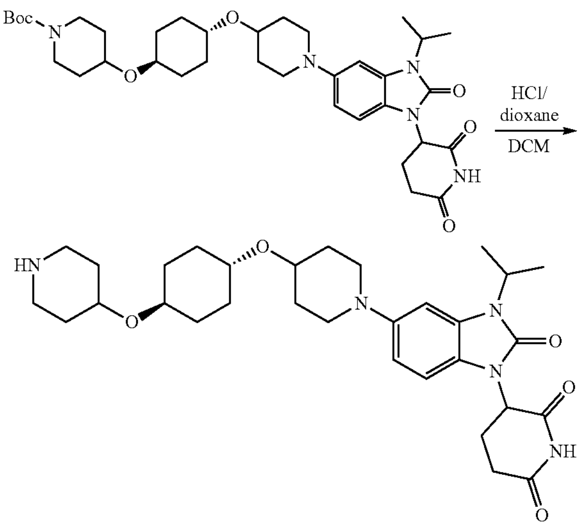

To a solution of tert-butyl 4-[4-[[1-[1-(2,6-dioxo-3-piperidyl)-3-isopropyl-2-oxo-benzimidazol-5-yl]-4-piperidyl]oxy]cyclohexoxy]piperidine-1-carboxylate (110 mg, 0.2 mmol) in dichloromethane (3 mL) was added HCl/dioxane (2 M, 4 mL). The mixture was stirred at 25° C. for 2 h, then concentrated under reduced pressure to afford 3-[3-isopropyl-2-oxo-5-[4-[4-(4-piperidyloxy)cyclohexoxy]-1-piperidyl]benzimidazol-1-yl]piperidine-2,6-dione (100 mg, crude, HCl salt) as a light yellow solid. MS (ESI) m/z: 568.3 [M+H]$^+$.

Step 7

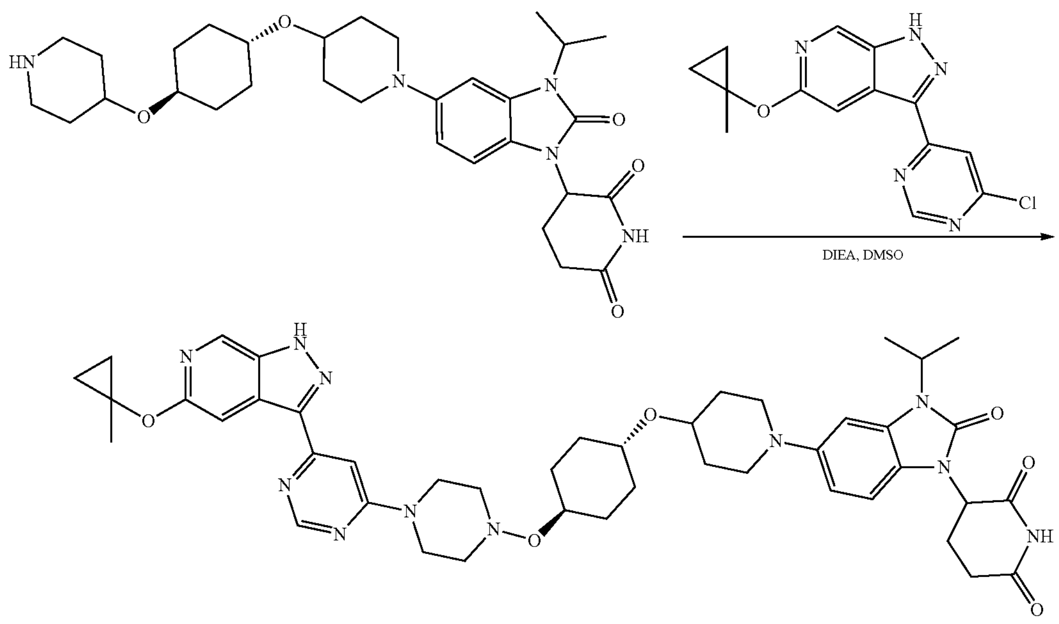

To a solution of 3-(6-chloropyrimidin-4-yl)-5-(1-methylcyclopropoxy)-1H-pyrazolo[3,4-c]pyridine (50 mg, 0.17 mmol) and 3-[3-isopropyl-2-oxo-5-[4-[4-(4-piperidyloxy)cyclohexoxy]-1-piperidyl]benzimidazol-1-yl]piperidine-2,6-dione (94.1 mg, 0.17 mmol) in DMSO (6 mL) was added DIEA (144 µL, 0.83 mmol). The mixture was stirred at 80° C. for 2 h, then filtered and the filtrate solution was purified by prep-HPLC (4%-44% acetonitrile in water (formic acid) over 25 min) to afford Compound 26 (29.7 mg, 21%) as an off-white solid. MS (ESI) m/z: 833.4 [M+H]$^+$.

Exemplary Synthesis of Compound 27:

To a solution of 3-(6-chloropyrimidin-4-yl)-5-isopropoxy-1H-indazole (prepared in a manner analogous to Compound 20, 50 mg, 0.17 mmol) and 3-[3-methyl-2-oxo-5-[4-[4-(4-piperidyloxy)cyclohexoxy]-1-piperidyl]benzimidazol-1-yl]piperidine-2,6-dione (synthesis described for Compound 25, 99.8 mg, 0.17 mmol, HCl) in DMSO (5 mL) was added DIEA (151 µL, 0.87 mmol). The mixture was stirred at 80° C. for 2 h, filtered and the resulting filtrate was purified by prep-HPLC (0%-40% acetonitrile in water (formic acid) over 25 min) to afford Compound 27 (62.6 mg, 43%) as an off-white solid. MS (ESI) m/z: 792.4 [M+H]$^+$.

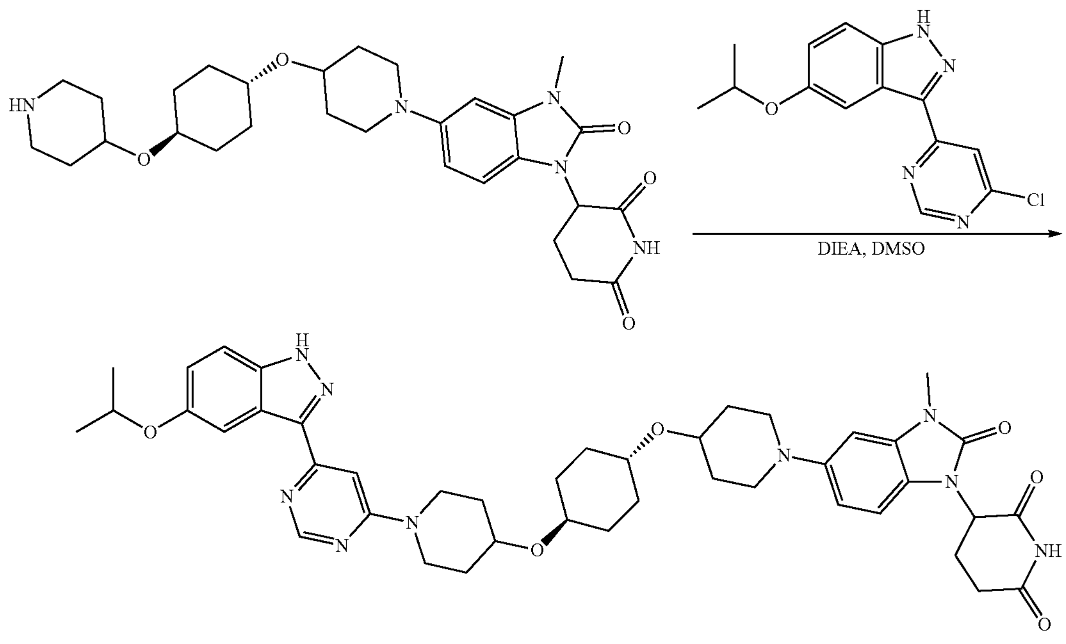

Exemplary Synthesis of Compound 28:

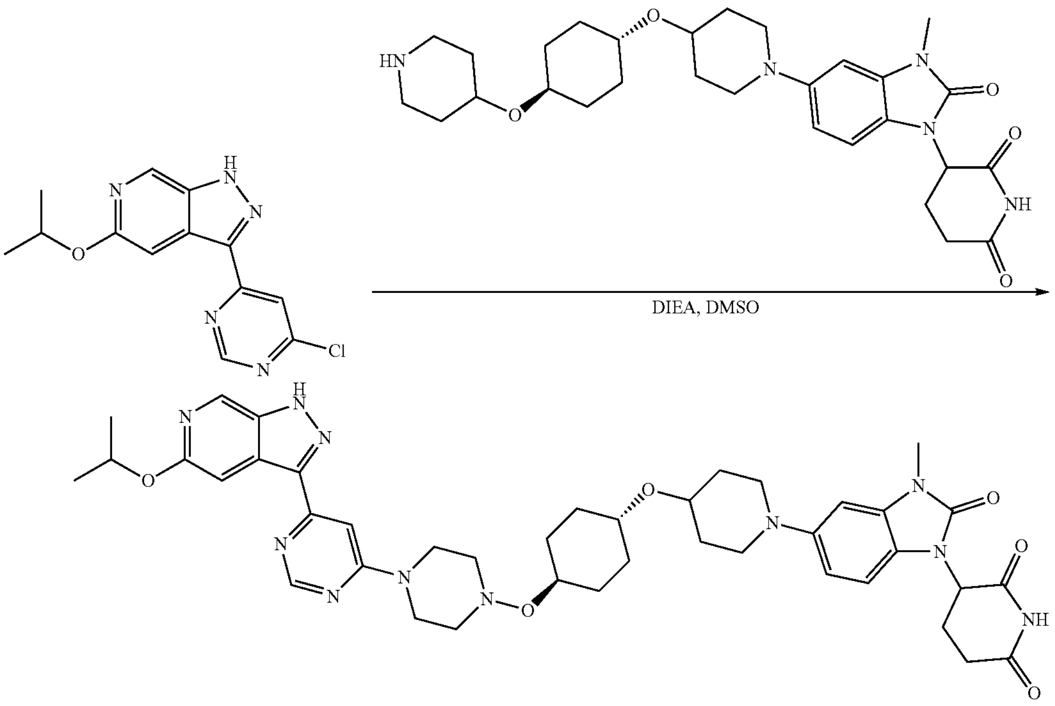

To a solution of 3-(6-chloropyrimidin-4-yl)-5-isopropoxy-1H-pyrazolo[3,4-c]pyridine (prepared in a manner analogous to Compound 20, 50 mg, 0.17 mmol) and 3-[3-methyl-2-oxo-5-[4-[4-(4-piperidyloxy)cyclohexoxy]-1-piperidyl]benzimidazol-1-yl]piperidine-2,6-dione (synthesis described for Compound 25, 93.1 mg, 0.17 mmol) in DMSO (5 mL) was added DIEA (150 μL, 0.86 mmol), the mixture was heated to 80° C. and stirred for 2 h. The reaction mixture was filtered and the filtrate solution was purified by prep-HPLC (2%-42% acetonitrile in water (formic acid) over 25 min) to afford Compound 28 (38.2 mg, 27%) as a brown solid. MS (ESI) m/z: 793.4 $[M+H]^+$.

Exemplary Synthesis of Compound 29:

Step 1

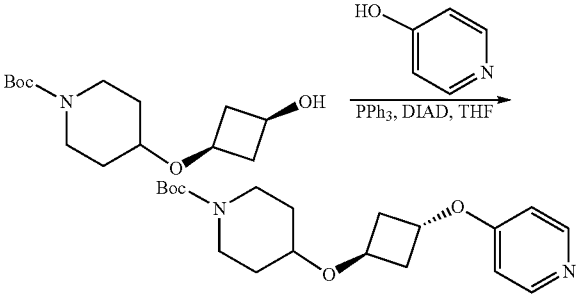

To a solution of tert-butyl 4-(3-hydroxycyclobutoxy)piperidine-1-carboxylate (5.0 g, 18 mmol) and pyridin-4-ol (2.10 g, 22 mmol) in THF (50 mL) was added triphenyl phosphine (5.8 g, 22 mmol). The mixture was stirred at 0° C. for 30 min before the dropwise addition of diisopropyl azodicarboxylate (4.3 mL, 22 mmol) at 0° C. under nitrogen atmosphere. The reaction mixture was stirred at 50° C. for 12 h under nitrogen atmosphere, then concentrated under reduced pressure. The residue was purified by silica gel chromatography (0-34% ethyl acetate/petroleum ether), the crude product was further triturated with methyl tert-butyl ether (5 mL×2) to afford tert-butyl 4-[3-(4-pyridyloxy)cyclobutoxy]piperidine-1-carboxylate (7.43 g, 96%) as yellow oil. MS (ESI) 349.2 $[M+H]^+$.

Step 2

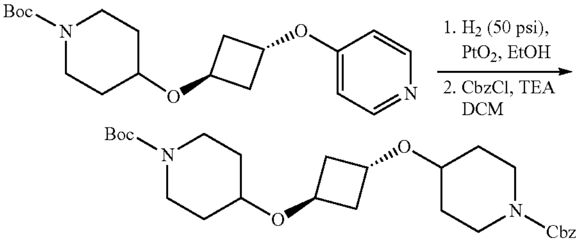

To a solution of tert-butyl 4-[3-(4-pyridyloxy)cyclobutoxy]piperidine-1-carboxylate (7.43 g, 20 mmol) and acetic acid (4.49 mL, 78 mmol) in EtOH (80 mL) was added platinum (IV) oxide (3.56 g, 16 mmol). The suspension was degassed and purged with hydrogen several times. The mixture was stirred under hydrogen (50 psi.) at 60° C. for 12 h, then filtered through celite, washed with EtOH (60 mL×5) and ethyl acetate (60 mL×5). The filtrate solution was concentrated under reduced pressure. The above residue was dissolved in dichloromethane (30 mL), triethylamine (6.0 mL, 43 mmol) and benzyl chloroformate (4.2 mL, 29 mmol) were added to the mixture at 0° C. under nitrogen atmosphere. The reaction mixture was stirred at 25° C. under nitrogen atmosphere for 2 h. Saturated sodium bicarbonate solution was added to the mixture to adjust the pH to 7-8.

The mixture was extracted with ethyl acetate (20 mL×3). The combined organic phase was washed with brine (20 mL×2), dried over anhydrous sodium sulfate, filtered and concentrated under reduced pressure. The residue was purified by silica gel chromatography (0-87% ethyl acetate/petroleum ether) to afford benzyl 4-[3-[(1-tert-butoxycarbonyl-4-piperidyl)oxy]cyclobutoxy]piperidine-1-carboxylate (2.74 g, 29%) as a colorless oil. MS (ESI) 389.1 [M−100+H]$^+$.

Step 3

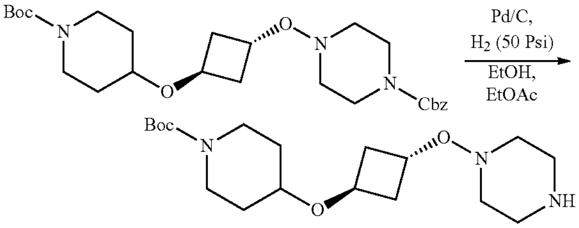

To a solution of benzyl 4-[3-[(1-tert-butoxycarbonyl-4-piperidyl)oxy]cyclobutoxy]piperidine-1-carboxylate (2.87 g, 6 mmol) in EtOH (15 mL) and ethyl acetate (15 mL) was added 10% palladium on carbon (312.5 mg). The suspension was degassed and purged with hydrogen several times. The mixture was stirred under hydrogen (50 psi.) at 50° C. for 12 h. The reaction mixture was filtered through celite, and the filter cake was washed with MeOH (100 mL×5) and ethyl acetate (100 mL×5). The filtrate solution was concentrated in vacuo to afford tert-butyl 4-[3-(4-piperidyloxy)cyclobutoxy]piperidine-1-carboxylate (2.06 g, 99%) as a colorless oil.

Step 4

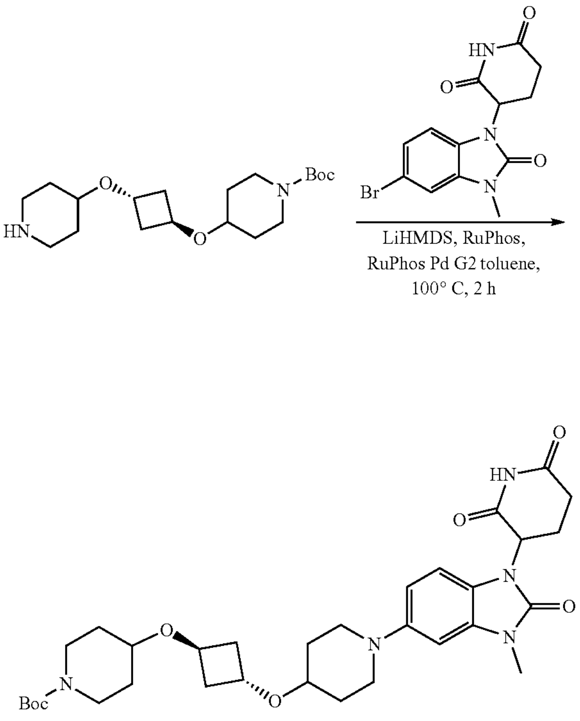

To a mixture of 3-(5-bromo-3-methyl-2-oxo-benzimidazol-1-yl)piperidine-2,6-dione (620 mg, 1.8 mmol) and tert-butyl 4-[3-(4-piperidyloxy)cyclobutoxy]piperidine-1-carboxylate (500 mg, 1.4 mmol) in toluene (5 mL) were added RuPhos (32.91 mg, 70 μmol) and [2-(2-aminophenyl)phenyl]-chloro-palladium; dicyclohexyl-[2-(2,6-diisopropoxyphenyl)phenyl]phosphane (54.78 mg, 70 μmol). To the above mixture was dropwise added lithium bis(trimethylsilyl)amide (1 M, 7.1 mL) at 0° C. under nitrogen atmosphere. The mixture was stirred at 100° C. for 2 h under nitrogen atmosphere. The reaction mixture was poured into acetic acid (4 mL) and water (40 mL) at 0° C., then diluted with saturated aqueous sodium bicarbonate solution (40 mL). The mixture was extracted with ethyl acetate (50 mL×2). The combined organic layers were washed with brine (50 mL×2) and dried over anhydrous sodium sulfate, filtered and concentrated. The residue was purified by silica gel chromatography (0-60% ethyl acetate/petroleum ether) to afford tert-butyl 4-[3-[[1-[1-(2,6-dioxo-3-piperidyl)-3-methyl-2-oxo-benzimidazol-5-yl]-4-piperidyl]oxy]cyclobutoxy]piperidine-1-carboxylate (450 mg, 52%) as an off-white solid. MS (ESI) 612.3 [M+H]$^+$.

Step 5

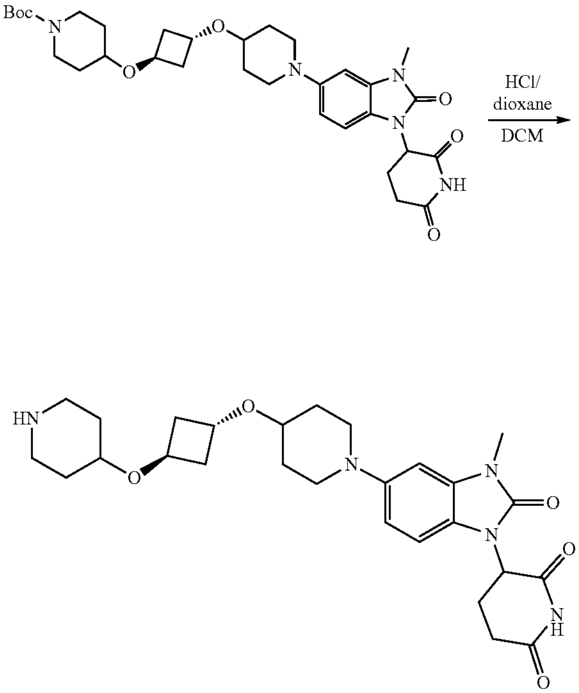

To a solution of tert-butyl 4-[3-[[1-[1-(2,6-dioxo-3-piperidyl)-3-methyl-2-oxo-benzimidazol-5-yl]-4-piperidyl]oxy]cyclobutoxy]piperidine-1-carboxylate (250 mg, 0.4 mmol) in dichloromethane (2 mL) was added HCl/dioxane (2 M, 6 mL). The mixture was stirred at 25° C. for 3.5 h, then concentrated under reduced pressure to afford 3-[3-methyl-2-oxo-5-[4-[3-(4-piperidyloxy)cyclobutoxy]-1-piperidyl]benzimidazol-1-yl]piperidine-2,6-dione (240 mg, crude, HCl salt) as an off-white solid. MS (ESI) 512.2 [M+H]$^+$.

Step 6

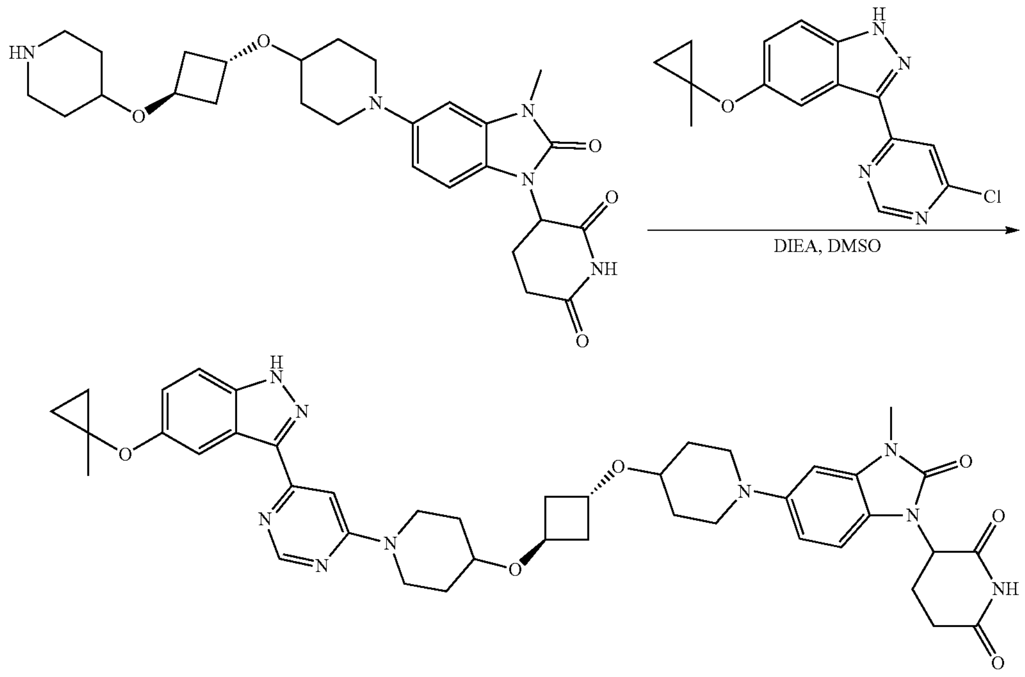

To a solution of 3-[3-methyl-2-oxo-5-[4-[3-(4-piperidyloxy)cyclobutoxy]-1-piperidyl]benzimidazol-1-yl]piperidine-2,6-dione (205.8 mg, 402 μmol) and 3-(6-chloropyrimidin-4-yl)-5-(1-methylcyclopropoxy)-1H-indazole (110 mg, 366 μmol) in DMSO (4 mL) was added DIEA (191 μL, 1.1 mmol). The mixture was stirred at 70° C. for 12 h, then cooled to 25° C., filtered and concentrated under reduced pressure. The residue was purified by prep-HPLC (2%-42% acetonitrile in water (TFA) over 20 min), the crude product was further purified by prep-HPLC (0%-60% acetonitrile in water (formic acid) over 20 min) to give Compound 29 (98.8 mg, 35%) as an off-white solid. MS (ESI) m/z: 776.4 $[M+H]^+$.

Exemplary Synthesis of Compound 30:

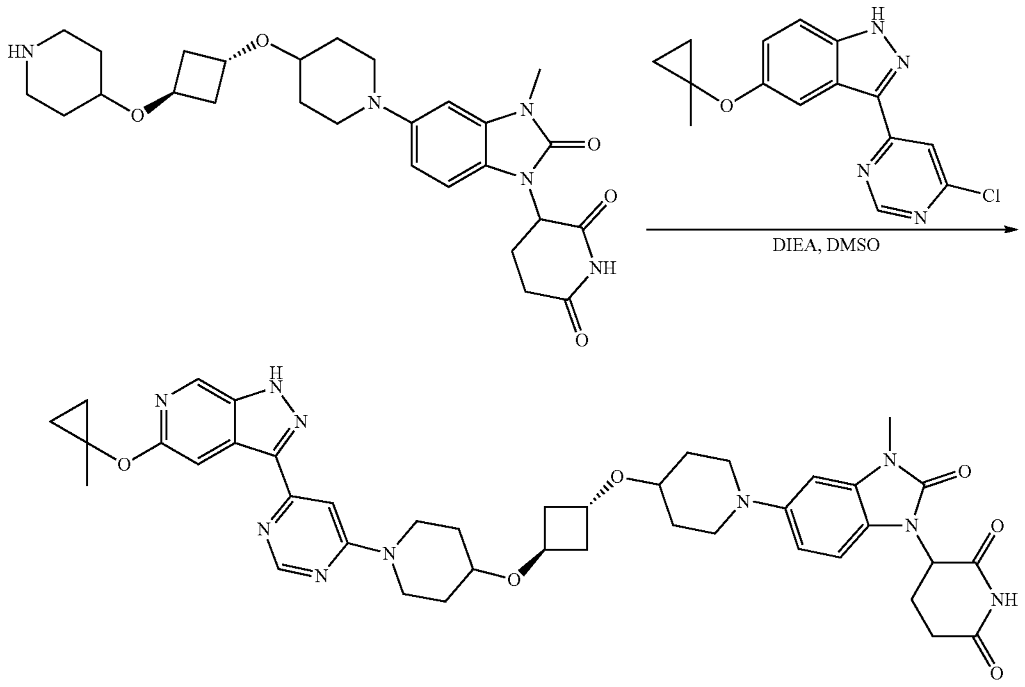

To a solution of 3-[3-methyl-2-oxo-5-[4-[3-(4-piperidyloxy)cyclobutoxy]-1-piperidyl]benzimidazol-1-yl]piperidine-2,6-dione (synthesis described for Compound 29, 205.8 mg, 402 μmol,) and 3-(6-chloropyrimidin-4-yl)-5-(1-methylcyclopropoxy)-1H-indazole (110 mg, 366 μmol) in DMSO (4 mL) was added DIEA (191 μL, 1.1 mmol). The mixture was stirred at 70° C. for 12 h, then allowed to cool to 25° C., filtered and concentrated under reduced pressure. The residue was purified by prep-HPLC (2%-42% acetonitrile in water (TFA) over 20 min), the crude product was further purified by prep-HPLC (0%-60% acetonitrile in water (formic acid) over 20 min) to afford Compound 30 (98.8 mg, 35%) as an off-white solid. MS (ESI) m/z: 776.4 [M+H]+.

Exemplary Synthesis of Compound 31:

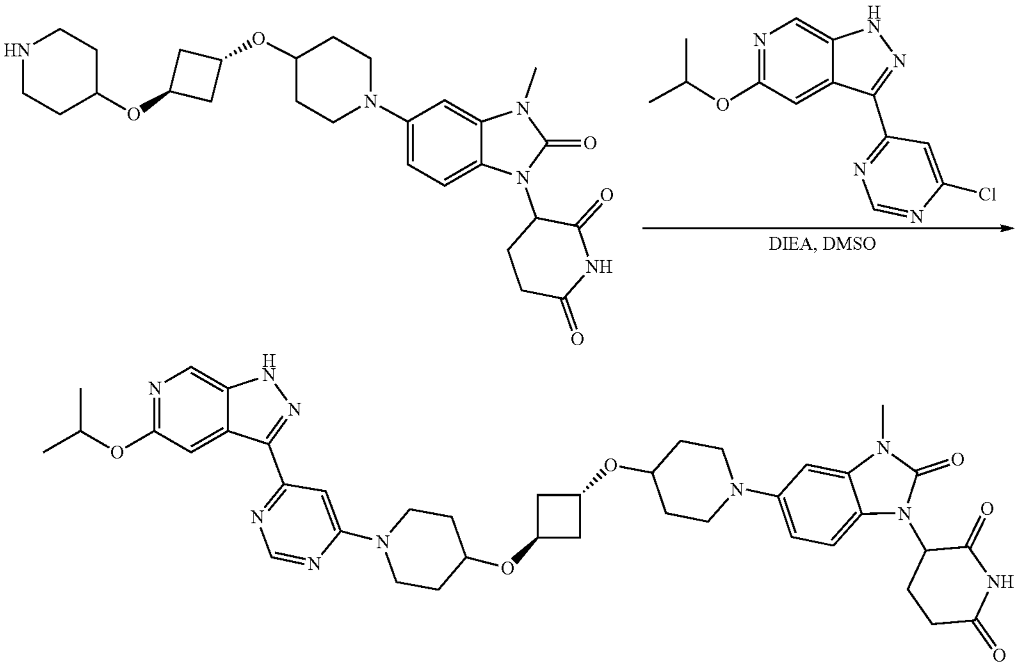

To a solution of 3-[3-methyl-2-oxo-5-[4-[3-(4-piperidyloxy)cyclobutoxy]-1-piperidyl]benzimidazol-1-yl]piperidine-2,6-dione (synthesis described for Compound 29, 137.7 mg, 269 μmol) and 3-(6-chloropyrimidin-4-yl)-5-isopropoxy-1H-pyrazolo[3,4-c]pyridine (60.0 mg, 207 μmol) in DMSO (5 mL) was added DIEA (108 μL, 0.6 mmol). The mixture was stirred at 80° C. for 2 h, then cooled to 25° C., filtered and concentrated under reduced pressure. The residue was purified by prep-HPLC (4%-44% acetonitrile in water (TFA) over 25 min), the crude product was further purified by prep-HPLC (2%-42% acetonitrile in water (formic acid) over 20.5 min) to afford Compound 31 (39.9 mg, 25% y) as a white solid. MS (ESI) m/z: 765.3 [M+H]+.

Exemplary Synthesis of Compound 32:

Step 1

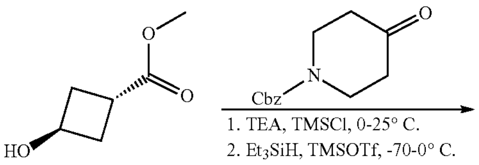

-continued

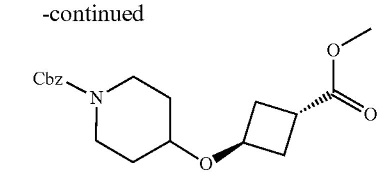

To a solution of methyl 3-hydroxycyclobutanecarboxylate (15 g, 0.1 mol) in THF (150 mL) were added chloro(trimethyl) silane (16.1 mL, 0.1 mol) and triethylamine (19.3 mL, 0.1 mol) at 0° C. under nitrogen atmosphere, the mixture was stirred at 25° C. for 1 h under nitrogen atmosphere. The reaction mixture was filtered and concentrated under reduced pressure. To a stirred solution of above residue and benzyl 4-oxopiperidine-1-carboxylate (27.5 mL, 0.1 mol) in dichloromethane (150 mL) were added triethylsilane (27.6 mL, 0.2 mol) and trimethylsilyl trifluoromethanesulfonate (11.5 mL, 63 mmol) dropwise at −70° C. under nitrogen atmosphere, the reaction mixture was stirred at 0° C. under nitrogen atmosphere for 2 h. The mixture was diluted with water (200 mL) and extracted with dichloromethane (200 mL×3). The combined organic layers were washed with brine (200 mL×2), dried over sodium sulfate, filtered and concentrated under reduced pressure. The residue was purified by silica gel chromatography (0-30% ethyl acetate/petroleum ether) to afford benzyl 4-(3-methoxycarbonylcyclobutoxy)piperidine-1-carboxylate (21.39 g, 53%) as a colorless oil. MS (ESI) 370.2 [M+23]+.

Step 2

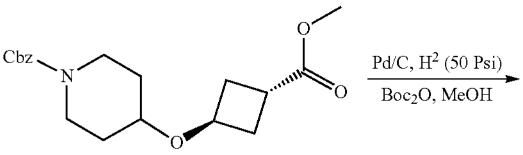

-continued

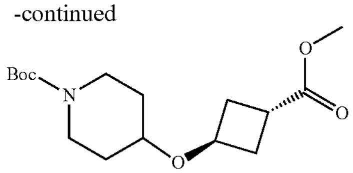

To a solution of benzyl 4-(3-methoxycarbonylcyclobutoxy)piperidine-1-carboxylate (21.4 g, 61 mmol) and di-tert-butyl dicarbonate (42.4 mL, 185 mmol) in MeOH (200 mL) was added palladium on carbon (3.28 g). The suspension was degassed and purged with hydrogen several times. The mixture was stirred under hydrogen (50 psi.) at 50° C. for 12 h. The reaction mixture was filtered through celite, washed with MeOH (100 mL×5) and ethyl acetate (100 mL×5), the filtrate solution was concentrated in vacuo. The residue was purified by silica gel chromatography (0-30% ethyl acetate/petroleum ether) to afford tert-butyl 4-(3-methoxycarbonylcyclobutoxy)piperidine-1-carboxylate (17.57 g, 91%) as a colorless oil.

Step 3

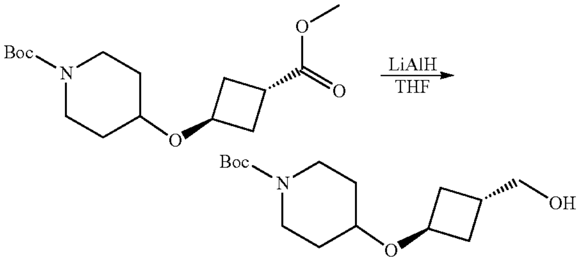

To a mixture of tert-butyl 4-(3-methoxycarbonylcyclobutoxy)piperidine-1-carboxylate (1 g, 3 mmol) in THF (10 mL) was dropwise added lithium aluminum chloride (2.5 M, 1.3 mL) at 0° C. under nitrogen atmosphere, the mixture was stirred at 0° C. for 2 h under nitrogen atmosphere. The reaction mixture was diluted with water (0.12 mL), followed by 15% aqueous sodium hydroxide solution (0.12 mL) and water (0.36 mL). The mixture was dried over anhydrous sodium sulfate, filtered, washed with THF (40 mL×4). The combined filtrate solution was concentrated under reduced pressure to afford tert-butyl 4-[3-(hydroxymethyl)cyclobutoxy]piperidine-1-carboxylate (900 mg, crude) as a colorless oil, which was used in the next step directly. MS (ESI) 230.2 $[M-55+H]^+$.

Step 4

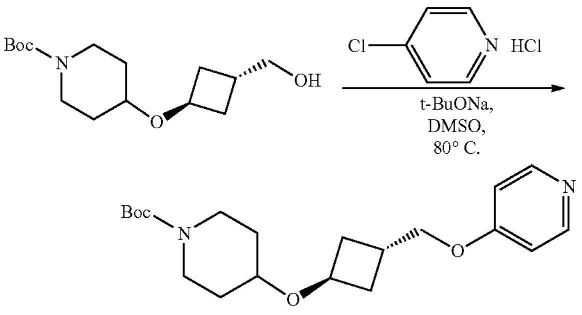

To a solution of sodium tert-butoxide (5.79 g, 60 mmol) in DMSO (50 mL) was added 4-chloropyridine hydrochloride (3.39 g, 23 mmol), the mixture was stirred at 40° C. for 0.5 h before the addition of tert-butyl 4-[3-(hydroxymethyl)cyclobutoxy]piperidine-1-carboxylate (4.3 g, 15 mmol). The reaction mixture was stirred at 80° C. for 12 h, then cooled to 0° C. and diluted with saturated ammonium chloride solution (100 mL). The mixture was extracted with ethyl acetate (100 mL×3). The combined organic phase was washed with brine (100 mL×3), dried over anhydrous sodium sulfate, filtered and concentrated under reduced pressure. The residue was purified by silica gel chromatography (0-77% ethyl acetate/petroleum ether) to afford tert-butyl 4-[3-(4-pyridyloxymethyl)cyclobutoxy]piperidine-1-carboxylate (3.26 g, 60%) as a white solid. MS (ESI) 363.0 $[M+H]^+$.

Step 5

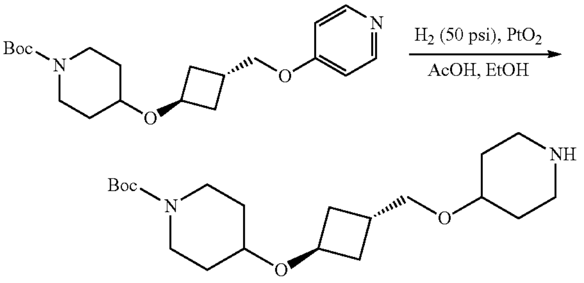

To a solution of tert-butyl 4-[3-(4-pyridyloxymethyl)cyclobutoxy]piperidine-1-carboxylate (3.26 g, 9 mmol) and acetic acid (1.54 mL, 27 mmol) in EtOH (30 mL) was added platinum (IV) oxide (1.63 g, 7 mmol). The suspension was degassed and purged with hydrogen several times. The mixture was stirred under hydrogen (50 psi.) at 50° C. for 16 h. The reaction mixture was filtered through celite and washed with EtOH (50 mL×5) and ethyl acetate (50 mL×5). The filtrate solution was concentrated to afford tert-butyl 4-[3-(4-piperidyloxymethyl)cyclobutoxy]piperidine-1-carboxylate (5 g, crude) as a colorless oil, which was used in the next step directly. MS (ESI) 369.6 $[M+H]^+$.

Step 6

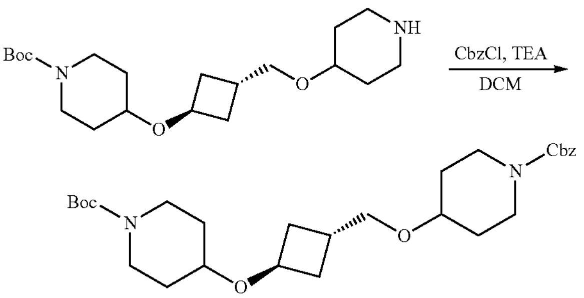

To a solution of tert-butyl 4-[3-(4-piperidyloxymethyl)cyclobutoxy]piperidine-1-carboxylate (3.3 g, 9 mmol) in dichloromethane (40 mL) were added triethylamine (3.74 mL, 27 mmol) and benzyl chloroformate (1.92 mL, 13 mmol) at 0° C. under nitrogen atmosphere. The mixture was stirred at 25° C. for 2 h under nitrogen atmosphere, then cooled to 0° C. and diluted with saturated aqueous sodium bicarbonate solution (60 mL). The mixture was extracted with ethyl acetate (60 mL×3). The combined organic phase was washed with brine (50 mL×3), dried over anhydrous sodium sulfate, filtered and concentrated under reduced pressure. The residue was purified by silica gel chromatography (0-25% ethyl acetate/petroleum ether) to afford benzyl 4-[[3-[(1-tert-butoxycarbonyl-4-piperidyl)oxy]cyclobutyl]methoxy]piperidine-1-carboxylate (1.19 g, 26%) as a colorless oil. MS (ESI) 403.3 [M−100+H]$^+$.

Step 7

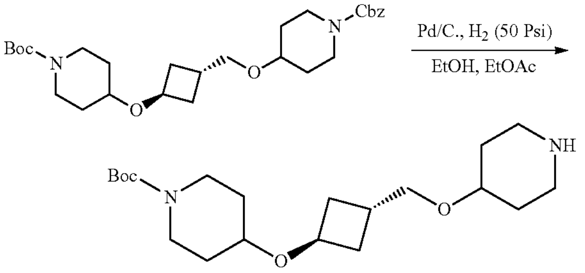

To a solution of benzyl 4-[[3-[(1-tert-butoxycarbonyl-4-piperidyl)oxy]cyclobutyl]methoxy]piperidine-1-carboxylate (970 mg, 2 mmol) in EtOH (10 mL) and ethyl acetate (10 mL) was added 10% palladium on carbon (102.7 mg). The suspension was degassed and purged with hydrogen several times. The mixture was stirred under hydrogen (50 psi.) at 50° C. for 12 h. The reaction mixture was filtered through celite, washed with MeOH (50 mL×5) and ethyl acetate (50 mL×5). The filtrate solution was concentrated in vacuo to afford tert-butyl 4-[3-(4-piperidyloxymethyl)cyclobutoxy]piperidine-1-carboxylate (750 mg, crude) as a colorless oil, which was used in the next step directly. MS (ESI) 369.2 [M+H]$^+$.

Step 8

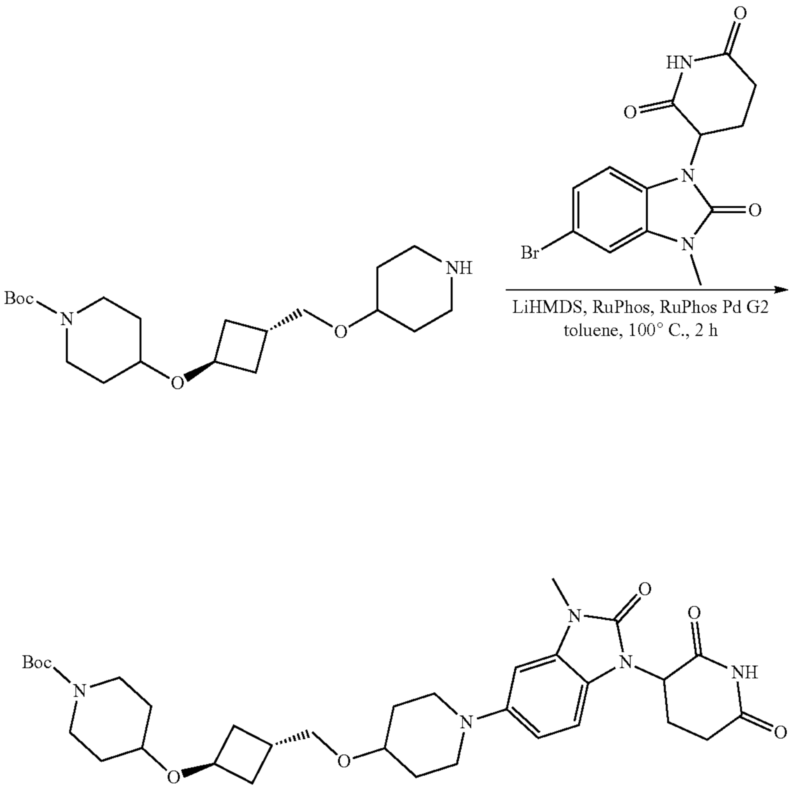

To a mixture of tert-butyl 4-[3-(4-piperidyloxymethyl)cyclobutoxy]piperidine-1-carboxylate (550 mg, 1.5 mmol) and 3-(5-bromo-3-methyl-2-oxo-benzimidazol-1-yl)piperidine-2,6-dione (1.31 g, 4 mmol) in toluene (10 mL) was added RuPhos (69.6 mg, 0.1 mmol) and RuPhos Pd $G_2$ (115.9 mg, 0.15 mmol), followed by the dropwise addition of lithium bis(trimethylsilyl)amide (1 M, 14.9 mL) at 0° C. for 15 min under nitrogen atmosphere. The mixture was stirred at 100° C. for 12 h under nitrogen atmosphere. The reaction mixture was poured into acetic acid (0.5 mL) and water (5 mL) at 0° C. The resulting mixture was diluted with saturated aqueous sodium bicarbonate solution (50 mL) and extracted with ethyl acetate (50 mL×3). The combined organic layers were washed with brine (50 mL×2), dried over anhydrous sodium sulfate, filtered and concentrated. The residue was purified by silica gel chromatography (0-50% THF/petroleum ether) to afford tert-butyl 4-[3-[[1-[1-(2,6-dioxo-3-piperidyl)-3-methyl-2-oxo-benzimidazol-5-yl]-4-piperidyl]oxymethyl]cyclobutoxy]piperidine-1-carboxylate (250 mg, 24%) as a green solid. MS (ESI) 626.6 [M+H]$^+$.

Step 9

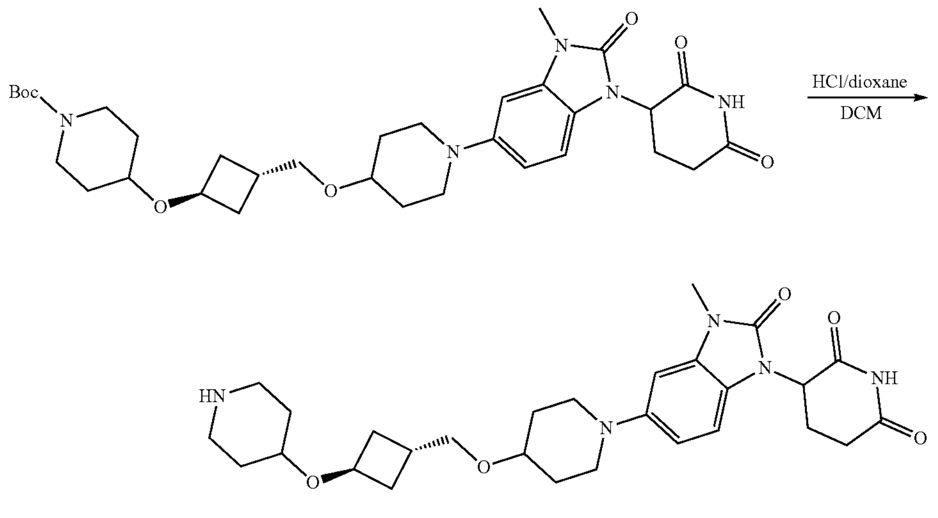

To a solution of tert-butyl 4-[3-[[1-[1-(2,6-dioxo-3-piperidyl)-3-methyl-2-oxo-benzimidazol-5-yl]-4-piperidyl]oxymethyl]cyclobutoxy]piperidine-1-carboxylate (250 mg, 0.4 mmol) in dichloromethane (4 mL) was added HCl/dioxane (2 M, 12 mL). The reaction mixture was stirred at 25° C. for 6 h, then concentrated under reduced pressure to afford 3-[3-methyl-2-oxo-5-[4-[[3-(4-piperidyloxy)cyclobutyl]methoxy]-1-piperidyl]benzimidazol-1-yl]piperidine-2,6-dione (250 mg, crude, HCl salt) as a brown solid. MS (ESI) 526.3 [M+H]$^+$.

Step 10

To a solution of 3-[3-methyl-2-oxo-5-[4-[[3-(4-piperidyloxy)cyclobutyl]methoxy]-1-piperidyl]benzimidazol-1-yl]piperidine-2,6-dione (87.1 mg, 0.16 mmol) and 3-(6-chloropyrimidin-4-yl)-5-(1-methylcyclopropoxy)-1H-pyrazolo[3,4-c]pyridine (50 mg, 0.16 mmol) in DMSO (5 mL) was added DIEA (86.6 μL, 0.5 mmol). The mixture was stirred at 80° C. for 2 h, then cooled to 25° C., filtered and concentrated under reduced pressure. The residue was purified by prep-HPLC (2%-42% acetonitrile in water (TFA) over 20 min), the crude product was further purified by prep-HPLC (0%-60% acetonitrile in water (formic acid)

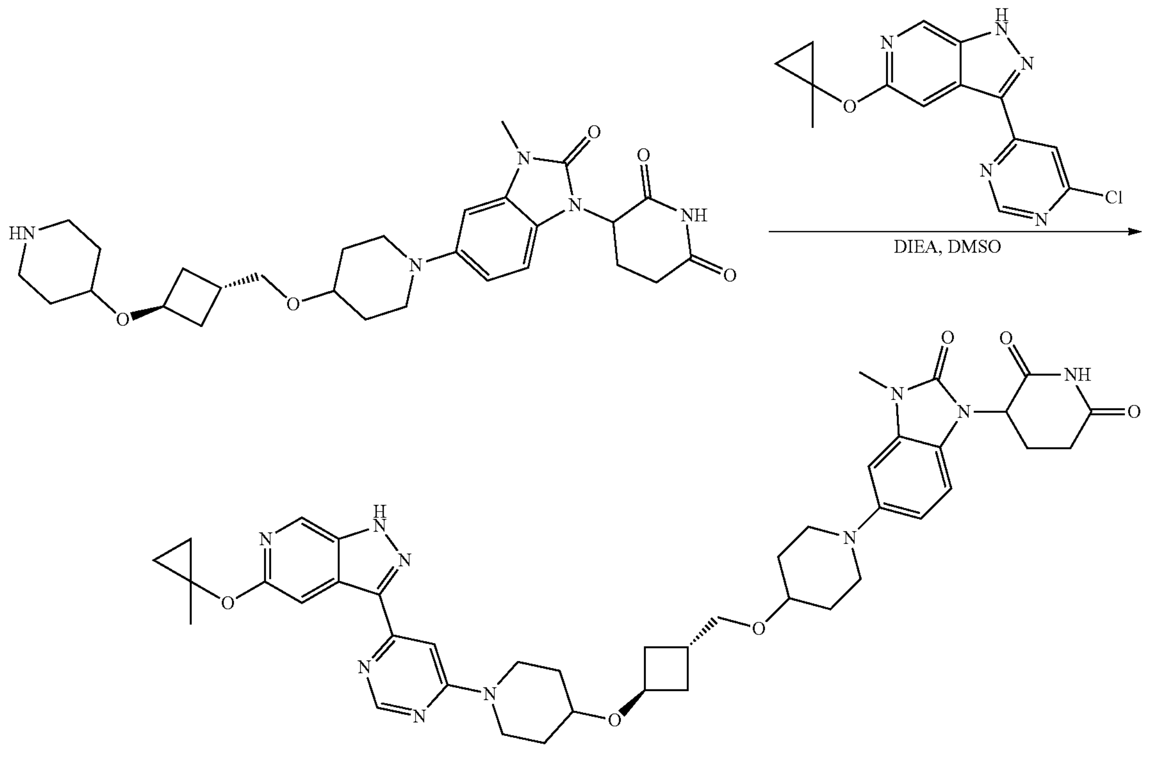

over 20 min) to give Compound 32 (33.5 mg, 26%) as an off-white solid. MS (ESI) m/z: 396.5 [M/2+H]$^+$.

Exemplary Synthesis of Compound 33:

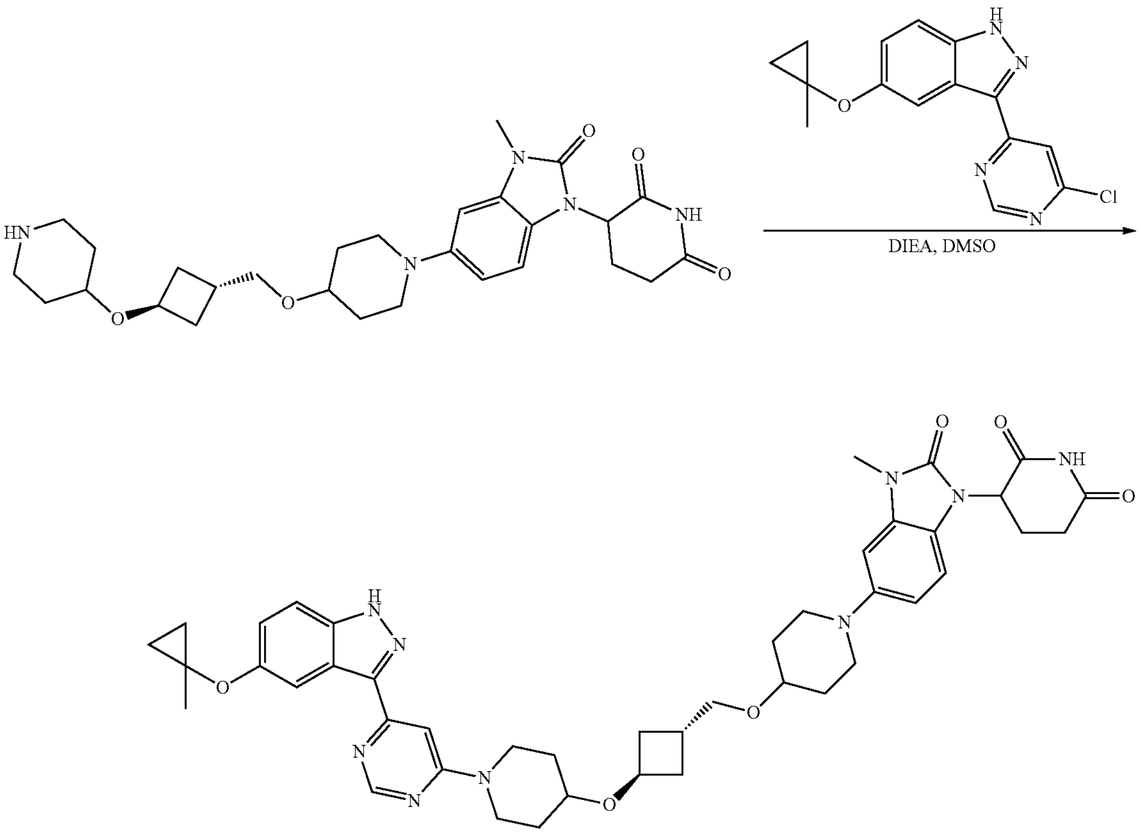

To a solution of 3-[3-methyl-2-oxo-5-[4-[[3-(4-piperidyloxy)cyclobutyl]methoxy]-1-piperidyl]benzimidazol-1-yl] piperidine-2,6-dione (synthesis described for Compound 32, 122 mg, 0.2 mmol) and 3-(6-chloropyrimidin-4-yl)-5-(1-methylcyclopropoxy)-1H-indazole (70 mg, 0.2 mmol) in DMSO (4 mL) was added DIEA (122 μL, 0.7 mmol). The mixture was stirred at 70° C. for 12 h, then cooled to 25° C., filtered and concentrated under reduced pressure. The residue was purified by prep-HPLC (0%-40% acetonitrile in water (TFA) over 20 min), the crude product was further purified by prep-HPLC (0%-60% acetonitrile in water (formic acid) over 20 min) to give Compound 33 (36.2 mg, 19%) as an off-white solid. MS (ESI) m/z: 789.3 [M+H]$^+$.

Exemplary Synthesis of Compound 34:

Step 1

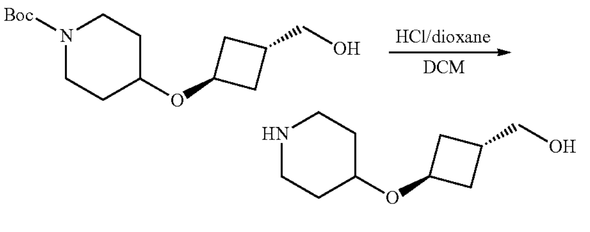

To a solution of tert-butyl 4-[3-(hydroxymethyl)cyclobutoxy]piperidine-1-carboxylate (2.7 g, 9 mmol) in dichloromethane (7 mL) was added HCl/dioxane (2 M, 22.7 mL). The mixture was stirred at 25° C. for 12 h, then concentrated under reduced pressure to afford [3-(4-piperidyloxy)cyclobutyl]methanol (2.05 g, crude, HCl salt) as a white solid, which was used in the next step directly.

Step 2

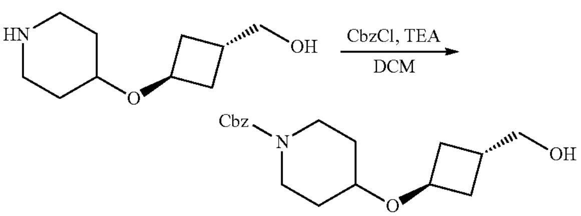

To a solution of [3-(4-piperidyloxy)cyclobutyl]methanol (2.05 g, 9 mmol, HCl) in dichloromethane (20 mL) was added triethylamine (3.9 mL, 28 mmol) at 0° C., followed by the dropwise addition of benzyl chloroformate (2.0 mL, 14 mmol) in dichloromethane (5 mL) at 0° C. under nitrogen atmosphere. The reaction mixture was stirred at 25° C. for 2 h under nitrogen atmosphere, then cooled to 0° C. The mixture was diluted with saturated aqueous sodium bicarbonate solution (60 mL) and extracted with ethyl acetate (60 mL×3). The combined organic phase was washed with brine (50 mL×3), dried over anhydrous sodium sulfate, filtered and concentrated under reduced pressure. The residue was purified by silica gel chromatography (0-80% methyl tert-butyl ether/petroleum ether) to afford benzyl 4-[3-(hydroxymethyl)cyclobutoxy]piperidine-1-carboxylate (1.55 g, 52%) as a colorless oil. MS (ESI) 320.1 $[M+H]^+$.

Step 3

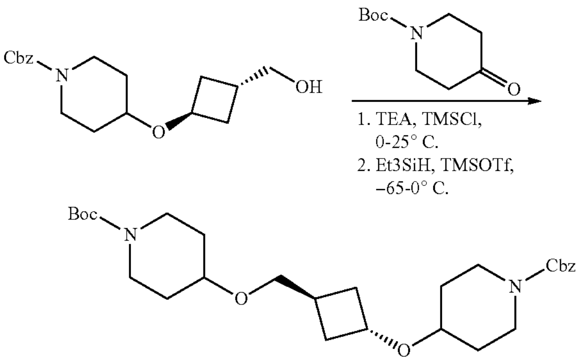

To a solution of ethyl benzyl 4-[3-(hydroxymethyl)cyclobutoxy]piperidine-1-carboxylate (1.5 g, 5 mmol) in THF (20 mL) were added chloro(trimethyl) silane (656 μL, 5 mmol) and triethylamine (784 μL, 6 mmol) at 0° C. under nitrogen atmosphere, the mixture was stirred at 25° C. for 1 h under nitrogen atmosphere. The reaction mixture was filtered, and the filtrate was concentrated under reduced pressure. To a stirred solution of the above residue and tert-butyl 4-oxopiperidine-1-carboxylate (2.81 g, 14 mmol) in dichloromethane (20 mL) were added triethylsilane (1.13 mL, 7 mmol) and trimethylsilyl trifluoromethanesulfonate (467 μL, 2.6 mmol) dropwise at −70° C. under nitrogen atmosphere. The reaction mixture was stirred at 0° C. under nitrogen atmosphere for 2 h, then diluted with water (20 mL) and extracted with dichloromethane (20 mL×3). The combined organic layers were washed with brine (20 mL×2), dried over sodium sulfate, filtered and concentrated under reduced pressure. The residue was purified by silica gel chromatography (0-23% THF/petroleum ether) to afford tert-butyl 4-[[3-[(1-benzyloxycarbonyl-4-piperidyl)oxy]cyclobutyl]methoxy]piperidine-1-carboxylate (320 mg, 14%) as a yellow oil. MS (ESI) 403.2 $[M-100+H]^+$.

Step 4

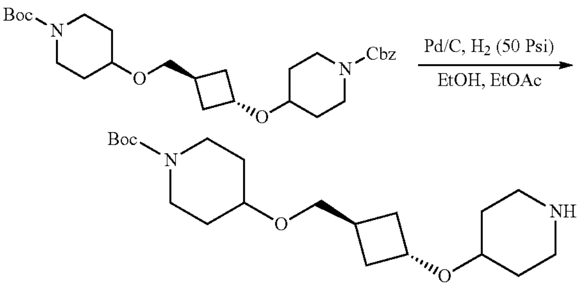

To a solution of tert-butyl 4-[[3-[(1-benzyloxycarbonyl-4-piperidyl)oxy]cyclobutyl]methoxy]piperidine-1-carboxylate (320 mg, 0.6 mmol) in EtOH (5 mL) and ethyl acetate (5 mL) was added 10% palladium on carbon (33.9 mg). The suspension was degassed and purged with hydrogen several times. The mixture was stirred under hydrogen (50 psi.) at 50° C. for 12 h. The reaction mixture was filtered through celite, washed with MeOH (50 mL×5) and ethyl acetate (50 mL×5), and concentrated in vacuo to afford tert-butyl 4-[[3-(4-piperidyloxy)cyclobutyl]methoxy]piperidine-1-carboxylate (210 mg, 75%, 84% purity) as a yellow oil. MS (ESI) 369.3 $[M+H]^+$.

Step 5

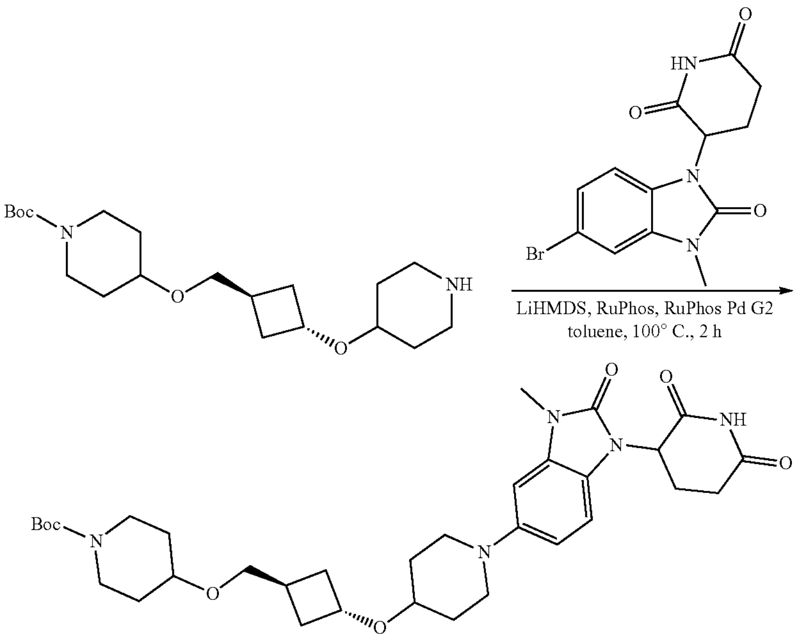

To a mixture of tert-butyl 4-[[3-(4-piperidyloxy)cyclobutyl]methoxy]piperidine-1-carboxylate (150 mg, 0.4 mmol) and 3-(5-bromo-3-methyl-2-oxo-benzimidazol-1-yl) piperidine-2,6-dione (151 mg, 0.4 mmol) in toluene (5 mL) were added RuPhos (9.5 mg, 20 μmol) and RuPhos Pd G2 (15.8 mg, 20 μmol), followed by the dropwise addition of lithium bis(trimethylsilyl)amide (1 M, 2 mL) at 0° C. under nitrogen atmosphere. The mixture was stirred at 100° C. for 2 h under nitrogen atmosphere. The reaction mixture was poured into acetic acid (0.3 mL) and water (5 mL) at 0° C., then diluted with saturated aqueous sodium bicarbonate solution (10 mL) and extracted with ethyl acetate (20 mL×3). The combined organic layers were washed with brine (20 mL×2) and dried over anhydrous sodium sulfate, filtered and concentrated. The residue was purified by silica gel chromatography (0-54% THF/petroleum ether) to afford tert-butyl 4-[[3-[[1-[1-(2,6-dioxo-3-piperidyl)-3-methyl-2-oxo-benzimidazol-5-yl]-4-piperidyl]oxy]cyclobutyl] methoxy]piperidine-1-carboxylate (110 mg, 23%, 53% purity) as a yellow solid. MS (ESI) 626.4 $[M+H]^+$.

Step 6

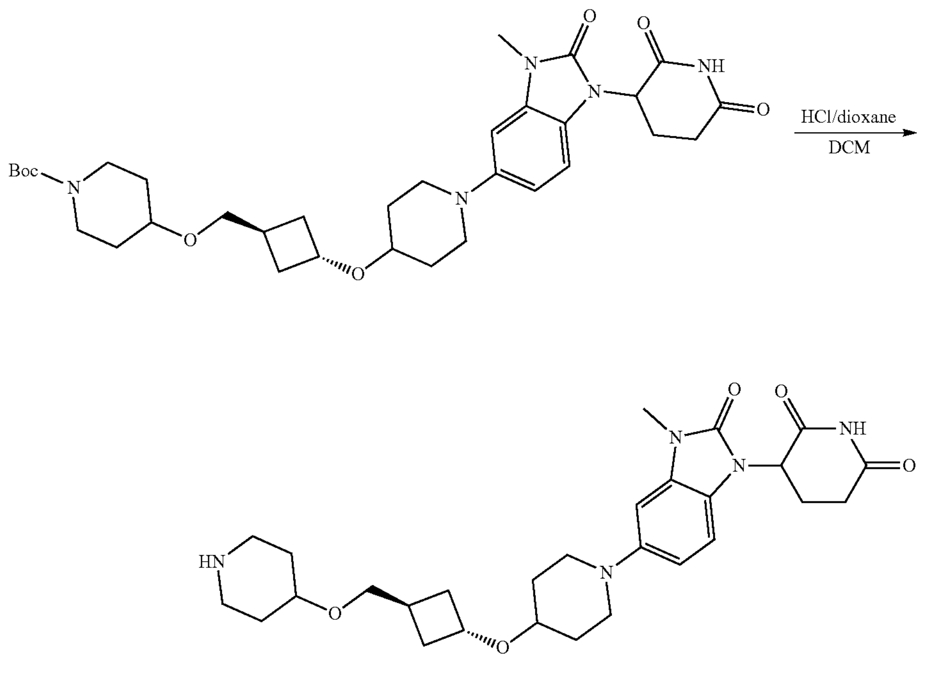

To a solution of tert-butyl 4-[[3-[[1-[1-(2,6-dioxo-3-piperidyl)-3-methyl-2-oxo-benzimidazol-5-yl]-4-piperidyl] oxy]cyclobutyl]methoxy]piperidine-1-carboxylate (110 mg, 0.2 mmol) in dichloromethane (4 mL) was added HCl/dioxane (2 M, 4 mL), and the solution was stirred at 25° C. for 1 h. The reaction solution was concentrated under reduced pressure and used in the next step directly.

Step 7

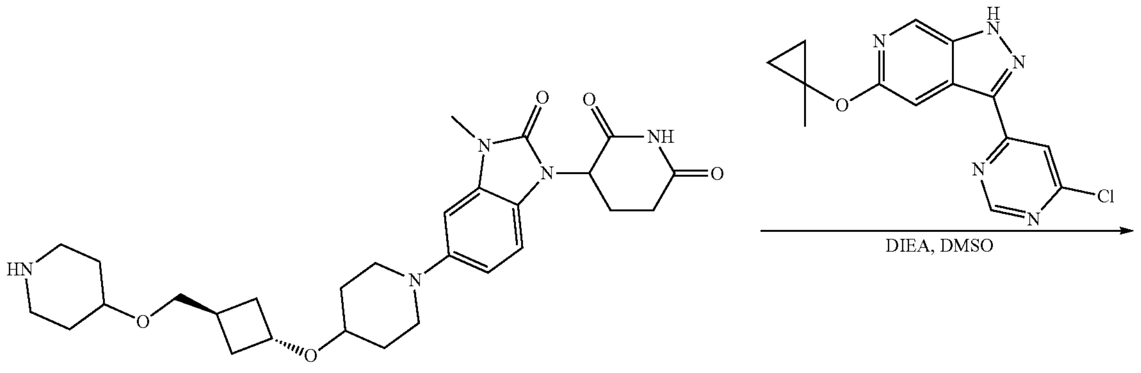

-continued

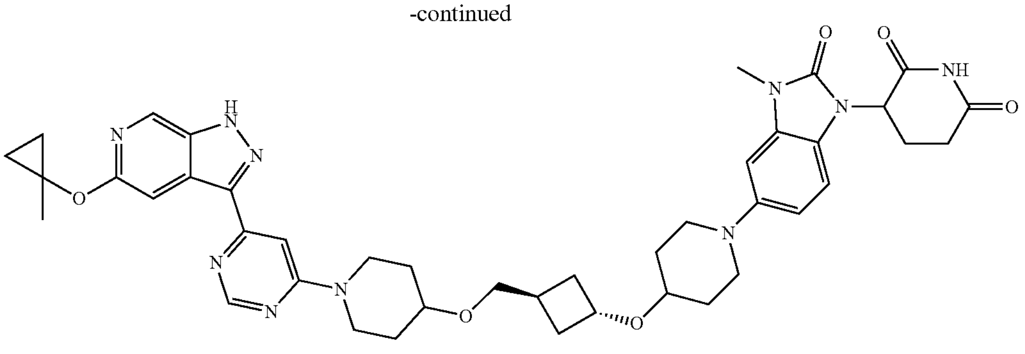

To the crude product from step 6 above and 3-(6-chloropyrimidin-4-yl)-5-(1-methylcyclopropoxy)-1H-pyrazolo[3,4-c]pyridine (53.04 mg, 0.17 mmol) in DMSO (10 mL) was added DIEA (153.1 μL, 0.9 mmol). The resulting solution was stirred at 70° C. for 16 h, then diluted with water (20 mL) and extracted with dichloromethane (2×30 mL). The organic layer was dried over sodium sulfate, filtered and concentrated under reduced pressure. The residue was purified by prep-TLC (dichloromethane:methanol=10:1) to give 100 mg crude product as yellow gum, which was further purified by prep-HPLC (2%-42% acetonitrile in water (formic acid) over 20 min) to give Compound 34 (24.2 mg, 17%) as a white solid. MS (ESI) m/z: 791.4 $[M+H]^+$.

Exemplary Synthesis of Compound 35:

Step 1

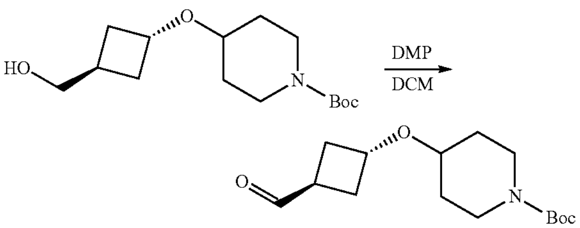

To a solution of tert-butyl 4-[3-(hydroxymethyl)cyclobutoxy]piperidine-1-carboxylate (2 g, 7 mmol) in dichloromethane (35 mL) was added Dess-Martin periodinane (3.26 mL, 10 mmol), the mixture was stirred at 25° C. for 1 h. The reaction mixture was diluted with saturated sodium bicarbonate solution until pH 8, saturated sodium thiosulfate solution (80 mL) was added, and the resulting mixture was extracted with dichloromethane (60 mL×3). The combined organic layers were washed with brine (80 mL), dried over sodium sulfate, filtered and concentrated under reduced pressure to afford tert-butyl 4-(3-formylcyclobutoxy)piperidine-1-carboxylate (1.74 g, 88%) as a colorless oil.

Step 2

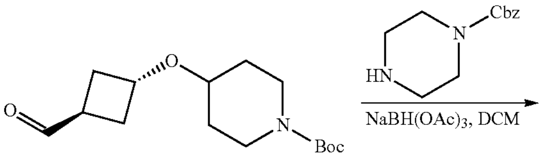

-continued

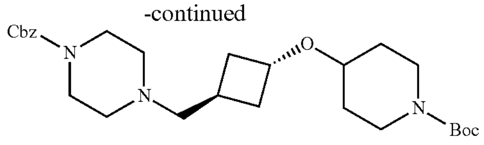

To a solution of benzyl piperazine-1-carboxylate (1.78 mL, 9 mmol) in dichloromethane (20 mL) were added acetic acid (351 μL, 6. mmol) and tert-butyl 4-(3-formylcyclobutoxy)piperidine-1-carboxylate (1.74 g, 6 mmol) in dichloromethane (20 mL) at 0° C. under nitrogen atmosphere. The solution was stirred at 0° C. for 0.5 h before the addition of sodium triacetoxyborohydride (3.90 g, 18 mmol). The reaction mixture was stirred at 0° C. under nitrogen atmosphere for 2 h. The mixture was diluted with saturated sodium bicarbonate solution until pH 8, the resulting mixture was extracted with dichloromethane (30 mL×3). The combined organic layers were washed with brine (30 mL), dried over sodium sulfate, filtered and concentrated under reduced pressure. The residue was purified by silica gel chromatography (0-90% ethyl acetate/petroleum ether) to afford benzyl 4-[[3-[(1-tert-butoxycarbonyl-4-piperidyl)oxy]cyclobutyl]methyl]piperazine-1-carboxylate (1.94 g, 65%) as a colorless gum.

Step 3

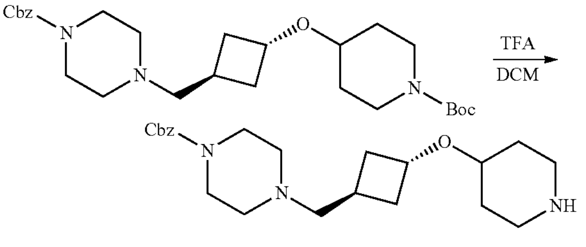

To a solution of benzyl 4-[[3-[(1-tert-butoxycarbonyl-4-piperidyl)oxy]cyclobutyl]methyl]piperazine-1-carboxylate (0.8 g, 2 mmol) in dichloromethane (4 mL) was added TFA (4 mL). The reaction solution was stirred at 25° C. for 1 h, then concentrated under reduced pressure. The residue was diluted with saturated sodium carbonate solution to adjust the pH to 12, the mixture was extracted with dichloromethane (40 mL×3). The combined organic layers were washed with brine (50 mL×2), dried over anhydrous sodium sulfate, filtered and concentrated under reduced pressure to afford benzyl 4-[[3-(4-piperidyloxy)cyclobutyl]methyl]piperazine-1-carboxylate (0.6 g, 94%) as a light yellow gum. MS (ESI) m/z: 388.3 $[M+H]^+$.

Step 4

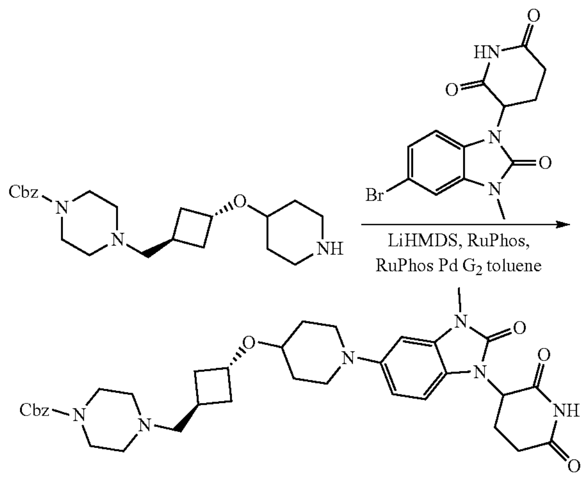

To a solution of benzyl 4-[[3-(4-piperidyloxy)cyclobutyl]methyl]piperazine-1-carboxylate (0.54 g, 1.4 mmol) and 3-(5-bromo-3-methyl-2-oxo-benzimidazol-1-yl)piperidine-2,6-dione (518 mg, 1.5 mmol) in toluene (30 mL) were added RuPhos (32.5 mg, 70 μmol), Ruphos Pd $G_2$ (54.1 mg, 70 μmol) and lithium bis(trimethylsilyl)amide (1 M, 7 mL), the mixture was stirred at 100° C. under nitrogen atmosphere for 2 h. The reaction mixture was slowly poured into acetic acid (40 mL) at 0° C., then diluted with saturated aqueous sodium bicarbonate solution until pH 8. The mixture was extracted with dichloromethane (40 mL×2). The combined organic layers were washed with brine (50 mL×2), dried over sodium sulfate, filtered and concentrated under reduced pressure. The residue was purified by silica gel chromatography (0-7% methanol in dichloromethane) to afford benzyl 4-[[3-[[1-[1-(2,6-dioxo-3-piperidyl)-3-methyl-2-oxo-benzimidazol-5-yl]-4-piperidyl]oxy]cyclobutyl]methyl]piperazine-1-carboxylate (150 mg, 13%, 75% purity) as a white solid. MS (ESI) m/z: 645.3 [M+H]$^+$.

Step 5

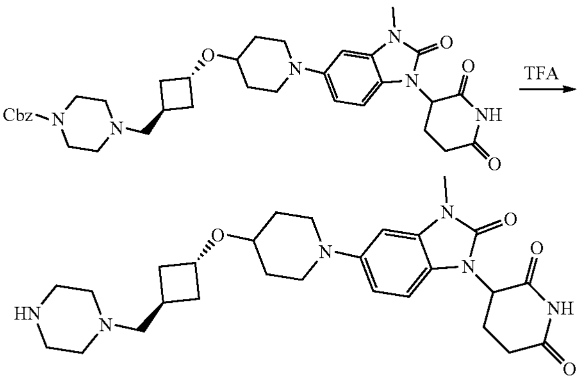

A solution of benzyl 4-[[3-[[1-[1-(2,6-dioxo-3-piperidyl)-3-methyl-2-oxo-benzimidazol-5-yl]-4-piperidyl]oxy]cyclobutyl]methyl]piperazine-1-carboxylate (0.14 g, 0.2 mmol) in TFA (3.5 mL) was stirred at 70° C. for 1 h, then concentrated under reduced pressure to afford 3-[3-methyl-2-oxo-5-[4-[3-(piperazin-1-ylmethyl)cyclobutoxy]-1-piperidyl]benzimidazol-1-yl]piperidine-2,6-dione (0.2 g, 81%, 55% purity, TFA salt) as a light yellow gum. MS (ESI) m/z: 511.3 [M+H]$^+$.

Step 6

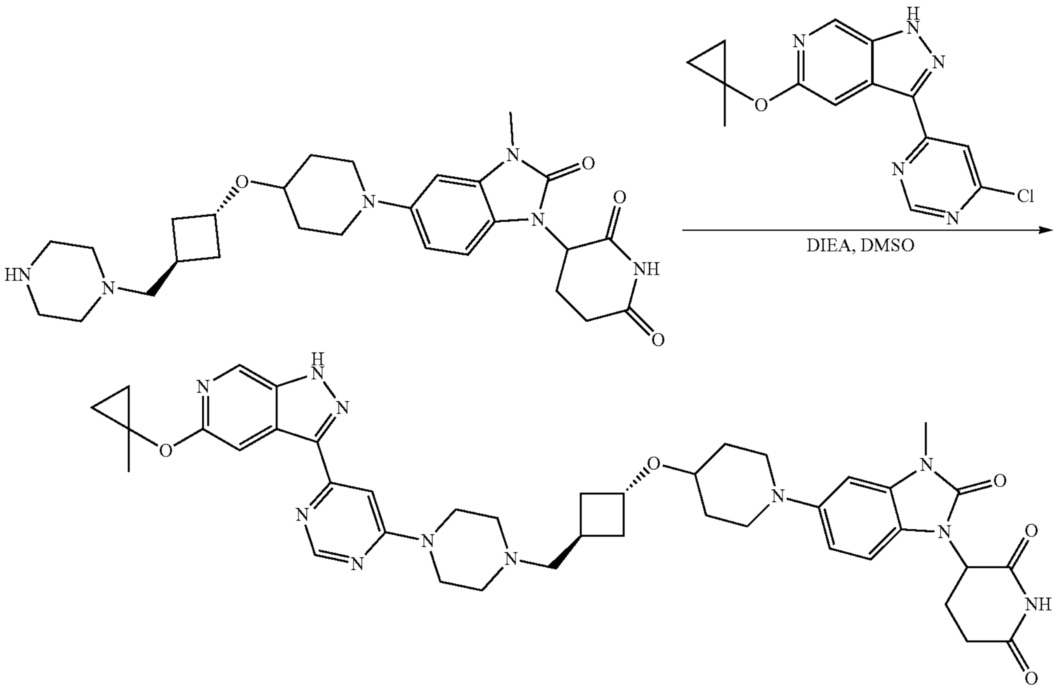

To a solution of 3-[3-methyl-2-oxo-5-[4-[3-(piperazin-1-ylmethyl)cyclobutoxy]-1-piperidyl]benzimidazol-1-yl]piperidine-2,6-dione (0.1 g, 0.2 mmol, TFA) and 3-(6-chloropyrimidin-4-yl)-5-(1-methylcyclopropoxy)-1H-pyrazolo[3,4-c]pyridine (53 mg, 0.2 mmol) in DMSO (5 mL) was added DIEA (2.0 mL, 12 mmol). The reaction mixture was stirred at 70° C. for 12 h, then filtered and concentrated under reduced pressure. The residue was purified by prep-HPLC (0%-32% acetonitrile in water (TFA) over 20 min), then further purified by prep-HPLC (22%-62% acetonitrile in water (ammonium bicarbonate) over 25 min) to afford Compound 35 (19.3 mg, 15%) as a white solid. MS (ESI) m/z: 776.4 $[M+H]^+$.

Exemplary Synthesis of Compound 36:

Step 1

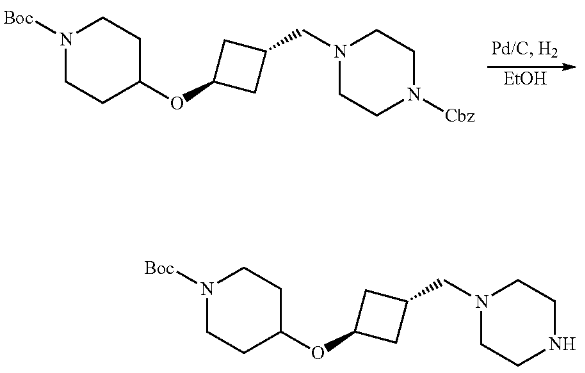

To a stirred solution of benzyl 4-[[3-[(1-tert-butoxycarbonyl-4-piperidyl)oxy]cyclobutyl]methyl]piperazine-1-carboxylate (0.5 g, 1 mmol) in EtOH (15 mL) was added 10% palladium on carbon (218 mg). The suspension was degassed and purged with hydrogen several times, then stirred at 40° C. under hydrogen (40 psi) for 4 h. The reaction mixture was filtered and concentrated under reduced pressure to afford tert-butyl 4-[3-(piperazin-1-ylmethyl)cyclobutoxy]piperidine-1-carboxylate (0.32 g, 88%) as a gray gum.

Step 2

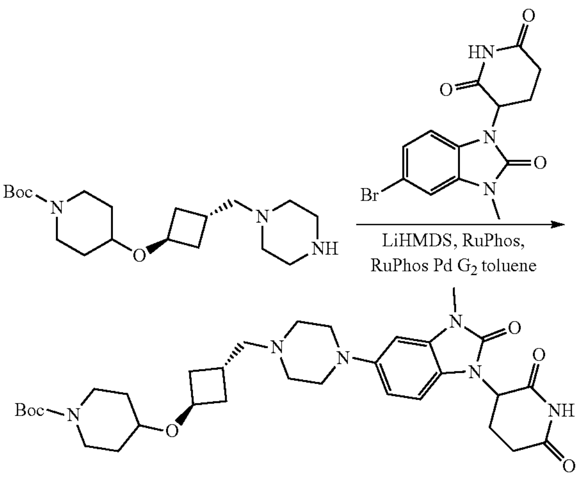

To a solution of tert-butyl 4-[3-(piperazin-1-ylmethyl)cyclobutoxy]piperidine-1-carboxylate (0.3 g, 0.8 mmol) and 3-(5-bromo-3-methyl-2-oxo-benzimidazol-1-yl)piperidine-2,6-dione (301 mg, 0.9 mmol) in toluene (20 mL) were added Ruphos Pd $G_2$ (33 mg, 42 μmol), RuPhos (19.8 mg, 42 μmol) and lithium bis(trimethylsilyl)amide (1 M, 4.24 mL) at 25° C. under nitrogen atmosphere, the mixture was stirred at 100° C. under nitrogen atmosphere for 2 h. The reaction mixture was slowly poured into acetic acid (40 mL) at 0° C. and diluted with saturated aqueous sodium bicarbonate solution until pH 8. The mixture was extracted with dichloromethane (40 mL×2). The combined organic layers were washed with brine (50 mL×2), dried over sodium sulfate, filtered and concentrated under reduced pressure. The residue was purified by silica gel chromatography (0-7% methanol in dichloromethane) to afford tert-butyl 4-[3-[[4-[1-(2,6-dioxo-3-piperidyl)-3-methyl-2-oxo-benzimidazol-5-yl]piperazin-1-yl]methyl]cyclobutoxy]piperidine-1-carboxylate (240 mg, 46%) as a light yellow solid.

Step 3

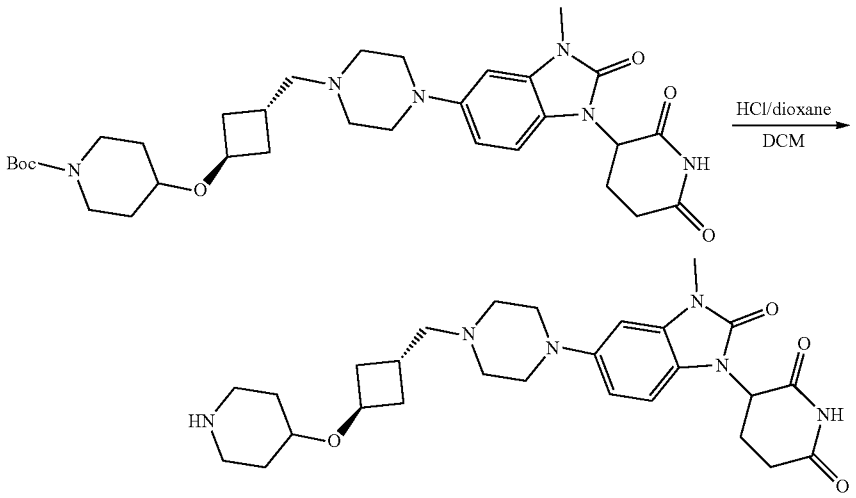

To a solution of tert-butyl 4-[3-[[4-[1-(2,6-dioxo-3-piperidyl)-3-methyl-2-oxo-benzimidazol-5-yl]piperazin-1-yl]methyl]cyclobutoxy]piperidine-1-carboxylate (0.2 g, 0.3 mmol) in dichloromethane (5 mL) was added HCl/dioxane (2 M, 5 mL). The reaction solution was stirred at 25° C. for 3 h, then concentrated under reduced pressure to afford 3-[3-methyl-2-oxo-5-[4-[[3-(4-piperidyloxy)cyclobutyl]methyl]piperazin-1-yl]benzimidazol-1-yl]piperidine-2,6-dione (170 mg, 92%, HCl salt) as a white solid. MS (ESI) m/z: 511.3 [M+H]$^+$.

Step 4

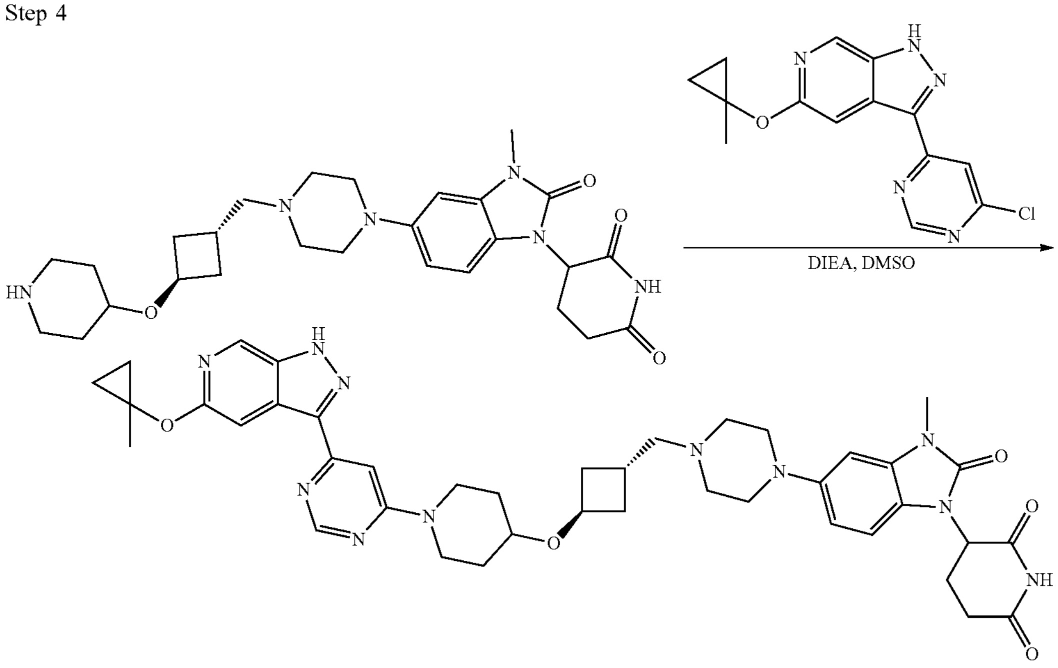

To a solution of 3-[3-methyl-2-oxo-5-[4-[[3-(4-piperidyloxy)cyclobutyl]methyl]piperazin-1-yl]benzimidazol-1-yl]piperidine-2,6-dione (141 mg, 0.26 mmol, HCl) and 3-(6-chloropyrimidin-4-yl)-5-(1-methylcyclopropoxy)-1H-pyrazolo[3,4-c]pyridine (60 mg, 0.2 mmol) in DMSO (3 mL) was added DIEA (346 μL, 2 mmol). The reaction mixture was stirred at 80° C. for 2 h, then filtered and concentrated under reduced pressure. The residue was purified by prep-HPLC (22%-62% acetonitrile in water (ammonium bicarbonate) over 25 min) to afford Compound 36 (35.1 mg, 22%) as a white solid. MS (ESI) m/z: 776.3 [M+H]$^+$.

Exemplary Synthesis of Compound 37:

Step 1

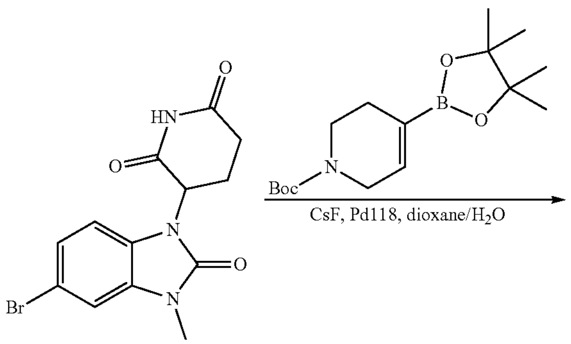

-continued

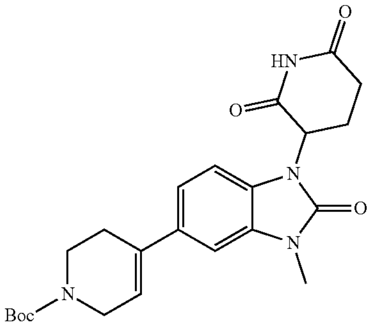

To a solution of 3-(5-bromo-3-methyl-2-oxo-benzimidazol-1-yl)piperidine-2,6-dione (3 g, 9 mmol) and tert-butyl 4-(4,4,5,5-tetramethyl-1,3,2-dioxaborolan-2-yl)-3,6-dihydro-2H-pyridine-1-carboxylate (2.74 g, 9 mmol) in dioxane (30 mL) and water (1.5 mL) were added cesium fluoride (4.04 g, 27 mmol) and Pd 118 (578 mg, 0.9 mmol) under nitrogen atmosphere. The mixture was stirred at 90° C. for 12 h under nitrogen atmosphere. The reaction mixture was cooled to 25° C., filtered and concentrated under reduced pressure. The residue was triturated with THF (10 mL) to afford tert-butyl 4-[1-(2,6-dioxo-3-piperidyl)-3-methyl-2-oxo-benzimidazol-5-yl]-3,6-dihydro-2H-pyridine-1-carboxylate (2 g, 51%) as a gray solid. MS (ESI) m/z: 441.2 [M+H]$^+$.

Step 2

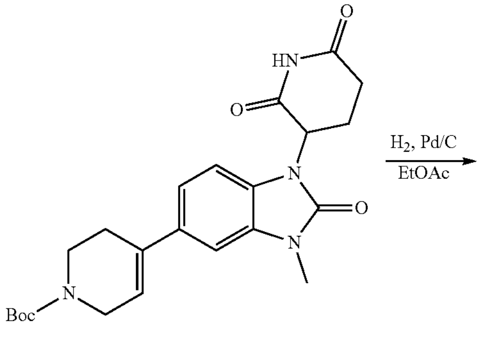

-continued

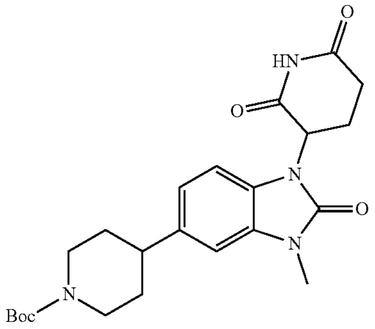

To a solution of tert-butyl 4-[1-(2,6-dioxo-3-piperidyl)-3-methyl-2-oxo-benzimidazol-5-yl]-3,6-dihydro-2H-pyridine-1-carboxylate (1 g, 2 mmol) in ethyl acetate (20 mL) and DMF (10 mL) were added 10% palladium on carbon (0.2 g) and 20% palladium hydroxide (0.2 g). The suspension was degassed and purged with hydrogen several times. The mixture was stirred under hydrogen (30 psi) at 40° C. for 12 h. The mixture was cooled to 25° C., filtered and concentrated in vacuo to afford tert-butyl 4-[1-(2,6-dioxo-3-piperidyl)-3-methyl-2-oxo-benzimidazol-5-yl]piperidine-1-carboxylate (0.9 g, 90%) as a white solid. MS (ESI) m/z: 387.2 $[M-56+H]^+$.

Step 3

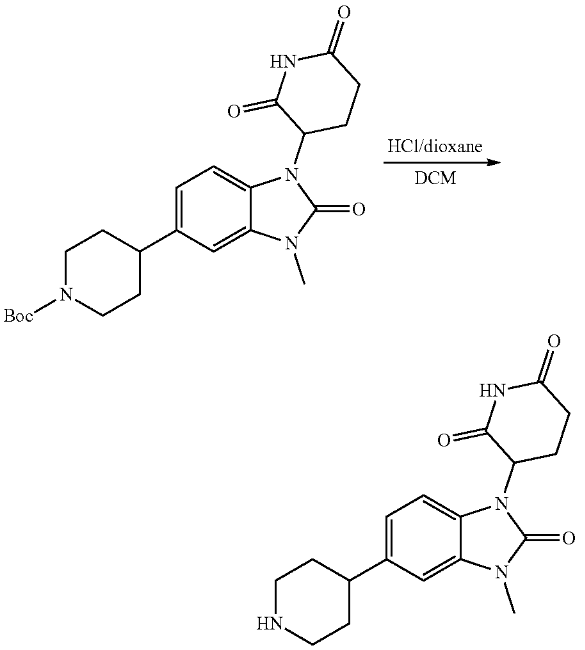

To a solution of tert-butyl 4-[1-(2,6-dioxo-3-piperidyl)-3-methyl-2-oxo-benzimidazol-5-yl]piperidine-1-carboxylate (0.9 g, 2 mmol) in dichloromethane (10 mL) was added HCl/dioxane (2 M, 10 mL). The reaction solution was stirred at 25° C. for 2 h, then concentrated under reduced pressure to afford 3-[3-methyl-2-oxo-5-(4-piperidyl)benzimidazol-1-yl]piperidine-2,6-dione (0.8 g, crude, HCl salt) as a white solid, which was used in the next step directly. MS (ESI) m/z: 343.1 $[M+H]^+$.

Step 4

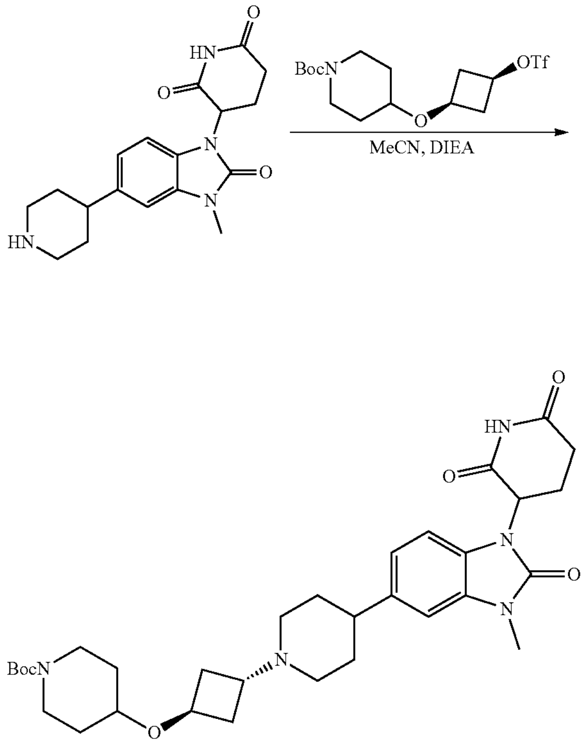

To a solution of 3-[3-methyl-2-oxo-5-(4-piperidyl)benzimidazol-1-yl]piperidine-2,6-dione (500 mg, 1.5 mmol) and tert-butyl 4-[3-(trifluoromethylsulfonyloxy)cyclobutoxy]piperidine-1-carboxylate (589 mg, 1.5 mmol) in acetonitrile (10 mL) and DMSO (2 mL) was added DIEA (1.27 mL, 7 mmol). The mixture was stirred at 35° C. for 12 h, then cooled to 25° C. and poured into water (100 mL). The mixture was extracted with ethyl acetate (100 mL×2). The combined organic phase was washed with brine (100 mL×2), dried over anhydrous sodium sulfate, filtered and concentrated under reduced pressure. The residue was purified by silica gel chromatography (0-80% THF/petroleum ether) to afford tert-butyl 4-[3-[4-[1-(2,6-dioxo-3-piperidyl)-3-methyl-2-oxo-benzimidazol-5-yl]-1-piperidyl]cyclobutoxy]piperidine-1-carboxylate (290 mg, 27%, 82% purity) as a light yellow solid. MS (ESI) m/z: 596.3 $[M+H]^+$.

Step 5

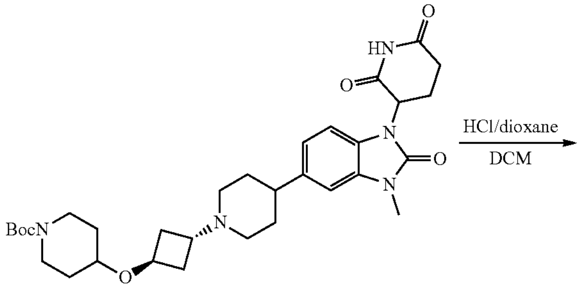

-continued

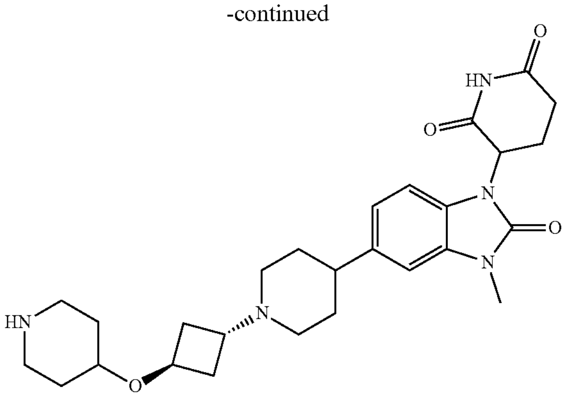

To a solution of tert-butyl 4-[3-[4-[1-(2,6-dioxo-3-piperidyl)-3-methyl-2-oxo-benzimidazol-5-yl]-1-piperidyl]cyclobutoxy]piperidine-1-carboxylate (0.29 g, 0.5 mmol) in dichloromethane (4 mL) was added HCl/dioxane (2 M, 8 mL). The reaction solution was stirred at 25° C. for 1 h, then concentrated under reduced pressure to afford 3-[3-methyl-2-oxo-5-[1-[3-(4-piperidyloxy)cyclobutyl]-4-piperidyl]benzimidazol-1-yl]piperidine-2,6-dione (300 mg, crude, HCl salt) as an off-white solid. MS (ESI) m/z: 496.4 $[M+H]^+$.

Step 6

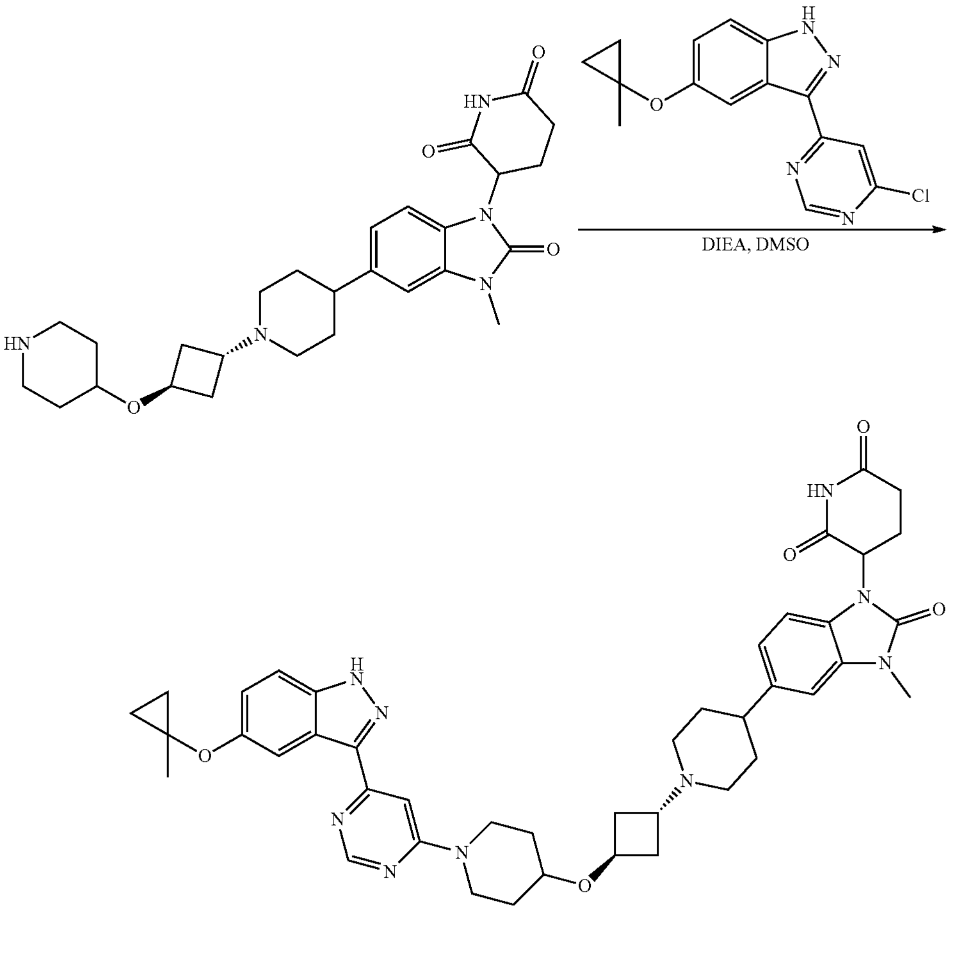

To a solution of 3-(6-chloropyrimidin-4-yl)-5-(1-methylcyclopropoxy)-1H-indazole (60 mg, 0.2 mmol) and 3-[3-methyl-2-oxo-5-[1-[3-(4-piperidyloxy)cyclobutyl]-4-piperidyl]benzimidazol-1-yl]piperidine-2,6-dione (98.9 mg, 0.2 mmol) in DMSO (10 mL) was added DIEA (257.9 mg, 347.5 μL, 2.00 mmol). The mixture was stirred at 80° C. for 2 h, filtered and concentrated under reduced pressure. The residue was purified by prep-HPLC (34%-74% acetonitrile in water (ammonium bicarbonate) over 25 min), the crude material was further purified by prep-HPLC (0%-38% acetonitrile in water (formic acid) over 25 min) to afford Compound 37 (30.4 mg, 20%) as a white solid. MS (ESI) m/z: 760.3 $[M+H]^+$.

The remaining compounds were prepared by procedures analogous to the above examples as follows:

Compound 10 was prepared in a manner analogous to compound 7. Compound 11 was prepared in a manner analogous to compound 7. Compound 13 was prepared in a manner analogous to compound 7. Compound 14 was prepared in a manner analogous to compound 2. Compound 15 was prepared in a manner analogous to compounds 7 and 8. Compound 17 was prepared in a manner analogous to compounds 5 and 16. Compounds 38-41 were prepared in a manner analogous to compound 13. Compounds 42-45 were prepared in a manner analogous to compounds 3 and 13. Compound 46 was prepared in a manner analogous to compounds 1 and 9. Compound 47 was prepared in a manner analogous to compounds 1 and 8. Compound 48 was prepared in a manner analogous to compounds 1 and 14. Compounds 49, 50, 54-57, 60, and 61 were prepared in a manner analogous to compound 6. Compound 51 was prepared in a manner analogous to compounds 1 and 2. Compounds 52, 53, 66, and 67 were prepared in a manner analogous to compound 1. Compound 58 was prepared in a manner analogous to compound 19. Compound 59 was prepared in a manner analogous to compound 20. Compound 62 was prepared in a manner analogous to compound 22. Compound 63 was prepared in a manner analogous to compound 23. Compounds 64-66 were prepared in a manner analogous to compound 23. Compound 69 was prepared in a manner analogous to compounds 3 and 10. Compound 70 was prepared in a manner analogous to compounds 3 and 11.

Characterization data for the compounds of the disclosure is presented below in Table 1.

TABLE 1

| Comp. No. | IUPAC Name | LCMS | $^1$H NMR (400 MHz, DMSO-$d_6$) |
|---|---|---|---|
| 1 | 3-[3-methyl-2-oxo-5-(4-{[(1r,4r)-4-[(4-{6-[5-(1-methylcyclopropoxy)-1H-pyrazolo[3,4-c]pyridin-3-yl]pyrimidin-4-yl}piperazin-1-yl)methyl]cyclohexyl]oxy}piperidin-1-yl)-2,3-dihydro-1H-1,3-benzodiazol-1-yl]piperidine-2,6-dione | 804.4 | δ = 13.89 (d, J = 0.9 Hz, 1H), 11.05 (s, 1H), 8.79 (s, 1H), 8.65 (s, 1H), 7.79 (s, 1H), 7.38 (s, 1H), 6.92 (d, J = 8.6 Hz, 1H), 6.83 (d, J = 2.1 Hz, 1H), 6.63 (dd, J = 2.0, 8.6 Hz, 1H), 5.28 (dd, J = 5.3, 12.8 Hz, 1H), 3.68 (s, 4H), 3.57 (dt, J = 4.2, 8.5 Hz, 1H), 3.45-3.39 (m, 2H), 3.30 (s, 3H), 2.90-2.78 (m, 3H), 2.74-2.60 (m, 2H), 2.42 (s, 4H), 2.12 (d, J = 7.0 Hz, 2H), 2.06-1.84 (m, 6H), 1.81 (d, J = 12.1 Hz, 2H), 1.61 (s, 3H), 1.59-1.47 (m, 3H), 1.22-1.12 (m, 2H), 0.95-0.87 (m, 4H), 0.78-0.74 (m, 2H) |
| 2 | 3-{5-[4-({3,3-dimethyl-4-[(1-{6-[5-(1-methylcyclopropoxy)-1H-indazol-3-yl]pyrimidin-4-yl}piperidin-4-yl)methyl]piperazin-1-yl}methyl)piperidin-1-yl]-2-oxo-3-(propan-2-yl)-2,3-dihydro-1H-1,3-benzodiazol-1-yl}piperidine-2,6-dione | 858.5 | δ = 13.37 (s, 1H), 11.05 (s, 1H), 8.61 (s, 1H), 8.28-8.01 (m, 2H), 7.50 (d, J = 9.0 Hz, 1H), 7.36 (s, 1H), 7.12-7.01 (m, 1H), 6.95-6.83 (m, 2H), 6.69-6.54 (m, 1H), 5.35-5.16 (m, 1H), 4.65-4.52 (m, 1H), 4.51-4.37 (m, 2H), 3.54 (br d, J = 11.1 Hz, 2H), 3.29-3.18 (m, 4H), 2.98-2.84 (m, 3H), 2.69-2.57 (m, 4H), 2.17-2.06 (m, 4H), 2.02-1.91 (m, 2H), 1.86-1.75 (m, 4H), 1.74-1.67 (m, 1H), 1.64-1.58 (m, 1H), 1.54 (s, 3H), 1.44 (d, J = 6.9 Hz, 6H), 1.29-1.20 (m, 2H), 1.11-1.00 (m, 2H), 0.95 (s, 8H), 0.79-0.73 (m, 2H) |
| 3 | 3-[4-(4-{[(1r,4r)-4-[(4-{6-[5-(1-methylcyclopropoxy)-1H-indazol-3-yl]pyrimidin-4-yl}piperazin-1-yl)methyl]cyclohexyl]oxy}piperidin-1-yl)-1H-1,3-benzodiazol-1-yl]piperidine-2,6-dione | 773.5 | δ = 13.42-13.35 (m, 1H), 11.22-11.12 (m, 1H), 8.67-8.60 (m, 1H), 8.18-8.14 (m, 1H), 8.12 (s, 1H), 7.54-7.47 (m, 1H), 7.41-7.35 (m, 1H), 7.10-7.05 (m, 2H), 6.98 (d, J = 8.0 Hz, 1H), 6.57-6.51 (m, 1H), 5.62 (dd, J = 5.2, 12.8 Hz, 1H), 4.07-3.99 (m, 2H), 3.71 (s, 4H), 3.58 (br d, J = 4.0 Hz, 1H), 3.08-3.02 (m, 2H), 2.71 (br d, J = 5.0 Hz, 1H), 2.59-2.56 (m, 1H), 2.54 (br d, J = 2.4 Hz, 4H), 2.45-2.40 (m, 5H), 2.25-2.16 (m, 2H), 2.15-2.09 (m, 2H), 2.00-1.90 (m, 5H), 1.85-1.79 (m, 2H), 1.54 (s, 3H), 1.20-1.17 (m, 1H), 1.15 (s, 1H), 0.95-0.93 (m, 2H), 0.79-0.75 (m, 2H) |
| 4 | 3-[6-(4-{[(1r,4r)-4-[(4-{6-[5-(1-methylcyclopropoxy)-1H-indazol-3-yl]pyrimidin-4-yl}piperazin-1-yl)methyl]cyclohexyl]oxy}piperidin-1-yl)-1H-1,3-benzodiazol-1-yl]piperidine-2,6-dione | 773.5 | δ = 13.39 (s, 1H), 11.20-11.08 (m, 1H), 8.64 (s, 1H), 8.15 (s, 1H), 8.05 (s, 1H), 7.49 (dd, J = 8.8, 14.4 Hz, 2H), 7.37 (s, 1H), 7.07 (dd, J = 2.4, 8.8 Hz, 1H), 7.03-6.98 (m, 1H), 6.93 (dd, J = 1.6, 8.8 Hz, 1H), 5.63 (dd, J = 4.2, 12.8 Hz, 1H), 3.72-3.63 (m, 4H), 3.62-3.54 (m, 2H), 3.49-3.43 (m, 4H), 2.91-2.83 (m, 3H), 2.78 (br dd, J = 3.2, 12.4 Hz, 1H), 2.74-2.64 (m, 2H), 2.42 (br s, 3H), 2.36-2.30 (m, 2H), 2.18 (br dd, J = 6.0, 10.4 Hz, 1H), 2.12 (br d, J = 6.8 Hz, 2H), 1.97-1.86 (m, 4H), 1.81 (br d, J = 12.0 Hz, 2H), 1.54 (s, 3H), 1.50-1.43 (m, 1H), 1.24-1.12 (m, 2H), 0.96-0.93 (m, 2H), 0.80-0.73 (m, 2H) |
| 5 | 3-[3-methyl-2-oxo-6-(4-{[(1r,4r)-4-[(4-{6-[5-(1-methylcyclopropoxy)-1H-indazol-3-yl]pyrimidin-4-yl}piperazin-1-yl)methyl]cyclohexyl]oxy}piperidin-1-yl)-2,3-dihydro-1H-1,3-benzodiazol-1-yl]piperidine-2,6-dione | 803.5 | δ = 13.41 (br s, 1H), 11.05 (s, 1H), 8.64 (s, 1H), 8.20 (s, 1H), 8.15 (d, J = 2.0 Hz, 1H), 7.50 (d, J = 9.0 Hz, 1H), 7.37 (s, 1H), 7.07 (dd, J = 2.4, 9.0 Hz, 1H), 6.99 (d, J = 8.4 Hz, 1H), 6.80 (br s, 1H), 6.73-6.62 (m, 1H), 5.32 (s, 1H), 3.66 (br s, 4H), 3.55 (br dd, J = 4.4, 8.2 Hz, 3H), 3.36 (br dd, J = 3.6, 10.6 Hz, 4H), 2.90-2.72 (m, 4H), 2.65 (br s, 1H), 2.41 (br s, 4H), 2.11 (br d, J = 7.0 Hz, 2H), 2.02-1.75 (m, 7H), 1.54 (s, 6H), 1.16 (br d, J = 13.4 Hz, 2H), 1.00-0.81 (m, 4H), 0.81-0.73 (m, 2H) |

TABLE 1-continued

| Comp. No. | IUPAC Name | LCMS | $^1H$ NMR (400 MHz, DMSO-$d_6$) |
|---|---|---|---|
| 6 | 3-[3-methyl-2-oxo-5-(4-{[(1r,4r)-4-[(4-{6-[5-(1-methylcyclopropoxy)-1H-indazol-3-yl]pyrimidin-4-yl}piperazin-1-yl)methyl]cyclohexyl]oxy}piperidin-1-yl)-2,3-dihydro-1H-1,3-benzodiazol-1-yl]piperidine-2,6-dione | 803.6 | δ = 13.72-13.36 (m, 1H), 11.11 (s, 1H), 9.67-9.13 (m, 1H), 8.76 (s, 1H), 8.13 (br s, 1H), 7.65-7.43 (m, 2H), 7.36-6.56 (m, 4H), 5.45-5.29 (m, 1H), 4.71-4.56 (m, 3H), 3.83-3.36 (m, 12H), 3.21-2.99 (m, 5H), 2.84-2.83 (m, 1H), 2.96-2.83 (m, 1H), 2.70-2.58 (m, 1H), 2.07-1.93 (m, 5H), 1.91-1.62 (m, 6H), 1.58-1.58 (m, 1H), 1.56 (s, 3H), 1.30-1.19 (m, 2H), 1.12-1.00 (m, 2H), 0.99-0.93 (m, 2H), 0.82-0.76 (m, 2H) |
| 7 | 3-{6-[4-({4-[(1-{6-[5-(1-methylcyclopropoxy)-1H-indazol-3-yl]pyrimidin-4-yl}piperidin-4-yl)methyl]piperazin-1-yl}methyl)piperidin-1-yl]-1H-1,3-benzodiazol-1-yl}piperidine-2,6-dione | 772.5 | δ = 11.16 (s, 1H), 8.64 (s, 1H), 8.19-8.12 (m, 2H), 8.08 (s, 1H), 7.50 (t, J = 9.2 Hz, 2H), 7.39 (s, 1H), 7.11-6.88 (m, 3H), 5.63 (br s, 1H), 4.47 (br dd, J = 3.8, 6.2 Hz, 2H), 3.66 (br d, J = 12.0 Hz, 2H), 3.51-3.37 (m, 6H), 3.03-2.62 (m, 13H), 2.20 (br d, J = 5.8 Hz, 1H), 1.83 (br d, J = 12.0 Hz, 6H), 1.54 (s, 3H), 1.41-1.26 (m, 2H), 1.15 (br dd, J = 1.4, 9.2 Hz, 2H), 0.99-0.91 (m, 2H), 0.81-0.73 (m, 2H) |
| 8 | 3-{4-[4-({3,3-dimethyl-4-[(1-{6-[5-(1-methylcyclopropoxy)-1H-indazol-3-yl]pyrimidin-4-yl}piperidin-4-yl)methyl]piperazin-1-yl}methyl)piperidin-1-yl]-3-methyl-2-oxo-2,3-dihydro-1H-1,3-benzodiazol-1-yl}piperidine-2,6-dione | 830.05 | δ = 13.39 (br s, 1H), 11.09 (s, 1H), 8.62 (s, 1H), 8.18-8.09 (m, 2H), 7.50 (d, J = 8.8 Hz, 1H), 7.38 (s, 1H), 7.07 (dd, J = 2.2, 9.0 Hz, 1H), 7.01-6.94 (m, 1H), 6.88 (br dd, J = 8.2, 12.0 Hz, 2H), 5.35 (br dd, J = 5.4, 12.8 Hz, 1H), 4.57-4.37 (m, 2H), 3.62 (s, 3H), 3.10 (br d, J = 9.2 Hz, 3H), 3.02-2.83 (m, 4H), 2.79-2.57 (m, 6H), 2.31-2.09 (m, 4H), 2.08-1.95 (m, 2H), 1.92-1.74 (m, 5H), 1.70-1.59 (m, 1H), 1.54 (s, 3H), 1.46-1.21 (m, 3H), 1.18-0.91 (m, 10H), 0.81-0.70 (m, 2H) |
| 9 | 3-[3-methyl-2-oxo-4-(4-{[(1r,4r)-4-[(4-{6-[5-(1-methylcyclopropoxy)-1H-indazol-3-yl]pyrimidin-4-yl}piperazin-1-yl)methyl]cyclohexyl]oxy}piperidin-1-yl)-2,3-dihydro-1H-1,3-benzodiazol-1-yl]piperidine-2,6-dione | 803.5 | δ = 13.57 (br s, 1H), 11.08 (s, 1H), 9.55 (br s, 1H), 8.75 (d, J = 0.6 Hz, 1H), 8.10 (d, J = 1.8 Hz, 1H), 7.62-7.46 (m, 2H), 7.11 (dd, J = 2.4, 9.0 Hz, 1H), 7.02-6.81 (m, 3H), 5.43-5.28 (m, 1H), 4.62 (br dd, J = 2.6, 12.8 Hz, 3H), 3.62 (s, 5H), 3.54-3.26 (m, 4H), 3.18-2.93 (m, 6H), 2.92-2.56 (m, 5H), 2.04-1.89 (m, 4H), 1.82 (br d, J = 11.8 Hz, 4H), 1.54 (s, 4H), 1.21 (br d, J = 8.2 Hz, 2H), 1.05 (br d, J = 11.6 Hz, 2H), 0.97-0.90 (m, 2H), 0.81-0.73 (m, 2H) |
| 10 | 3-{6-[4-({3,3-dimethyl-4-[(1-{6-[5-(1-methylcyclopropoxy)-1H-indazol-3-yl]pyrimidin-4-yl}piperidin-4-yl)methyl]piperazin-1-yl}methyl)piperidin-1-yl]-1H-1,3-benzodiazol-1-yl}piperidine-2,6-dione | 800.5 | δ = 13.49 (br s, 1H), 11.22 (s, 1H), 8.69-8.63 (m, 1H), 8.53-8.41 (m, 1H), 8.18-8.00 (m, 2H), 7.62-7.48 (m, 2H), 7.42 (s, 1H), 7.21-6.97 (m, 3H), 5.75 (br s, 1H), 4.63-4.40 (m, 2H), 3.70 (br d, J = 7.2 Hz, 4H), 3.08-2.65 (m, 12H), 2.36-1.97 (m, 6H), 1.81 (br d, J = 9.8 Hz, 4H), 1.54 (s, 3H), 1.33 (br s, 10H), 0.99-0.90 (m, 2H), 0.81-0.72 (m, 2H) |
| 11 | 3-{5-[4-({4-[(1-{6-[5-(1-methylcyclopropoxy)-1H-indazol-3-yl]pyrimidin-4-yl}piperidin-4-yl)methyl]piperazin-1-yl}methyl)piperidin-1-yl]-1H-1,3-benzodiazol-1-yl}piperidine-2,6-dione | 772.5 | δ = 13.38 (br s, 1H), 11.16 (s, 1H), 8.62 (s, 1H), 8.21-8.05 (m, 2H), 7.50 (d, J = 8.8 Hz, 1H), 7.41-7.28 (m, 2H), 7.13 (s, 1H), 7.07 (dd, J = 1.6, 9.0 Hz, 1H), 7.00 (br d, J = 8.8 Hz, 1H), 5.58 (br s, 1H), 4.43 (br s, 2H), 3.57 (br d, J = 11.0 Hz, 3H), 3.48-3.41 (m, 3H), 3.02-2.56 (m, 9H), 2.47-2.38 (m, 2H), 2.34-2.13 (m, 5H), 1.81 (br d, J = 12.8 Hz, 5H), 1.66 (br s, 1H), 1.54 (s, 3H), 1.28 (br d, J = 10.2 Hz, 2H), 1.09 (br d, J = 12.8 Hz, 2H), 0.99-0.90 (m, 2H), 0.81-0.72 (m, 2H) |
| 12 | 3-{3-methyl-5-[4-({4-[(1-{6-[5-(1-methylcyclopropoxy)-1H-indazol-3-yl]pyrimidin-4-yl}piperidin-4-yl)methyl]piperazin-1-yl}methyl)piperidin-1-yl]-2-oxo-2,3-dihydro-1H-1,3-benzodiazol-1-yl}piperidine-2,6-dione | 802.6 | δ = 13.60-13.15 (m, 1H), 11.06 (s, 1H), 8.62 (s, 1H), 8.24-8.08 (m, 3H), 7.50 (d, J = 8.8 Hz, 1H), 7.37 (s, 1H), 7.06 (dd, J = 2.4, 8.8 Hz, 1H), 6.92 (d, J = 8.8 Hz, 1H), 6.81 (d, J = 1.6 Hz, 1H), 6.62 (dd, J = 1.6, 8.8 Hz, 1H), 5.28 (dd, J = 5.2, 12.8 Hz, 1H), 4.54-4.35 (m, 2H), 3.57 (br d, J = 11.6 Hz, 5H), 3.00-2.82 (m, 4H), 2.70-2.55 (m, 4H), 2.39 (br d, J = 1.2 Hz, 7H), 2.17 (br t, J = 8.0 Hz, 4H), 2.02-1.94 (m, 1H), 1.89-1.74 (m, 5H), 1.69-1.57 (m, 1H), 1.54 (s, 3H), 1.31-1.17 (m, 2H), 1.14-1.01 (m, 2H), 0.99-0.89 (m, 2H), 0.81-0.72 (m, 2H). |
| 13 | 3-{5-[4-({3,3-dimethyl-4-[(1-{6-[5-(1-methylcyclopropoxy)-1H-indazol-3-yl]pyrimidin-4-yl}piperidin-4-yl)methyl]piperazin-1- | 800.03 | δ = 13.38 (s, 1H), 11.16 (s, 1H), 8.62 (s, 1H), 8.23-8.03 (m, 2H), 7.50 (d, J = 9.0 Hz, 1H), 7.40-7.31 (m, 2H), 7.13 (d, J = 1.8 Hz, 1H), 7.07 (dd, J = 2.4, 9.0 Hz, 1H), 7.03-6.95 (m, 1H), 5.61 (s, 1H), 4.46 (br s, 2H), 3.56 (br s, 2H), 3.31-3.18 (m, 5H), 3.09-2.55 (m, 10H), 2.25-2.10 (m, 4H), |

TABLE 1-continued

| Comp. No. | IUPAC Name | LCMS | $^1$H NMR (400 MHz, DMSO-$d_6$) |
| --- | --- | --- | --- |
| | yl}methyl)piperidin-1-yl]-1H-1,3-benzodiazol-1-yl}piperidine-2,6-dione | | 1.95-1.70 (m, 5H), 1.63 (br d, J = 5.2 Hz, 1H), 1.54 (s, 3H), 1.34-1.20 (m, 2H), 1.18-0.99 (m, 7H), 0.96-0.92 (m, 2H), 0.80-0.74 (m, 2H) |
| 14 | 3-{5-[4-({3,3-dimethyl-4-[(1-{6-[5-(1-methylcyclopropoxy)-1H-indazol-3-yl]pyrimidin-4-yl}piperidin-4-yl)methyl]piperazin-1-yl}methyl)piperidin-1-yl]-3-methyl-2-oxo-2,3-dihydro-1H-1,3-benzodiazol-1-yl}piperidine-2,6-dione | 830.7 | δ = 14.21-13.34 (m, 1H), 11.11 (s, 1H), 8.70 (s, 1H), 8.13-7.78 (m, 1H), 7.76-7.51 (m, 1H), 7.41 (s, 1H), 7.41-7.40 (m, 1H), 7.39-6.52 (m, 4H), 5.45-5.29 (m, 1H), 4.66-4.57 (m, 2H), 3.66-3.52 (m, 3H), 3.32-2.57 (m, 12H), 2.35-2.09 (m, 5H), 2.07-1.64 (m, 7H), 1.63-1.44 (m, 5H), 1.43-1.02 (m, 10H), 1.00-0.95 (m, 2H), 0.82-0.74 (m, 2H) |
| 15 | 3-{3-methyl-4-[4-({4-[(1-{6-[5-(1-methylcyclopropoxy)-1H-indazol-3-yl]pyrimidin-4-yl}piperidin-4-yl)methyl]piperazin-1-yl}methyl)piperidin-1-yl]-2-oxo-2,3-dihydro-1H-1,3-benzodiazol-1-yl}piperidine-2,6-dione | 802.00 | δ = 13.37 (br s, 1H), 11.08 (s, 1H), 8.62 (s, 1H), 8.21-8.11 (m, 2H), 7.50 (d, J = 8.8 Hz, 1H), 7.37 (s, 1H), 7.06 (dd, J = 2.4, 9.0 Hz, 1H), 7.00-6.94 (m, 1H), 6.94-6.79 (m, 2H), 5.35 (br s, 1H), 4.46 (br s, 2H), 3.62 (s, 3H), 3.09 (br s, 2H), 2.94 (br s, 4H), 2.77-2.61 (m, 4H), 2.39 (br d, J = 1.8 Hz, 6H), 2.25-2.12 (m, 4H), 2.04-1.94 (m, 1H), 1.80 (br d, J = 12.6 Hz, 5H), 1.54 (s, 4H), 1.31 (br s, 2H), 1.09 (br s, 2H), 0.98-0.91 (m, 2H), 0.81-0.71 (m, 2H) |
| 16 | 3-{3-methyl-6-[4-({4-[(1-{6-[5-(1-methylcyclopropoxy)-1H-indazol-3-yl]pyrimidin-4-yl}piperidin-4-yl)methyl]piperazin-1-yl}methyl)piperidin-1-yl]-2-oxo-2,3-dihydro-1H-1,3-benzodiazol-1-yl}piperidine-2,6-dione | 802.6 | δ = 13.38 (br s, 1H), 11.06 (s, 1H), 8.62 (s, 1H), 8.22-8.08 (m, 2H), 7.51 (d, J = 9.2 Hz, 1H), 7.37 (s, 1H), 7.07 (dd, J = 2.4, 9.2 Hz, 1H), 6.99 (d, J = 8.8 Hz, 1H), 6.78 (br s, 1H), 6.68 (dd, J = 1.6, 8.8 Hz, 1H), 5.33 (dd, J = 5.2, 12.8 Hz, 1H), 4.52-4.36 (m, 2H), 3.51-3.46 (m, 5H), 3.03-2.67 (m, 5H), 2.66-2.51 (m, 4H), 2.38 (br s, 6H), 2.16 (br t, J = 8.0 Hz, 4H), 1.99 (br d, J = 5.6 Hz, 1H), 1.90- 1.71 (m, 5H), 1.54 (s, 4H), 1.32-1.01 (m, 4H), 0.99-0.89 (m, 2H), 0.82-0.72 (m, 2H) |
| 17 | 3-{6-[4-({3,3-dimethyl-4-[(1-{6-[5-(1-methylcyclopropoxy)-1H-indazol-3-yl]pyrimidin-4-yl}piperidin-4-yl)methyl]piperazin-1-yl}methyl)piperidin-1-yl]-3-methyl-2-oxo-2,3-dihydro-1H-1,3-benzodiazol-1-yl}piperidine-2,6-dione | 830.7 | δ = 13.37 (br s, 1H), 11.05 (s, 1H), 8.62 (s, 1H), 8.21-8.09 (m, 3H), 7.50 (d, J = 9.2 Hz, 1H), 7.37 (s, 1H), 7.06 (dd, J = 2.4, 9.2 Hz, 1H), 6.99 (d, J = 8.4 Hz, 1H), 6.78 (br s, 1H), 6.67 (dd, J = 1.6, 8.4 Hz, 1H), 5.32 (br s, 1H), 4.46 (br s, 2H), 3.78-3.71 (m, 2H), 3.03-2.69 (m, 6H), 2.63-2.51 (m, 6H), 2.35-1.94 (m, 8H), 1.78 (br d, J = 11.6 Hz, 5H), 1.54 (s, 4H), 1.31-1.15 (m, 2H), 1.12-0.89 (m, 10H), 0.81-0.73 (m, 2H) |
| 18 | 3-{3-methyl-4-[3-({1-[(1-{6-[5-(1-methylcyclopropoxy)-1H-indazol-3-yl]pyrimidin-4-yl}piperidin-4-yl)methyl]piperidin-4-yl}oxy)prop-1-yn-1-yl]-2-oxo-2,3-dihydro-1H-1,3-benzodiazol-1-yl}piperidine-2,6-dione | | δ = 13.46-13.31 (m, 1H), 11.26-10.99 (m, 1H), 8.64-8.58 (m, 1H), 8.17-8.15 (m, 1H), 8.15-8.10 (m, 1H), 7.54-7.46 (m, 1H), 7.38-7.34 (m, 1H), 7.20-7.00 (m, 4H), 5.44-5.34 (m, 1H), 4.53-4.37 (m, 4H), 3.64 (br s, 3H), 3.00-2.82 (m, 4H), 2.73-2.59 (m, 4H), 2.19-2.01 (m, 4H), 1.95-1.73 (m, 6H), 1.54 (s, 3H), 1.50 (br d, J = 1.6 Hz, 1H), 1.13-1.01 (m, 2H), 0.94 (br s, 2H), 0.77 (br s, 2H) |
| 19 | rel-3-[3-methyl-2-oxo-5-(4-{[(1r,4r)-4-[(4-{6-[5-(tert-butoxy)-1H-pyrazolo[3,4-c]pyridin-3-yl]pyrimidin-4-yl}piperazin-1-yl)methyl]cyclohexyl]oxy}piperidin-1-yl)-2,3-dihydro-1H-1,3-benzodiazol-1-yl]piperidine-2,6-dione | 806.5 | δ = 14.15-13.21 (m, 1H), 11.16-10.96 (m, 1H), 8.77 (d, J = 1.0 Hz, 1H), 8.65 (s, 1H), 7.71 (d, J = 1.0 Hz, 1H), 7.39 (s, 1H), 6.93 (d, J = 8.6 Hz, 1H), 6.84 (d, J = 2.0 Hz, 1H), 6.67-6.59 (m, 1H), 5.35-5.22 (m, 1H), 3.68 (br s, 4H), 3.61-3.56 (m, 1H), 3.48-3.38 (m, 4H), 2.95-2.76 (m, 3H), 2.71-2.63 (m, 2H), 2.60-2.53 (m, 2H), 2.43 (br s, 4H), 2.13 (br d, J = 6.4 Hz, 2H), 2.04-1.88 (m, 5H), 1.86-1.77 (m, 2H), 1.60-1.45 (m, 12H), 1.22-1.08 (m, 2H), 0.99-0.80 (m, 2H) |
| 20 | rel-3-[3-methyl-2-oxo-5-(4-{[(1r,4r)-4-[(4-{6-[5-(propan-2-yloxy)-1H-pyrazolo[3,4-c]pyridin-3-yl]pyrimidin-4-yl}piperazin-1-yl)methyl]cyclohexyl]oxy} | 792.4 | δ = 13.98-13.73 (m, 1H), 11.13-10.98 (m, 1H), 8.82-8.71 (m, 1H), 8.69-8.56 (m, 1H), 8.19-8.12 (m, 1H), 7.73-7.57 (m, 1H), 7.41-7.31 (m, 1H), 6.98-6.86 (m, 1H), 6.85-6.79 (m, 1H), 6.66-6.59 (m, 1H), 5.32-5.24 (m, 1H), 5.24-5.14 (m, 1H), 3.72-3.63 (m, 4H), 3.61-3.55 (m, 1H), 3.46-3.41 (m, 2H), 3.30-3.30 (m, 3H), 2.93-2.77 (m, |

TABLE 1-continued

| Comp. No. | IUPAC Name | LCMS | $^1$H NMR (400 MHz, DMSO-$d_6$) |
|---|---|---|---|
| | piperidin-1-yl)-2,3-dihydro-1H-1,3-benzodiazol-1-yl]piperidine-2,6-dione | | 3H), 2.73-2.62 (m, 2H), 2.54-2.52 (m, 1H), 2.44-2.39 (m, 4H), 2.17-2.08 (m, 2H), 2.00-1.86 (m, 5H), 1.84-1.75 (m, 2H), 1.62-1.45 (m, 3H), 1.32-1.25 (m, 6H), 1.23-1.10 (m, 2H), 1.00-0.85 (m, 2H) |
| 21 | rel-3-[3-methyl-2-oxo-5-(4-{[(1r,4r)-4-{[4-(6-{5-methoxy-1H-pyrazolo[3,4-c]pyridin-3-yl}pyrimidin-4-yl)piperazin-1-yl]methyl}cyclohexyl]oxy}piperidin-1-yl)-2,3-dihydro-1H-1,3-benzodiazol-1-yl]piperidine-2,6-dione | 764.4 | δ = 14.28-13.40 (m, 1H), 11.06 (s, 1H), 8.78 (d, J = 0.9 Hz, 1H), 8.65 (s, 1H), 8.15 (s, 1H), 7.70 (d, J = 1.0 Hz, 1H), 7.38 (s, 1H), 6.92 (d, J = 8.6 Hz, 1H), 6.83 (d, J = 1.9 Hz, 1H), 6.67-6.58 (m, 1H), 5.39-5.11 (m, 1H), 3.91 (s, 3H), 3.68 (br s, 4H), 3.59-3.53 (m, 1H), 3.44-3.39 (m, 2H), 3.36-3.34 (m, 1H), 3.30 (s, 3H), 2.95-2.78 (m, 3H), 2.71-2.61 (m, 2H), 2.42 (br s, 4H), 2.12 (br d, J = 6.9 Hz, 2H), 2.01-1.85 (m, 5H), 1.81 (br d, J = 12.9 Hz, 2H), 1.60-1.40 (m, 3H), 1.17 (br d, J = 13.5 Hz, 2H), 0.99-0.79 (m, 2H) |
| 22 | rel-1-{3-[6-(4-{[(1r,4r)-4-({1-[1-(2,6-dioxopiperidin-3-yl)-3-methyl-2-oxo-2,3-dihydro-1H-1,3-benzodiazol-5-yl]piperidin-4-yl}oxy)cyclohexyl]methyl}piperazin-1-yl)pyrimidin-4-yl]-1H-pyrazolo[3,4-c]pyridin-5-yl}cyclobutane-1-carbonitrile | 813.4 | δ = 11.24-10.83 (m, 1H), 9.24 (s, 1H), 8.76-8.65 (m, 1H), 8.59-8.50 (m, 1H), 8.23-8.19 (m, 1H), 7.44 (s, 1H), 6.97-6.89 (m, 1H), 6.85-6.77 (m, 1H), 6.67-6.52 (m, 1H), 5.28 (dd, J = 5.3, 12.8 Hz, 1H), 3.69 (br s, 4H), 3.60-3.58 (m, 1H), 3.48-3.46 (m, 2H), 3.30 (s, 3H), 2.87-2.71 (m, 7H), 2.70-2.61 (m, 2H), 2.42 (br s, 4H), 2.37-2.25 (m, 2H), 2.14-2.03 (m, 3H), 2.01-1.85 (m, 5H), 1.85-1.76 (m, 2H), 1.64-1.43 (m, 3H), 1.23-1.09 (m, 2H), 0.99-0.82 (m, 2H) |
| 23 | rel-1-{3-[6-(4-{[(1r,4r)-4-({1-[1-(2,6-dioxopiperidin-3-yl)-3-methyl-2-oxo-2,3-dihydro-1H-1,3-benzodiazol-5-yl]piperidin-4-yl}oxy)cyclohexyl]methyl}piperazin-1-yl)pyrimidin-4-yl]-1H-pyrazolo[3,4-c]pyridin-5-yl}cyclopropane-1-carbonitrile | 799.4 | δ = 11.43-10.60 (m, 1H), 9.13-8.96 (m, 1H), 8.76-8.68 (m, 1H), 8.68-8.58 (m, 1H), 8.22-8.12 (m, 1H), 7.50-7.32 (m, 1H), 6.96-6.86 (m, 1H), 6.86-6.79 (m, 1H), 6.70-6.51 (m, 1H), 5.35-5.19 (m, 1H), 3.69 (br s, 4H), 3.59 (br s, 1H), 3.40 (br s, 4H), 3.35 (br s, 1H), 3.30 (s, 3H), 2.92-2.85 (m, 1H), 2.84-2.75 (m, 2H), 2.71-2.59 (m, 2H), 2.45-2.39 (m, 4H), 2.16-2.06 (m, 2H), 2.02-1.85 (m, 5H), 1.85-1.76 (m, 4H), 1.75-1.65 (m, 2H), 1.62-1.39 (m, 3H), 1.25-1.08 (m, 2H) |
| 24 | rel-5-{3-[6-(4-{[(1r,4r)-4-({1-[1-(2,6-dioxopiperidin-3-yl)-3-methyl-2-oxo-2,3-dihydro-1H-1,3-benzodiazol-5-yl]piperidin-4-yl}oxy)cyclohexyl]methyl}piperazin-1-yl)pyrimidin-4-yl]-1H-pyrazolo[3,4-c]pyridin-5-yl}spiro[2.3]hexane-5-carbonitrile | 420.4 $[M/2]^+$ | δ = 14.62-13.79 (m, 1H), 11.21-10.79 (m, 1H), 9.30-9.11 (m, 1H), 8.77-8.66 (m, 1H), 8.66-8.56 (m, 1H), 7.52-7.37 (m, 1H), 6.97-6.87 (m, 1H), 6.86-6.78 (m, 1H), 6.71-6.47 (m, 1H), 5.36-5.21 (m, 1H), 3.78-3.61 (m, 4H), 3.59-3.51 (m, 1H), 3.48-3.39 (m, 2H), 3.37-3.35 (m, 1H), 3.30 (s, 3H), 3.12-3.02 (m, 2H), 2.95-2.85 (m, 1H), 2.85-2.77 (m, 4H), 2.59 (br s, 2H), 2.46-2.38 (m, 4H), 2.16-2.06 (m, 2H), 2.02-1.86 (m, 5H), 1.84-1.72 (m, 2H), 1.61-1.38 (m, 3H), 1.25-1.08 (m, 2H), 0.98-0.81 (m, 2H), 0.80-0.66 (m, 2H), 0.60-0.43 (m, 2H) |
| 25 | rel-3-[3-methyl-2-oxo-5-(4-{[(1r,4r)-4-[(1-{6-[5-(1-methylcyclopropoxy)-1H-pyrazolo[3,4-c]pyridin-3-yl]pyrimidin-4-yl}piperidin-4-yl)oxy]cyclohexyl]oxy}piperidin-1-yl)-2,3-dihydro-1H-1,3-benzodiazol-1-yl]piperidine-2,6-dione | 805.3 | δ = 11.32-10.85 (m, 1H), 8.81-8.75 (m, 1H), 8.67-8.59 (m, 1H), 8.24-8.22 (m, 1H), 7.85-7.76 (m, 1H), 7.44-7.34 (m, 1H), 6.95-6.88 (m, 1H), 6.84-6.77 (m, 1H), 6.69-6.55 (m, 1H), 5.34-5.21 (m, 1H), 4.15-4.00 (m, 2H), 3.78-3.66 (m, 1H), 3.58-3.50 (m, 1H), 3.37 (br s, 6H), 3.30 (br s, 3H), 2.96-2.76 (m, 3H), 2.74-2.59 (m, 2H), 2.03-1.94 (m, 1H), 1.94-1.82 (m, 8H), 1.65-1.59 (m, 3H), 1.59-1.49 (m, 2H), 1.48-1.36 (m, 2H), 1.31-1.21 (m, 4H), 0.98-0.89 (m, 2H), 0.79-0.71 (m, 2H) |
| 26 | rel-3-[2-oxo-3-(propan-2-yl)-5-(4-{[(1r,4r)-4-[(1-{6-[5-(1-methylcyclopropoxy)-1H-pyrazolo[3,4-c]pyridin-3-yl]pyrimidin-4-yl}piperidin-4-yl)oxy]cyclohexyl]oxy}piperidin-1-yl)-2,3-dihydro-1H-1,3-benzodiazol-1-yl]piperidine-2,6-dione | 833.4 | δ = 14.06-13.78 (m, 1H), 11.16-10.91 (m, 1H), 8.81-8.77 (m, 1H), 8.66-8.61 (m, 1H), 8.15-8.13 (m, 1H), 7.88-7.73 (m, 1H), 7.50-7.38 (m, 1H), 7.00-6.84 (m, 2H), 6.51 (br d, J = 2.9 Hz, 1H), 5.32-5.17 (m, 1H), 4.65-4.53 (m, 1H), 4.16-3.99 (m, 2H), 3.80-3.66 (m, 1H), 3.59-3.49 (m, 1H), 3.49-3.34 (m, 6H), 2.92-2.75 (m, 3H), 2.70-2.57 (m, 2H), 2.04-1.96 (m, 1H), 1.96-1.81 (m, 8H), 1.65-1.59 (m, 3H), 1.59-1.51 (m, 2H), 1.49-1.39 (m, 8H), 1.32-1.22 (m, 4H), 0.98-0.88 (m, 2H), 0.80-0.69 (m, 2H) |
| 27 | rel-3-[3-methyl-2-oxo-5-(4-{[(1r,4r)-4-[(1-{6-[5-(propan-2-yloxy)-1H- | 792.4 | δ = 13.44-13.28 (m, 1H), 11.13-10.98 (m, 1H), 8.69-8.55 (m, 1H), 8.20-8.17 (m, 1H), 8.00-7.95 (m, 1H), 7.53-7.47 (m, 1H), 7.42-7.36 (m, |

TABLE 1-continued

| Comp. No. | IUPAC Name | LCMS | $^1H$ NMR (400 MHz, DMSO-$d_6$) |
|---|---|---|---|
| | indazol-3-yl]pyrimidin-4-yl}piperidin-4-yl)oxy]cyclohexyl]oxy}piperidin-1-yl)-2,3-dihydro-1H-1,3-benzodiazol-1-yl]piperidine-2,6-dione | | 1H), 7.08-7.01 (m, 1H), 6.92 (d, J = 8.6 Hz, 1H), 6.84-6.80 (m, 1H), 6.67-6.58 (m, 1H), 5.34-5.19 (m, 1H), 4.67-4.51 (m, 1H), 4.15-3.99 (m, 2H), 3.78-3.66 (m, 1H), 3.57-3.50 (m, 1H), 3.47-3.38 (m, 6H), 3.30-3.29 (m, 3H), 2.95-2.79 (m, 3H), 2.73-2.60 (m, 2H), 2.03-1.95 (m, 1H), 1.94-1.83 (m, 8H), 1.61-1.48 (m, 2H), 1.47-1.37 (m, 2H), 1.34-1.29 (m, 6H), 1.29-1.22 (m, 4H) |
| 28 | rel-3-[3-methyl-2-oxo-5-(4-{[(1r,4r)-4-[(1-{6-[5-(propan-2-yloxy)-1H-pyrazolo[3,4-c]pyridin-3-yl]pyrimidin-4-yl}piperidin-4-yl)oxy]cyclohexyl]oxy}piperidin-1-yl)-2,3-dihydro-1H-1,3-benzodiazol-1-yl]piperidine-2,6-dione | 793.4 | δ = 13.99-13.65 (m, 1H), 11.15-10.91 (m, 1H), 8.79-8.71 (m, 1H), 8.65-8.57 (m, 1H), 8.22-8.18 (m, 1H), 7.66 (d, J = 1.0 Hz, 1H), 7.43-7.32 (m, 1H), 6.96-6.88 (m, 1H), 6.85-6.80 (m, 1H), 6.68-6.60 (m, 1H), 5.33-5.25 (m, 1H), 5.23-5.12 (m, 1H), 4.14-3.99 (m, 2H), 3.76-3.65 (m, 1H), 3.57-3.51 (m, 1H), 3.49-3.38 (m, 5H), 3.30 (s, 3H), 2.95-2.77 (m, 3H), 2.67-2.55 (m, 3H), 2.03-1.96 (m, 1H), 1.94-1.82 (m, 8H), 1.61-1.50 (m, 2H), 1.47-1.38 (m, 2H), 1.33-1.29 (m, 6H), 1.29-1.21 (m, 4H) |
| 29 | rel-3-(3-methyl-2-oxo-5-{4-[(1r,3r)-3-[(1-{6-[5-(1-methylcyclopropoxy)-1H-indazol-3-yl]pyrimidin-4-yl}piperidin-4-yl)oxy]cyclobutoxy]piperidin-1-yl}-2,3-dihydro-1H-1,3-benzodiazol-1-yl)piperidine-2,6-dione | 776.4 | δ = 13.38 (br s, 1H), 11.06 (br s, 1H), 8.63 (d, J = 0.6 Hz, 1H), 8.17 (s, 1H), 8.15 (d, J = 2.0 Hz, 1H), 7.50 (d, J = 9.0 Hz, 1H), 7.39 (s, 1H), 7.07 (dd, J = 2.4, 9.0 Hz, 1H), 6.92 (d, J = 8.6 Hz, 1H), 6.83 (d, J = 2.1 Hz, 1H), 6.62 (dd, J = 2.1, 8.6 Hz, 1H), 5.28 (dd, J = 5.3, 12.8 Hz, 1H), 4.31-4.21 (m, 2H), 4.10 (br d, J = 13.1 Hz, 2H), 3.57 (br dd, J = 4.1, 8.0 Hz, 1H), 3.41 (dt, J = 4.4, 8.4 Hz, 4H), 3.34 (br s, 2H), 3.30-3.24 (m, 2H), 2.87 (br d, J = 16.6 Hz, 1H), 2.83-2.74 (m, 2H), 2.72-2.57 (m, 2H), 2.18 (t, J = 5.6 Hz, 4H), 2.03-1.95 (m, 1H), 1.88 (br d, J = 3.8 Hz, 4H), 1.63-1.50 (m, 5H), 1.48-1.37 (m, 2H), 0.97-0.92 (m, 2H), 0.79-0.74 (m, 2H) |
| 30 | rel-3-(3-methyl-2-oxo-5-{4-[(1r,3r)-3-[(1-{6-[5-(1-methylcyclopropoxy)-1H-pyrazolo[3,4-c]pyridin-3-yl]pyrimidin-4-yl}piperidin-4-yl)oxy]cyclobutoxy]piperidin-1-yl}-2,3-dihydro-1H-1,3-benzodiazol-1-yl)piperidine-2,6-dione | 777.4 | δ = 13.38 (br s, 1H), 11.06 (br s, 1H), 8.63 (d, J = 0.6 Hz, 1H), 8.17 (s, 1H), 8.15 (d, J = 2.0 Hz, 1H), 7.50 (d, J = 9.0 Hz, 1H), 7.39 (s, 1H), 7.07 (dd, J = 2.4, 9.0 Hz, 1H), 6.92 (d, J = 8.6 Hz, 1H), 6.83 (d, J = 2.1 Hz, 1H), 6.62 (dd, J = 2.1, 8.6 Hz, 1H), 5.28 (dd, J = 5.3, 12.8 Hz, 1H), 4.31-4.21 (m, 2H), 4.10 (br d, J = 13.1 Hz, 2H), 3.57 (br dd, J = 4.1, 8.0 Hz, 1H), 3.41 (dt, J = 4.4, 8.4 Hz, 4H), 3.34 (br s, 2H), 3.30-3.24 (m, 2H), 2.87 (br d, J = 16.6 Hz, 1H), 2.83-2.74 (m, 2H), 2.72-2.57 (m, 2H), 2.18 (t, J = 5.6 Hz, 4H), 2.03-1.95 (m, 1H), 1.88 (br d, J = 3.8 Hz, 4H), 1.63-1.50 (m, 5H), 1.48-1.37 (m, 2H), 0.97-0.92 (m, 2H), 0.79-0.74 (m, 2H) |
| 31 | rel-3-(3-methyl-2-oxo-5-{4-[(1r,3r)-3-[(1-{6-[5-(propan-2-yloxy)-1H-pyrazolo[3,4-c]pyridin-3-yl]pyrimidin-4-yl}piperidin-4-yl)oxy]cyclobutoxy]piperidin-1-yl}-2,3-dihydro-1H-1,3-benzodiazol-1-yl)piperidine-2,6-dione | 765.3 | δ = 13.97-13.76 (m, 1H), 11.20-10.89 (m, 1H), 8.77 (d, J = 0.9 Hz, 1H), 8.63 (d, J = 0.8 Hz, 1H), 7.66 (d, J = 1.0 Hz, 1H), 7.39 (s, 1H), 6.92 (d, J = 8.6 Hz, 1H), 6.84 (d, J = 2.0 Hz, 1H), 6.63 (dd, J = 2.1, 8.6 Hz, 1H), 5.29 (br dd, J = 5.6, 12.8 Hz, 1H), 5.23-5.15 (m, 1H), 4.33-4.21 (m, 2H), 4.18-4.02 (m, 2H), 3.59 (td, J = 4.1, 8.2 Hz, 1H), 3.49-3.39 (m, 4H), 3.30 (br s, 3H), 2.94-2.71 (m, 4H), 2.58 (br d, J = 3.3 Hz, 2H), 2.18 (t, J = 5.7 Hz, 4H), 2.04-1.96 (m, 1H), 1.90 (br s, 4H), 1.60-1.50 (m, 2H), 1.48-1.38 (m, 2H), 1.31 (d, J = 6.1 Hz, 6H) |
| 32 | rel-3-[3-methyl-2-oxo-5-(4-{[(1r,3r)-3-[(1-{6-[5-(1-methylcyclopropoxy)-1H-pyrazolo[3,4-c]pyridin-3-yl]pyrimidin-4-yl}piperidin-4-yl)oxy]cyclobutyl]methoxy}piperidin-1-yl)-2,3-dihydro-1H-1,3-benzodiazol-1-yl]piperidine-2,6-dione | 396.5 $[M/2]^+$ | δ = 14.35-13.30 (m, 1H), 11.05 (br s, 1H), 8.78 (s, 1H), 8.63 (s, 1H), 8.18 (s, 1H), 7.79 (s, 1H), 7.39 (s, 1H), 6.93 (d, J = 8.6 Hz, 1H), 6.84 (d, J = 1.8 Hz, 1H), 6.64 (dd, J = 1.8, 8.6 Hz, 1H), 5.28 (br dd, J = 5.2, 12.8 Hz, 1H), 4.23 (br t, J = 7.0 Hz, 1H), 4.09 (br d, J = 12.5 Hz, 2H), 3.57 (td, J = 4.1, 7.9 Hz, 1H), 3.46 (br d, J = 7.0 Hz, 3H), 3.40 (br d, J = 12.9 Hz, 4H), 3.33 (br s, 4H), 2.94-2.81 (m, 3H), 2.71-2.56 (m, 2H), 2.38-2.24 (m, 1H), 2.06-1.99 (m, 4H), 1.97-1.92 (m, 2H), 1.90-1.79 (m, 2H), 1.64-1.54 (m, 5H), 1.48-1.37 (m, 2H), 0.96-0.90 (m, 2H), 0.79-0.72 (m, 2H) |
| 33 | rel-3-[3-methyl-2-oxo-5-(4-{[(1r,3r)-3-[(1-{6-[5-(1-methylcyclopropoxy)-1H-indazol-3-yl]pyrimidin-4-yl}piperidin-4-yl)oxy]cyclobutyl]methoxy} | 396.0 $[M/2]^+$ | δ = 13.38 (s, 1H), 11.06 (s, 1H), 8.63 (d, J = 0.6 Hz, 1H), 8.16 (d, J = 2.3 Hz, 1H), 8.14 (s, 1H), 7.50 (d, J = 9.0 Hz, 1H), 7.39 (s, 1H), 7.07 (dd, J = 2.3, 9.0 Hz, 1H), 6.93 (d, J = 8.6 Hz, 1H), 6.85 (d, J = 2.0 Hz, 1H), 6.64 (dd, J = 2.0, 8.6 Hz, 1H), 5.29 (dd, J = 5.4, 12.9 Hz, 1H), 4.24 (t, J = 7.0 Hz, |

TABLE 1-continued

| Comp. No. | IUPAC Name | LCMS | $^1$H NMR (400 MHz, DMSO-$d_6$) |
|---|---|---|---|
| | piperidin-1-yl)-2,3-dihydro-1H-1,3-benzodiazol-1-yl]piperidine-2,6-dione | | 1H), 4.15-4.04 (m, 2H), 3.62-3.53 (m, 1H), 3.51-3.43 (m, 3H), 3.43-3.38 (m, 2H), 3.35 (br d, J = 3.0 Hz, 1H), 3.31 (br s, 4H), 2.94-2.82 (m, 3H), 2.72-2.58 (m, 2H), 2.35-2.28 (m, 1H), 2.07-1.92 (m, 7H), 1.90-1.80 (m, 2H), 1.67-1.57 (m, 2H), 1.55 (s, 3H), 1.48-1.36 (m, 2H), 0.98-0.91 (m, 2H), 0.80-0.75 (m, 2H) |
| 34 | rel-3-(3-methyl-2-oxo-5-{4-[(1r,3r)-3-{[(1-{6-[5-(1-methylcyclopropoxy)-1H-pyrazolo[3,4-c]pyridin-3-yl]pyrimidin-4-yl}piperidin-4-yl)oxy]methyl}cyclobutoxy]piperidin-1-yl}-2,3-dihydro-1H-1,3-benzodiazol-1-yl)piperidine-2,6-dione | 791.4 | δ = 14.11-13.78 (m, 1H), 11.06 (s, 1H), 8.79 (d, J = 1.1 Hz, 1H), 8.65 (d, J = 1.0 Hz, 1H), 8.35-8.20 (m, 1H), 7.80 (d, J = 1.0 Hz, 1H), 7.42 (s, 1H), 6.92 (d, J = 8.6 Hz, 1H), 6.83 (d, J = 2.1 Hz, 1H), 6.69-6.53 (m, 1H), 5.38-5.20 (m, 1H), 4.28-4.17 (m, 1H), 4.10-3.96 (m, 2H), 3.66-3.58 (m, 1H), 3.51-3.38 (m, 8H), 2.96-2.85 (m, 1H), 2.79 (br t, J = 9.8 Hz, 2H), 2.70-2.57 (m, 2H), 2.35-2.26 (m, 1H), 2.10-1.79 (m, 10H), 1.65-1.39 (m, 8H), 0.99-0.90 (m, 2H), 0.81-0.73 (m, 2H) |
| 35 | rel-3-(3-methyl-2-oxo-5-{4-[(1r,3r)-3-[(4-{6-[5-(1-methylcyclopropoxy)-1H-pyrazolo[3,4-c]pyridin-3-yl]pyrimidin-4-yl}piperazin-1-yl)methyl]cyclobutoxy]piperidin-1-yl}-2,3-dihydro-1H-1,3-benzodiazol-1-yl)piperidine-2,6-dione | 776.4 | δ = 14.06-13.70 (m, 1H), 11.17-10.96 (m, 1H), 8.93-8.74 (m, 1H), 8.69-8.48 (m, 1H), 7.86-7.69 (m, 1H), 7.47-7.30 (m, 1H), 6.97-6.88 (m, 1H), 6.87-6.76 (m, 1H), 6.67-6.50 (m, 1H), 5.35-5.20 (m, 1H), 3.98 (br s, 1H), 3.79-3.50 (m, 4H), 3.46-3.38 (m, 3H), 3.31-3.29 (m, 3H), 2.96-2.84 (m, 1H), 2.84-2.75 (m, 2H), 2.59 (br s, 2H), 2.48-2.28 (m, 8H), 2.08-1.94 (m, 2H), 1.94-1.81 (m, 2H), 1.65-1.60 (m, 3H), 1.59 (br s, 4H), 1.00-0.88 (m, 2H), 0.81-0.69 (m, 2H) |
| 36 | rel-3-[3-methyl-2-oxo-5-(4-{[(1r,3r)-3-[(1-{6-[5-(1-methylcyclopropoxy)-1H-pyrazolo[3,4-c]pyridin-3-yl]pyrimidin-4-yl}piperidin-4-yl)oxy]cyclobutyl]methyl}piperazin-1-yl)-2,3-dihydro-1H-1,3-benzodiazol-1-yl]piperidine-2,6-dione | 776.3 | δ = 14.31-13.03 (m, 1H), 11.30-10.66 (m, 1H), 8.83-8.73 (m, 1H), 8.68-8.58 (m, 1H), 7.84-7.72 (m, 1H), 7.45-7.33 (m, 1H), 6.98-6.88 (m, 1H), 6.86-6.78 (m, 1H), 6.68-6.55 (m, 1H), 5.39-5.16 (m, 1H), 4.18-4.00 (m, 2H), 4.00-3.89 (m, 1H), 3.64-3.56 (m, 1H), 3.39-3.36 (m, 1H), 3.35-3.33 (m, 4H), 3.30-3.28 (m, 3H), 3.11-2.99 (m, 4H), 2.93-2.83 (m, 1H), 2.56 (br d, J = 18.6 Hz, 3H), 2.33 (br s, 4H), 2.11-1.92 (m, 2H), 1.91-1.76 (m, 2H), 1.66-1.58 (m, 3H), 1.58-1.49 (m, 2H), 1.49-1.36 (m, 2H), 1.00-0.87 (m, 2H), 0.82-0.64 (m, 2H) |
| 37 | rel-3-(3-methyl-2-oxo-5-{1-[(1r,3r)-3-[(1-{6-[5-(1-methylcyclopropoxy)-1H-indazol-3-yl]pyrimidin-4-yl}piperidin-4-yl)oxy]cyclobutyl]piperidin-4-yl}-2,3-dihydro-1H-1,3-benzodiazol-1-yl)piperidine-2,6-dione | 760.3 | δ = 13.45-13.31 (m, 1H), 11.18-10.93 (m, 1H), 8.71-8.57 (m, 1H), 8.20-8.10 (m, 2H), 7.54-7.47 (m, 1H), 7.42-7.35 (m, 1H), 7.13-7.09 (m, 1H), 7.09-7.04 (m, 1H), 7.02-6.97 (m, 1H), 6.95-6.88 (m, 1H), 5.38-5.26 (m, 1H), 4.24-4.16 (m, 1H), 4.14-4.03 (m, 2H), 3.67-3.59 (m, 1H), 3.39-3.36 (m, 3H), 3.29-3.28 (m, 2H), 3.05-2.99 (m, 2H), 2.99-2.76 (m, 3H), 2.76-2.60 (m, 2H), 2.22-2.12 (m, 2H), 2.07-1.95 (m, 3H), 1.94-1.84 (m, 2H), 1.83-1.63 (m, 6H), 1.58-1.51 (m, 3H), 1.50-1.37 (m, 2H), 0.99-0.91 (m, 2H), 0.81-0.71 (m, 2H) |
| 38 | 3-{5-[4-({3,3-dimethyl-4-[(1-{6-[5-(1-methylcyclopropoxy)-1H-indazol-3-yl]pyrimidin-4-yl}piperidin-4-yl)methyl]piperazin-1-yl}methyl)piperidin-1-yl]-2-methyl-1H-1,3-benzodiazol-1-yl}piperidine-2,6-dione | 814.4 | δ = 13.37 (br s, 1H), 11.19 (s, 1H), 8.61 (s, 1H), 8.15 (s, 2H), 7.50 (d, J = 9.0 Hz, 1H), 7.37 (s, 1H), 7.17 (br d, J = 6.1 Hz, 1H), 7.09-7.04 (m, 1H), 7.02 (d, J = 1.4 Hz, 1H), 6.89-6.79 (m, 1H), 5.54 (br d, J = 7.6 Hz, 1H), 4.53-4.37 (m, 2H), 3.52 (br d, J = 10.0 Hz, 4H), 3.04-2.83 (m, 4H), 2.78-2.52 (m, 6H), 2.45 (s, 3H), 2.37-2.28 (m, 1H), 2.22-2.02 (m, 6H), 1.80 (br d, J = 10.4 Hz, 4H), 1.70 (br d, J = 2.8 Hz, 1H), 1.64-1.56 (m, 1H), 1.56-1.49 (m, 3H), 1.33-1.19 (m, 2H), 1.08-0.98 (m, 2H), 0.96 (s, 6H), 0.94-0.93 (m, 1H), 0.81-0.74 (m, 2H) |
| 39 | 3-{5-[4-({3,3-dimethyl-4-[(1-{6-[5-(1-methylcyclopropoxy)-1H-indazol-3-yl]pyrimidin-4-yl}piperidin-4-yl)methyl]piperazin-1-yl}methyl)piperidin-1-yl]-7-fluoro-1H-1,3-benzodiazol-1-yl}piperidine-2,6-dione | 818.4 | δ = 13.37 (s, 1H), 11.19 (s, 1H), 8.61 (s, 1H), 8.17 (s, 1H), 8.16-8.12 (m, 2H), 7.50 (d, J = 9.1 Hz, 1H), 7.36 (s, 1H), 7.06 (dd, J = 2.3, 8.9 Hz, 1H), 6.94 (d, J = 1.8 Hz, 1H), 6.85 (d, J = 13.4 Hz, 1H), 5.62 (dd, J = 5.5, 13.0 Hz, 1H), 4.53-4.37 (m, 2H), 3.65-3.59 (m, 2H), 3.01-2.81 (m, 4H), 2.75-2.57 (m, 4H), 2.46-2.35 (m, 2H), 2.35-2.22 (m, 3H), 2.09 (d, J = 7.0 Hz, 3H), 1.85-1.75 (m, 4H), 1.75-1.56 (m, 3H), 1.54 (s, 3H), 1.28-1.18 (m, 2H), 1.04 (d, J = 9.6 Hz, 2H), 0.95 (s, 9H), 0.79-0.75 (m, 2H) |
| 40 | 3-{5-[4-({3,3-dimethyl-4-[(1-{6-[5-(1- | 818.4 | δ = 13.44-13.28 (m, 1H), 11.25-11.05 (m, 1H), 8.66-8.58 (m, 1H), 8.17 (s, 2H), 7.54-7.47 (m, |

TABLE 1-continued

| Comp. No. | IUPAC Name | LCMS | $^1H$ NMR (400 MHz, DMSO-$d_6$) |
|---|---|---|---|
| | methylcyclopropoxy)-1H-indazol-3-yl]pyrimidin-4-yl}piperidin-4-yl)methyl]piperazin-1-yl}methyl)piperidin-1-yl]-6-fluoro-1H-1,3-benzodiazol-1-yl}piperidine-2,6-dione | | 1H), 7.46-7.40 (m, 1H), 7.39-7.35 (m, 1H), 7.32-7.26 (m, 1H), 7.10-7.03 (m, 1H), 5.66-5.52 (m, 1H), 4.57-4.38 (m, 2H), 3.27-3.21 (m, 4H), 3.02-2.87 (m, 3H), 2.87-2.75 (m, 2H), 2.70-2.58 (m, 3H), 2.22-2.16 (m, 2H), 2.15-2.05 (m, 4H), 1.87-1.75 (m, 4H), 1.71-1.60 (m, 2H), 1.54 (s, 3H), 1.36-1.22 (m, 3H), 1.12-0.99 (m, 3H), 0.97-0.95 (m, 6H), 0.94-0.86 (m, 2H), 0.79-0.75 (m, 2H) |
| 41 | 3-{5-[4-({3,3-dimethyl-4-[(1-{6-[5-(1-methylcyclopropoxy)-1H-indazol-3-yl]pyrimidin-4-yl}piperidin-4-yl)methyl]piperazin-1-yl}methyl)piperidin-1-yl]-4-fluoro-1H-1,3-benzodiazol-1-yl}piperidine-2,6-dione | 818.4 | δ = 13.48-13.19 (m, 1H), 11.31-11.12 (m, 1H), 8.64-8.56 (m, 1H), 8.25-8.20 (m, 1H), 8.17-8.10 (m, 2H), 7.54-7.47 (m, 1H), 7.39-7.33 (m, 1H), 7.29-7.23 (m, 1H), 7.11-7.01 (m, 2H), 5.73-5.56 (m, 1H), 4.53-4.37 (m, 2H), 3.27-3.24 (m, 4H), 2.93 (br t, J = 12.1 Hz, 3H), 2.87-2.76 (m, 2H), 2.75 (br s, 4H), 2.55-2.53 (m, 1H), 2.27-2.18 (m, 2H), 2.17-2.07 (m, 4H), 1.88-1.76 (m, 4H), 1.75-1.60 (m, 2H), 1.57-1.49 (m, 3H), 1.37-1.25 (m, 2H), 1.12-1.00 (m, 2H), 0.98-0.91 (m, 8H), 0.81-0.74 (m, 2H) |
| 42 | rel-3-[2-methyl-5-(4-{[(1r,4r)-4-[(4-{6-[5-(1-methylcyclopropoxy)-1H-indazol-3-yl]pyrimidin-4-yl}piperazin-1-yl)methyl]cyclohexyl]oxy}piperidin-1-yl)-1H-1,3-benzodiazol-1-yl]piperidine-2,6-dione | 787.4 | δ = 13.40 (s, 1H), 11.19 (s, 1H), 8.65 (s, 1H), 8.15 (s, 1H), 7.51 (d, J = 9.0 Hz, 1H), 7.38 (s, 1H), 7.23-7.14 (m, 1H), 7.10-7.05 (m, 1H), 7.03 (d, J = 1.9 Hz, 1H), 6.87 (br d, J = 8.9 Hz, 1H), 5.55 (br d, J = 8.4 Hz, 1H), 3.67 (br s, 4H), 3.58-3.53 (m, 1H), 3.45-3.39 (m, 4H), 2.97-2.87 (m, 1H), 2.79 (br t, J = 10.2 Hz, 2H), 2.72-2.61 (m, 2H), 2.47-2.42 (m, 6H), 2.13 (br d, J = 7.4 Hz, 3H), 1.99-1.87 (m, 4H), 1.82 (br d, J = 12.6 Hz, 2H), 1.61-1.46 (m, 5H), 1.22-1.11 (m, 2H), 0.99-0.86 (m, 4H), 0.80-0.74 (m, 2H) |
| 43 | rel-3-[7-fluoro-5-(4-{[(1r,4r)-4-[(4-{6-[5-(1-methylcyclopropoxy)-1H-indazol-3-yl]pyrimidin-4-yl}piperazin-1-yl)methyl]cyclohexyl]oxy}piperidin-1-yl)-1H-1,3-benzodiazol-1-yl]piperidine-2,6-dione | 791.4 | δ = 13.39 (s, 1H), 11.19 (s, 1H), 8.64 (s, 1H), 8.15 (d, J = 3.1 Hz, 2H), 7.50 (d, J = 8.9 Hz, 1H), 7.37 (s, 1H), 7.07 (dd, J = 2.4, 9.0 Hz, 1H), 6.96 (d, J = 1.5 Hz, 1H), 6.86 (dd, J = 1.3, 14.6 Hz, 1H), 5.62 (dd, J = 5.3, 13.0 Hz, 1H), 3.67 (s, 4H), 3.61-3.55 (m, 1H), 3.46 (d, J = 11.9 Hz, 3H), 2.92-2.81 (m, 3H), 2.69 (d, J = 16.8 Hz, 1H), 2.42 (s, 4H), 2.30 (dd, J = 5.9, 11.4 Hz, 1H), 2.12 (d, J = 7.0 Hz, 2H), 1.97-1.86 (m, 4H), 1.81 (d, J = 11.6 Hz, 2H), 1.66-1.37 (m, 7H), 1.22-1.11 (m, 2H), 0.97-0.86 (m, 4H), 0.80-0.75 (m, 2H) |
| 44 | rel-3-[6-fluoro-5-(4-{[(1r,4r)-4-[(4-{6-[5-(1-methylcyclopropoxy)-1H-indazol-3-yl]pyrimidin-4-yl}piperazin-1-yl)methyl]cyclohexyl]oxy}piperidin-1-yl)-1H-1,3-benzodiazol-1-yl]piperidine-2,6-dione | 791.4 | δ = 13.51-13.24 (m, 1H), 11.31-10.98 (m, 1H), 8.68-8.58 (m, 1H), 8.20-8.12 (m, 2H), 7.54-7.48 (m, 1H), 7.47-7.41 (m, 1H), 7.40-7.35 (m, 1H), 7.33-7.27 (m, 1H), 7.10-7.03 (m, 1H), 5.73-5.48 (m, 1H), 3.81-3.53 (m, 6H), 3.24-3.12 (m, 2H), 2.92-2.64 (m, 5H), 2.46-2.37 (m, 4H), 2.24-2.16 (m, 1H), 2.15-2.08 (m, 2H), 2.03-1.88 (m, 4H), 1.87-1.75 (m, 2H), 1.66-1.40 (m, 6H), 1.27-1.10 (m, 2H), 1.01-0.83 (m, 4H), 0.81-0.71 (m, 2H) |
| 45 | rel-3-[4-fluoro-5-(4-{[(1r,4r)-4-[(4-{6-[5-(1-methylcyclopropoxy)-1H-indazol-3-yl]pyrimidin-4-yl}piperazin-1-yl)methyl]cyclohexyl]oxy}piperidin-1-yl)-1H-1,3-benzodiazol-1-yl]piperidine-2,6-dione | 791.4 | δ = 13.47-13.31 (m, 1H), 11.32-11.09 (m, 1H), 8.67-8.61 (m, 1H), 8.27-8.20 (m, 1H), 8.18-8.12 (m, 1H), 7.54-7.47 (m, 1H), 7.42-7.34 (m, 1H), 7.29-7.22 (m, 1H), 7.15-6.99 (m, 2H), 5.72-5.57 (m, 1H), 3.67 (br s, 4H), 3.62-3.54 (m, 1H), 3.41-3.35 (m, 1H), 3.24-3.14 (m, 2H), 2.92-2.76 (m, 4H), 2.74-2.67 (m, 1H), 2.45-2.37 (m, 4H), 2.27-2.19 (m, 1H), 2.17-2.09 (m, 2H), 2.02-1.88 (m, 4H), 1.86-1.76 (m, 2H), 1.66-1.57 (m, 2H), 1.56-1.53 (m, 3H), 1.52-1.44 (m, 1H), 1.26-1.13 (m, 2H), 1.00-0.88 (m, 4H), 0.81-0.73 (m, 2H) |
| 46 | rel-3-[3-methyl-2-oxo-4-(4-{[(1r,4r)-4-[(4-{6-[5-(1-methylcyclopropoxy)-1H-pyrazolo[3,4-c]pyridin-3-yl]pyrimidin-4-yl}piperazin-1-yl)methyl]cyclohexyl]oxy}piperidin-1-yl)-2,3-dihydro-1H-1,3-benzodiazol-1-yl]piperidine-2,6-dione | 804.4 | δ = 14.09-13.65 (m, 1H), 11.09 (br s, 1H), 8.79 (s, 1H), 8.65 (s, 1H), 7.80 (s, 1H), 7.39 (s, 1H), 7.02-6.94 (m, 1H), 6.92-6.83 (m, 2H), 5.35 (dd, J = 5.6, 12.6 Hz, 1H), 3.68 (br s, 4H), 3.63 (s, 3H), 3.14-2.99 (m, 2H), 2.92-2.83 (m, 1H), 2.80-2.59 (m, 4H), 2.42 (br s, 5H), 2.13 (br d, J = 7.3 Hz, 2H), 2.07-1.90 (m, 5H), 1.88-1.73 (m, 3H), 1.69-1.42 (m, 6H), 1.27-1.14 (m, 2H), 0.99-0.86 (m, 4H), 0.79-0.73 (m, 2H) |
| 47 | 3-{4-[4-({3,3-dimethyl-4-[(1-{6-[5-(1- | 831.5 | δ = 0.73-0.79 (m, 2 H) 0.90-0.97 (m, 8 H) 0.99-1.10 (m, 2 H) 1.22-1.37 (m, 2 H) 1.61 (s, 3 H) |

TABLE 1-continued

| Comp. No. | IUPAC Name | LCMS | $^1$H NMR (400 MHz, DMSO-$d_6$) |
|---|---|---|---|
| | methylcyclopropoxy)-1H-pyrazolo[3,4-c]pyridin-3-yl]pyrimidin-4-yl}piperidin-4-yl)methyl]piperazin-1-yl}methyl)piperidin-1-yl]-3-methyl-2-oxo-2,3-dihydro-1H-1,3-benzodiazol-1-yl}piperidine-2,6-dione | | 1.66-1.73 (m, 1 H) 1.75-1.87 (m, 4 H) 1.94-2.05 (m, 2 H) 2.06-2.18 (m, 4 H) 2.43 (br d, J = 9.51 Hz, 4 H) 2.61-2.74 (m, 4 H) 2.81-3.01 (m, 4 H) 3.10 (br d, J = 9.38 Hz, 3 H) 3.59-3.63 (m, 3 H) 4.33-4.60 (m, 2 H) 5.28-5.40 (m, 1 H) 6.82-6.92 (m, 2 H) 6.93-7.00 (m, 1 H) 7.33-7.40 (m, 1 H) 7.76-7.82 (m, 1 H) 8.16-8.17 (m, 1 H) 8.59-8.64 (m, 1 H) 8.76-8.80 (m, 1 H) 11.04-11.14 (m, 1 H) 13.75-14.02 (m, 1 H) |
| 48 | 3-{5-[4-({3,3-dimethyl-4-[(1-{6-[5-(1-methylcyclopropoxy)-1H-pyrazolo[3,4-c]pyridin-3-yl]pyrimidin-4-yl}piperidin-4-yl)methyl]piperazin-1-yl}methyl)piperidin-1-yl]-3-methyl-2-oxo-2,3-dihydro-1H-1,3-benzodiazol-1-yl}piperidine-2,6-dione | 831.4 | δ = 14.07-13.68 (m, 1H), 11.04 (s, 1H), 8.78 (s, 1H), 8.62 (s, 1H), 8.15 (s, 1H), 7.79 (s, 1H), 7.37 (s, 1H), 6.91 (d, J = 8.5 Hz, 1H), 6.81 (s, 1H), 6.62 (br d, J = 8.6 Hz, 1H), 5.28 (br dd, J = 5.5, 12.8 Hz, 1H), 4.53-4.34 (m, 2H), 3.57 (br d, J = 11.6 Hz, 2H), 3.30 (br s, 6H), 3.02-2.82 (m, 4H), 2.69-2.58 (m, 4H), 2.29-2.02 (m, 6H), 2.01-1.94 (m, 1H), 1.79 (br d, J = 11.0 Hz, 4H), 1.70 (br d, J = 2.1 Hz, 1H), 1.61 (s, 4H), 1.31-1.16 (m, 2H), 1.04 (br d, J = 10.9 Hz, 2H), 0.95 (s, 6H), 0.94-0.90 (m, 2H), 0.76 (s, 2H) |
| 49 | rel-3-[2-oxo-3-(propan-2-yl)-5-(4-{[(1r,4r)-4-[(4-{6-[5-(1-methylcyclopropoxy)-1H-indazol-3-yl]pyrimidin-4-yl}piperazin-1-yl)methyl]cyclohexyl]oxy}piperidin-1-yl)-2,3-dihydro-1H-1,3-benzodiazol-1-yl]piperidine-2,6-dione | 831.4 | δ = 13.58-13.18 (m, 1H), 11.31-10.71 (m, 1H), 8.64 (s, 1H), 8.22 (s, 1H), 8.15 (d, J = 1.9 Hz, 1H), 7.50 (d, J = 9.0 Hz, 1H), 7.37 (s, 1H), 7.12-7.02 (m, 1H), 6.95-6.83 (m, 2H), 6.67-6.57 (m, 1H), 5.40-5.12 (m, 1H), 4.70-4.43 (m, 1H), 3.67 (br s, 4H), 3.60-3.51 (m, 2H), 2.96-2.75 (m, 4H), 2.71-2.60 (m, 2H), 2.42 (br s, 4H), 2.16-2.07 (m, 2H), 2.00-1.86 (m, 5H), 1.81 (br d, J = 11.9 Hz, 2H), 1.63-1.48 (m, 5H), 1.44 (d, J = 6.9 Hz, 6H), 1.27-1.21 (m, 1H), 1.20-1.10 (m, 2H), 0.99-0.87 (m, 4H), 0.80-0.71 (m, 2H) |
| 50 | rel-3-[2-oxo-3-(propan-2-yl)-5-(4-{[(1r,4r)-4-[(4-{6-[5-(1-methylcyclopropoxy)-1H-indazol-3-yl]pyrimidin-4-yl}piperazin-1-yl)methyl]cyclohexyl]oxy}piperidin-1-yl)-2,3-dihydro-1H-1,3-benzodiazol-1-yl]piperidine-2,6-dione | 416.5 $[M/2]^+$ | δ = 13.40 (br s, 1H), 11.29-10.84 (m, 1H), 8.64 (s, 1H), 8.22 (s, 1H), 8.15 (s, 1H), 7.50 (d, J = 8.9 Hz, 1H), 7.37 (s, 1H), 7.12-7.02 (m, 1H), 6.97-6.86 (m, 2H), 6.63 (br d, J = 8.6 Hz, 1H), 5.39-5.10 (m, 1H), 4.71-4.44 (m, 1H), 3.67 (br s, 4H), 3.53-3.47 (m, 2H), 2.96-2.76 (m, 4H), 2.70-2.60 (m, 2H), 2.43 (br s, 4H), 2.17 (br d, J = 7.0 Hz, 2H), 2.05-1.81 (m, 4H), 1.75-1.67 (m, 2H), 1.66-1.60 (m, 1H), 1.58-1.50 (m, 5H), 1.44 (br d, J = 6.8 Hz, 8H), 1.34-1.22 (m, 3H), 0.98-0.90 (m, 2H), 0.82-0.71 (m, 2H) |
| 51 | 3-{5-[4-({3,3-dimethyl-4-[(1-{6-[5-(1-methylcyclopropoxy)-1H-pyrazolo[3,4-c]pyridin-3-yl]pyrimidin-4-yl}piperidin-4-yl)methyl]piperazin-1-yl}methyl)piperidin-1-yl]-2-oxo-3-(propan-2-yl)-2,3-dihydro-1H-1,3-benzodiazol-1-yl}piperidine-2,6-dione | 859.5 | δ = 14.02-13.68 (m, 1H), 11.04 (s, 1H), 8.78 (s, 1H), 8.62 (s, 1H), 8.15 (s, 1H), 7.79 (s, 1H), 7.37 (s, 1H), 6.99-6.82 (m, 2H), 6.62 (br d, J = 8.6 Hz, 1H), 5.25 (dd, J = 5.4, 12.8 Hz, 1H), 4.64-4.54 (m, 1H), 4.46 (br dd, J = 3.6, 5.7 Hz, 2H), 3.54 (br d, J = 11.6 Hz, 2H), 3.31-3.27 (m, 3H), 3.05-2.81 (m, 4H), 2.70-2.55 (m, 4H), 2.22-1.92 (m, 7H), 1.80 (br d, J = 10.6 Hz, 4H), 1.70 (br s, 1H), 1.61 (s, 4H), 1.44 (d, J = 6.9 Hz, 6H), 1.30-1.18 (m, 2H), 1.03 (br d, J = 11.4 Hz, 2H), 0.95 (s, 6H), 0.94-0.91 (m, 2H), 0.79-0.72 (m, 2H) |
| 52 | rel-3-[2-oxo-3-(propan-2-yl)-5-(4-{[(1r,4r)-4-[(4-{6-[5-(1-methylcyclopropoxy)-1H-pyrazolo[3,4-c]pyridin-3-yl]pyrimidin-4-yl}piperazin-1-yl)methyl]cyclohexyl]oxy}piperidin-1-yl)-2,3-dihydro-1H-1,3-benzodiazol-1-yl]piperidine-2,6-dione | 832.4 | δ = 11.29-10.89 (m, 1H), 8.79 (s, 1H), 8.70-8.59 (m, 1H), 8.22 (s, 1H), 7.80 (s, 1H), 7.39 (s, 1H), 7.00-6.83 (m, 2H), 6.72-6.54 (m, 1H), 5.34-5.12 (m, 1H), 4.67-4.50 (m, 1H), 3.75-3.64 (m, 4H), 3.61-3.49 (m, 2H), 2.95-2.76 (m, 4H), 2.73-2.56 (m, 3H), 2.45-2.38 (m, 4H), 2.13 (br d, J = 7.1 Hz, 2H), 2.02-1.87 (m, 5H), 1.85-1.77 (m, 2H), 1.62 (s, 3H), 1.59-1.49 (m, 3H), 1.45 (d, J = 6.8 Hz, 6H), 1.24-1.11 (m, 2H), 1.00-0.86 (m, 4H), 0.85-0.72 (m, 2H) |
| 53 | rel-3-[2-oxo-3-(propan-2-yl)-5-(4-{[(1r,4r)-4-[(4-{6-[5-(1-methylcyclopropoxy)-1H-pyrazolo[3,4-c]pyridin-3-yl]pyrimidin-4-yl}piperazin-1- | 832.4 | δ = 11.30-10.87 (m, 1H), 8.90-8.73 (m, 1H), 8.79 (s, 1H), 8.65 (s, 1H), 8.20 (s, 1H), 7.80 (s, 1H), 7.39 (s, 1H), 6.96-6.81 (m, 2H), 6.63 (br d, J = 9.4 Hz, 1H), 5.32-5.14 (m, 1H), 4.68-4.49 (m, 1H), 3.67 (br s, 6H), 2.95-2.77 (m, 3H), 2.73-2.57 (m, 2H), 2.54-2.51 (m, 2H), 2.43 (br s, 4H), 2.16 (br d, J = 6.9 Hz, 2H), 2.04-1.83 (m, 3H), |

TABLE 1-continued

| Comp. No. | IUPAC Name | LCMS | $^1$H NMR (400 MHz, DMSO-$d_6$) |
|---|---|---|---|
| | yl)methyl]cyclohexyl]oxy}piperidin-1-yl)-2,3-dihydro-1H-1,3-benzodiazol-1-yl]piperidine-2,6-dione | | 1.74-1.66 (m, 2H), 1.63-1.38 (m, 12H), 1.36-1.14 (m, 3H), 1.00-0.89 (m, 2H), 0.85-0.70 (m, 2H) |
| 54 | rel-3-[3-methyl-2-oxo-5-(4-{[(1r,4r)-4-[(4-{6-[5-(tert-butoxy)-1H-indazol-3-yl]pyrimidin-4-yl}piperazin-1-yl)methyl]cyclohexyl]oxy}piperidin-1-yl)-2,3-dihydro-1H-1,3-benzodiazol-1-yl]piperidine-2,6-dione | 805.5 | δ = 13.54-13.37 (m, 1H), 11.08-10.97 (m, 1H), 8.71-8.56 (m, 1H), 8.15-8.12 (m, 1H), 8.11-8.06 (m, 1H), 7.53-7.47 (m, 1H), 7.41-7.35 (m, 1H), 7.13-7.05 (m, 1H), 6.95-6.89 (m, 1H), 6.85-6.80 (m, 1H), 6.66-6.59 (m, 1H), 5.28 (dd, J = 5.4, 12.9 Hz, 1H), 3.74-3.63 (m, 4H), 3.62-3.56 (m, 1H), 3.46-3.41 (m, 3H), 3.30-3.27 (m, 3H), 2.91-2.77 (m, 3H), 2.71-2.61 (m, 2H), 2.44-2.37 (m, 4H), 2.17-2.09 (m, 2H), 2.03-1.87 (m, 5H), 1.84-1.75 (m, 2H), 1.61-1.45 (m, 3H), 1.35-1.29 (m, 9H), 1.22-1.10 (m, 2H), 0.99-0.83 (m, 2H) |
| 55 | rel-3-[3-methyl-2-oxo-5-(4-{[(1r,4r)-4-[(4-{6-[5-(propan-2-yloxy)-1H-indazol-3-yl]pyrimidin-4-yl}piperazin-1-yl)methyl]cyclohexyl]oxy}piperidin-1-yl)-2,3-dihydro-1H-1,3-benzodiazol-1-yl]piperidine-2,6-dione | 791.4 | δ = 13.39 (br s, 1H), 11.06 (br s, 1H), 8.65 (s, 1H), 8.17 (s, 1H), 7.97 (s, 1H), 7.50 (d, J = 9.0 Hz, 1H), 7.37 (s, 1H), 7.09-7.00 (m, 1H), 6.92 (d, J = 8.6 Hz, 1H), 6.83 (d, J = 1.9 Hz, 1H), 6.69-6.56 (m, 1H), 5.45-5.11 (m, 1H), 4.72-4.44 (m, 1H), 3.74-3.62 (m, 4H), 3.60-3.54 (m, 1H), 3.47-3.37 (m, 4H), 3.30 (br s, 3H), 2.83 (br d, J = 11.9 Hz, 2H), 2.75-2.61 (m, 2H), 2.42 (br s, 4H), 2.12 (br d, J = 7.0 Hz, 2H), 2.00-1.86 (m, 5H), 1.81 (br d, J = 12.4 Hz, 2H), 1.61-1.46 (m, 3H), 1.30 (d, J = 6.0 Hz, 6H), 1.22-1.10 (m, 2H), 0.97-0.83 (m, 2H) |
| 56 | rel-3-[2-oxo-3-(propan-2-yl)-5-(4-{[(1r,4r)-4-[(4-{6-[5-(tert-butoxy)-1H-indazol-3-yl]pyrimidin-4-yl}piperazin-1-yl)methyl]cyclohexyl]oxy}piperidin-1-yl)-2,3-dihydro-1H-1,3-benzodiazol-1-yl]piperidine-2,6-dione | 833.5 | δ = 13.46 (s, 1H), 11.05 (s, 1H), 8.65 (s, 1H), 8.17 (s, 1H), 8.09 (d, J = 1.8 Hz, 1H), 7.50 (d, J = 8.8 Hz, 1H), 7.39 (s, 1H), 7.08 (dd, J = 2.1, 8.9 Hz, 1H), 6.96-6.85 (m, 2H), 6.66-6.58 (m, 1H), 5.26 (br dd, J = 5.2, 12.8 Hz, 1H), 4.64-4.51 (m, 1H), 3.67 (br s, 4H), 3.56 (td, J = 4.3, 8.1 Hz, 1H), 3.41 (br s, 3H), 2.94-2.77 (m, 4H), 2.65-2.59 (m, 2H), 2.42 (br s, 4H), 2.13 (br d, J = 6.6 Hz, 2H), 1.99-1.86 (m, 5H), 1.82 (br d, J = 12.0 Hz, 2H), 1.58-1.51 (m, 2H), 1.45 (d, J = 6.8 Hz, 6H), 1.32 (s, 9H), 1.17 (br d, J = 11.4 Hz, 2H), 0.97-0.82 (m, 2H) |
| 57 | rel-3-[2-oxo-3-(propan-2-yl)-5-(4-{[(1r,4r)-4-[(4-{6-[5-(propan-2-yloxy)-1H-indazol-3-yl]pyrimidin-4-yl}piperazin-1-yl)methyl]cyclohexyl]oxy}piperidin-1-yl)-2,3-dihydro-1H-1,3-benzodiazol-1-yl]piperidine-2,6-dione | 819.4 | δ = 8.65 (s, 1H), 7.97 (s, 1H), 7.50 (d, J = 9.0 Hz, 1H), 7.37 (s, 1H), 7.05 (dd, J = 2.3, 8.9 Hz, 1H), 6.97-6.84 (m, 2H), 6.62 (br d, J = 8.6 Hz, 1H), 5.26 (br dd, J = 5.6, 12.2 Hz, 1H), 4.66-4.53 (m, 2H), 3.66 (br s, 4H), 3.60-3.49 (m, 1H), 3.37 (br d, J = 8.0 Hz, 3H), 2.80 (br t, J = 10.3 Hz, 2H), 2.67-2.61 (m, 1H), 2.42 (br s, 4H), 2.12 (br d, J = 7.0 Hz, 2H), 2.00-1.86 (m, 5H), 1.84-1.77 (m, 2H), 1.55 (br d, J = 9.6 Hz, 2H), 1.44 (br d, J = 6.8 Hz, 6H), 1.31 (d, J = 6.0 Hz, 6H), 1.23 (s, 3H), 1.19-1.11 (m, 2H), 0.94-0.83 (m, 2H) |
| 58 | rel-3-[2-oxo-3-(propan-2-yl)-5-(4-{[(1r,4r)-4-[(4-{6-[5-(tert-butoxy)-1H-pyrazolo[3,4-c]pyridin-3-yl]pyrimidin-4-yl}piperazin-1-yl)methyl]cyclohexyl]oxy}piperidin-1-yl)-2,3-dihydro-1H-1,3-benzodiazol-1-yl]piperidine-2,6-dione | 834.4 | δ = 14.65-13.29 (m, 1H), 11.33-10.92 (m, 1H), 8.77 (s, 1H), 8.65 (s, 1H), 7.70 (s, 1H), 7.38 (s, 1H), 6.98-6.80 (m, 2H), 6.62 (br d, J = 8.6 Hz, 1H), 5.33-5.20 (m, 1H), 4.66-4.47 (m, 1H), 3.67 (br s, 4H), 3.56 (br s, 2H), 2.88-2.74 (m, 3H), 2.70-2.52 (m, 4H), 2.41 (br s, 4H), 2.12 (br d, J = 6.5 Hz, 2H), 2.03-1.87 (m, 5H), 1.81 (br d, J = 11.6 Hz, 2H), 1.58-1.39 (m, 17H), 1.23-1.11 (m, 2H), 0.97-0.83 (m, 2H) |
| 59 | rel-3-[2-oxo-3-(propan-2-yl)-5-(4-{[(1r,4r)-4-[(4-{6-[5-(propan-2-yloxy)-1H-pyrazolo[3,4-c]pyridin-3-yl]pyrimidin-4-yl}piperazin-1-yl)methyl]cyclohexyl]oxy}piperidin-1-yl)-2,3-dihydro-1H-1,3-benzodiazol-1-yl]piperidine-2,6-dione | 820.4 | δ = 13.87 (s, 1H), 11.06 (s, 1H), 8.77 (s, 1H), 8.64 (s, 1H), 7.66 (s, 1H), 7.38 (s, 1H), 7.03-6.81 (m, 2H), 6.63 (br d, J = 8.6 Hz, 1H), 5.34-5.12 (m, 2H), 4.66-4.50 (m, 1H), 3.74-3.64 (m, 4H), 3.60-3.54 (m, 1H), 3.45-3.38 (m, 4H), 2.89-2.76 (m, 3H), 2.65-2.57 (m, 2H), 2.42 (br s, 4H), 2.13 (br d, J = 6.8 Hz, 2H), 1.98-1.86 (m, 5H), 1.84-1.77 (m, 2H), 1.60-1.52 (m, 2H), 1.45 (d, J = 6.8 Hz, 6H), 1.31 (d, J = 6.1 Hz, 6H), 1.21-1.12 (m, 2H), 0.98-0.85 (m, 2H) |
| 60 | rel-3-[3-methyl-2-oxo-5-(4-{[(1r,4r)-4-({4-[6-(5-methoxy-1H-indazol-3-yl)pyrimidin-4- | 763.3 | δ = 13.53-13.26 (m, 1H), 11.19-10.90 (m, 1H), 8.72-8.57 (m, 1H), 8.24-8.12 (m, 1H), 8.03-7.85 (m, 1H), 7.60-7.46 (m, 1H), 7.43-7.32 (m, 1H), 7.12-7.02 (m, 1H), 6.97-6.89 (m, 1H), 6.86- |

TABLE 1-continued

| Comp. No. | IUPAC Name | LCMS | $^1H$ NMR (400 MHz, DMSO-$d_6$) |
|---|---|---|---|
| | yl]piperazin-1-yl}methyl)cyclohexyl]oxy}piperidin-1-yl)-2,3-dihydro-1H-1,3-benzodiazol-1-yl]piperidine-2,6-dione | | 6.74 (m, 1H), 6.68-6.50 (m, 1H), 5.35-5.20 (m, 1H), 3.92-3.77 (m, 3H), 3.75-3.60 (m, 4H), 3.60-3.54 (m, 1H), 3.47-3.38 (m, 4H), 3.22-3.12 (m, 1H), 2.97-2.86 (m, 1H), 2.86-2.76 (m, 2H), 2.59 (br s, 3H), 2.45-2.37 (m, 4H), 2.18-2.08 (m, 2H), 2.04-1.85 (m, 5H), 1.85-1.72 (m, 2H), 1.62-1.41 (m, 3H), 1.27-1.09 (m, 2H), 1.02-0.79 (m, 2H) |
| 61 | rel-3-[3-methyl-2-oxo-5-(4-{[(1r,4r)-4-({4-[6-(5-ethoxy-1H-indazol-3-yl)pyrimidin-4-yl]piperazin-1-yl}methyl)cyclohexyl]oxy}piperidin-1-yl)-2,3-dihydro-1H-1,3-benzodiazol-1-yl]piperidine-2,6-dione | 777.4 | δ = 13.51-13.28 (m, 1H), 11.12-10.87 (m, 1H), 8.70-8.54 (m, 1H), 8.20-8.17 (m, 0.11H), 8.00-7.85 (m, 1H), 7.55-7.44 (m, 1H), 7.41-7.30 (m, 1H), 7.10-6.98 (m, 1H), 6.95-6.87 (m, 1H), 6.86-6.76 (m, 1H), 6.69-6.51 (m, 1H), 5.34-5.22 (m, 1H), 4.12-3.98 (m, 2H), 3.77-3.59 (m, 4H), 3.58-3.53 (m, 1H), 3.48-3.44 (m, 1H), 3.42-3.40 (m, 2H), 3.30-3.29 (m, 3H), 2.95-2.76 (m, 3H), 2.70-2.58 (m, 2H), 2.44-2.39 (m, 4H), 2.18-2.05 (m, 2H), 2.05-1.84 (m, 5H), 1.84-1.69 (m, 2H), 1.63-1.42 (m, 3H), 1.42-1.31 (m, 3H), 1.26-1.04 (m, 2H), 1.00-0.78 (m, 2H) |
| 62 | rel-1-{3-[6-(4-{[(1r,4r)-4-({1-[1-(2,6-dioxopiperidin-3-yl)-3-methyl-2-oxo-2,3-dihydro-1H-1,3-benzodiazol-5-yl]piperidin-4-yl}oxy)cyclohexyl]methyl}piperazin-1-yl)pyrimidin-4-yl]-1H-indazol-5-yl}cyclobutane-1-carbonitrile | 812.4 | δ = 13.76-13.56 (m, 1H), 11.16-10.94 (m, 1H), 8.71-8.64 (m, 1H), 8.60-8.55 (m, 1H), 8.24-8.17 (m, 1H), 7.74-7.64 (m, 1H), 7.54-7.45 (m, 1H), 7.44-7.35 (m, 1H), 6.98-6.88 (m, 1H), 6.86-6.78 (m, 1H), 6.68-6.56 (m, 1H), 5.36-5.22 (m, 1H), 3.75-3.65 (m, 4H), 3.62-3.56 (m, 1H), 3.46-3.42 (m, 2H), 3.29-3.26 (m, 3H), 2.90-2.76 (m, 5H), 2.74-2.62 (m, 4H), 2.45-2.39 (m, 4H), 2.27 (br s, 2H), 2.16-2.10 (m, 2H), 2.07-1.86 (m, 6H), 1.85-1.76 (m, 2H), 1.62-1.43 (m, 3H), 1.24-1.08 (m, 2H), 0.97-0.82 (m, 2H) |
| 63 | rel-1-{3-[6-(4-{[(1r,4r)-4-({1-[1-(2,6-dioxopiperidin-3-yl)-3-methyl-2-oxo-2,3-dihydro-1H-1,3-benzodiazol-5-yl]piperidin-4-yl}oxy)cyclohexyl]methyl}piperazin-1-yl)pyrimidin-4-yl]-1H-indazol-5-yl}cyclopropane-1-carbonitrile | 798.5 | δ = 13.62 (br s, 1H), 11.05 (s, 1H), 8.69 (s, 1H), 8.61 (d, J = 1.1 Hz, 1H), 8.15 (s, 1H), 7.63 (d, J = 8.9 Hz, 1H), 7.41 (s, 1H), 7.36 (dd, J = 1.9, 8.8 Hz, 1H), 6.92 (d, J = 8.6 Hz, 1H), 6.83 (d, J = 2.0 Hz, 1H), 6.63 (dd, J = 1.9, 8.7 Hz, 1H), 5.28 (dd, J = 5.3, 12.8 Hz, 1H), 3.68 (br s, 4H), 3.56 (br d, J = 4.0 Hz, 2H), 3.43-3.41 (m, 2H), 3.30 (br s, 3H), 2.91-2.78 (m, 3H), 2.71-2.60 (m, 2H), 2.42 (br s, 4H), 2.13 (br d, J = 6.9 Hz, 2H), 2.02-1.86 (m, 5H), 1.85-1.74 (m, 4H), 1.61-1.43 (m, 5H), 1.17 (br d, J = 13.5 Hz, 2H), 0.98-0.85 (m, 2H) |
| 64 | rel-5-{3-[6-(4-{[(1r,4r)-4-({1-[1-(2,6-dioxopiperidin-3-yl)-3-methyl-2-oxo-2,3-dihydro-1H-1,3-benzodiazol-5-yl]piperidin-4-yl}oxy)cyclohexyl]methyl}piperazin-1-yl)pyrimidin-4-yl]-1H-indazol-5-yl}spiro[2.3]hexane-5-carbonitrile | 838.4 | δ = 13.78-13.53 (m, 1H), 11.13-10.86 (m, 1H), 8.78-8.59 (m, 2H), 7.76-7.63 (m, 1H), 7.61-7.52 (m, 1H), 7.49-7.32 (m, 1H), 6.98-6.87 (m, 1H), 6.86-6.77 (m, 1H), 6.68-6.56 (m, 1H), 5.35-5.19 (m, 1H), 3.58 (br s, 4H), 3.58-3.49 (m, 1H), 3.46-3.38 (m, 2H), 3.37-3.33 (m, 1H), 3.30 (s, 3H), 2.97-2.92 (m, 2H), 2.91-2.85 (m, 2H), 2.85-2.74 (m, 3H), 2.70-2.57 (m, 2H), 2.47-2.31 (m, 4H), 2.19-2.03 (m, 2H), 2.01-1.86 (m, 5H), 1.81 (br d, J = 11.9 Hz, 2H), 1.60-1.43 (m, 3H), 1.22-1.06 (m, 2H), 1.00-0.81 (m, 2H), 0.79-0.65 (m, 2H), 0.63-0.47 (m, 2H) |
| 65 | (1R**)-1-{3-[6-(4-{[(1r*,4r*)-4-({1-[1-(2,6-dioxopiperidin-3-yl)-3-methyl-2-oxo-2,3-dihydro-1H-1,3-benzodiazol-5-yl]piperidin-4-yl}oxy)cyclohexyl]methyl}piperazin-1-yl)pyrimidin-4-yl]-1H-indazol-5-yl}spiro[2.2]pentane-1-carbonitrile | 824.4 | δ = 13.61 (br s, 1H), 11.05 (s, 1H), 8.78-8.53 (m, 2H), 8.17 (s, 1H), 7.64 (d, J = 8.9 Hz, 1H), 7.41 (s, 1H), 7.32-7.21 (m, 1H), 6.93 (d, J = 8.5 Hz, 1H), 6.83 (d, J = 2.0 Hz, 1H), 6.67-6.47 (m, 1H), 5.39-5.19 (m, 1H), 3.68 (br s, 4H), 3.62-3.52 (m, 3H), 3.48-3.43 (m, 4H), 2.95-2.88 (m, 1H), 2.85-2.78 (m, 2H), 2.74-2.61 (m, 2H), 2.43 (br s, 4H), 2.28 (d, J = 5.0 Hz, 1H), 2.13 (br d, J = 6.8 Hz, 2H), 2.04-1.87 (m, 6H), 1.82 (br d, J = 12.1 Hz, 2H), 1.63-1.43 (m, 3H), 1.27-1.11 (m, 5H), 1.01-0.85 (m, 3H) |
| 66 | (1R**)-1-{3-[6-(4-{[(1r*,4r*)-4-({1-[1-(2,6-dioxopiperidin-3-yl)-3-methyl-2-oxo-2,3-dihydro-1H-1,3-benzodiazol-5-yl]piperidin-4-yl}oxy)cyclohexyl]methyl}piperazin-1-yl)pyrimidin-4-yl]-1H-indazol-5-yl}spiro[2.2]pentane-1-carbonitrile | 824.4 | δ = 13.60 (s, 1H), 11.04 (s, 1H), 8.73-8.53 (m, 2H), 8.12 (s, 1H), 7.62 (d, J = 8.8 Hz, 1H), 7.41 (s, 1H), 7.29-7.19 (m, 1H), 6.91 (d, J = 8.5 Hz, 1H), 6.82 (d, J = 2.0 Hz, 1H), 6.65-6.58 (m, 1H), 5.33-5.19 (m, 1H), 3.76-3.48 (m, 5H), 3.46-3.33 (m, 4H), 3.22 (br s, 2H), 2.93-2.75 (m, 3H), 2.70-2.60 (m, 2H), 2.36 (br s, 4H), 2.27 (d, J = 5.1 Hz, 1H), 2.22-2.08 (m, 2H), 2.02-1.86 (m, 6H), 1.81 (br d, J = 12.6 Hz, 2H), 1.61-1.40 (m, 3H), 1.24-1.10 (m, 5H), 1.00-0.82 (m, 3H) |

TABLE 1-continued

| Comp. No. | IUPAC Name | LCMS | $^1$H NMR (400 MHz, DMSO-$d_6$) |
|---|---|---|---|
| 67 | rel-3-[6-bromo-3-methyl-2-oxo-5-(4-{[(1r,4r)-4-[(4-{6-[5-(1-methylcyclopropoxy)-1H-pyrazolo[3,4-c]pyridin-3-yl]pyrimidin-4-yl}piperazin-1-yl)methyl]cyclohexyl]oxy}piperidin-1-yl)-2,3-dihydro-1H-1,3-benzodiazol-1-yl]piperidine-2,6-dione | 884.3 | δ = 13.89 (br s, 1H), 11.06 (s, 1H), 8.78 (s, 1H), 8.65 (s, 1H), 7.80 (s, 1H), 7.48-7.34 (m, 2H), 7.08 (s, 1H), 5.42-5.24 (m, 1H), 3.79-3.48 (m, 5H), 3.39-3.32 (m, 4H), 3.13-3.05 (m, 2H), 2.91-2.81 (m, 1H), 2.79-2.72 (m, 2H), 2.68-2.56 (m, 2H), 2.42 (br s, 4H), 2.13 (br d, J = 6.5 Hz, 2H), 2.00-1.88 (m, 5H), 1.82 (br d, J = 11.6 Hz, 2H), 1.68-1.57 (m, 5H), 1.54-1.42 (m, 1H), 1.27-1.09 (m, 2H), 1.01-0.87 (m, 4H), 0.82-0.68 (m, 2H) |
| 68 | 3-[3-methyl-2-oxo-5-(4-{[(1s,4s)-4-[(4-{6-[5-(1-methylcyclopropoxy)-1H-pyrazolo[3,4-c]pyridin-3-yl]pyrimidin-4-yl}piperazin-1-yl)methyl]cyclohexyl]oxy}piperidin-1-yl)-2,3-dihydro-1H-1,3-benzodiazol-1-yl]piperidine-2,6-dione | 804.6 | δ = 13.91 (br t, J = 12.0 Hz, 1H), 11.27-10.92 (m, 1H), 8.79 (d, J = 0.8 Hz, 1H), 8.64 (d, J = 0.8 Hz, 1H), 7.79 (s, 1H), 7.38 (s, 1H), 6.92 (d, J = 8.4 Hz, 1H), 6.83 (d, J = 2.0 Hz, 1H), 6.63 (dd, J = 2.0, 8.4 Hz, 1H), 5.28 (br dd, J = 5.2, 12.4 Hz, 1H), 3.67 (br s, 5H), 3.56-3.47 (m, 1H), 3.46-3.38 (m, 2H), 3.30 (s, 3H), 2.95-2.79 (m, 3H), 2.71-2.56 (m, 2H), 2.43 (br s, 4H), 2.23-2.12 (m, 2H), 2.03-1.95 (m, 1H), 1.89 (br d, J = 10.4 Hz, 2H), 1.70 (br dd, J = 3.2, 8.4 Hz, 2H), 1.61 (s, 3H), 1.60-1.38 (m, 7H), 1.36-1.20 (m, 2H), 0.98-0.89 (m, 2H), 0.80-0.72 (m, 2H) |
| 69 | 3-{4-[4-({3,3-dimethyl-4-[(1-{6-[5-(1-methylcyclopropoxy)-1H-indazol-3-yl]pyrimidin-4-yl}piperidin-4-yl)methyl]piperazin-1-yl}methyl)piperidin-1-yl]-1H-1,3-benzodiazol-1-yl}piperidine-2,6-dione | 800.6 | δ = 13.38 (s, 1H), 11.17 (s, 1H), 8.64 (s, 1H), 8.15 (d, J = 2.0 Hz, 1H), 8.13 (s, 1H), 8.11 (s, 1H), 7.51 (d, J = 5.2 Hz, 1H), 7.43-7.35 (m, 1H), 7.12-7.03 (m, 2H), 6.98 (d, J = 8.0 Hz, 1H), 6.59-6.48 (m, 1H), 5.71-5.49 (m, 1H), 4.61-4.37 (m, 2H), 4.37-4.17 (m, 2H), 3.30 (br s, 4H), 3.06-2.84 (m, 5H), 2.81-2.69 (m, 5H), 2.25-2.14 (m, 4H), 1.89-1.63 (m, 6H), 1.54 (s, 3H), 1.41-1.22 (m, 6H), 1.17-0.99 (m, 4H), 0.96-0.93 (m, 2H), 0.79-0.75 (m, 2H) |
| 70 | 3-{4-[4-({4-[(1-{6-[5-(1-methylcyclopropoxy)-1H-indazol-3-yl]pyrimidin-4-yl}piperidin-4-yl)methyl]piperazin-1-yl}methyl)piperidin-1-yl]-1H-1,3-benzodiazol-1-yl}piperidine-2,6-dione | 772.6 | δ = 13.37 (s, 1H), 11.17 (s, 1H), 8.63 (s, 1H), 8.15 (s, 1H), 8.13 (s, 1H), 8.12 (s, 1H), 7.51 (d, J = 9.2 Hz, 1H), 7.38 (s, 1H), 7.14-7.03 (m, 2H), 7.01-6.92 (m, 1H), 6.60-6.48 (m, 1H), 5.62 (dd, J = 5.2, 12.8 Hz, 1H), 4.57-4.36 (m, 2H), 4.34-4.23 (m, 2H), 3.20-2.84 (m, 7H), 2.83-2.69 (m, 6H), 2.30-2.12 (m, 5H), 1.83 (br d, J = 12.0 Hz, 8H), 1.54 (s, 3H), 1.43-1.29 (m, 2H), 1.21-1.06 (m, 2H), 0.97-0.91 (m, 2H), 0.80-0.75 (m, 2H) |

Biological Assays

Exemplary Assay for Testing LRRK2 Degradation Driven by Exemplary Hetero-Bifunctional Compounds Designed to Target LRRK2

The assay measures the degradation of LRRK2 in cells where the C-terminus (3') of the endogenous gene has been tagged with a HiBit sequence in HEK293 cells. The cells also express firefly lucisferase, expressed from a Cytomegalovirus promoter and introduced into the HiBit tagged cells and stably expressed. The Nano-Glo® Dual Luciferase Reporter Assay System (Promega™, Madison, WI) was utilized.

Day 1—Preparation of Compound and Assay Plates. Two sets of plates were prepared: a triplicate set for the HiBit assay in white 384-well plates and a triplicate set of plate in black 384-well plates for the Alamar Blue cell viability assay. Briefly, the growth media (DMEM+Glutamax-10% fetal bovine serum-1% Penicillin-Streptomicin) from two T128 flasks was aspirated from the flasks. Cells were washed with Dulbecco's Phosphate Buffered Saline (dPBS) and aspirated. Trypsin (3 mL per flask) was added and the flasks were incubated for 2-3 minutes.

Ten mL of OptiMEM—10% fetal bovine-1% penicillin-streptomycin (hereinafter, "OptiMEM media") was added to the flask and the cells and transferred to a 50 ml conical tube. A cell count (25 ul of cell into Effendorf vial+25 ul of Trypan Blue Stain) was performed and the cell density adjusted to 15,000 cell/45 μl/well (3.33×10^5/mL) in OptiMEM media.

Forty-five microliters of the cell suspension (15,000 cells) was aliquoted to each well of the white 384-well plate. The plates incubated at room temperature for 10 minutes before being placed in the 37° C.+5% $CO_2$ incubator overnight Day 2—Compound Treatment. Exemplary compounds were prepared at a 1 mM starting concentration and 1:3 serial dilution for 11 points CRC prepared and stored in the freezer. The Master Compound Plate was thawed overnight at room temperature. DMSO (20 μL) was added into column 24 of the Master Compound Plate for negative control and 20 μL of 300 μM of Compound 4 in column 23 as positive control.

Intermediate Compound Plate with 4% DMSO in OptiMEM Media. DMSO was added to warm OptiMEM media to achieve a 4% DMSO solution (approximately 50 mL/plate). One-hundred microliters of the OptiMEM-4% DMSO was aliquoted to each well of 384-Well Deep Well Microplates.

The Master Compound Plate and the Intermediate Compound Plate were spun down.

One microliter of compound from the Master Compound Plate was transferred into the Intermediate plate (a 1:100 dilution). The diluted mixture was mixed and 5 μL transferred into the assay plate (a 1:10 dilution) for the final starting concentration of 1 μM. The Treated Assay plates were incubated for 24 hours at 37° C.+5% $CO_2$. The Master Compound Plate was sealed and store at room temperature for a second run that was performed within a week.

Day 3—HiBit Assay. Five microliters of Alamar Blue was added to each well of the black 384-well plates. The plates were incubated for 2 hours in the incubator (37° C.+5% $CO_2$) and at room temperature for one hour. Fluorescence of each plate was read on a plated reader for the Alamar Blue viability assay.

One set of white assay plates was warmed to room temperature (45 minute).

The One Glo luciferase mixture was prepared. The media from white 384-well assay plates was aspirated. Twenty-five μL of the One Glo luciferase mixture was added to each well of the assay plates. The plates were incubated on the bench (room temperature) for 45 minutes, including 10 minutes of shaking at 700 rpm. The luminescence of each plate was read on a plate reader.

1:100 DLR substrate and 1:100 LgBiT Protein dilution were added to the Promega Stop and Glo buffer and mixed just before addition to assay plates. Twenty-five microliters of Stop and Glo mixture was added to each well. Assay plates incubated for at least 45 minutes, including 10 minutes of shaking at 700 rpm. The luminescence of each plate was read on a plate reader.

Analysis of LRRK2 HiBit Screening assays. As mentioned above, plates were run in triplicate and the assay repeated twice (total of 6 replicate for exemplary compounds). For each treatment, measurements were taken for firefly luciferase for cell number, cell viability (Alamar Blue), and Nanoluc for the LRRK2-HiBit quantification.

The LRRK2 HiBit and alamar blue signal was normalized to % DMSO median value for each plate. Curve fitting was performed on each compound for replicates across three plates.

Data for compounds disclosed herein is provided in Table 2.

TABLE 2

| Compound No. | WT LRRK2 *$DC_{50}$ (nM) | WT LRRK2 **Dmax (%) |
|---|---|---|
| 1 | 0.14 | 53 |
| 2 | 0.18 | 55 |
| 3 | 28 | 30 |
| 4 | 7.5 | 62 |
| 5 | 1000 | NT |
| 6 | 0.17 | 58 |
| 7 | 6.4 | 64 |
| 8 | 1.2 | 65 |
| 9 | 1.2 | 66 |
| 10 | 4.5 | 69 |
| 11 | 1.6 | 62 |
| 12 | 0.17 | 64 |
| 13 | 1 | 64 |
| 14 | 0.22 | 58 |
| 15 | 1.5 | 59 |
| 16 | 1000 | ***nd |
| 17 | 1000 | ***nd |
| 18 | 3.9 | 74 |
| 19 | 28 | 76 |
| 20 | 0.56 | 40 |
| 21 | 1000 | ***nd |
| 22 | 0.14 | 46 |
| 23 | 0.56 | 45 |
| 24 | 0.46 | 49 |
| 25 | 0.32 | 48 |
| 26 | 1.1 | 69 |
| 27 | 0.25 | 57 |
| 28 | 17 | 60 |
| 29 | 0.16 | 54 |
| 30 | 0.065 | 48 |
| 31 | 160 | 61 |
| 32 | 0.33 | 51 |
| 33 | 0.14 | 62 |
| 34 | 0.42 | 57 |
| 35 | 0.052 | 50 |
| 36 | 0.079 | 60 |
| 37 | 0.053 | 64 |
| 38 | 1.2 | 53 |
| 39 | 4.9 | 56 |
| 40 | 4.2 | 59 |
| 41 | 3.7 | 49 |
| 42 | 5.2 | 42 |
| 43 | 6.2 | 49 |
| 44 | 6.3 | 50 |
| 45 | 3.9 | 56 |
| 46 | 2.1 | 90 |
| 47 | 24 | 100 |
| 48 | 0.14 | 56 |
| 49 | 0.44 | 55 |
| 50 | 0.48 | 43 |
| 51 | 1.1 | 64 |
| 52 | 0.28 | 53 |
| 53 | 0.59 | 54 |
| 54 | 0.33 | 53 |
| 55 | 1.5 | 53 |
| 56 | 0.95 | 43 |
| 57 | 0.64 | 51 |
| 58 | 33 | 70 |
| 59 | 0.74 | 41 |
| 60 | 0.67 | 38 |
| 61 | 0.51 | 48 |
| 62 | 0.3 | 54 |
| 63 | 0.13 | 56 |
| 64 | 0.16 | 63 |
| 65 | 0.13 | 64 |
| 66 | 0.14 | 61 |
| 67 | 5.9 | 90 |
| 68 | 1.2 | 35 |
| 69 | 5 | 50 |
| 70 | 20 | 33 |

NT = Not Tested

As shown below in Table 3, certain compounds comprising a 3-(3-methyl-2-oxo-2,3-dihydro-1H-benzo[d]imidazol-1-yl)piperidine-2,6-dione group attached to variable (L), in the described compounds had improved activity over the following direct comparators, in particular those bearing a 3-(4-methoxy-1-oxoisoindolin-2-yl)piperidine-2,6-dione group. For example, Compound 1 showed over a 40-fold increase in WT LRRK2 $DC_{50}$ activity when compared to Comparator Example 1, which comprises a 3-(4-methoxy-1-oxoisoindolin-2-yl)piperidine-2,6-dione group attached to variable (L) n. Compounds 6, 12, 14, and 48 when compared to Comparator Examples 2, 4, 5, and 6, respectively, all showed a similar trend. These data, along with the additional data presented in Table 3 evidence activity improvements arising from the use of the 3-(3-methyl-2-oxo-2,3-dihydro-1H-benzo[d]imidazol-1-yl)piperidine-2,6-dione group.

TABLE 3
| Compound | WT LRRK2 *$DC_{50}$ (nM) | WT LRRK2 **Dmax (%) |
|---|---|---|
| 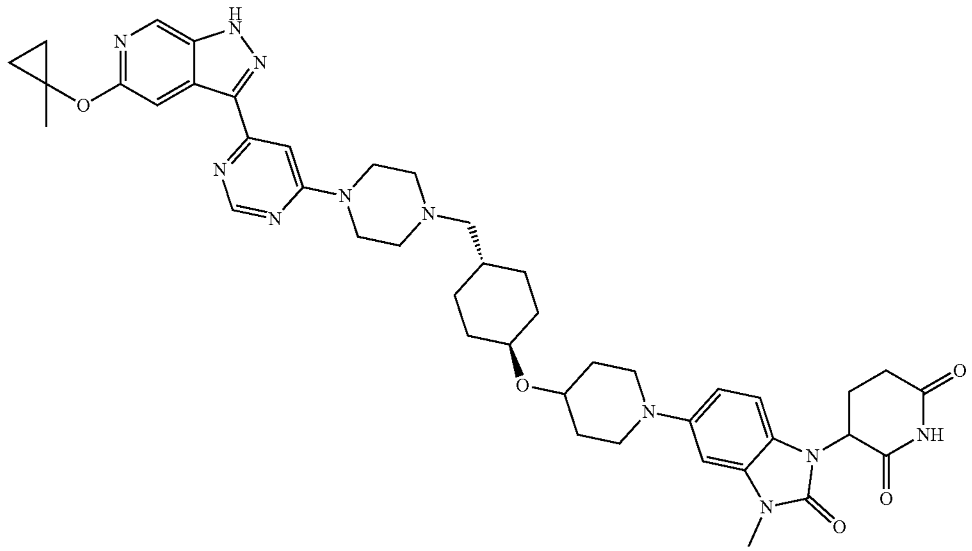 [SMILES: Cn1c(=O)n(C2CCC(=O)NC2=O)c2ccc(N3CCC(O[C@H]4CC[C@H](CN5CCN(c6cc(-c7n[nH]c8cnc(OC9(C)CC9)cc78)ncn6)CC5)CC4)CC3)cc21] Compound No. 1 | 0.14 | 53 |
| 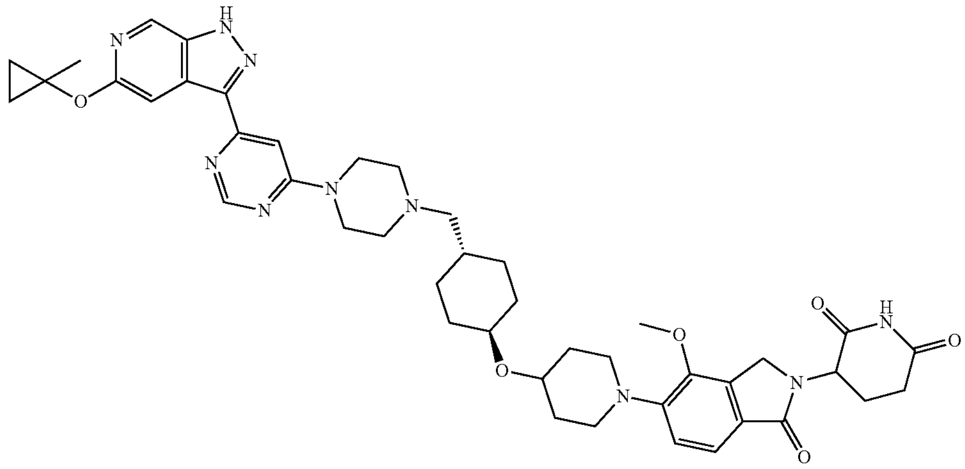 [SMILES: COc1c(N2CCC(O[C@H]3CC[C@H](CN4CCN(c5cc(-c6n[nH]c7cnc(OC8(C)CC8)cc67)ncn5)CC4)CC3)CC2)ccc2c1CN(C1CCC(=O)NC1=O)C2=O] Comparative Example 1 | 5.6 | 52 |

TABLE 3-continued
| Compound | WT LRRK2 *$DC_{50}$ (nM) | WT LRRK2 **Dmax (%) |
| --- | --- | --- |
| 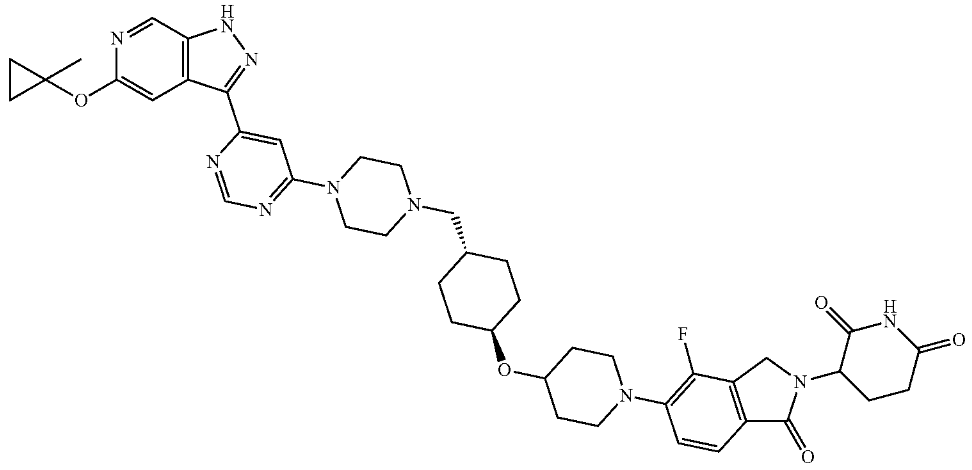 [SMILES: CC1(Oc2cc3c(-c4cc(N5CCN(C[C@H]6CC[C@H](OC7CCN(c8ccc9c(c8F)CN(C8CCC(=O)NC8=O)C9=O)CC7)CC6)CC5)ncn4)n[nH]c3cn2)CC1] Comparative Example 3 | 4.3 | 65 |
| 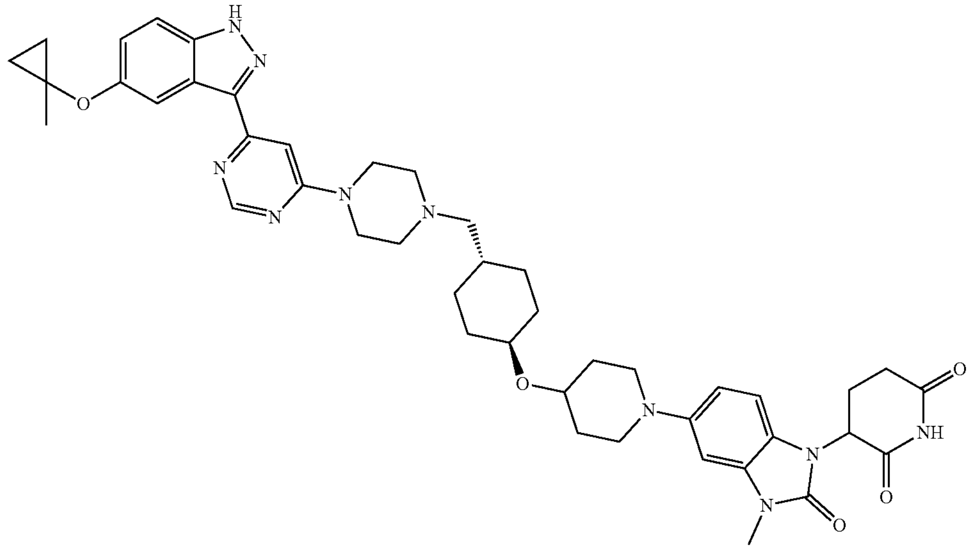 [SMILES: Cn1c(=O)n(C2CCC(=O)NC2=O)c2ccc(N3CCC(O[C@H]4CC[C@H](CN5CCN(c6cc(-c7n[nH]c8ccc(OC9(C)CC9)cc78)ncn6)CC5)CC4)CC3)cc21] Compound No. 6 | 0.17 | 58 |

TABLE 3-continued
| Compound | WT LRRK2 *$DC_{50}$ (nM) | WT LRRK2 **Dmax (%) |
|---|---|---|
| 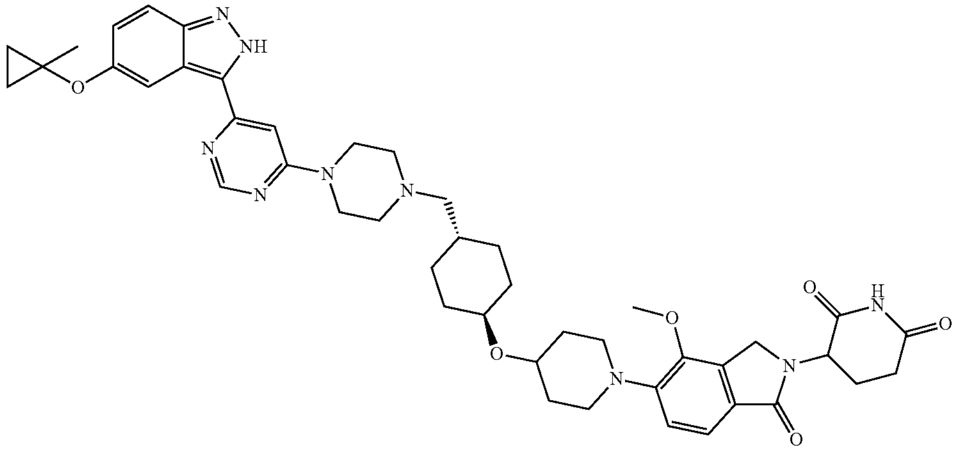 [SMILES: COc1c(N2CCC(O[C@H]3CC[C@H](CN4CCN(c5cc(-c6[nH]nc7ccc(OC8(C)CC8)cc67)ncn5)CC4)CC3)CC2)ccc2c1CN(C1CCC(=O)NC1=O)C2=O] Comparative Example 2 | 3 | 62 |
| 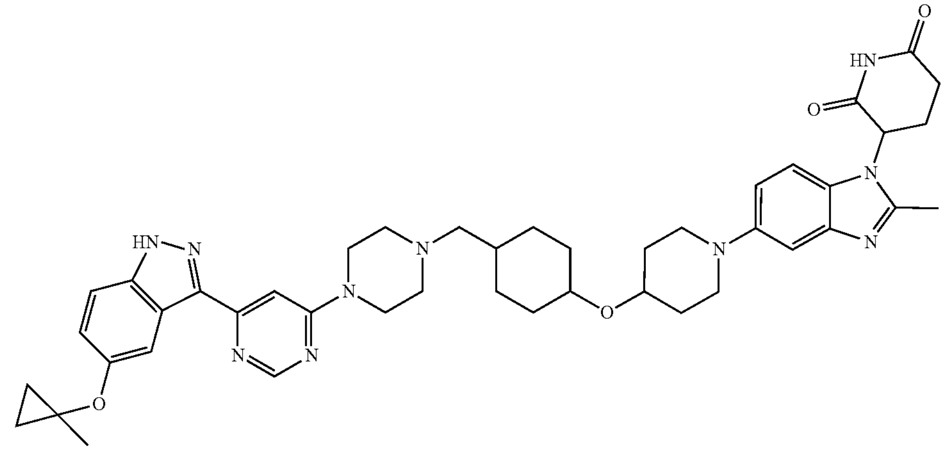 [SMILES: Cc1nc2cc(N3CCC(OC4CCC(CN5CCN(c6cc(-c7n[nH]c8ccc(OC9(C)CC9)cc78)ncn6)CC5)CC4)CC3)ccc2n1C1CCC(=O)NC1=O] Compound No. 42 | 5.2 | 52 |
| 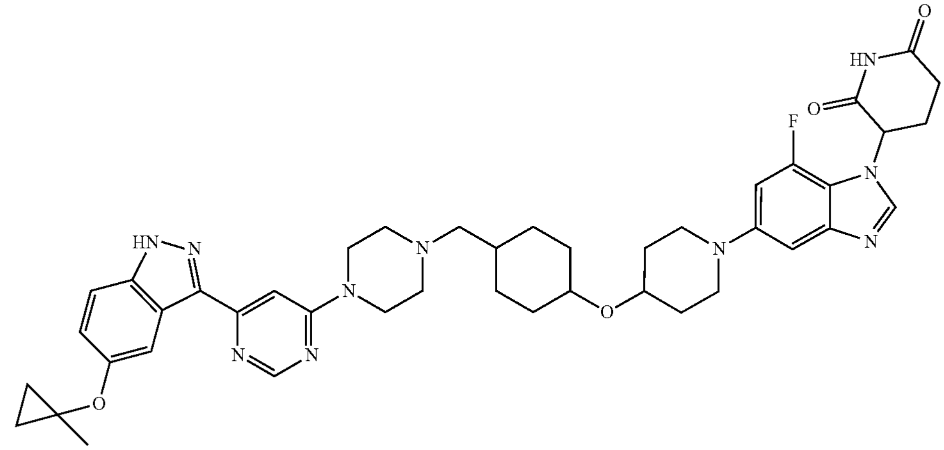 [SMILES: CC1(Oc2ccc3[nH]nc(-c4cc(N5CCN(CC6CCC(OC7CCN(c8cc(F)c9c(c8)ncn9C8CCC(=O)NC8=O)CC7)CC6)CC5)ncn4)c3c2)CC1] Compound No. 43 | 6.2 | 49 |

TABLE 3-continued
| Compound | WT LRRK2 *$DC_{50}$ (nM) | WT LRRK2 **Dmax (%) |
|---|---|---|
| 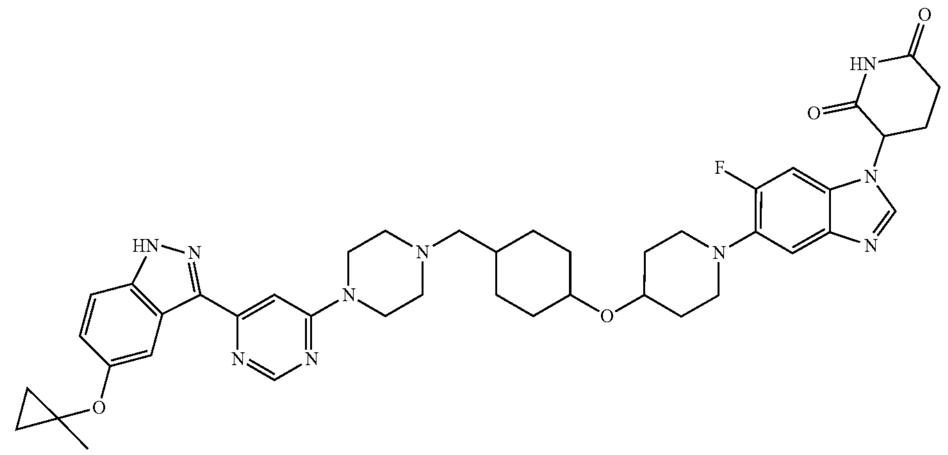 [SMILES: CC1(Oc2ccc3[nH]nc(-c4cc(N5CCN(CC6CCC(OC7CCN(c8cc9ncn(C%10CCC(=O)NC%10=O)c9cc8F)CC7)CC6)CC5)ncn4)c3c2)CC1] Compound No. 44 | 6.3 | 50 |
| 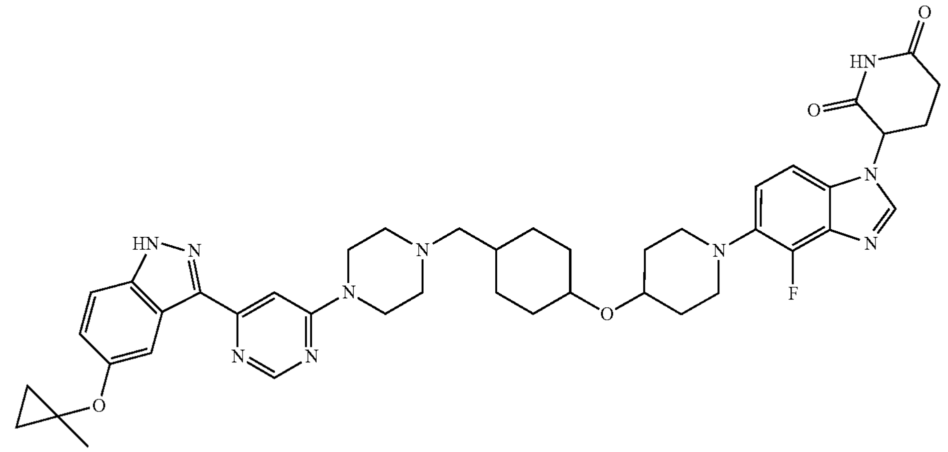 [SMILES: CC1(Oc2ccc3[nH]nc(-c4cc(N5CCN(CC6CCC(OC7CCN(c8ccc9c(ncn9C9CCC(=O)NC9=O)c8F)CC7)CC6)CC5)ncn4)c3c2)CC1] Compound No. 45 | 3.9 | 56 |
| 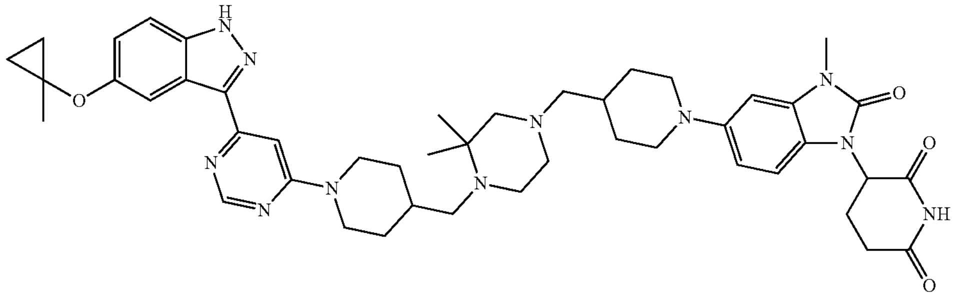 [SMILES: Cn1c(=O)n(C2CCC(=O)NC2=O)c2ccc(N3CCC(CN4CCN(CC5CCN(c6cc(-c7n[nH]c8ccc(OC9(C)CC9)cc78)ncn6)CC5)C(C)(C)C4)CC3)cc21] Compound No. 14 | 0.22 | 58 |

TABLE 3-continued
| Compound | WT LRRK2 *$DC_{50}$ (nM) | WT LRRK2 **Dmax (%) |
|---|---|---|
| 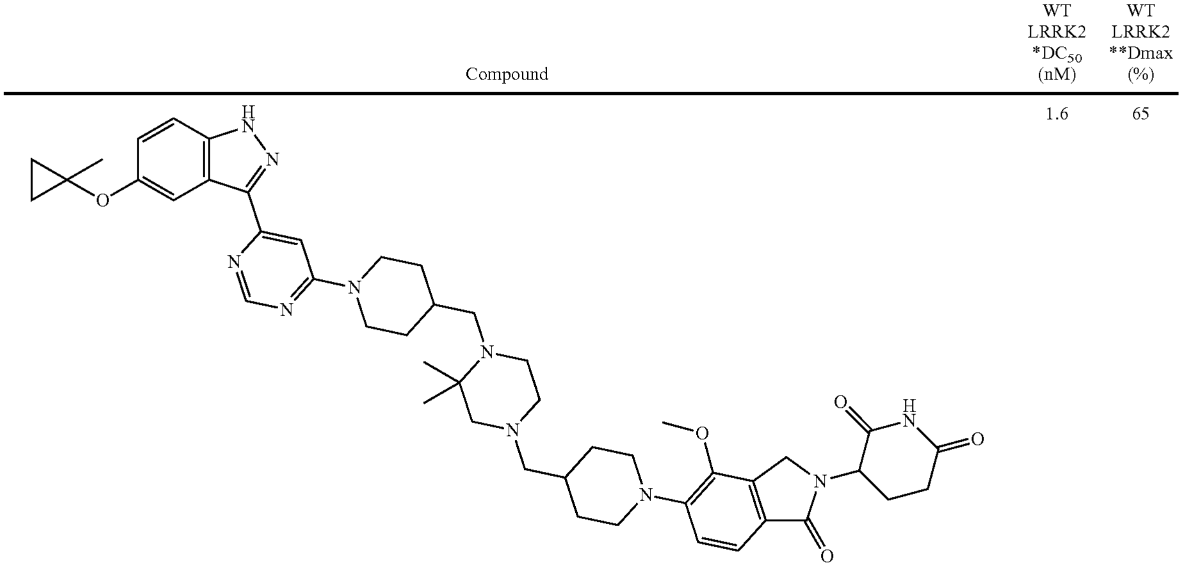 Comparative Example 5 | 1.6 | 65 |
| 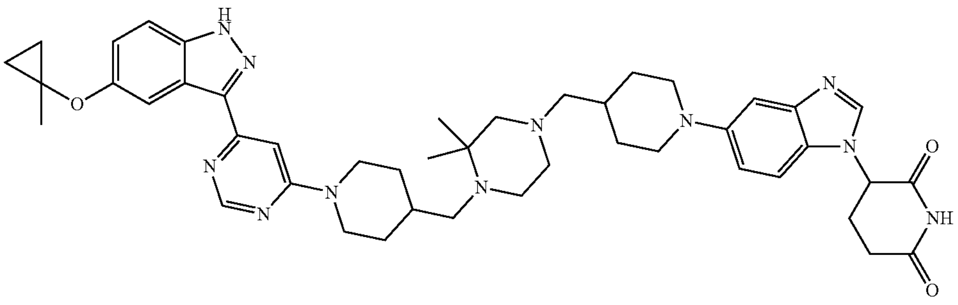 [SMILES: CC1(Oc2ccc3[nH]nc(-c4cc(N5CCC(CN6CCN(CC7CCN(c8ccc9c(c8)ncn9C8CCC(=O)NC8=O)CC7)CC6(C)C)CC5)ncn4)c3c2)CC1] Compound No. 13 | 1 | 64 |
| 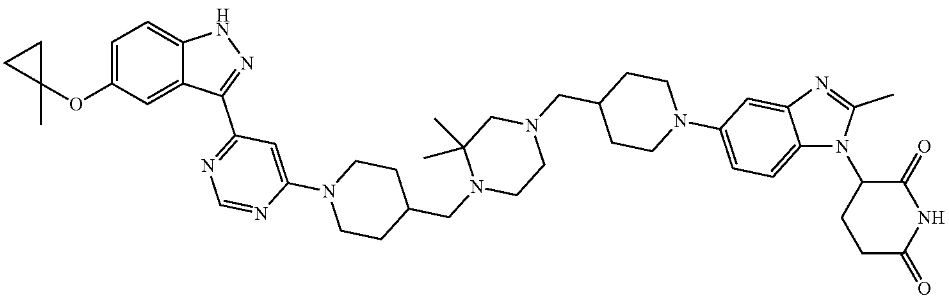 [SMILES: Cc1nc2cc(N3CCC(CN4CCN(CC5CCN(c6cc(-c7n[nH]c8ccc(OC9(C)CC9)cc78)ncn6)CC5)C(C)(C)C4)CC3)ccc2n1C1CCC(=O)NC1=O] Compound No. 38 | 1.2 | 53 |
| 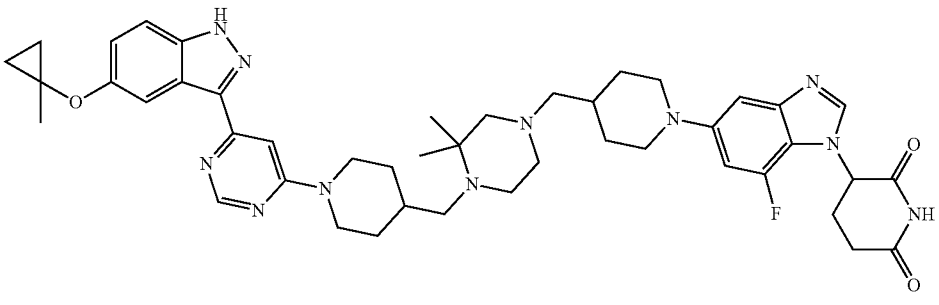 Compound No. 39 | 4.9 | 56 |

TABLE 3-continued
| Compound | WT LRRK2 *$DC_{50}$ (nM) | WT LRRK2 **Dmax (%) |
|---|---|---|
| 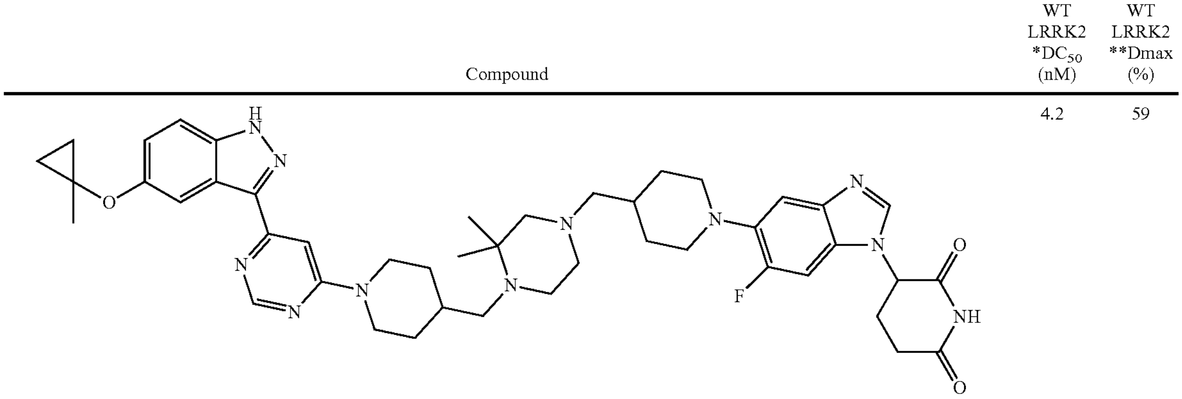 Compound No. 40 | 4.2 | 59 |
| 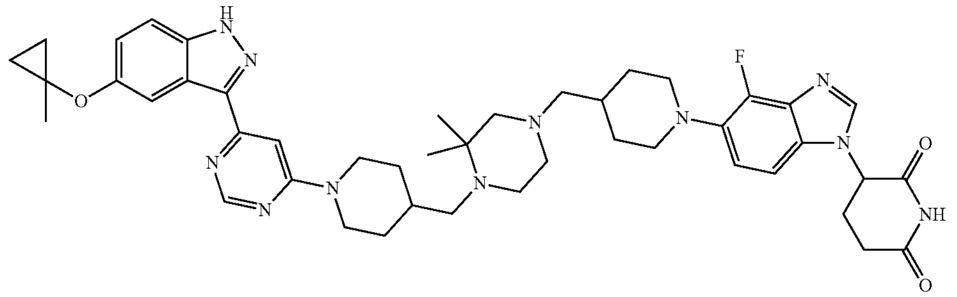 [SMILES: CC1(Oc2ccc3[nH]nc(-c4cc(N5CCC(CN6CCN(CC7CCN(c8ccc9c(ncn9C9CCC(=O)NC9=O)c8F)CC7)CC6(C)C)CC5)ncn4)c3c2)CC1] Compound No. 41 | 3.7 | 49 |
| 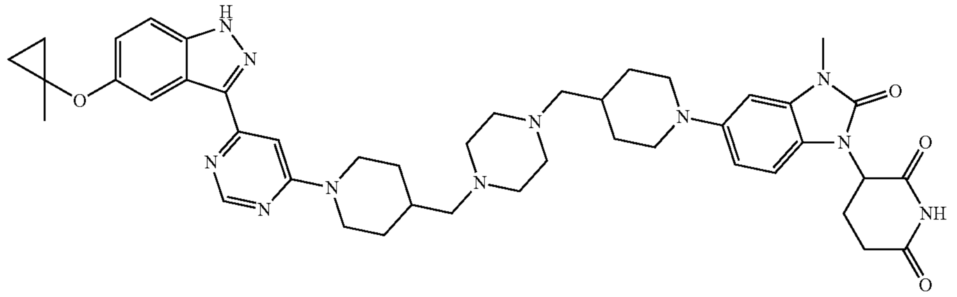 [SMILES: Cn1c(=O)n(C2CCC(=O)NC2=O)c2ccc(N3CCC(CN4CCN(CC5CCN(c6cc(-c7n[nH]c8ccc(OC9(C)CC9)cc78)ncn6)CC5)CC4)CC3)cc21] Compound No. 12 | 0.17 | 64 |
| 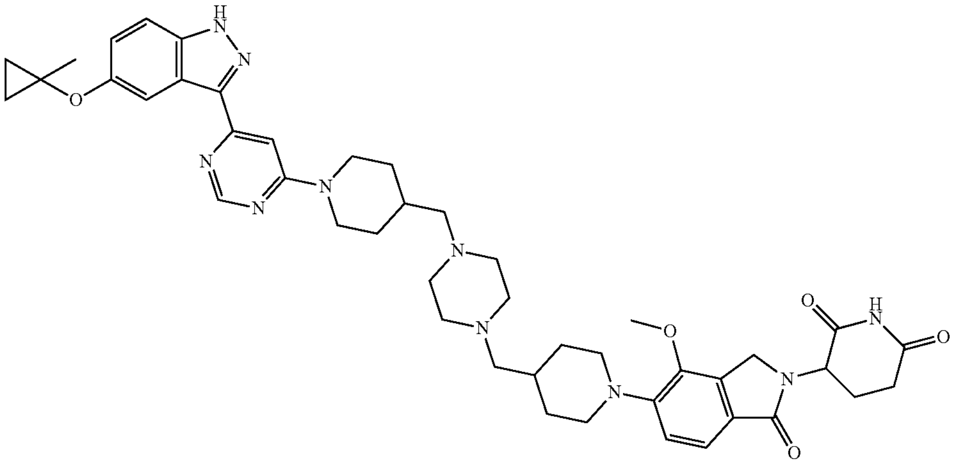 [SMILES: COc1c(N2CCC(CN3CCN(CC4CCN(c5cc(-c6n[nH]c7ccc(OC8(C)CC8)cc67)ncn5)CC4)CC3)CC2)ccc2c1CN(C1CCC(=O)NC1=O)C2=O] Comparative Example 4 | 0.79 | 80 |

TABLE 3-continued
| Compound | WT LRRK2 *$DC_{50}$ (nM) | WT LRRK2 **Dmax (%) |
|---|---|---|
| 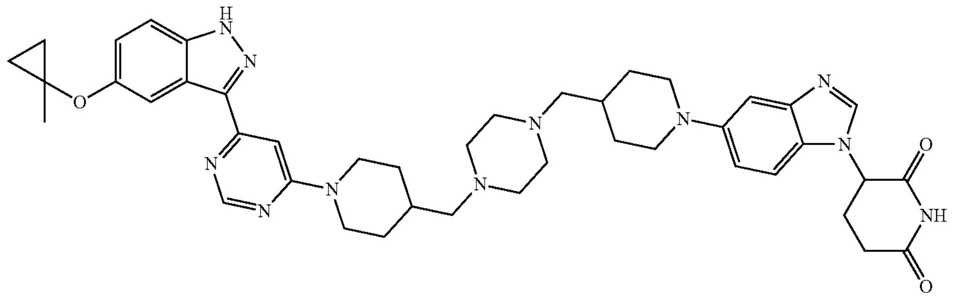 [SMILES: CC1(Oc2ccc3[nH]nc(-c4cc(N5CCC(CN6CCN(CC7CCN(c8ccc9c(c8)ncn9C8CCC(=O)NC8=O)CC7)CC6)CC5)ncn4)c3c2)CC1] Compound No. 11 | 1.6 | 62 |
| 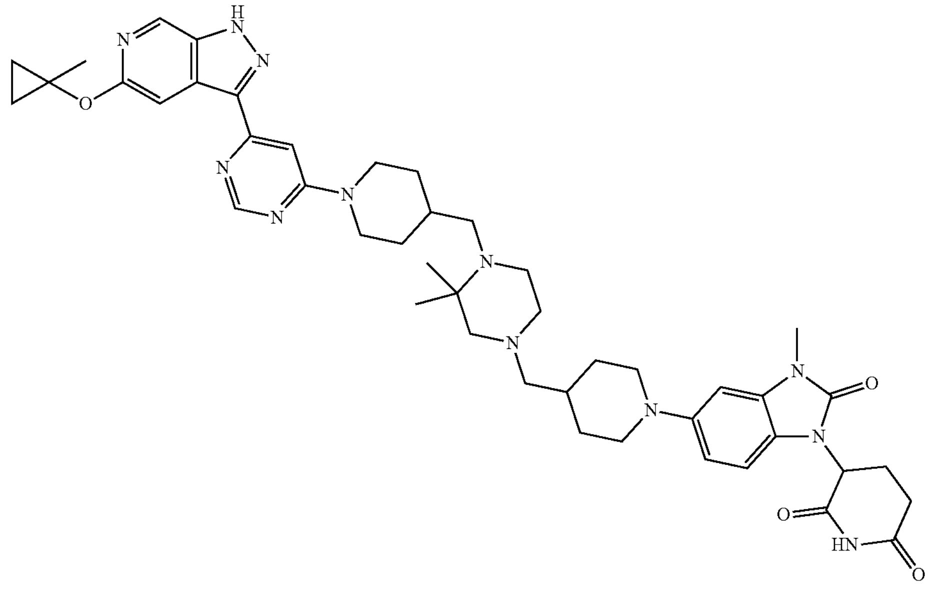 [SMILES: Cn1c(=O)n(C2CCC(=O)NC2=O)c2ccc(N3CCC(CN4CCN(CC5CCN(c6cc(-c7n[nH]c8cnc(OC9(C)CC9)cc78)ncn6)CC5)C(C)(C)C4)CC3)cc21] Compound No. 48 | 0.14 | 56 |
| 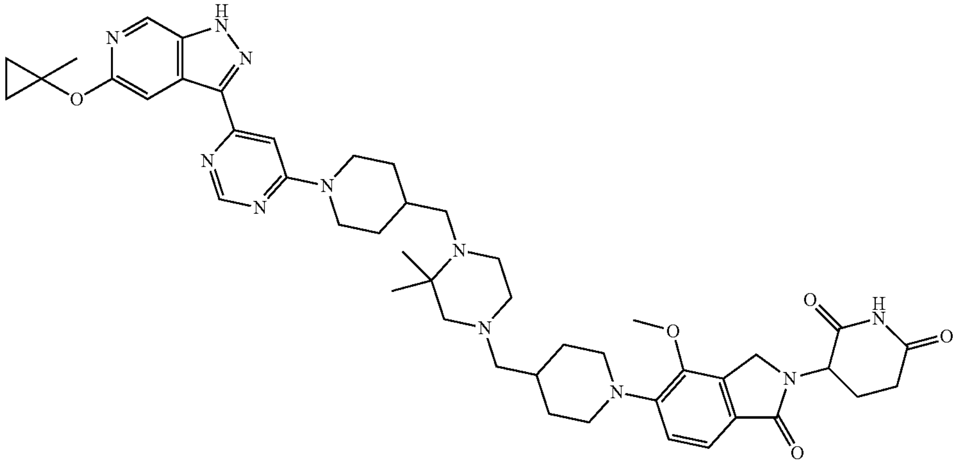 [SMILES: COc1c(N2CCC(CN3CCN(CC4CCN(c5cc(-c6n[nH]c7cnc(OC8(C)CC8)cc67)ncn5)CC4)C(C)(C)C3)CC2)ccc2c1CN(C1CCC(=O)NC1=O)C2=O] Comparative Example 6 | 1.7 | 68 |

TABLE 3-continued
| Compound | WT LRRK2 *$DC_{50}$ (nM) | WT LRRK2 **Dmax (%) |
| --- | --- | --- |
| 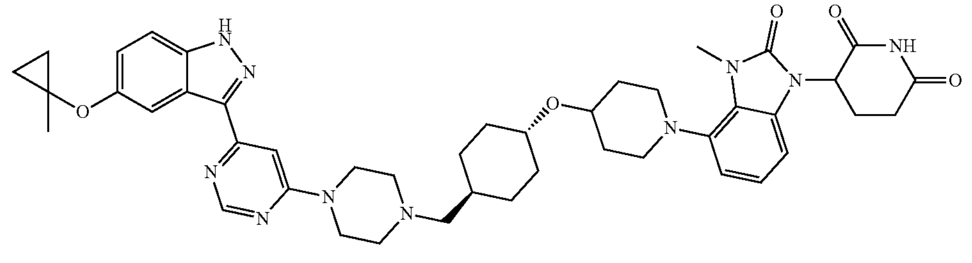 [SMILES: Cn1c(=O)n(C2CCC(=O)NC2=O)c2cccc(N3CCC(O[C@H]4CC[C@H](CN5CCN(c6cc(-c7n[nH]c8ccc(OC9(C)CC9)cc78)ncn6)CC5)CC4)CC3)c21] Compound No. 9 | 1.2 | 66 |
| 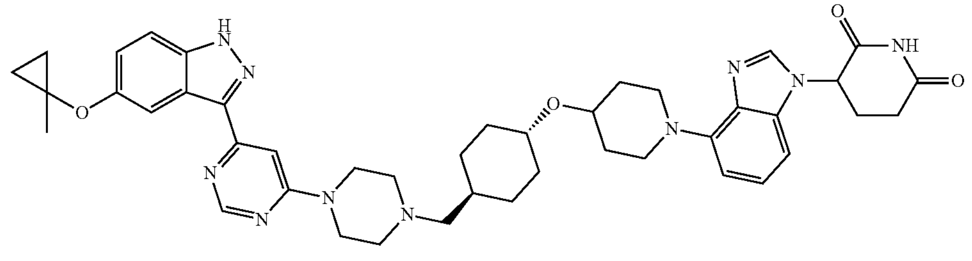 [SMILES: CC1(Oc2ccc3[nH]nc(-c4cc(N5CCN(C[C@H]6CC[C@H](OC7CCN(c8cccc9c8ncn9C8CCC(=O)NC8=O)CC7)CC6)CC5)ncn4)c3c2)CC1] Compound No. 3 | 28 | 30 |
| 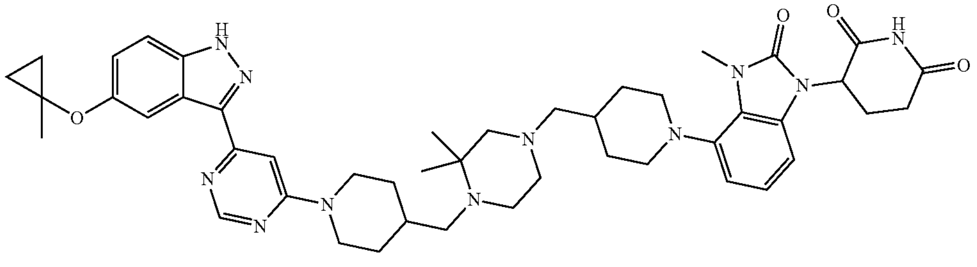 [SMILES: Cn1c(=O)n(C2CCC(=O)NC2=O)c2cccc(N3CCC(CN4CCN(CC5CCN(c6cc(-c7n[nH]c8ccc(OC9(C)CC9)cc78)ncn6)CC5)C(C)(C)C4)CC3)c21] Compound No. 8 | 1.2 | 65 |
| 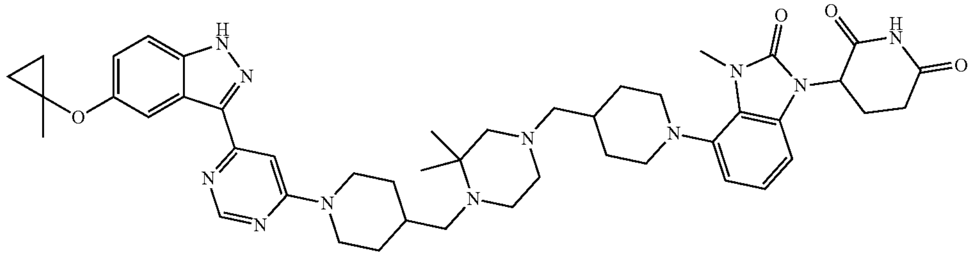 [SMILES: Cn1c(=O)n(C2CCC(=O)NC2=O)c2cccc(N3CCC(CN4CCN(CC5CCN(c6cc(-c7n[nH]c8ccc(OC9(C)CC9)cc78)ncn6)CC5)C(C)(C)C4)CC3)c21] Compound No. 69 | 5 | 50 |
| 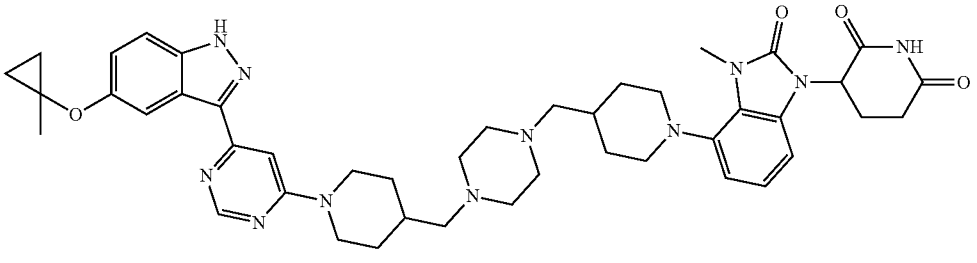 [SMILES: Cn1c(=O)n(C2CCC(=O)NC2=O)c2cccc(N3CCC(CN4CCN(CC5CCN(c6cc(-c7n[nH]c8ccc(OC9(C)CC9)cc78)ncn6)CC5)CC4)CC3)c21] Compound No. 15 | 1.5 | 59 |

TABLE 3-continued

| Compound | WT LRRK2 *$DC_{50}$ (nM) | WT LRRK2 **Dmax (%) |
|---|---|---|
| 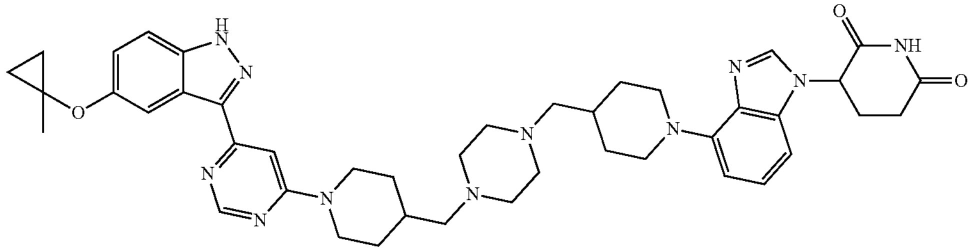 [SMILES: CC1(Oc2ccc3[nH]nc(-c4cc(N5CCC(CN6CCN(CC7CCN(c8cccc9c8ncn9C8CCC(=O)NC8=O)CC7)CC6)CC5)ncn4)c3c2)CC1] Compound No. 70 | 20 | 33 |

The disclosed subject matter is not to be limited in scope by the specific embodiments and examples described herein. Indeed, various modifications of the disclosure in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes. Other embodiments are within the following claims.

What is claimed is:

1. A compound, wherein the compound is:

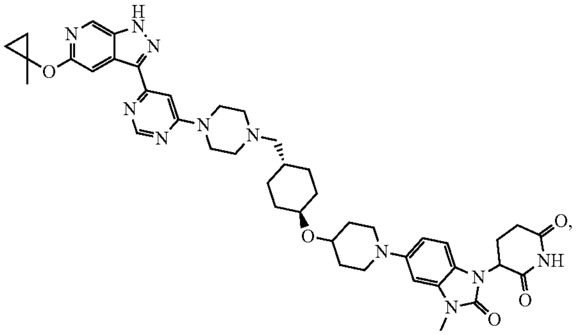

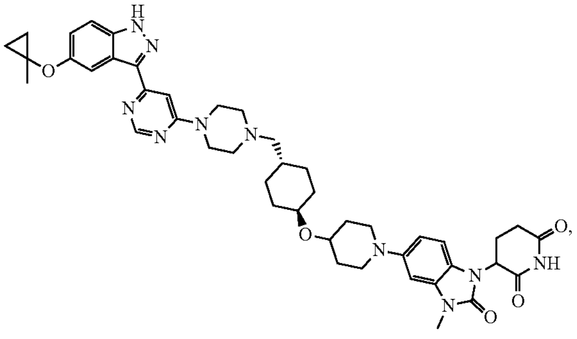

-continued

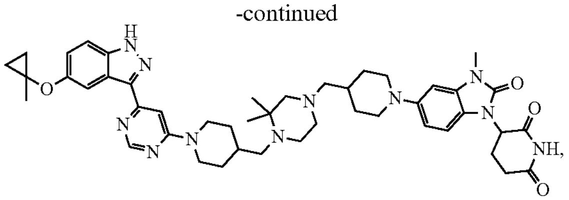

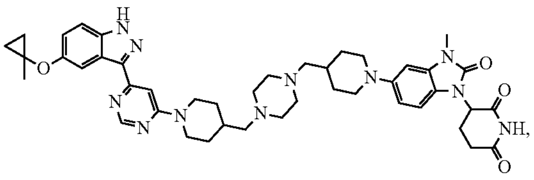

or

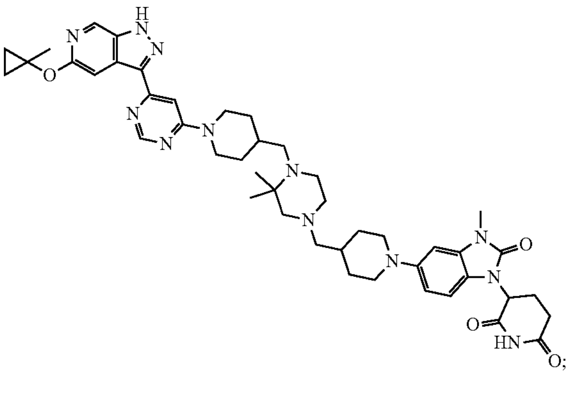

or a pharmaceutically acceptable salt thereof.

2. The compound of claim 1, wherein the compound is:
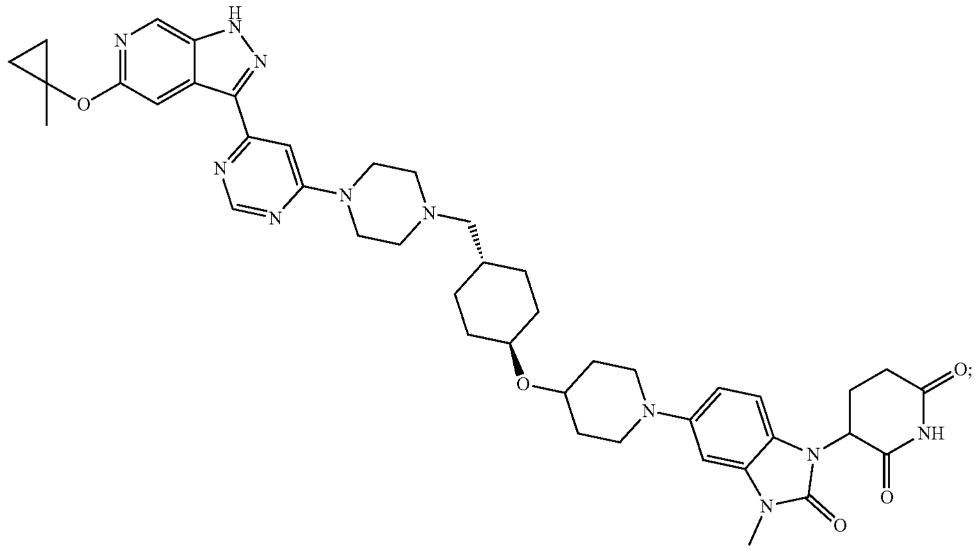 [SMILES: Cn1c(=O)n(C2CCC(=O)NC2=O)c2ccc(N3CCC(O[C@H]4CC[C@H](CN5CCN(c6cc(-c7n[nH]c8cnc(OC9(C)CC9)cc78)ncn6)CC5)CC4)CC3)cc21]
or a pharmaceutically acceptable salt thereof.
3. The compound of claim 1, wherein the compound is:
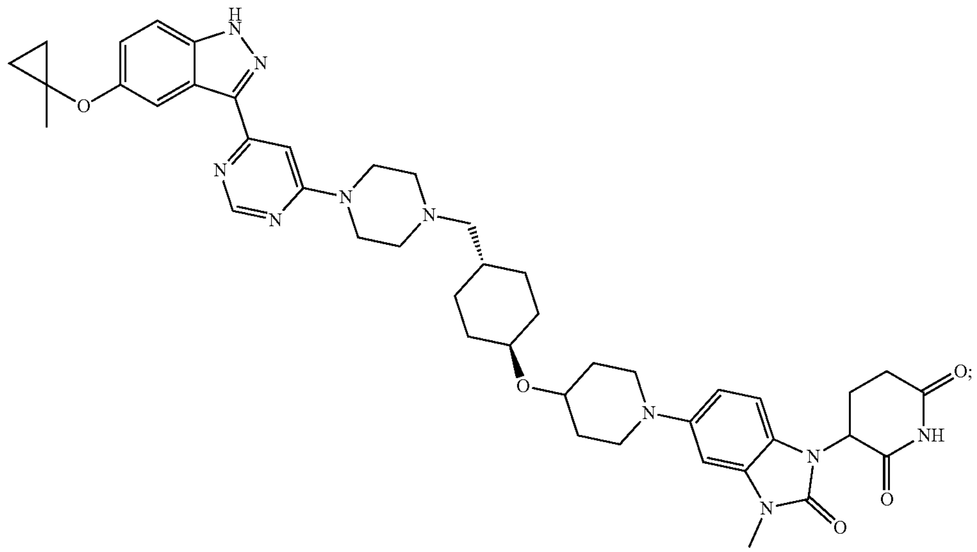 [SMILES: Cn1c(=O)n(C2CCC(=O)NC2=O)c2ccc(N3CCC(O[C@H]4CC[C@H](CN5CCN(c6cc(-c7n[nH]c8ccc(OC9(C)CC9)cc78)ncn6)CC5)CC4)CC3)cc21]
or a pharmaceutically acceptable salt thereof.

4. The compound of claim 1, wherein the compound is:

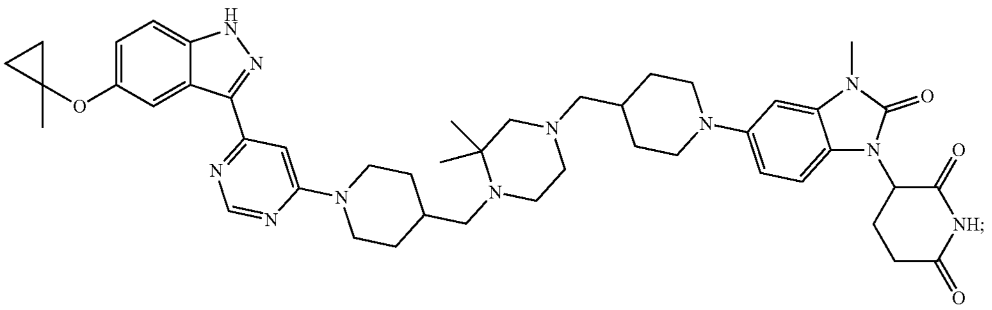 [SMILES: Cn1c(=O)n(C2CCC(=O)NC2=O)c2ccc(N3CCC(CN4CCN(CC5CCN(c6cc(-c7n[nH]c8ccc(OC9(C)CC9)cc78)ncn6)CC5)C(C)(C)C4)CC3)cc21]

or a pharmaceutically acceptable salt thereof.

5. The compound of claim 1, wherein the compound is:

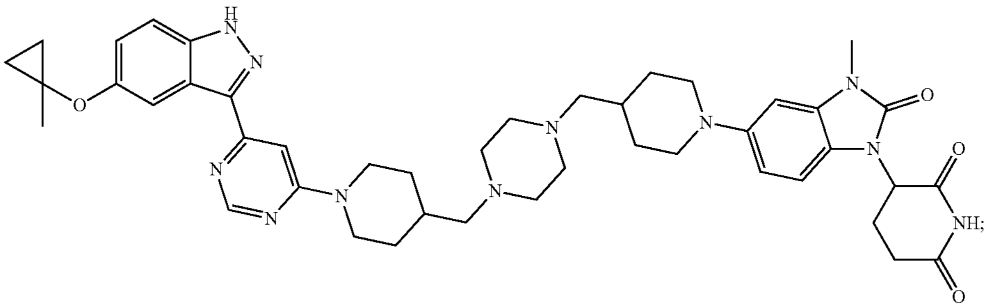 [SMILES: Cn1c(=O)n(C2CCC(=O)NC2=O)c2ccc(N3CCC(CN4CCN(CC5CCN(c6cc(-c7n[nH]c8ccc(OC9(C)CC9)cc78)ncn6)CC5)CC4)CC3)cc21]

or a pharmaceutically acceptable salt thereof.

6. The compound of claim 1, wherein the compound is:

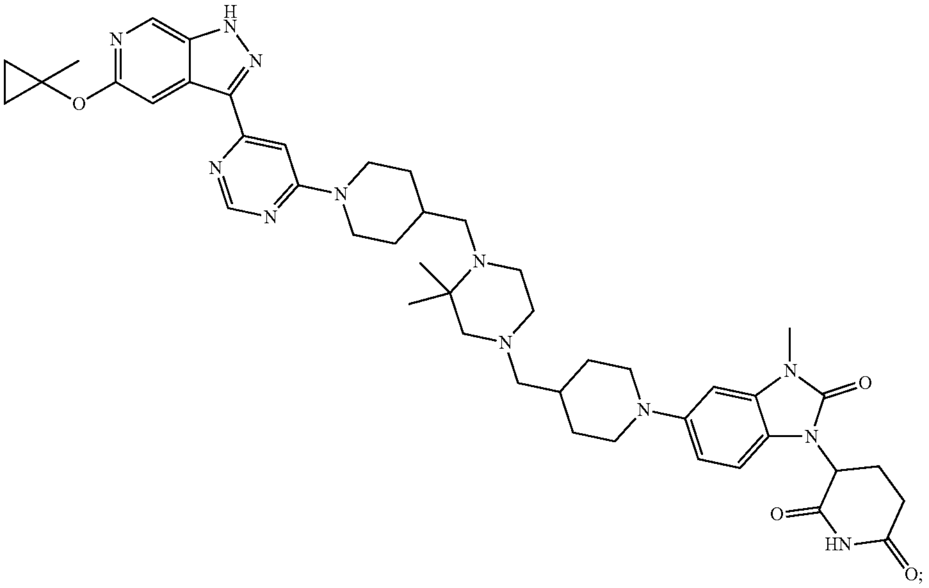 [SMILES: Cn1c(=O)n(C2CCC(=O)NC2=O)c2ccc(N3CCC(CN4CCN(CC5CCN(c6cc(-c7n[nH]c8cnc(OC9(C)CC9)cc78)ncn6)CC5)C(C)(C)C4)CC3)cc21]

or a pharmaceutically acceptable salt thereof.

7. A pharmaceutical composition comprising the compound of claim 1, or a pharmaceutically acceptable salt thereof, and a pharmaceutically acceptable carrier.

8. A pharmaceutical composition comprising the compound of claim 2, or a pharmaceutically acceptable salt thereof, and a pharmaceutically acceptable carrier.

9. A pharmaceutical composition comprising the compound of claim 3, or a pharmaceutically acceptable salt thereof, and a pharmaceutically acceptable carrier.

10. A pharmaceutical composition comprising the compound of claim 4, or a pharmaceutically acceptable salt thereof, and a pharmaceutically acceptable carrier.

11. A pharmaceutical composition comprising the compound of claim 5, or a pharmaceutically acceptable salt thereof, and a pharmaceutically acceptable carrier.

12. A pharmaceutical composition comprising the compound of claim 6, or a pharmaceutically acceptable salt thereof, and a pharmaceutically acceptable carrier.

* * * * *